United States Patent
Bulik-Sullivan et al.

(10) Patent No.: US 11,264,117 B2
(45) Date of Patent: Mar. 1, 2022

(54) NEOANTIGEN IDENTIFICATION USING HOTSPOTS

(71) Applicant: Gritstone bio, Inc., Emeryville, CA (US)

(72) Inventors: Brendan Bulik-Sullivan, Cambridge, MA (US); Thomas Francis Boucher, Boston, MA (US); Roman Yelensky, Newton, MA (US)

(73) Assignee: GRITSTONE BIO, INC., Emeryville, CA (US)

( * ) Notice: Subject to any disclaimer, the term of this patent is extended or adjusted under 35 U.S.C. 154(b) by 0 days.

(21) Appl. No.: 16/403,331

(22) Filed: May 3, 2019

(65) Prior Publication Data

US 2019/0279742 A1    Sep. 12, 2019

Related U.S. Application Data

(63) Continuation of application No. PCT/US2018/055283, filed on Oct. 10, 2018.

(60) Provisional application No. 62/570,569, filed on Oct. 10, 2017.

(51) Int. Cl.
| | |
|---|---|
| G16B 40/00 | (2019.01) |
| G01N 33/50 | (2006.01) |
| G01N 33/68 | (2006.01) |
| C12Q 1/6886 | (2018.01) |
| G01N 33/574 | (2006.01) |
| G01N 33/569 | (2006.01) |

(52) U.S. Cl.
CPC .......... *G16B 40/00* (2019.02); *C12Q 1/6886* (2013.01); *G01N 33/50* (2013.01); *G01N 33/56977* (2013.01); *G01N 33/574* (2013.01); *G01N 33/6878* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 4,235,871 A | 11/1980 | Papahadjopoulos et al. |
| 4,452,773 A | 6/1984 | Molday |
| 4,501,728 A | 2/1985 | Geho et al. |
| 4,656,127 A | 4/1987 | Mundy |
| 4,722,848 A | 2/1988 | Paoletti et al. |
| 4,795,698 A | 1/1989 | Owen et al. |
| 4,837,028 A | 6/1989 | Allen |
| 5,019,369 A | 5/1991 | Presant et al. |
| 5,130,538 A | 7/1992 | Fenn et al. |
| 5,200,084 A | 4/1993 | Liberti et al. |
| 5,204,244 A | 4/1993 | Fell et al. |
| 5,204,253 A | 4/1993 | Sanford et al. |
| 5,279,833 A | 1/1994 | Rose |
| 5,504,329 A | 4/1996 | Mann et al. |
| 5,514,578 A | 5/1996 | Hogness et al. |
| 5,534,615 A | 7/1996 | Baker et al. |
| 5,580,859 A | 12/1996 | Felgner et al. |
| 5,581,080 A | 12/1996 | Fenn et al. |
| 5,589,466 A | 12/1996 | Felgner et al. |
| 5,608,217 A | 3/1997 | Franzen et al. |
| 5,686,726 A | 11/1997 | Fenn et al. |
| 5,849,589 A | 12/1998 | Tedder et al. |
| 6,040,177 A | 3/2000 | Riddell et al. |
| 6,245,531 B1 | 6/2001 | Hogness et al. |
| 6,405,917 B1 | 6/2002 | Mann |
| 6,864,089 B2 | 3/2005 | Figeys et al. |
| 7,091,038 B2 | 8/2006 | Palli et al. |
| 7,283,337 B2 | 10/2007 | Sakai et al. |
| 7,695,725 B2 | 4/2010 | Dubensky, Jr. et al. |
| 7,731,648 B2 | 6/2010 | Ivkov |
| 7,833,775 B2 | 11/2010 | Dubensky, Jr. et al. |
| 7,842,289 B2 | 11/2010 | Dubensky, Jr. et al. |
| 7,935,804 B2 | 5/2011 | Dubensky, Jr. et al. |
| 7,981,420 B2 | 7/2011 | Mueller et al. |
| 8,053,552 B2 | 11/2011 | Von Knebel-Doeberitz et al. |
| 8,121,797 B2 | 2/2012 | Heckerman et al. |

(Continued)

FOREIGN PATENT DOCUMENTS

| | | |
|---|---|---|
| CN | 103180730 A | 6/2013 |
| EP | 0434792 A1 | 7/1991 |

(Continued)

OTHER PUBLICATIONS

Inza et al Bioinformatics Methods in Clinical Research, Methods in Molecular Biology 593, p. 25-48.*
Larranga et al. Briefings in Bioinformatics, vol. 7, Issue 1,86-112, 2006.*
Deniger et al. Molecular Therapy vol. 24, Supplement 1, May 2016, S155.*
Rajasagi, M et al. "Systemic Identification of Personal Tumor-Specific Neoantigens in Chronic Lymphocytic Leukemia, Blood" Jun. 2, 2014; vol. 124, No. 3, pp. 453-462.
International Search Report and Written Opinion issued for PCT/US2018/055283, dated Jan. 17, 2019.

(Continued)

*Primary Examiner* — Michael L Borin
(74) *Attorney, Agent, or Firm* — Goodwin Procter LLP

(57) ABSTRACT

A method for identifying neoantigens that are likely to be presented on a surface of tumor cells of a subject. Peptide sequences of tumor neoantigens are obtained by sequencing the tumor cells of the subject. The peptide sequence of each of the neoantigens is associated with one or more k-mer blocks of a plurality of k-mer blocks of the nucleotide sequencing data of the subject; The peptide sequences and the associated k-mer blocks are input into a machine-learned presentation model to generate presentation likelihoods for the tumor neoantigens, each presentation likelihood representing the likelihood that a neoantigen is presented by an MHC allele on the surfaces of the tumor cells of the subject. A subset of the neoantigens is selected based on the presentation likelihoods.

29 Claims, 57 Drawing Sheets

Specification includes a Sequence Listing.

(56) References Cited

U.S. PATENT DOCUMENTS

| | | |
|---|---|---|
| 8,287,883 B2 | 10/2012 | Dubensky, Jr. et al. |
| 8,583,380 B2 | 11/2013 | Stephan et al. |
| 8,680,239 B2 | 3/2014 | Mueller et al. |
| 8,741,556 B2 | 6/2014 | Mann et al. |
| 8,768,629 B2 | 7/2014 | Von Hoff et al. |
| 8,796,414 B2 | 8/2014 | Johnston |
| 8,821,864 B2 | 9/2014 | Von Knebel-Doeberitz et al. |
| 8,840,881 B2 | 9/2014 | Jooss et al. |
| 8,926,993 B2 | 1/2015 | Dubensky, Jr. et al. |
| 9,017,660 B2 | 4/2015 | Shahabi et al. |
| 9,063,149 B2 | 6/2015 | Mann et al. |
| 9,084,747 B2 | 7/2015 | Shahabi et al. |
| 9,115,402 B2 | 8/2015 | Hacohen et al. |
| 9,161,974 B2 | 10/2015 | Dubensky et al. |
| 9,175,088 B2 | 11/2015 | Sahin et al. |
| 9,194,004 B2 | 11/2015 | Sahin et al. |
| 9,198,960 B2 | 12/2015 | Dubensky, Jr. et al. |
| 9,267,177 B2 | 2/2016 | Tureci et al. |
| 9,289,478 B2 | 3/2016 | Lewandrowski et al. |
| 9,308,244 B2 | 4/2016 | Singh et al. |
| 9,389,235 B2 | 7/2016 | Weinschenk et al. |
| 9,463,227 B2 | 10/2016 | Rothman et al. |
| 9,498,512 B2 | 11/2016 | Rammensee et al. |
| 9,499,602 B2 | 11/2016 | Paterson et al. |
| 9,511,128 B2 | 12/2016 | Singh et al. |
| 9,527,916 B2 | 12/2016 | Van Eenennaam et al. |
| 9,533,043 B2 | 1/2017 | Tureci et al. |
| 9,549,973 B2 | 1/2017 | Paterson et al. |
| 9,587,020 B2 | 3/2017 | Wu et al. |
| 2002/0076817 A1 | 6/2002 | Figeys et al. |
| 2002/0155447 A1 | 10/2002 | Zauderer et al. |
| 2002/0192708 A1 | 12/2002 | Steen et al. |
| 2003/0171290 A1 | 9/2003 | Carr et al. |
| 2003/0175722 A1 | 9/2003 | Mann et al. |
| 2004/0002112 A1 | 1/2004 | Mann et al. |
| 2004/0102376 A1 | 5/2004 | Mueller et al. |
| 2005/0164326 A1 | 7/2005 | Figeys et al. |
| 2006/0190226 A1* | 8/2006 | Jojic ............... G16B 40/00 703/11 |
| 2006/0252077 A1 | 11/2006 | Buzby |
| 2009/0093050 A1 | 4/2009 | Wu et al. |
| 2010/0127110 A1 | 5/2010 | Hagedorn et al. |
| 2010/0286070 A1 | 11/2010 | Verheyden et al. |
| 2011/0003380 A1 | 1/2011 | Miltenyi et al. |
| 2011/0112280 A1 | 5/2011 | Mueller et al. |
| 2011/0287055 A1 | 11/2011 | Lauer et al. |
| 2011/0293637 A1 | 12/2011 | Hacohen et al. |
| 2012/0077696 A1 | 3/2012 | Admon et al. |
| 2012/0100173 A1 | 4/2012 | Leclair et al. |
| 2012/0208706 A1 | 8/2012 | Downing et al. |
| 2012/0264154 A1 | 10/2012 | Mann et al. |
| 2013/0072667 A1 | 3/2013 | Mueller et al. |
| 2013/0138414 A1 | 5/2013 | Bangera et al. |
| 2013/0259883 A1 | 10/2013 | Hunt et al. |
| 2013/0303594 A1 | 11/2013 | Kappei et al. |
| 2013/0315950 A1 | 11/2013 | Dubensky et al. |
| 2014/0037662 A1 | 2/2014 | Lauer et al. |
| 2014/0072991 A1 | 3/2014 | Mann et al. |
| 2014/0178438 A1 | 6/2014 | Sahin et al. |
| 2014/0186387 A1 | 7/2014 | Lauer et al. |
| 2014/0205653 A1 | 7/2014 | Dubensky, Jr. et al. |
| 2014/0234370 A1 | 8/2014 | Shahabi |
| 2014/0248304 A1 | 9/2014 | Paterson et al. |
| 2014/0314708 A1 | 10/2014 | Maciag et al. |
| 2014/0315314 A1 | 10/2014 | Dubensky, Jr. et al. |
| 2014/0335120 A1 | 11/2014 | Maciag et al. |
| 2015/0044246 A1 | 2/2015 | Weinschenk et al. |
| 2015/0056224 A1 | 2/2015 | Dubensky, Jr. et al. |
| 2015/0079119 A1 | 3/2015 | Johnston |
| 2015/0098964 A1 | 4/2015 | Singh et al. |
| 2015/0125465 A1 | 5/2015 | Binder et al. |
| 2015/0125477 A1 | 5/2015 | Kuttruff-Coqui et al. |
| 2015/0125485 A1 | 5/2015 | Dubensky, Jr. et al. |
| 2015/0140041 A1 | 5/2015 | Vitiello |
| 2015/0238584 A1 | 8/2015 | Shahabi et al. |
| 2015/0241420 A1 | 8/2015 | Johnston et al. |
| 2015/0278441 A1 | 10/2015 | Min et al. |
| 2015/0297702 A1 | 10/2015 | Shahabi et al. |
| 2015/0307567 A1 | 10/2015 | Leclair et al. |
| 2015/0320848 A1 | 11/2015 | Rammensee et al. |
| 2015/0335721 A1 | 11/2015 | Paterson et al. |
| 2015/0343047 A1 | 12/2015 | Paterson et al. |
| 2015/0346068 A1 | 12/2015 | Kulak et al. |
| 2015/0366955 A9 | 12/2015 | Shahabi et al. |
| 2015/0368298 A1 | 12/2015 | Stickel et al. |
| 2015/0376718 A1 | 12/2015 | Tureci et al. |
| 2016/0002738 A1 | 1/2016 | Sahin et al. |
| 2016/0008447 A1 | 1/2016 | Hacohen et al. |
| 2016/0022814 A1 | 1/2016 | Petit et al. |
| 2016/0024173 A1 | 1/2016 | Paterson et al. |
| 2016/0051654 A1 | 2/2016 | Singh et al. |
| 2016/0058853 A1 | 3/2016 | Sahin et al. |
| 2016/0069895 A1 | 3/2016 | Delamarre et al. |
| 2016/0074491 A1 | 3/2016 | Lauer et al. |
| 2016/0101170 A1 | 4/2016 | Hacohen et al. |
| 2016/0115212 A1 | 4/2016 | Dengjel |
| 2016/0117441 A1 | 4/2016 | Bremel |
| 2016/0125129 A1 | 5/2016 | Sahin et al. |
| 2016/0151472 A1 | 6/2016 | Jooss et al. |
| 2016/0168200 A1 | 6/2016 | Weinschenk et al. |
| 2016/0175357 A1 | 6/2016 | Weinschenk et al. |
| 2016/0175414 A1 | 6/2016 | Sahin et al. |
| 2016/0175415 A1 | 6/2016 | Dubensky, Jr. et al. |
| 2016/0185870 A1 | 6/2016 | Van Eenennaam et al. |
| 2016/0194402 A1 | 7/2016 | Van Eenennaam et al. |
| 2016/0195539 A1 | 7/2016 | Tureci et al. |
| 2016/0201137 A1 | 7/2016 | Wirtz et al. |
| 2016/0202267 A1 | 7/2016 | Van Eenennaam et al. |
| 2016/0215351 A1 | 7/2016 | Sahin et al. |
| 2016/0220652 A1 | 8/2016 | Petit et al. |
| 2016/0244825 A1 | 8/2016 | Vigneault et al. |
| 2016/0250307 A1 | 9/2016 | Weinschenk et al. |
| 2016/0250323 A1 | 9/2016 | Sahin et al. |
| 2016/0264674 A1 | 9/2016 | van Eenennaam et al. |
| 2016/0265050 A1 | 9/2016 | Sahin et al. |
| 2016/0272711 A1 | 9/2016 | Sahin et al. |
| 2016/0279214 A1 | 9/2016 | Mahr et al. |
| 2016/0279215 A1 | 9/2016 | Mahr et al. |
| 2016/0279216 A1 | 9/2016 | Mahr et al. |
| 2016/0279217 A1 | 9/2016 | Mahr et al. |
| 2016/0279218 A1 | 9/2016 | Mahr et al. |
| 2016/0280738 A1 | 9/2016 | Mahr et al. |
| 2016/0280752 A1 | 9/2016 | Mahr et al. |
| 2016/0280757 A1 | 9/2016 | Mahr et al. |
| 2016/0280758 A1 | 9/2016 | Mahr et al. |
| 2016/0280759 A1 | 9/2016 | Mahr et al. |
| 2016/0280760 A1 | 9/2016 | Mahr et al. |
| 2016/0287687 A1 | 10/2016 | Mahr et al. |
| 2016/0289296 A1 | 10/2016 | Mahr et al. |
| 2016/0298185 A1 | 10/2016 | Shukla et al. |
| 2016/0324903 A1 | 11/2016 | Rothman et al. |
| 2016/0331821 A1 | 11/2016 | Levey et al. |
| 2016/0331822 A1 | 11/2016 | Hacohen et al. |
| 2016/0339090 A1 | 11/2016 | Hacohen et al. |
| 2016/0339092 A1 | 11/2016 | Schoor et al. |
| 2016/0346369 A1 | 12/2016 | Lauer et al. |
| 2016/0346371 A1 | 12/2016 | Schoor et al. |
| 2016/0347798 A1 | 12/2016 | Poma et al. |
| 2016/0347808 A1 | 12/2016 | Schoor et al. |
| 2016/0347815 A1 | 12/2016 | Sahin et al. |
| 2016/0347847 A1 | 12/2016 | Van Dijk et al. |
| 2016/0361401 A1 | 12/2016 | Shahabi et al. |
| 2016/0368965 A1 | 12/2016 | Mahr et al. |
| 2016/0368989 A1 | 12/2016 | Dijk et al. |
| 2017/0002055 A1 | 1/2017 | Mahr et al. |
| 2017/0022251 A1 | 1/2017 | Rammensee et al. |
| 2017/0028044 A1* | 2/2017 | Soon-Shiong ...... A61K 39/0011 |
| 2017/0029486 A1 | 2/2017 | Mahr et al. |
| 2017/0035807 A1 | 2/2017 | Schuster et al. |
| 2017/0037089 A1 | 2/2017 | Mahr et al. |
| 2017/0037092 A1 | 2/2017 | Mahr et al. |
| 2017/0037093 A1 | 2/2017 | Mahr et al. |
| 2017/0037094 A1 | 2/2017 | Mahr et al. |
| 2017/0037095 A1 | 2/2017 | Mahr et al. |

(56) References Cited

U.S. PATENT DOCUMENTS

| | | |
|---|---|---|
| 2017/0037096 A1 | 2/2017 | Mahr et al. |
| 2017/0037097 A1 | 2/2017 | Mahr et al. |
| 2017/0037098 A1 | 2/2017 | Mahr et al. |
| 2017/0037107 A1 | 2/2017 | Mahr et al. |
| 2017/0037110 A1 | 2/2017 | Mahr et al. |
| 2017/0037111 A1 | 2/2017 | Mahr et al. |
| 2017/0042996 A1 | 2/2017 | Wallecha et al. |
| 2017/0052187 A1 | 2/2017 | Sahin et al. |
| 2017/0056486 A1 | 3/2017 | Mahr et al. |
| 2017/0056487 A1 | 3/2017 | Mahr et al. |
| 2017/0056488 A1 | 3/2017 | Mahr et al. |
| 2017/0116371 A1 | 4/2017 | Dimon et al. |
| 2017/0166877 A1 | 6/2017 | Bayle et al. |
| 2017/0199961 A1 | 7/2017 | Yelensky et al. |
| 2017/0212984 A1 | 7/2017 | Yelensky et al. |
| 2017/0221176 A1 | 8/2017 | Munteanu et al. |
| 2018/0330055 A1 | 11/2018 | Yelensky et al. |
| 2020/0105377 A1 | 4/2020 | Bulik-Sullivan et al. |
| 2021/0098077 A1 | 4/2021 | Yelensky et al. |
| 2021/0113673 A1 | 4/2021 | Boucher et al. |
| 2021/0166784 A1 | 6/2021 | Yelensky et al. |

FOREIGN PATENT DOCUMENTS

| | | |
|---|---|---|
| EP | 452342 A1 | 10/1991 |
| EP | 0517805 A1 | 12/1992 |
| EP | 1021537 A1 | 7/2000 |
| EP | 1290450 A2 | 3/2003 |
| EP | 1355666 A2 | 10/2003 |
| EP | 1419518 A2 | 5/2004 |
| EP | 1575643 A2 | 9/2005 |
| EP | 1592441 A2 | 11/2005 |
| EP | 1603936 A2 | 12/2005 |
| EP | 1608321 A2 | 12/2005 |
| EP | 1708741 A2 | 10/2006 |
| EP | 1991263 A2 | 11/2008 |
| EP | 2002263 A2 | 12/2008 |
| EP | 2091046 A1 | 8/2009 |
| EP | 2134363 A2 | 12/2009 |
| EP | 2155243 A2 | 2/2010 |
| EP | 2172212 A2 | 4/2010 |
| EP | 2178557 A1 | 4/2010 |
| EP | 2266608 A2 | 12/2010 |
| EP | 2266613 A2 | 12/2010 |
| EP | 2267013 A2 | 12/2010 |
| EP | 2280082 A2 | 2/2011 |
| EP | 2283112 A1 | 2/2011 |
| EP | 2288379 A2 | 3/2011 |
| EP | 2309262 A1 | 4/2011 |
| EP | 2311860 A2 | 4/2011 |
| EP | 2331118 A1 | 6/2011 |
| EP | 2341927 A2 | 7/2011 |
| EP | 2385062 A2 | 11/2011 |
| EP | 2403528 A2 | 1/2012 |
| EP | 2413953 A2 | 2/2012 |
| EP | 2486405 A1 | 8/2012 |
| EP | 2498808 A2 | 9/2012 |
| EP | 2508537 A1 | 10/2012 |
| EP | 2547691 A1 | 1/2013 |
| EP | 2567707 A2 | 3/2013 |
| EP | 2574346 A1 | 4/2013 |
| EP | 2576614 A2 | 4/2013 |
| EP | 2576791 A1 | 4/2013 |
| EP | 2591001 A1 | 5/2013 |
| EP | 2616482 A1 | 7/2013 |
| EP | 2619585 A2 | 7/2013 |
| EP | 2640842 A1 | 9/2013 |
| EP | 2643698 A1 | 10/2013 |
| EP | 2694556 A1 | 2/2014 |
| EP | 2744513 A1 | 6/2014 |
| EP | 2767834 A2 | 8/2014 |
| EP | 2772262 A1 | 9/2014 |
| EP | 2825195 A1 | 1/2015 |
| EP | 2853269 A1 | 4/2015 |
| EP | 2859899 A1 | 4/2015 |
| EP | 2859901 A1 | 4/2015 |
| EP | 2860253 A2 | 4/2015 |
| EP | 2865387 A2 | 4/2015 |
| EP | 2931738 A1 | 10/2015 |
| EP | 2934749 A2 | 10/2015 |
| EP | 2938627 A1 | 11/2015 |
| EP | 2959021 A1 | 12/2015 |
| EP | 2966082 A1 | 1/2016 |
| EP | 2994159 A1 | 3/2016 |
| EP | 2996473 A1 | 3/2016 |
| EP | 3027203 A1 | 6/2016 |
| EP | 3027210 A1 | 6/2016 |
| EP | 3030255 A1 | 6/2016 |
| EP | 3041867 A1 | 7/2016 |
| EP | 3041868 A2 | 7/2016 |
| EP | 3042914 A1 | 7/2016 |
| EP | 3049065 A1 | 8/2016 |
| EP | 3058947 A2 | 8/2016 |
| EP | 3060679 A1 | 8/2016 |
| EP | 3066115 A2 | 9/2016 |
| EP | 3069728 A1 | 9/2016 |
| EP | 3095791 A1 | 11/2016 |
| EP | 3099706 A1 | 12/2016 |
| EP | 3099708 A1 | 12/2016 |
| EP | 3103476 A2 | 12/2016 |
| EP | 3106175 A1 | 12/2016 |
| EP | 3107566 A1 | 12/2016 |
| EP | 3110942 A2 | 1/2017 |
| EP | 3111952 A1 | 1/2017 |
| EP | 3113794 A1 | 1/2017 |
| EP | 3120868 A1 | 1/2017 |
| EP | 3120869 A1 | 1/2017 |
| EP | 3120870 A1 | 1/2017 |
| EP | 3124043 A1 | 2/2017 |
| EP | 3132801 A1 | 2/2017 |
| EP | 2845604 B1 | 3/2017 |
| EP | 3134510 A1 | 3/2017 |
| WO | 1990/014148 A1 | 11/1990 |
| WO | 91/02087 A1 | 2/1991 |
| WO | 1991/06309 A1 | 5/1991 |
| WO | 92/15712 A1 | 9/1992 |
| WO | 1993/24640 A2 | 12/1993 |
| WO | 96/18372 A2 | 6/1996 |
| WO | 1999/019484 A1 | 4/1999 |
| WO | 2001/025268 A1 | 4/2001 |
| WO | 2001/094935 A2 | 12/2001 |
| WO | 2002/037121 A2 | 5/2002 |
| WO | 2002/051438 A2 | 7/2002 |
| WO | 2002/080649 A2 | 10/2002 |
| WO | 2003/038055 A2 | 5/2003 |
| WO | 2003/087162 A2 | 10/2003 |
| WO | 2007/101227 A2 | 9/2007 |
| WO | 2008/109155 A2 | 9/2008 |
| WO | 2008/140812 A2 | 11/2008 |
| WO | 2009/072003 A2 | 6/2009 |
| WO | 2009/143167 A2 | 11/2009 |
| WO | 2010/028288 A2 | 3/2010 |
| WO | 2010/033140 A3 | 5/2010 |
| WO | 2010/104749 A2 | 9/2010 |
| WO | 2011/042467 A1 | 4/2011 |
| WO | 2011/060260 A2 | 5/2011 |
| WO | 2011/100754 A1 | 8/2011 |
| WO | 2011/143656 A2 | 11/2011 |
| WO | 2011/149852 A2 | 12/2011 |
| WO | 2012/035066 A1 | 3/2012 |
| WO | 2012/068360 A1 | 5/2012 |
| WO | 2012/136737 A2 | 10/2012 |
| WO | 2012/138377 A2 | 10/2012 |
| WO | 2013/025925 A1 | 2/2013 |
| WO | 2013/138337 A1 | 9/2013 |
| WO | 2013/158611 A1 | 10/2013 |
| WO | 2014/082729 A1 | 6/2014 |
| WO | 2014/093936 A1 | 6/2014 |
| WO | 2014/096136 A2 | 6/2014 |
| WO | 2014/106123 A1 | 7/2014 |
| WO | 2015/030585 A2 | 3/2015 |
| WO | 2015/095811 A2 | 6/2015 |
| WO | 2015/103037 A2 | 7/2015 |
| WO | 2015/126921 A1 | 8/2015 |

(56) References Cited

FOREIGN PATENT DOCUMENTS

| | | |
|---|---|---|
| WO | 2015/130810 A2 | 9/2015 |
| WO | 2015/134722 A2 | 9/2015 |
| WO | 2015/169945 A2 | 11/2015 |
| WO | 2015/172843 A1 | 11/2015 |
| WO | 2015/172960 A1 | 11/2015 |
| WO | 2015/173317 A1 | 11/2015 |
| WO | 2015/193359 A2 | 12/2015 |
| WO | 2016/011320 A1 | 1/2016 |
| WO | 2016/011357 A1 | 1/2016 |
| WO | 2016/011362 A1 | 1/2016 |
| WO | 2016/040900 A1 | 3/2016 |
| WO | 2016/044530 A1 | 3/2016 |
| WO | 2016/054013 A1 | 4/2016 |
| WO | 2016/062323 A1 | 4/2016 |
| WO | 2016/062659 A1 | 4/2016 |
| WO | 2016/069283 A1 | 5/2016 |
| WO | 2016/074915 A1 | 5/2016 |
| WO | 2016/081947 A2 | 5/2016 |
| WO | 2016/100929 A1 | 6/2016 |
| WO | 2016/100975 A1 | 6/2016 |
| WO | 2016/100977 A1 | 6/2016 |
| WO | 2016/102272 A1 | 6/2016 |
| WO | 2016/110584 A1 | 7/2016 |
| WO | 2016/110587 A1 | 7/2016 |
| WO | 2016/126876 A3 | 8/2016 |
| WO | 2016/128060 A1 | 8/2016 |
| WO | 2016/128316 A1 | 8/2016 |
| WO | 2016/128376 A1 | 8/2016 |
| WO | 2016/131875 A1 | 8/2016 |
| WO | 2016/141121 A1 | 9/2016 |
| WO | 2016/144976 A1 | 9/2016 |
| WO | 2016/146035 A1 | 9/2016 |
| WO | 2016/146751 A1 | 9/2016 |
| WO | 2016/154412 A2 | 9/2016 |
| WO | 2016/155809 A1 | 10/2016 |
| WO | 2016/156202 A1 | 10/2016 |
| WO | 2016/156230 A1 | 10/2016 |
| WO | 2016/156398 A1 | 10/2016 |
| WO | 2016/168198 A1 | 10/2016 |
| WO | 2016/168214 A2 | 10/2016 |
| WO | 2016/170139 A1 | 10/2016 |
| WO | 2016/172624 A1 | 10/2016 |
| WO | 2016/174085 A1 | 11/2016 |
| WO | 2016/177784 A1 | 11/2016 |
| WO | 2016/179517 A1 | 11/2016 |
| WO | 2016/180467 A1 | 11/2016 |
| WO | 2016/180778 A1 | 11/2016 |
| WO | 2016/183361 A1 | 11/2016 |
| WO | 2016/183486 A1 | 11/2016 |
| WO | 2016/191545 A1 | 12/2016 |
| WO | 2016/196237 A1 | 12/2016 |
| WO | 2016/202963 A2 | 12/2016 |
| WO | 2016/207164 A2 | 12/2016 |
| WO | 2016/207859 A1 | 12/2016 |
| WO | 2016/187508 A3 | 1/2017 |
| WO | 2017/001491 A2 | 1/2017 |
| WO | 2017/005733 A2 | 1/2017 |
| WO | 2017/005898 A1 | 1/2017 |
| WO | 2017/009400 A1 | 1/2017 |
| WO | 2017/017232 A1 | 2/2017 |
| WO | 2017/021527 A2 | 2/2017 |
| WO | 2017/024006 A1 | 2/2017 |
| WO | 2017/030956 A1 | 2/2017 |
| WO | 2017/036936 A1 | 3/2017 |
| WO | 2017/040790 A1 | 3/2017 |
| WO | WO-2017/106638 A1 | 6/2017 |
| WO | 2017/184590 A1 | 10/2017 |
| WO | 2018/098362 A1 | 5/2018 |
| WO | 2018/195357 A1 | 10/2018 |
| WO | 2018/227030 A1 | 12/2018 |
| WO | 2019/050994 A1 | 3/2019 |
| WO | 2019/075112 A1 | 4/2019 |
| WO | 2019/104203 A1 | 5/2019 |
| WO | 2019/168984 A1 | 9/2019 |

OTHER PUBLICATIONS

Lundegaard, C., Hoof, I., Lund, O. & Nielsen, M. State of the art and challenges in sequence based T-cell epitope prediction. Immunome Res. 6 Suppl 2, S3 (2010).

Maguire, S. L. et al. SF3B1 mutations constitute a novel therapeutic target in breast cancer. J. Pathol. 235, 571-580 (2015).

Maretty, L., Sibbesen, J. A. & Krogh, A. Bayesian transcriptome assembly. Genome Biol. 15, 501 (2014).

Mayor, N. P. et al. HLA Typing for the Next Generation. PloS One 10, e0127153 (2015).

McGranahan, N., Rosenthal, R., Hiley, C.T., Rowan, A.J., Watkins, T.B.K., Wilson, G.A., Birkbak, N.J., Veeriah, S., Van Loo, P., Herrero, J., et al. (2017). Allele-Specific HLA Loss and Immune Escape in Lung Cancer Evolution. Cell 171, 1259-1271.e11.

Miller et al., Correlation Between Somatic Mutation Burden, Neoantigen Load and Progression Free Survival in Multiple Myeloma: Analysis of MMRF CoMMpass Study Blood, Dec. 2016, vol. 128 No. 22 pp. 193.

Mommen et al., Sampling From the Proteome to the Human Leukocyte Antigen-DR (HLA-DR) Ligandome Proceeds Via High Specificity. Mol Cell Proteomics 15(4): 1412-1423, Apr. 2016.

Moon, EKCarpenito, CSun, JWang, LCKapoor, VPredina, J Expression of a functional CCR2 receptor enhances tumor localization and tumor eradication by retargeted human T-cells expressing a mesothelin-specific chimeric antibody receptor.Clin Cancer Res. 2011; 17: 4719-4730.

Mose, L. E., Wilkerson, M. D., Hayes, D. N., Perou, C. M. & Parker, J. S. ABRA: improved coding indel detection via assembly-based realignment. Bioinforma. Oxf. Engl. 30, 2813-2815 (2014).

Nielsen, et al., NN-align—An artificial neural network-based alignment algorithm for MHC class II peptide binding prediction. BMC Bioinformatics 10:296, Sep. 2009.

Nielsen, et al., "Prediction of MHC class II binding affinity using SMM-align, a novel stabilization matrix alignment method.," BMC Bioinformatics 8:238, Jul. 2007.

Nielsen M., Lundegaard, C., Lund, O. & Kesmir, C. The role of the proteasome in generating cytotoxic T-cell epitopes: Insights obtained from improved predictions of proteasomal cleavage. Immunogenetics 57, 33-41 (2005).

No Author, "The problem with neoantigen prediction," Nat. Biotechnol. 35, 97-97 (2017).

Ochi, Novel adoptive T-cell immunotherapy using a WT1-speci?c TCR vector encoding silencers for endogenous TCRs shows marked antileukemia reactivity and safety, Blood. Aug. 11, 2011;118(6):1495-503.

Office Action, U.S. Appl. No. 15/381,375, dated Apr. 11, 2019, 2019, 33 pages.

Office Action, U.S. Appl. No. 15/381,375, dated Sep. 5, 2019, 34 pages.

Office Action, U.S. Appl. No. 15/466,729, dated Jun. 20, 2017, 13 pages.

Office Action, U.S. Appl. No. 15/466,729, dated Oct. 19, 2017, 12 pages.

Office Action, U.S. Appl. No. 16/001,569, dated Feb. 4, 2019, 13 pages.

Office Action, U.S. Appl. No. 16/040,409, dated Dec. 27, 2018, 12 pages.

Office Action, U.S. Appl. No. 16/040,409, dated May 22, 2019, 12 pages.

Office Action, U.S. Appl. No. 16/128,421, dated Apr. 3, 2019, 29 pages.

Office Action, U.S. Appl. No. 16/128,421, dated Sep. 6, 2019, 31 pages.

Office Action, U.S. Appl. No. 16/403,331, dated Oct. 25, 2019, 29 pages.

Okamoto, A promising vector for TCR gene therapy: differential effect of siRNA, 2A peptide, and disulfide bond on the introduced TCR expression, Mol Ther Nucleic Acids. Dec. 2012; 1(12): e63.

Ooi, J. D. et al. Dominant protection from HLA-linked autoimmunity by antigen-specific regulatory T-cells. Nature 545, 243-247 (2017).

Ott, P. A. et al., "An immunogenic personal neoantigen vaccine for patients with melanoma," Nature 547, 217-221 (2017).

(56) References Cited

OTHER PUBLICATIONS

O'Donnell, T. J. et al., "MHCflurry: Open-Source Class I MHC Binding Affinity Prediction," Cell Syst. (2018). doi:10.1016/j.cels.2018.05.014.
Pasetto, A. et al. Tumor- and Neoantigen-Reactive T-cell Receptors Can Be Identified Based on Their Frequency in Fresh Tumor. Cancer Immunol. Res. 4, 734-743 (2016).
PCT International Search Report and Written Opinion, PCT Application No. PCT/US17/63133, dated Apr. 6, 2018, 20 pages.
PCT International Search Report and Written Opinion, PCT Application No. PCT/US18/036571, dated Oct. 3, 2018, 9 pages.
PCT International Search Report and Written Opinion, PCT Application No. PCT/US18/049614, dated Jan. 4, 2019, 9 pages.
PCT International Search Report and Written Opinion, PCT Application No. PCT/US19/019836, dated Jun. 26, 2019, 12 pages.
PCT International Search Report and Written Opinion, PCT Application No. PCT/US19/019836, dated Jun. 26, 2019.
PCT International Search Report and Written Opinion, PCT Application No. PCT/US2016/067159, dated Apr. 27, 2017, 14 pages.
PCT International Search Report and Written Opinion, PCT Application No. PCT/US2017/63133, dated Apr. 6, 2018, 20 pages.
PCT International Search Report and Written Opinion, PCT Application No. PCT/US2018/028438, dated Aug. 1, 2018, 7 pages.
PCT International Search Report and Written Opinion, PCT Application No. PCT/US2018/036571, dated Jun. 8, 2018, 4 pages.
PCT International Search Report and Written Opinion, PCT Application No. PCT/US2018/049614, dated Jan. 4, 2019, 5 pages.
PCT International Search Report and Written Opinion, PCT Application No. PCT/US2018/055283, dated Jan. 17, 2019, 15 pages.
PCT International Search Report and Written Opinion, PCT Application No. PCT/US2019/019836, dated Jun. 26, 2019, 5 pages.
Pearson, et al., MHC Class I-Associated Peptides Derive from Selective Regions of the Human Genome, The Journal of Clinical Investigation, Dec. 2016, vol. 126, No. 12, pp. 4690-4701.
Pertea, M. et al. StringTie enables improved reconstruction of a transcriptome from RNA-seq reads. Nat. Biotechnol. 33, 290-295 (2015).
Polyakova et al., "Proteogenomics meets cancer immunology; mass spectrometric discovery and analysis of neoantigens," Expert Review of Proteomics, vol. 12, No. 5, Jul. 15, 2015, pp. 533-541.
Pritchard, A.L. et al., "Exome Sequencing to Predict Neoantigens in Melanoma," Cancer Immunology Research, Sep. 2015, pp. 992-998, vol. 3, No. 9.
Purcell et al., "Immunoproteomics: Mass Spectrometry-Based Methods to Study the Targets of the Immune Response," Molecular & Cellular Proteomics, American Society for Biochemistry and Molecular Biology, US, vol. 3, No. 3, Mar. 1, 2004, pp. 193-208.
Quintarelli C, Vera JF, Savoldo B, Giordano Attianese GM, Pule M, Foster AE, Co-expression of cytokine and suicide genes to enhance the activity and safety of tumor-specific cytotoxic T lymphocytes. Blood. 2007;110:2793-802.
Rammensee et al., "HLA Ligandome Tumor Antigen Discovery for Personalized Vaccine Approach," Expert Review of Vaccines, vol. 12, No. 10, Oct. 1, 2013, pp. 1211-1127.
Rivas, M. A. et al. Human genomics. Effect of predicted protein-truncating genetic variants on the human transcriptome. Science 348, 666-669 (2015).
http://www.cbs.dtu.dk/services/NetMHCpan/ May 14, 2020.
Juliane Liepe, Fabio Marino, John Sidney, Anita Jeko, Daniel E. Bunting, Alessandro Sette, Peter M. Kloetzel, Michael P. H. Stumpf, Albert J. R. Heck, Michele Mishto. A large fraction of HLA class I ligands are proteasome-generated spliced peptides. Science, 21, Oct. 2016.
Käll, L., Storey, J. D., MacCoss, M. J. & Noble, W. S. Assigning significance to peptides identified by tandem mass spectrometry using decoy databases. J. Proteome Res. 7, 29-34 (2008).
Office Action, U.S. Appl. No. 16/001,569, dated Jun. 18, 2019, 12 pages.
Office Action, U.S. Appl. No. 16/001,569, dated Mar. 12, 2020, 28 pages.

Office Action, U.S. Appl. No. 16/040,409, dated Mar. 12, 2020, 28 pages.
PCT International Preliminary Report on Patentability, PCT Application No. PCT/US2018/055283, dated Apr. 23, 2020, 13 pages.
PCT International Search Report and Written Opinion, PCT Application No. PCT/US18/055283, dated Jan. 17, 2019, 15 pages.
PCT International Search Report and Written Opinion, PCT Application No. PCT/US18/62294, dated Nov. 21, 2018, 24 pages.
PCT International Search Report and Written Opinion, PCT Application No. PCT/US19/019836, dated Jun. 26, 2019, 5 pages.
Supplementary European Search Report, EP16876766, dated Nov. 29, 2019, 8 pages.
Target Capture for NextGen Sequencing—IDT. at <http://www.idtdna.com/pages/products/nextgen/target-capture>, May 19, 2020.
Fritsch, E.F. et al., "HLA-Binding Properties of Tumor Neoepitopes in Humans," Cancer Immunology Research, Jun. 1, 2014, pp. 522-529, vol. 2, No. 6.
Furney, S. J. et al. SF3B1 mutations are associated with alternative splicing in uveal melanoma. Cancer Discov. (2013). doi:10.1158/2159-8290.CD-13-0330.
Garrison, E. & Marth, G. Haplotype-based variant detection from short-read sequencing. arXiv (2012).
Gillette, M. A. & Carr, S. A. Quantitative analysis of peptides and proteins in biomedicine by targeted mass spectrometry. Nat. Methods 10, 28-34 (2013).
Glanville, J. et al. Identifying specificity groups in the T-cell receptor repertoire. Nature 547, 94-98 (2017).
Glorot, X. & Bengio, Y. Understanding the difficulty of training deep feedforward neural networks. in Proceedings of the Thirteenth International Conference on Artificial Intelligence and Statistics 249-256 (2010).
Godin et al., Microfluidics and photonics for Bio-System-on-a-Chip: A review of advancements in technology towards a microfluidic flow cytometry chip, (2008) J Biophoton. 1(5):355-376.
Goldman JM, et al., HLA-DR monoclonal antibodies inhibit the proliferation of normal and chronic granulocytic leukaemia myeloid progenitor cells. Br J Haematol. Nov. 1982; 52(3):411-20.
Griffioen Retroviral transfer of human CD20 as a suicide gene for adoptive T-cell therapy, Haematologica. Sep. 2009; 94(9): 1316-1320.
Gros, A. et al., "Prospective identification of neoantigen-specific lymphocytes in the peripheral blood of melanoma patients," Nat. Med. 22, 433-438 (2016).
Gubin, et al. "Tumor neoantigens: building a framework for personalized cancer immunotherapy," J. Clin. Invest. 125, 3413-3421 (2015).
Hall M, Liu H, Malafa M, et al. Expansion of tumor-infiltrating lymphocytes (TIL) from human pancreatic tumors. Journal for Immunotherapy of Cancer. 2016;4:61. doi:10.1186/s40425-016-0164-7.
Han et al., Linking T-cell receptor sequence to functional phenotype at the single-cell level, Nat Biotech 2014 (PMID 24952902, doi 10.1038/nbt.2938).
Hegde et al., The surprising complexity of signal sequences, Trends Biochem Sci. Oct. 31, 2006(10):563-71. Epub Aug. 21, 2006.
Howie et al., High-throughput pairing of T cell receptor alpha and beta sequences, Science Translational Medicine 2015 (doi: 10.1126/scitranslmed.aac5624) vol. Issue 301, 301ra131.
Hsu C, Hughes MS, Zheng Z, Bray RB, Rosenberg SA, Morgan RA. Primary human T lymphocytes engineered with a codon-optimized IL-15 gene resist cytokine withdrawal-induced apoptosis and persist long-term in the absence of exogenous cytokine. J Immunol. 2005;175:7226-34.
Hsu C, Jones SA, Cohen CJ, Zheng Z, Kerstann K, Zhou J, Cytokine-independent growth and clonal expansion of a primary human CD8+ T-cell clone following retroviral transduction with the IL-15 gene. Blood. 2007;109:5168-77.
http://www.cbs.dtu.dk/services/NetMHCpan/.
Hunt et al., Characterization of peptides bound to the class I MHC molecule HLA-A2.1 by mass spectrometry. Science 1992. 255: 1261-1263.

(56) References Cited

OTHER PUBLICATIONS

Hunt, D. F. et al. Pillars article: Characterization of peptides bound to the class I MHC molecule HLA-A2.1 by mass spectrometry. Science 1992. 255: 1261-1263, . J. Immunol. Baltim. Md 1950 179, 2669-2671 (2007).
Integrated DNA Technologies, Hybridization capture, https://www.idtdna.com/pages/products/next-generation-sequencing/hybridization-capture.
International Search Report and Written Opinion for PCT/US18/028438 dated Aug. 1, 2018.
International Search Report and Written Opinion for PCT/US18/036571 dated Oct. 3, 2018.
Janetzki, S. et al. Guidelines for the automated evaluation of Elispot assays. Nat. Protoc. 10, 1098-1115 (2015).
Janetzki, S., et al., Standardization and validation issues of the ELISPOT assay. Methods Mol. Biol. Clifton NJ 302, 51-86 (2005).
Jensen, Kamilla Kjaergaard, et al. "Improved Methods for Prediting Peptide Binding Affinity to MHC Class II Molecules." Immunology, 2018, doi:10.1111/imm.12889.
Johnson, D. B. et al. Melanoma-specific MHC-II expression represents a tumour-autonomous phenotype and predicts response to anti-PD-1/PD-L1 therapy. Nat. Commun. 7, 10582 (2016).
Jurtz et al., "NetMHCpan-4.0: Improved Peptide-MHC Class I Interaction Predictions Integrating Eluted Ligand and Peptide binding Affinity Data," The Journal of Immunology, Nov. 1, 2017, vol. 199, No. 9, pp. 3360-3368.
Jørgensen, K. W., Rasmussen, M., Buus, S. & Nielsen, M. NetMHCstab—predicting stability of peptide-MHC-I complexes; impacts for cytotoxic T lymphocyte epitope discovery. Immunology 141, 18-26 (2014).
Karosiene, E. et al. NetMHCIIpan-3.0, a common pan-specific MHC class II prediction method including all three human MHC class II isotypes, HLA-DR, HLA-DP and HLA-DQ. Immunogenetics 65, 711-724 (2013).
Kelderman, S. , Heemskerk, B. , Fanchi, L. , Philips, D. , Toebes, M. , Kvistborg, P. , Buuren, M. M., Rooij, N. , Michels, S. , Germeroth, L. , Haanen, J. B. and Schumacher, N. M. (2016), Antigen-specific TIL therapy for melanoma: A flexible platform for personalized cancer immunotherapy. Eur. J. Immunol., 46: 1351-1360. doi:10.1002/eji.201545849.
Kingma, D. & Ba, J. Adam: A method for stochastic optimization. ArXiv Prepr. ArXiv14126980 (2014).
Klebanoff et al., Sorting through subsets which T-Cell populations mediate highly effective adoptive immunotherapy, (2012) J Immunother. 35(9): 651-660.
Kosaloglu-Yalçin, Z. et al. Predicting T cell recognition of MHC class I restricted neoepitopes. J. OncoImmunology, 1-15 (2018).
Kreiter et al., "Mutant MHC class II epitopes drive therapeutic immune responses to cancer," Nature 520, 692-696, Apr. 2015.
Käll, L., et al., Semi-supervised learning for peptide identification from shotgun proteomics datasets. Nat. Methods 4, 923-925 (2007).
Käll, L., et al., Assigning significance to peptides identified by tandem mass spectrometry using decoy databases. J. Proteome Res. 7, 29-34 (2008).
Käll, L., et al., Non-parametric estimation of posterior error probabilities associated with peptides identified by tandem mass spectrometry. Bioinforma. Oxf. Engl. 24, i42-48 (2008).
Lam, H. Y. K. et al. Nucleotide-resolution analysis of structural variants using BreakSeq and a breakpoint library. Nat. Biotechnol. 28, 47-55 (2010).
Larsen, M. V. et al. An integrative approach to CTL epitope prediction: a combined algorithm integrating MHC class I binding, TAP transport efficiency, and proteasomal cleavage predictions. Eur. J. Immunol. 35, 2295-2303 (2005).
Legut, CRISPR-mediated TCR replacement generates superior anti-cancer transgenic T cells Blood. Jan. 18, 2018;131(3):311-322. doi: 10.1182/blood-2017-05-787598.
Li et al., Increasing the safety and efficacy of chimeric antigen receptor T cell therapy, Protein Cell. Aug. 2017; 8(8): 573-589.

Li, B. & Dewey, C. N. RSEM: accurate transcript quantification from RNA-Seq data with or without a reference genome. BMC Bioinformatics 12, 323 (2011).
Li, H. et al., Fast and accurate short read alignment with Burrows-Wheeler transform. Bioinforma. Oxf. Engl. 25, 1754-1760 (2009).
Liepe et al., A large fraction of HLA class I ligands are proteasome-generated spliced peptides. Science, 21, Oct. 2016.
Lin Cereghino et al., New selectable marker/auxotrophic host strain combinations for molecular genetic manipulation of Pichia pastoris, Gene, Jan. 24, 2001;263(1-2):159-69.
Liu, C. et al. ATHLATES: accurate typing of human leukocyte antigen through exome sequencing. Nucleic Acids Res. 41, e142 (2013).
Liu, et al., Systematic comparison of 2A peptides for cloning multi-genes in a polycistronic vector, Scientific Reports vol. 7, Article No. 2193 (2017) doi:10.1038/s41598-017-02460-2.
Lorente, E. et al., "Diversity of Natural Self-Derived Ligands Presented by Different HLA Class I Molecules in Transporter Antigen Processing-Deficient Cells," PLoS One, Mar. 26, 2013, pp. 1-10, vol. 8, e59118.
Robbins, P. F. et al. A Pilot Trial Using Lymphocytes Genetically Engineered with an NY-ESO-1-Reactive T-cell Receptor: Long-term Follow-up and Correlates with Response. Clin. Cancer Res. 21, 1019-1027 (2015).
Roberts, A., et al., Identification of novel transcripts in annotated genomes using RNA-Seq. Bioinforma. Oxf. Engl. (2011). doi:10.1093/bioinformatics/btr355.
Roy, C. K., Olson, S., Graveley, B. R., Zamore, P. D. & Moore, M. J. Assessing long-distance RNA sequence connectivity via RNA-templated DNA-DNA ligation. eLife 4, (2015).
Rubinsteyn, A., O'Donnell, T., Damaraju, N. & Hammerbacher, J. Predicting Peptide-MHC Binding Affinities With Imputed Training Data. biorxiv (2016). doi:https://doi.org/10.1101/054775.
Sahin, U. et al., "Personalized RNA mutanome vaccines mobilize poly-specific therapeutic immunity against cancer," Nature 547, 222-226 (2017).
Saunders, C. T. et al., Strelka: accurate somatic small-variant calling from sequenced tumor-normal sample pairs. Bioinforma. Oxf. Engl. 28, 1811-1817 (2012).
Schneider, T. D. & Stephens, R. M. Sequence logos: a new way to display consensus sequences. Nucleic Acids Res. 18, 6097-6100 (1990).
Scholz, E. M. et al. Human Leukocyte Antigen (HLA)-DRB1*15:01 and HLA-DRB5*01:01 Present Complementary Peptide Repertoires. Front. Immunol. 8, 984 (2017).
Schumacher, T.N. et al., "Neoantigens in Cancer Immunotherapy," Science, Apr. 3, 2015, pp. 69-74, vol. 348, Issue 6230.
Sette, A. et al., "The relationship between class I binding affinity and immunogenicity of potential cytotoxic T-cell epitopes," J. Immunol. Baltim. Md 1950 153, 5586-5592 (1994).
Shukla, S.A., Rooney, M.S., Rajasagi, M., Tiao, G., Dixon, P.M., Lawrence, M.S., Stevens, J., Lane, W.J., Dellagatta, J.L., Steelman, S., et al. (2015). Comprehensive analysis of cancer-associated somatic mutations in class I HLA genes. Nat. Biotechnol. 33, 1152-1158.
Skelly, D. A., Johansson, M., Madeoy, J., Wakefield, J. & Akey, J. M. A powerful and flexible statistical framework for testing hypotheses of allele-specific gene expression from RNA-seq data. Genome Res. 21, 1728-1737 (2011).
Snyder, A. et al. Genetic basis for clinical response to CTLA-4 blockade in melanoma. N. Engl. J. Med. 371, 2189-2199 (2014).
Song, L. & Florea, L. CLASS: constrained transcript assembly of RNA-seq reads. BMC Bioinformatics 14 Suppl 5, S14 (2013).
Stevanovic, S. et al. Landscape of immunogenic tumor antigens in successful immunotherapy of virally induced epithelial cancer. Science 356, 200-205 (2017).
Stranzl, T. et al., "NetCTLpan: Pan-Specific MHC Class I Pathway Epitope Predictions," Immunogenetics, 62, 2010, pp. 357-368, vol. 62.
Strønen et al., "Targeting of cancer neoantigens with donor-derived T-cell receptor repertoires," Science 352, 1337-1341 (2016).
Suri, A. et al., "Specificity of Peptide Selection by Antigen-Presenting Cells Homozygous or Heterozygous for Expression of

(56) References Cited

OTHER PUBLICATIONS

Class II MHC Molecules: The Lack of Competition," Proceedings of the National Academy of Sciences, Apr. 29, 2003, pp. 5330-5335, vol. 100, No. 9.
Szolek, A. et al. OptiType: precision HLA typing from next-generation sequencing data. Bioinforma. Oxf. Engl. 30, 3310-3316 (2014).
Terakura et al., Generation of CD19-chimeric antigen receptor modified CD8+ T cells derived from virus-specific central memory T cells, (2012) Blood, 1:72-82.
Torikai, A foundation for universal T-cell based immunotherapy: T cells engineered to express a CD19-specii¬?c chimeric-antigen-receptor and eliminate expression of endogenous TCR, Blood. Jun. 14, 2012; 119(24): 5697-5705.
Torikai, Hiroki et al "HLA and TCR Knockout by Zinc Finger Nucleases: Toward "off-the-Shelf" Allogeneic T-Cell Therapy for CD19+ Malignancies," Blood 116.21 (2010): 3766.
Tran et al., "Cancer immunotherapy based on mutation-specific CD4+ T-cells in a patient with epithelial cancer," Science 344(6184) 641-645, May 2014.
Tran, E. et al., "Immunogenicity of somatic mutations in human gastrointestinal cancers," Science 350, 1387-1390 (2015).
Tran, E. et al.,"T-Cell Transfer Therapy Targeting Mutant KRAS in Cancer," N. Engl. J. Med. 375, 2255-2262 (2016).
Trolle, T. et al., "The Length Distribution of Class I-Restricted T-cell Epitopes is Determined by Both Peptide Supply and MHC Allele-Specific Binding Preference," J. Immunol. Baltim. Md 1950 196, 1480-1487 (2016).
Turtle et al., "Artificial Antigen Presenting Cells for Use in Adoptive Immunotherapy," Cancer J. 2010; 16(4): 374-381.
United States Office Action, U.S. Appl. No. 15/466,729, dated Jun. 20, 2017, 13 pages.
U.S. Appl. No. 62/268,333, filed Dec. 16, 2015, Inventors: Yelensky et al.
Van Allen, E. M. et al., "Genomic correlates of response to CTLA-4 blockade in metastatic melanoma.," Science 350, 207-211 (2015).
Van Loo, P., Nordgard, S.H., Lingjærde, O.C., Russnes, H.G., Rye, I.H., Sun, W., Weigman, V.J., Marynen, P., Zetterberg, A., Naume, B., et al. (2010). Allele-specific copy number analysis of tumors. Proc. Natl. Acad. Sci. U. S. A. 107, 16910-16915.
Vita, R. et al., "The immune epitope database (IEDB) 3.0," Nucleic Acids Res. 43, D405-412 (2015).
Vitiello, A. & Zanetti, M., "Neoantigen prediction and the need for validation," Nat. Biotechnol. 35, 815-817 (2017).
Vitting-Seerup, K., Porse, B. T., Sandelin, A. & Waage, J. spliceR: an R package for classification of alternative splicing and prediction of coding potential from RNA-seq data. BMC Bioinformatics 15, 81 (2014).
Walter, M. J. et al. Clonal architecture of secondary acute myeloid leukemia. N. Engl. J. Med. 366, 1090-1098 (2012).
Wang et al., Phenotypic and functional attributes of Lentivirus-modified CD19-specific human CD8+ central memory T cells manufactured at clinical scale, (2012) J Immunother. 35(9):689-701.
Weinmann, H. "Cancer Immunotherapy: Selected Targets and Small-Molecule Modulators" published Feb. 2, 2016, vol. 11, issue 5 450-466, ChemMedChem (DOI: 10.1002/cmdc.201500566), with Corrigendum ChemMedChem </journal/18607187>vol. 11, Issue 14 </toc/18607187/2016/11/14>, <https://doi.org/10.1002/cmdc.201600319>.
Wilkerson, M. D. et al. Integrated RNA and DNA sequencing improves mutation detection in low purity tumors. Nucleic Acids Res. 42, e107 (2014).
Wu et al., Remote control of therapeutic T cells through a small molecule-gated chimeric receptor, Science. Oct. 16, 2015; 350(6258): aab4077.
Xu, G. et al. RNA CoMPASS: a dual approach for pathogen and host transcriptome analysis of RNA-seq datasets. PloS One 9, e89445 (2014).

Yadav el al., Predicting Immunogenic Tumour Mutations by Combining Mass Spectrometry and Exome Sequencing, Nature, Nov. 27, 2014, vol. 515, No. 7528, pp. 572-576.
Ye, K., et al., Pindel: a pattern growth approach to detect break points of large deletions and medium sized insertions from paired-end short reads. Bioinforma. Oxf. Engl. 25, 2865-2871 (2009).
Yoshida, et al., Splicing factor mutations and cancer. Wiley Interdiscip. Rev. RNA 5, 445-459 (2014).
Zacharakis, N. et al., "Immune recognition of somatic mutations leading to complete durable regression in metastatic breast cancer," Nat. Med. 24, 714-730 (2018).
Zarling, A. L. et al. Identification of class I MHC-associated phosphopeptides as targets for cancer immunotherapy. Proc. Natl. Acad. Sci. U. S. A. 103, 14889-14894 (2006).
Zhang et al., "MULTIPRED2: A Computational Systems for Large-Scale Identification of Peptides to Bind to HLA Supertypes and Alleles," J Immunol Methods, 374:53-61, 2011.
Zhang, J. et al. Intratumor heterogeneity in localized lung adenocarcinomas delineated by multiregion sequencing. Science 346, 256-259 (2014).
Zhang, J., et al. "PEAKS DB: de novo sequencing assisted database search for sensitive and accurate peptide identification. Molecular & Cellular Proteomics," 11(4):1-8. Jan. 2, 2012.
Zhou, Q. et al. A chemical genetics approach for the functional assessment of novel cancer genes. Cancer Res. (2015). dol: 10.1158/0008-5472.CAN-14-2930.
Abelin, J. G. et al. Complementary IMAC enrichment methods for HLA-associated phosphopeptide identification by mass spectrometry. Nat. Protoc. 10, 1308-1318 (2015).
Abelin, J.G. et al., "Mass Spectrometry Profiling of HLA-Associated Peptidomes in Mono-Allelic Cells Enables More Accurate Epitope Prediction," Immunity, Feb. 21, 2017, pp. 315-326, vol. 46.
Altschul et al., Basic local alignment search tool, J. Mol. Biol. 215:403-410 (1990).
An, et al. "Construction of a New Anti-CD19 Chimeric Antigen Receptor and the Anti-Leukemia Function Study of the Transduced T-cells." Oncotarget 7.9 (2016): 10638-10649. PMC. Web. Aug. 16, 2018.
Anagnostou, V. et al. Evolution of Neoantigen Landscape during Immune Checkpoint Blockade in Non-Small Cell Lung Cancer. Cancer Discov. 7, 264-276 (2017).
Anders, S., Pyl, P. T. & Huber, W. HTSeq—a Python framework to work with high-throughput sequencing data. Bioinforma. Oxf. Engl. 31, 166-169 (2015).
Andreatta et al., Accurate Pan-Specific Prediction of Peptide-MHC Class II Binding Affinity with Improved Binding Core Identification, Immunogenetics, Nov. 1, 2015, vol. 67. pp. 641-650.
Andreatta, M. & Nielsen, M, "Gapped sequence alignment using artificial neural networks: application to the MHC class I system," Bioinforma. Oxf. Engl. 32, 511-517 (2016).
Andreatta, M., Alvarez, B. & Nielsen, M., "GibbsCluster: unsupervised clustering and alignment of peptide sequences," Nucleic Acids Res. (2017). doi:10.1093/nar/gkx248.
Andreatta, M., Lund, O. & Nielsen, M., "Simultaneous alignment and clustering of peptide data using a Gibbs sampling approach," Bioinforma. Oxf. Engl. 29, 8-14 (2013).
Barnstable, C. J. et al. Production of monoclonal antibodies to group A erythrocytes, HLA and other human cell surface antigens—new tools for genetic analysis. Cell 14, 9-20 (1978).
Bassani-Stemberg et al, Mass Spectrometry of Human Leukocyte Antigen Class I Peptidomes Reveals Strong Effects of Protein Abundance and Turnover on Antigen Presentation, Mol Cell Proteomics, 14:658-673, 2015.
Bassani-Sternberg, M. et al., "Unsupervised HLA Peptide Deconvolution Improves Ligand Prediction Accuracy and Predicts Cooperative Effects in Peptide—HLA Interactions," The Journal of Immunology, 2016, pp. 2492-2499, vol. 197.
Bassani-Sternberg, M. et al., "Deciphering HLA-I motifs across HLA peptidomes improves neo-antigen predictions and identifies allostery regulating HLA specificity," PLoS Comput. Biol. 13, e1005725 (2017).

(56) References Cited

OTHER PUBLICATIONS

Bassani-Sternberg, M. et al., "Direct identification of clinically relevant neoepitopes presented on native human melanoma tissue by mass spectrometry," Nat. Commun. 7, 13404 (2016).
Bentzen, A. K. et al., "Large-scale detection of antigen-specific T-cells using peptide-MHC-I multimers labeled with DNA barcodes," Nat. Biotechnol. 34, 1037-1045 (2016).
Bodini, M. et al. The hidden genomic landscape of acute myeloid leukemia: subclonal structure revealed by undetected mutations. Blood 125, 600-605 (2015).
Boegel, S. et al. HLA typing from RNA-Seq sequence reads. Genome Med. 4, 102 (2012).
Boegel, S., et al., A catalog of HLA type, HLA expression, and neo-epitope candidates in human cancer cell lines. Oncoimmunology 3, e954893 (2014).
Boisvert, F.-M. et al. A Quantitative Spatial Proteomics Analysis of Proteome Turnover in Human Cells. Mol. Cell. Proteomics 11, M111.011429-M111.011429 (2012).
Briggs A, Goldfless S, Timberlake S, et al. Tumor-infiltrating immune repertoires captured by single-cell barcoding in emulsion. bioRxiv. 2017. doi.org/10.1101/134841.
Calis, J. J. A. et al. Properties of MHC class I presented peptides that enhance immunogenicity. PLoS Comput. Biol. 9, e1003266 (2013).
Cancer Genome Atlas Research Network. Comprehensive molecular profiling of lung adenocarcinoma. Nature 511, 543-550 (2014).
Carithers, L. J. et al. A Novel Approach to High-Quality Postmortem Tissue Procurement: The GTEx Project. Biopreservation Biobanking 13, 311-319 (2015).
Caron et al., "Analysis of Major Histocompatibility Complex (MHC) Immunopeptides Using Mass Spectrometry," Molecular Cellular Proteomics, Oct. 19, 2015, vol. 14, pp. 3105-3117.
Carreno, B. M. et al. Cancer immunotherapy. A dendritic cell vaccine increases the breadth and diversity of melanoma neoantigen-specific T-cells. Science 348, 803-808 (2015).
Carter, S.L., Cibulskis, K., Heiman, E., McKenna, A., Shen, H., Zack, T., Laird, P.W., Onofrio, R.C., Winckler, W., Weir, B.A., et al. (2012). Absolute quantification of somatic DNA alterations in human cancer. Nat. Biotechnol. 30, 413-421.
Chang, K.Y. et al., "Prediction of HLA-DQ8 ß Cell Peptidome Using a Computational Program and Its Relationship to Autoreactive T Cells," International Immunology, Jun. 14, 2009, pp. 705-713, vol. 21.
Cho et al. Human mammalian cell sorting using a highly integrated micro-fabricated fluorescence-activated cell sorter (mFACS), (2010) Lab Chip 10, 1567-1573.
Chollet, F. et al., Keras: The Python Deep Learning library (2015), <https://keras.io/>.
Chudley, L. et al., "Harmonisation of short-term in vitro culture for the expansion of antigen-specific CD8+ T-cells with detection by ELISPOT and HLA-multimer staining," Cancer Immunol. Immunother. 63, 1199-1211 (2014).
Cibulskis, K. et al. Sensitive detection of somatic point mutations in impure and heterogeneous cancer samples. Nat. Biotechnol. 31, 213-219 (2013).
Cieslik, M. et al. The use of exome capture RNA-seq for highly degraded RNA with application to clinical cancer sequencing. Genome Res. 25, 1372-1381 (2015).
Cingolani, P. et al. A program for annotating and predicting the effects of single nucleotide polymorphisms, SnpEff: SNPs in the genome of Drosophila melanogaster strain w1118; iso-2; iso-3. Fly (Austin) 6, 80-92 (2012).
Clarke, Immunomagnetic Cell Separation, From: Methods in Molecular Medicine, vol. 58: Metastasis Research Protocols, vol. 2: Cell Behavior in Vitro and in Vivo, p. 17-25 Edited by: S. A. Brooks and U. Schumacher Humana Press Inc., Totowa, N.J.
Cohen CJ, et al., Isolation of neoantigen-specific T cells from tumor and peripheral lymphocytes. The Journal of Clinical Investigation. 2015;125(10):3981-3991. doi:10.1172/JCI82416.
Craddock, JALu, ABear, APule, MBrenner, MKRooney, CM et al. Enhanced tumor trafficking of GD2 chimeric antigen receptor T-cells by expression of the chemokine receptor CCR2b., J Immunother. 2010; 33: 780-788.
Dash, P. et al. Quantifiable predictive features define epitope-specific T-cell receptor repertoires. Nature 547, 89-93 (2017).
DePristo, M. A. et al. A framework for variation discovery and genotyping using next-generation DNA sequencing data. Nat. Genet. 43, 491-498 (2011).
Desrichard, A., Snyder, A. & Chan, T. A. Cancer Neoantigens and Applications for Immunotherapy. Clin. Cancer Res. Off. J. Am. Assoc. Cancer Res. (2015). doi:10.1158/1078-0432.CCR-14-3175.
Di Marco, M. et al, "Unveiling the Peptide Motifs of HLA-C and HLA-G from Naturally Presented Peptides and Generation of Binding Prediction Matrices," J. Immunol. Baltim. Md 1950 199, 2639-2651 (2017).
DTU Bioinformatics http://www.cbs.dtu.dk/services/NetMHCpan/.
Duan, et al, Genomic and Bioinformatic Profiling of Mutational Neopitopes Reveals New rules to Predict Anticancer Immunogenicity, The Journal of Experimental Medicine, Sep. 22, 2014, vol. 211, No. 11, pp. 2231-2248, p. 2240, col. 1, paragraph 3.
Dudley et al., Generation of Tumor-Infiltrating Lymphocyte Cultures for Use in Adoptive Transfer Therapy for Melanoma Patients. Journal of Immunotherapy 2003; 26(4):332-342.
Dudley ME, Gross CA, Langhan MM, et al. CD8+ enriched "young" tumor infiltrating lymphocytes can mediate regression of metastatic melanoma. Clinical cancer research?: an official journal of the American Association for Cancer Research. 2010;16(24):6122-6131. doi:10.1158/1078-0432.CCR-10-1297.
Eng, J. K. et al. A deeper look into Comet—implementation and features. J. Am. Soc. Mass Spectrom. 26, 1865-1874 (2015).
Eng, J. K., Jahan, T. A. & Hoopmann, M. R. Comet: an open-source MS/MS sequence database search tool. Proteomics 13, 22-24 (2013).
Fleri et al., The Immune Eitope Database and Analysis Resource in Epitope Discovery and Synthetic Vaccine Design, Frontiers in Immunology, Mar. 14, 2017, vol. 8, No. 278; pp. 1-16; p. 4, col. 1, paragraph 3, p. 8, col. 1, paragraph 7, p. 8, col. 2, paragraph 3.
Fortier, M.-H. et al., "The MHC class I peptide repertoire is molded by the transcriptome," J. Exp. Med. 205, 595-610 (2008).
Frampton, G. M. et al. Development and validation of a clinical cancer genomic profiling test based on massively parallel DNA sequencing. Nat. Biotechnol. 31, 1023-1031 (2013).
Freudenmann, LK et al., "Mapping the tumour human leukocyte antigen (HLA) ligandome by mass spectrometry." Immunology. Jul. 2018, Epub May 8, 2018, vol. 154, No. 3; pp. 331-345; DOI: 10.1111/imm.12936.
Rizvi, N. A. et al., "Cancer immunology Mutational landscape determines sensitivity to PD-1 blockade in non-small cell lung cancer," Science 348, 124-128 (2015).
De Groot et al., "HIV vaccine development by computer assisted design: the GAIA vaccine." Vaccine 23, No. 17-18 (2005): 2136-2148.
Toussaint et al., "Universal peptide vaccines-optimal peptide vaccine design based on viral sequence conservation." Vaccine 29, No. 47 (2011): 8745-8753.
Notification of Transmittal of the International Search Report and the Written Opinion of the International Searching Authority, or the Declaration, Int'l Application No. PCT/US2019/019836, dated Jun. 26, 2019, 17 pages.
Caron et al., "Analysis of Major Histocompatability Complex (MHC) Immunopeptidomes Using Mass Spectrometry," Molecular & Cellular Proteomics, Oct. 19, 2015, vol. 14, pp. 2015-3117.
Johanns et al., "Targeting Neoantigens in Glioblastoma: An Overview of Cancer Immunogenomics and Translational Implications," Neurosurgery, Sep. 1, 2017, vol. 64, pp. 165-176.
Jurtz et al., "NetMHCpan-4.0: Improved Peptide-MHC Class 1 Interaction Predictions Integrating Eluted Ligand and Peptide Binding Affinity Data," The journal of Immunology, Nov. 1, 2017, vol. 199, No. 9, pp. 3360-3368.
Cooper et al. "Rescue of splicing-mediated intron loss maximizes expression in lentiviral vectors containing the human ubiquitin C promoter," Nucleic acids research, 2015, 43(1):682-690.

(56) References Cited

OTHER PUBLICATIONS

Felgner et al. "Lipofection: a highly efficient, lipid-mediated DNA-transfection procedure," Proceedings of the National Academy of Sciences of the United States of America, 1987, 84(21):7413-7417.
Hu et al. "Immunization delivered by lentiviral vectors for cancer and infectious diseases," Immunological reviews, 2011, 239(1):45-61.
Komher et al. "Mutation detection using nucleotide analogs that alter electrophoretic mobility," Nucleic acids research, 1989, 17(19):7779-7784.
Kuppuswamy et al. "Single nucleotide primer extension to detect genetic diseases: experimental application to hemophilia B (factor IX) and cystic fibrosis genes," Proceedings of the National Academy of Sciences of the United States of America, 1991, 88(4):1143-1147.
Lu et al. "Efficient identification of mutated cancer antigens recognized by T-cells associated with durable tumor regressions," Clinical Cancer Research, 2014, 20(13):3401-3410.
Needleman et al. "A general method applicable to the search for similarities in the amino acid sequence of two proteins," Journal of Molecular Biology, 1970,48(3):443-453.
Pearson et al. "Improved tools for biological sequence comparison," Proceedings of the National Academy of Sciences of the United States of America, 1988, 85(8):2444-2448.
Smith et al. "Comparison of biosequences," Advances in Applied Mathematics, 1981, 2(4):482-489.
Sokolov. "Primer extension technique for the detection of single nucleotide in genomic DNA," Nucleic acids research, 1990, 18(12):3671.
Stover et al. "New use of BCG for recombinant vaccines," Nature, 1991, 351(6326):456-460.
Syvänen et al. "Identification of individuals by analysis of biallelic DNA markers, using PCR and solid-phase minisequencing," American journal of human genetics, 1993, 52(1):46-59.
Szoka et al. "Comparative properties and methods of preparation of lipid vesicles (liposomes)," Annual review of biophysics and bioengineering, 1980, 9:467-508.
Tatsis et al. "Adenoviruses as vaccine vectors," Molecular therapy: the journal of the American Society of Gene Therapy, 2004, 10(4):616-629.
Wolff et al. "Direct gene transfer into mouse muscle in vivo," Science (New York, N.Y.), 1990, 247(4949 Pt 1):1465-1468.
Zufferey et al. "Self-inactivating lentivirus vector for safe and efficient in vivo gene delivery," Journal of virology, 1998, 72(12):9873-9880.
Allison, "The mode of action of immunological adjuvants," Developments in biological standardization, 1998, 92:3-11.
Coos Verhoef et al. "Des-enkephalin-gamma-endorphin (DE gamma E): biotransformation in rat, dog and human plasma," European journal of drug metabolism and pharmacokinetics, 1986, 11(4):291-302.
Dupuis et al. "Dendritic cells internalize vaccine adjuvant after intramuscular injection," Cellular immunology, 1998, 186(1):18-27.
Mannino et al. "Liposome mediated gene transfer," BioTechniques, 1988, 6(7):682-690.
Merrifield. "Solid phase synthesis," Science, 1986, 232(4748):341-347.
Sakuma et al. "Lentiviral vectors: basic to translational," The Biochemical journal, 2012,443(3):603-618.
Syvänen et al. "A primer-guided nucleotide incorporation assay in the genotyping of apolipoprotein E," Genomics, 1990, 8(4):684-692.
Ugozzoli et al. "Detection of specific alleles by using allele-specific primer extension followed by capture on solid support," Genetic analysis, techniques and applications, 1992, 9(4): 107-112.
Gabrilovich et al. "IL-12 and mutant P53 peptide-pulsed dendritic cells for the specific immunotherapy of cancer," Journal of immunotherapy with emphasis on tumor immunology: official journal of the Society for Biological Therapy, 1996, 19(6):414-418.
Nyren et al. "Solid phase DNA minisequencing by an enzymatic luminometric inorganic pyrophosphate detection assay," Analytical biochemistry, 1993, 208(1):171-175.
Prezant et al. "Trapped-oligonucleotide nucleotide incorporation (TONI) assay, a simple method for screening point mutations," Human mutation, 1992, 1(2):159-164.
Bulik-Sullivan et al., "Deep Learning Using Tumor HLA Pepride Mass Spectrometry Datasets Improves Neoantigan Identification," Nature Biotechnology, vol. 37, No. 1, Jan. 2019, 17 pages.
Liu et al., "Applications of Immunogenomics to Cancer," Cell 168, Feb. 9, 2017, pp. 600-612.

\* cited by examiner

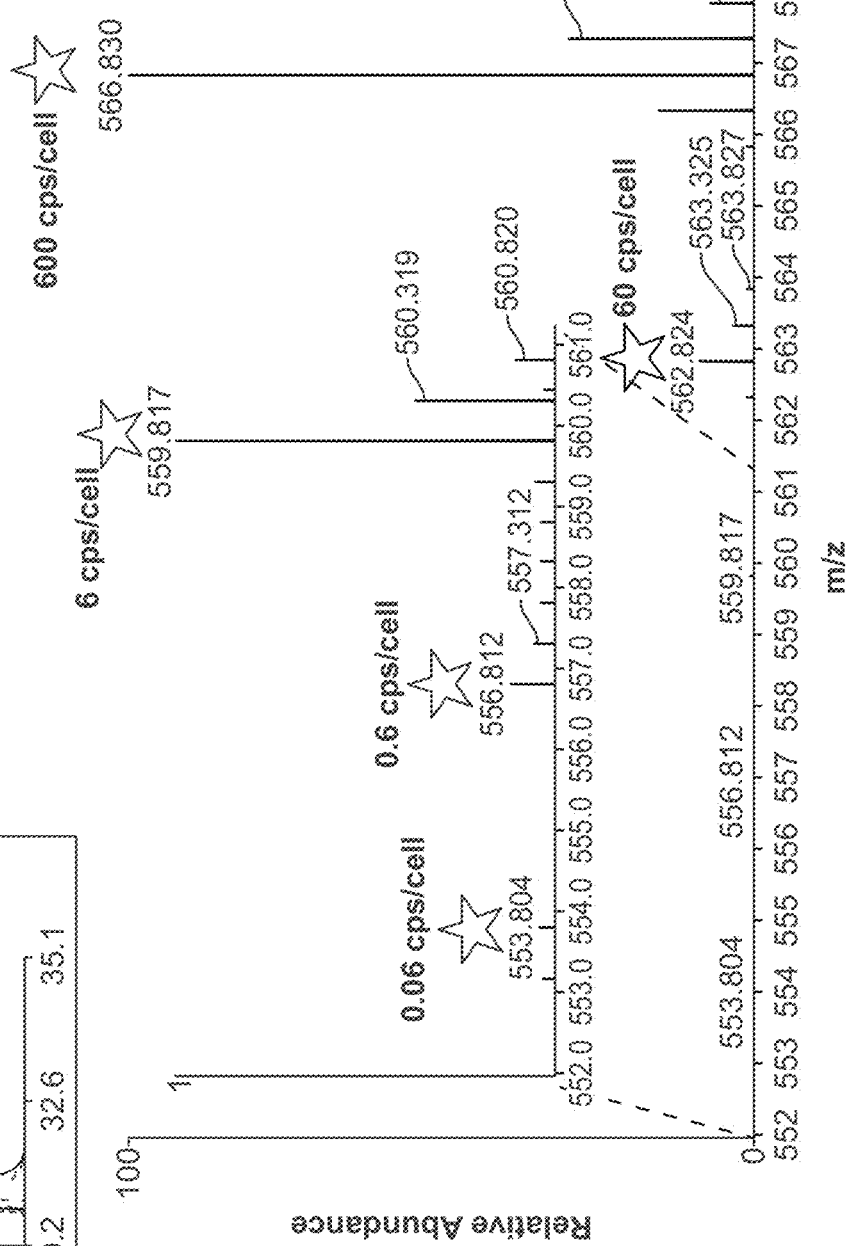
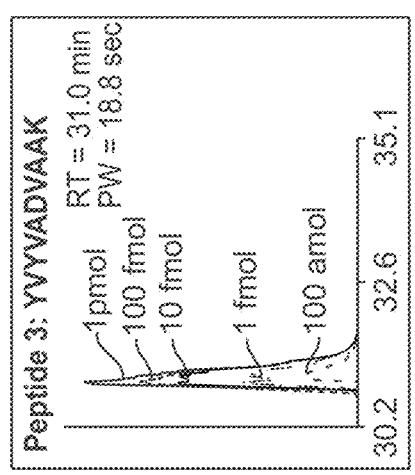
FIG. 1F

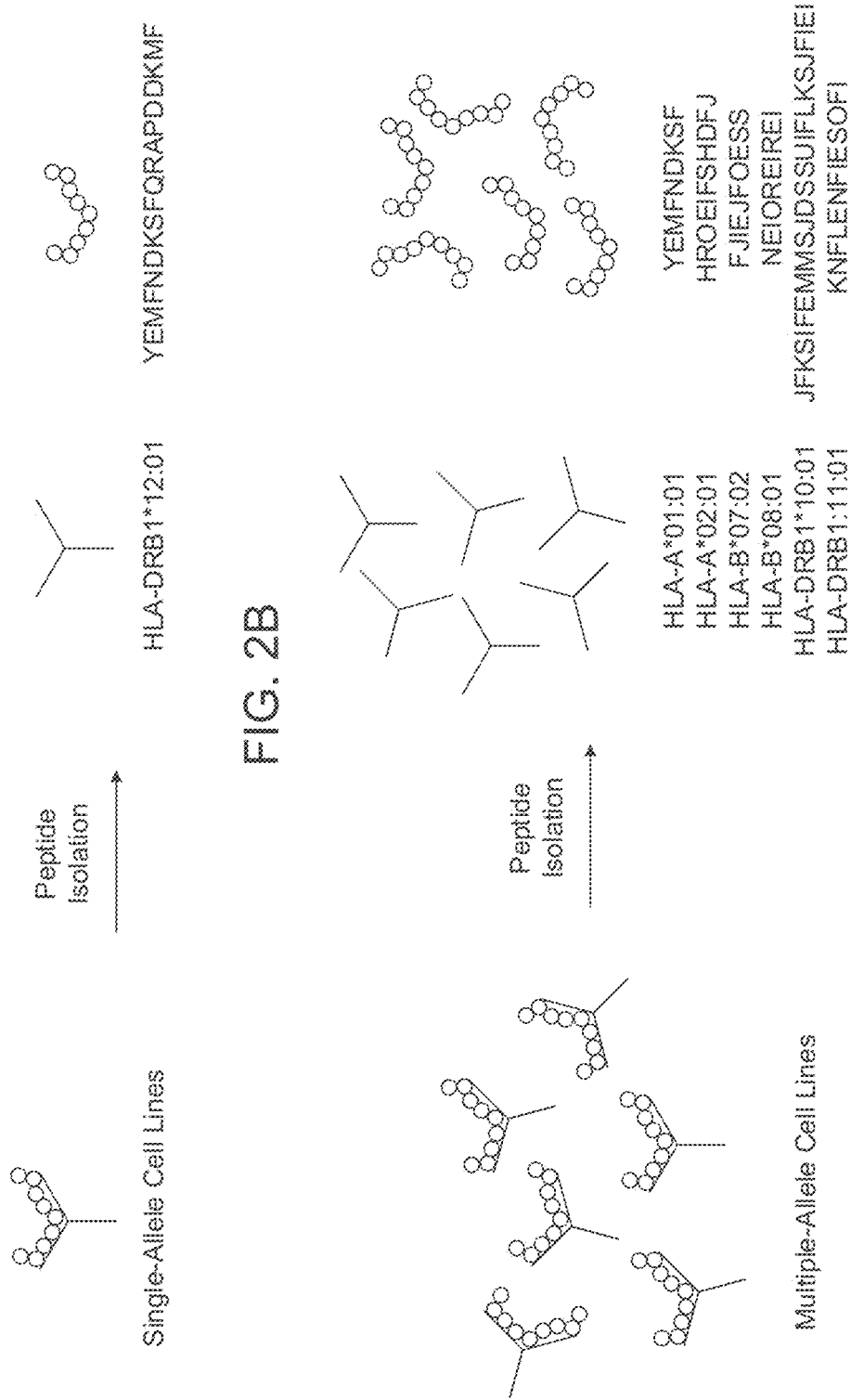

| | Allele-Dependent ($x^i$) | | | Allele-Independent ($w^i$) | | |
|---|---|---|---|---|---|---|
| Peptide Sequence ($p^i$) | Affinity ($b^i$-nM) | Stability ($s^i$-h) | Allele ($a^i$) | C-Flanking Sequence ($c^i$) | mRNA Q. ($m^i$-TPM) | Label ($y^i$) |
| QCEIOWAREFLKEIGJ | 1000 | 1 | HLA-DRB3:01:01 | FJELFISBOSJFIE | $10^2$ | Not Presented |
| FIEUHFWI | 1500 | 15 | HLA-C*01:03 | FEGRKUOOI | $10^{-3}$ | Presented |
| FEWRHRJTRUJR | 650 | 20 | HLA-C*01:03 | PJFIOEJOIJGEIO | $10^1$ | Presented |
| | 500 | 1 | HLA-B*07:02 | | | |
| QIEJOEIJE | 600 | 14 | HLA-C*01:03 | PJFIOEJOIJGEIO | 1 | Presented |
| | 1200 | 7 | HLA-A*01:01 | | | |

Training Data 170A

SEQUENCE LISTING

<160> NUMBER OF SEQ ID NOS: 232

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Tyr Val Tyr Val Ala Asp Val Ala Ala Lys
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Glu Met Phe Asn Asp Lys Ser Gln Arg Ala Pro Asp Asp Lys Met
1               5                   10                  15

Phe

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Glu Met Phe Asn Asp Lys Ser Phe
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pyrrolysine
<220> FEATURE:
<221> NAME/KEY: MOD_RES
<222> LOCATION: (11)..(11)
<223> OTHER INFORMATION: Ile or Leu

<400> SEQUENCE: 4

His Arg Xaa Glu Ile Phe Ser His Asp Phe Xaa
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile or Leu
<220> FEATURE:
<221> NAME/KEY: MOD_RES
<222> LOCATION: (5)..(5)
<223> OTHER INFORMATION: Ile or Leu
<220> FEATURE:
<221> NAME/KEY: MOD_RES
<222> LOCATION: (7)..(7)
<223> OTHER INFORMATION: Pyrrolysine

<400> SEQUENCE: 5

Phe Xaa Ile Glu Xaa Phe Xaa Glu Ser Ser
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pyrrolysine

<400> SEQUENCE: 6

Asn Glu Ile Xaa Arg Glu Ile Arg Glu Ile
1               5                   10

<210> SEQ ID NO 7
<211> LENGTH: 27
<212> TYPE: PRT
<213> ORGANISM: Artificial Sequence
<220> FEATURE:
<223> OTHER INFORMATION: Description of Artificial Sequence: Synthetic

```
            peptide
<220> FEATURE:
<221> NAME/KEY: MOD_RES
<222> LOCATION: (1)..(1)
<223> OTHER INFORMATION: Ile or Leu
<220> FEATURE:
<221> NAME/KEY: MOD_RES
<222> LOCATION: (11)..(11)
<223> OTHER INFORMATION: Ile or Leu
<220> FEATURE:
<221> NAME/KEY: MOD_RES
<222> LOCATION: (15)..(15)
<223> OTHER INFORMATION: Selenocysteine
<220> FEATURE:
<221> NAME/KEY: MOD_RES
<222> LOCATION: (21)..(21)
<223> OTHER INFORMATION: Ile or Leu
<220> FEATURE:
<221> NAME/KEY: MOD_RES
<222> LOCATION: (27)..(27)
<223> OTHER INFORMATION: Ile or Leu

<400> SEQUENCE: 7

Xaa Phe Lys Ser Ile Phe Glu Met Met Ser Xaa Asp Ser Ser Xaa Ile
1               5                   10                  15

Phe Leu Lys Ser Xaa Phe Ile Glu Ile Phe Xaa
            20                  25

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Pyrrolysine

<400> SEQUENCE: 8

Lys Asn Phe Leu Glu Asn Phe Ile Glu Ser Xaa Phe Ile
1               5                   10

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Pyrrolysine
<220> FEATURE:
<221> NAME/KEY: MOD_RES
<222> LOCATION: (14)..(14)
<223> OTHER INFORMATION: Ile or Leu

<400> SEQUENCE: 9

Phe Xaa Glu Ile Phe Asn Asp Lys Ser Leu Asp Lys Phe Xaa Ile
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (5)..(5)
<223> OTHER INFORMATION: Pyrrolysine
<220> FEATURE:
<221> NAME/KEY: MOD_RES
<222> LOCATION: (16)..(16)
<223> OTHER INFORMATION: Ile or Leu

<400> SEQUENCE: 10

Gln Cys Glu Ile Xaa Trp Ala Arg Glu Phe Leu Lys Glu Ile Gly Xaa
1               5                   10                  15

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Selenocysteine

<400> SEQUENCE: 11

Phe Ile Glu Xaa His Phe Trp Ile
1               5

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ile or Leu
<220> FEATURE:
<221> NAME/KEY: MOD_RES
<222> LOCATION: (10)..(10)
<223> OTHER INFORMATION: Selenocysteine
<220> FEATURE:
<221> NAME/KEY: MOD_RES
<222> LOCATION: (11)..(11)
<223> OTHER INFORMATION: Ile or Leu

<400> SEQUENCE: 12

Phe Glu Trp Arg His Arg Xaa Thr Arg Xaa Xaa Arg
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ile or Leu
<220> FEATURE:
<221> NAME/KEY: MOD_RES
<222> LOCATION: (5)..(5)
<223> OTHER INFORMATION: Pyrrolysine
<220> FEATURE:
<221> NAME/KEY: MOD_RES
<222> LOCATION: (8)..(8)
<223> OTHER INFORMATION: Ile or Leu

<400> SEQUENCE: 13
```

```
Gln Ile Glu Xaa Xaa Glu Ile Xaa Glu
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Pyrrolysine

<400> SEQUENCE: 14

Gln Cys Glu Ile Xaa Trp Ala Arg Glu
1               5

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile or Leu
<220> FEATURE:
<221> NAME/KEY: MOD_RES
<222> LOCATION: (9)..(9)
<223> OTHER INFORMATION: Pyrrolysine
<220> FEATURE:
<221> NAME/KEY: MOD_RES
<222> LOCATION: (11)..(11)
<223> OTHER INFORMATION: Ile or Leu

<400> SEQUENCE: 15

Phe Xaa Glu Leu Phe Ile Ser Asx Xaa Ser Xaa Phe Ile Glu
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Pyrrolysine
<220> FEATURE:
<221> NAME/KEY: MOD_RES
<222> LOCATION: (9)..(9)
<223> OTHER INFORMATION: Ile or Leu

<400> SEQUENCE: 16

Ile Glu Phe Arg Xaa Glu Ile Phe Xaa Glu Phe
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (5)..(5)
<223> OTHER INFORMATION: Pyrrolysine
<220> FEATURE:
<221> NAME/KEY: MOD_RES
<222> LOCATION: (9)..(9)
<223> OTHER INFORMATION: Ile or Leu

<400> SEQUENCE: 17

Ile Glu Phe Arg Xaa Glu Ile Phe Xaa
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pyrrolysine
<220> FEATURE:
<221> NAME/KEY: MOD_RES
<222> LOCATION: (8)..(8)
<223> OTHER INFORMATION: Ile or Leu

<400> SEQUENCE: 18

Glu Phe Arg Xaa Glu Ile Phe Xaa Glu
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pyrrolysine
<220> FEATURE:
<221> NAME/KEY: MOD_RES
<222> LOCATION: (7)..(7)
<223> OTHER INFORMATION: Ile or Leu

<400> SEQUENCE: 19

Phe Arg Xaa Glu Ile Phe Xaa Glu Phe
1               5

<210> SEQ ID NO 20
<211> LENGTH: 9
<212> TYPE: PRT
<213> ORGANISM: Homo sapiens

<400> SEQUENCE: 20

Tyr Glu His Glu Asp Val Lys Glu Ala
1               5

<210> SEQ ID NO 21
<211> LENGTH: 9
<212> TYPE: PRT
<213> ORGANISM: Homo sapiens

<400> SEQUENCE: 21

Ser Ser Ala Ala Ala Pro Phe Pro Leu
1               5
```

<210> SEQ ID NO 22
<211> LENGTH: 10
<212> TYPE: PRT
<213> ORGANISM: Homo sapiens

<400> SEQUENCE: 22

Phe Val Ser Thr Ser Asp Ile Lys Ser Met
1               5                   10

<210> SEQ ID NO 23
<211> LENGTH: 9
<212> TYPE: PRT
<213> ORGANISM: Homo sapiens

<400> SEQUENCE: 23

Asp Glu Asn Ile Thr Thr Ile Gln Phe
1               5

<210> SEQ ID NO 24
<211> LENGTH: 9
<212> TYPE: PRT
<213> ORGANISM: Homo sapiens

<400> SEQUENCE: 24

Gln Asp Val Ser Val Gln Val Glu Arg
1               5

<210> SEQ ID NO 25
<211> LENGTH: 10
<212> TYPE: PRT
<213> ORGANISM: Homo sapiens

<400> SEQUENCE: 25

Glu Val Ala Asp Ala Ala Thr Leu Thr Met
1               5                   10

<210> SEQ ID NO 26
<211> LENGTH: 10
<212> TYPE: PRT
<213> ORGANISM: Homo sapiens

<400> SEQUENCE: 26

Asp Thr Val Glu Tyr Pro Tyr Thr Ser Phe
1               5                   10

<210> SEQ ID NO 27
<211> LENGTH: 10
<212> TYPE: PRT
<213> ORGANISM: Homo sapiens

<400> SEQUENCE: 27

Gly Thr Lys Lys Asp Val Asp Val Leu Lys
1               5                   10

<210> SEQ ID NO 28
<211> LENGTH: 9
<212> TYPE: PRT
<213> ORGANISM: Homo sapiens

<400> SEQUENCE: 28

His Ser Pro Phe Thr Ala Thr Ser Leu
1               5

<210> SEQ ID NO 29

```
<211> LENGTH: 9
<212> TYPE: PRT
<213> ORGANISM: Homo sapiens

<400> SEQUENCE: 29

Asp Pro Glu Glu Val Leu Val Thr Val
1               5

<210> SEQ ID NO 30
<211> LENGTH: 10
<212> TYPE: PRT
<213> ORGANISM: Homo sapiens

<400> SEQUENCE: 30

Glu Leu Asp Pro Asp Ile Gln Leu Glu Tyr
1               5                   10

<210> SEQ ID NO 31
<211> LENGTH: 9
<212> TYPE: PRT
<213> ORGANISM: Homo sapiens

<400> SEQUENCE: 31

Thr Pro Leu Thr Lys Asp Val Thr Leu
1               5

<210> SEQ ID NO 32
<211> LENGTH: 8
<212> TYPE: PRT
<213> ORGANISM: Homo sapiens

<400> SEQUENCE: 32

Asp Gly Val Gly Lys Ser Ala Leu
1               5

<210> SEQ ID NO 33
<211> LENGTH: 9
<212> TYPE: PRT
<213> ORGANISM: Homo sapiens

<400> SEQUENCE: 33

Tyr Thr Thr Val Arg Ala Leu Thr Leu
1               5

<210> SEQ ID NO 34
<211> LENGTH: 9
<212> TYPE: PRT
<213> ORGANISM: Homo sapiens

<400> SEQUENCE: 34

Thr Pro Ser Ala Ala Val Lys Leu Ile
1               5

<210> SEQ ID NO 35
<211> LENGTH: 8
<212> TYPE: PRT
<213> ORGANISM: Homo sapiens

<400> SEQUENCE: 35

Trp Pro Val Leu Leu Leu Asn Val
1               5

<210> SEQ ID NO 36
<211> LENGTH: 9
<212> TYPE: PRT
```

-continued

<213> ORGANISM: Homo sapiens

<400> SEQUENCE: 36

Glu Leu Asn Ala Arg Arg Cys Ser Phe
1               5

<210> SEQ ID NO 37
<211> LENGTH: 9
<212> TYPE: PRT
<213> ORGANISM: Homo sapiens

<400> SEQUENCE: 37

Gln Met Lys Asn Pro Ile Leu Glu Leu
1               5

<210> SEQ ID NO 38
<211> LENGTH: 9
<212> TYPE: PRT
<213> ORGANISM: Homo sapiens

<400> SEQUENCE: 38

Leu Thr Glu Lys Val Ser Leu Leu Lys
1               5

<210> SEQ ID NO 39
<211> LENGTH: 8
<212> TYPE: PRT
<213> ORGANISM: Homo sapiens

<400> SEQUENCE: 39

Ser Pro Phe Thr Ala Thr Ser Leu
1               5

<210> SEQ ID NO 40
<211> LENGTH: 9
<212> TYPE: PRT
<213> ORGANISM: Homo sapiens

<400> SEQUENCE: 40

Asn Val Asp Met Arg Thr Ile Ser Phe
1               5

<210> SEQ ID NO 41
<211> LENGTH: 9
<212> TYPE: PRT
<213> ORGANISM: Homo sapiens

<400> SEQUENCE: 41

Thr Ser Ile Val Val Ser Gln Thr Leu
1               5

<210> SEQ ID NO 42
<211> LENGTH: 9
<212> TYPE: PRT
<213> ORGANISM: Homo sapiens

<400> SEQUENCE: 42

His Ile Lys Ile Glu Pro Val Ala Ile
1               5

<210> SEQ ID NO 43
<211> LENGTH: 9
<212> TYPE: PRT
<213> ORGANISM: Homo sapiens

```
<400> SEQUENCE: 43

Asp Ser Pro Asp Gly Ser Asn Gly Leu
1               5

<210> SEQ ID NO 44
<211> LENGTH: 10
<212> TYPE: PRT
<213> ORGANISM: Homo sapiens

<400> SEQUENCE: 44

Tyr Thr Ala Val His Tyr Ala Ala Ser Tyr
1               5                   10

<210> SEQ ID NO 45
<211> LENGTH: 11
<212> TYPE: PRT
<213> ORGANISM: Homo sapiens

<400> SEQUENCE: 45

Val Gly Ala Asp Gly Val Gly Lys Ser Ala Leu
1               5                   10

<210> SEQ ID NO 46
<211> LENGTH: 8
<212> TYPE: PRT
<213> ORGANISM: Homo sapiens

<400> SEQUENCE: 46

Met Met Pro Pro Leu Pro Gly Ile
1               5

<210> SEQ ID NO 47
<211> LENGTH: 9
<212> TYPE: PRT
<213> ORGANISM: Homo sapiens

<400> SEQUENCE: 47

Phe Pro Tyr Pro Gly Met Thr Asn Gln
1               5

<210> SEQ ID NO 48
<211> LENGTH: 9
<212> TYPE: PRT
<213> ORGANISM: Homo sapiens

<400> SEQUENCE: 48

Val Thr Asn His Ala Pro Leu Ser Trp
1               5

<210> SEQ ID NO 49
<211> LENGTH: 10
<212> TYPE: PRT
<213> ORGANISM: Homo sapiens

<400> SEQUENCE: 49

Gly Leu Asn Val Pro Val Gln Ser Asn Lys
1               5                   10

<210> SEQ ID NO 50
<211> LENGTH: 10
<212> TYPE: PRT
<213> ORGANISM: Homo sapiens

<400> SEQUENCE: 50
```

```
Val Val Val Gly Ala Cys Gly Val Gly Lys
1               5                  10

<210> SEQ ID NO 51
<211> LENGTH: 10
<212> TYPE: PRT
<213> ORGANISM: Homo sapiens

<400> SEQUENCE: 51

Ala Gln Phe Ala Gly Lys Asp Gln Thr Tyr
1               5                  10

<210> SEQ ID NO 52
<211> LENGTH: 11
<212> TYPE: PRT
<213> ORGANISM: Homo sapiens

<400> SEQUENCE: 52

Lys Val Val Leu Pro Ser Asp Val Thr Ser Tyr
1               5                  10

<210> SEQ ID NO 53
<211> LENGTH: 9
<212> TYPE: PRT
<213> ORGANISM: Homo sapiens

<400> SEQUENCE: 53

Met Leu Met Lys Asn Ile Ser Thr Lys
1               5

<210> SEQ ID NO 54
<211> LENGTH: 9
<212> TYPE: PRT
<213> ORGANISM: Homo sapiens

<400> SEQUENCE: 54

Asp Leu Ala Gly Gly Thr Phe Asp Val
1               5

<210> SEQ ID NO 55
<211> LENGTH: 10
<212> TYPE: PRT
<213> ORGANISM: Homo sapiens

<400> SEQUENCE: 55

Leu Ile Phe Asp Leu Ala Gly Gly Thr Phe
1               5                  10

<210> SEQ ID NO 56
<211> LENGTH: 8
<212> TYPE: PRT
<213> ORGANISM: Homo sapiens

<400> SEQUENCE: 56

Asn Val Leu Ile Phe Asp Leu Ala
1               5

<210> SEQ ID NO 57
<211> LENGTH: 9
<212> TYPE: PRT
<213> ORGANISM: Homo sapiens

<400> SEQUENCE: 57

Val Val Gly Ala Cys Gly Val Gly Lys
1               5
```

<210> SEQ ID NO 58
<211> LENGTH: 9
<212> TYPE: PRT
<213> ORGANISM: Homo sapiens

<400> SEQUENCE: 58

Val Ile Met Leu Asn Gly Thr Lys Lys
1               5

<210> SEQ ID NO 59
<211> LENGTH: 8
<212> TYPE: PRT
<213> ORGANISM: Homo sapiens

<400> SEQUENCE: 59

Leu Ala Gly Gly Thr Phe Asp Val
1               5

<210> SEQ ID NO 60
<211> LENGTH: 9
<212> TYPE: PRT
<213> ORGANISM: Homo sapiens

<400> SEQUENCE: 60

Leu Arg Asn Ser Gly Gly Glu Val Phe
1               5

<210> SEQ ID NO 61
<211> LENGTH: 10
<212> TYPE: PRT
<213> ORGANISM: Homo sapiens

<400> SEQUENCE: 61

Val Val Leu Pro Ser Asp Val Thr Ser Tyr
1               5                   10

<210> SEQ ID NO 62
<211> LENGTH: 9
<212> TYPE: PRT
<213> ORGANISM: Homo sapiens

<400> SEQUENCE: 62

Ile Phe Asp Leu Ala Gly Gly Thr Phe
1               5

<210> SEQ ID NO 63
<211> LENGTH: 11
<212> TYPE: PRT
<213> ORGANISM: Homo sapiens

<400> SEQUENCE: 63

Gly Leu Leu Asp Glu Ala Lys Arg Leu Leu Tyr
1               5                   10

<210> SEQ ID NO 64
<211> LENGTH: 11
<212> TYPE: PRT
<213> ORGANISM: Homo sapiens

<400> SEQUENCE: 64

Ser Val Leu Leu Pro Glu Asn Tyr Ile Thr Lys
1               5                   10

```
<210> SEQ ID NO 65
<211> LENGTH: 10
<212> TYPE: PRT
<213> ORGANISM: Homo sapiens

<400> SEQUENCE: 65

Asp Leu Ala Gly Gly Thr Phe Asp Val Ser
1               5                   10

<210> SEQ ID NO 66
<211> LENGTH: 11
<212> TYPE: PRT
<213> ORGANISM: Homo sapiens

<400> SEQUENCE: 66

Ile Phe Asp Leu Ala Gly Gly Thr Phe Asp Val
1               5                   10

<210> SEQ ID NO 67
<211> LENGTH: 11
<212> TYPE: PRT
<213> ORGANISM: Homo sapiens

<400> SEQUENCE: 67

Ala Glu Trp Arg Asn Gly Ser Thr Ser Ser Leu
1               5                   10

<210> SEQ ID NO 68
<211> LENGTH: 11
<212> TYPE: PRT
<213> ORGANISM: Homo sapiens

<400> SEQUENCE: 68

Tyr Val Ser Glu Lys Asp Val Ile Ser Ala Lys
1               5                   10

<210> SEQ ID NO 69
<211> LENGTH: 10
<212> TYPE: PRT
<213> ORGANISM: Homo sapiens

<400> SEQUENCE: 69

Glu Gly Ser Leu Gly Ile Ser His Thr Arg
1               5                   10

<210> SEQ ID NO 70
<211> LENGTH: 9
<212> TYPE: PRT
<213> ORGANISM: Homo sapiens

<400> SEQUENCE: 70

Ile Pro Ala Ser Val Ser Ala Pro Lys
1               5

<210> SEQ ID NO 71
<211> LENGTH: 11
<212> TYPE: PRT
<213> ORGANISM: Homo sapiens

<400> SEQUENCE: 71

Leu Val Val Val Gly Ala Ser Gly Val Gly Lys
1               5                   10

<210> SEQ ID NO 72
<211> LENGTH: 8
```

```
<212> TYPE: PRT
<213> ORGANISM: Homo sapiens

<400> SEQUENCE: 72

Arg Ala Thr Ile Val Pro Glu Leu
1               5

<210> SEQ ID NO 73
<211> LENGTH: 11
<212> TYPE: PRT
<213> ORGANISM: Homo sapiens

<400> SEQUENCE: 73

Gly Val Ser Lys Ile Ile Gly Gly Asn Pro Lys
1               5                   10

<210> SEQ ID NO 74
<211> LENGTH: 11
<212> TYPE: PRT
<213> ORGANISM: Homo sapiens

<400> SEQUENCE: 74

Glu Gln Asn Phe Val Ser Thr Ser Asp Ile Lys
1               5                   10

<210> SEQ ID NO 75
<211> LENGTH: 11
<212> TYPE: PRT
<213> ORGANISM: Homo sapiens

<400> SEQUENCE: 75

Arg Thr Gln Asp Val Ser Val Gln Val Glu Arg
1               5                   10

<210> SEQ ID NO 76
<211> LENGTH: 10
<212> TYPE: PRT
<213> ORGANISM: Homo sapiens

<400> SEQUENCE: 76

Glu Ala Gly Asn Asn Ser Arg Val Pro Arg
1               5                   10

<210> SEQ ID NO 77
<211> LENGTH: 9
<212> TYPE: PRT
<213> ORGANISM: Homo sapiens

<400> SEQUENCE: 77

Arg Tyr Val Leu His Val Val Ala Ala
1               5

<210> SEQ ID NO 78
<211> LENGTH: 10
<212> TYPE: PRT
<213> ORGANISM: Homo sapiens

<400> SEQUENCE: 78

Val Ser Lys Ile Ile Gly Gly Asn Pro Lys
1               5                   10

<210> SEQ ID NO 79
<211> LENGTH: 9
<212> TYPE: PRT
<213> ORGANISM: Homo sapiens
```

```
<400> SEQUENCE: 79

Gln Pro Ser Gly Val Pro Thr Ser Leu
1               5

<210> SEQ ID NO 80
<211> LENGTH: 8
<212> TYPE: PRT
<213> ORGANISM: Homo sapiens

<400> SEQUENCE: 80

Asp Val Ser Val Gln Val Glu Arg
1               5

<210> SEQ ID NO 81
<211> LENGTH: 9
<212> TYPE: PRT
<213> ORGANISM: Homo sapiens

<400> SEQUENCE: 81

Phe Pro Val Val Asn Ser His Ser Leu
1               5

<210> SEQ ID NO 82
<211> LENGTH: 10
<212> TYPE: PRT
<213> ORGANISM: Homo sapiens

<400> SEQUENCE: 82

Ala Pro Phe Pro Leu Gly Asp Ser Ala Leu
1               5                   10

<210> SEQ ID NO 83
<211> LENGTH: 10
<212> TYPE: PRT
<213> ORGANISM: Homo sapiens

<400> SEQUENCE: 83

Ala Thr Ile Val Pro Glu Leu Asn Glu Ile
1               5                   10

<210> SEQ ID NO 84
<211> LENGTH: 9
<212> TYPE: PRT
<213> ORGANISM: Homo sapiens

<400> SEQUENCE: 84

Gln Glu Phe Ala Pro Leu Gly Thr Val
1               5

<210> SEQ ID NO 85
<211> LENGTH: 8
<212> TYPE: PRT
<213> ORGANISM: Homo sapiens

<400> SEQUENCE: 85

Met Asn Gln Val Leu His Ala Tyr
1               5

<210> SEQ ID NO 86
<211> LENGTH: 8
<212> TYPE: PRT
<213> ORGANISM: Homo sapiens

<400> SEQUENCE: 86
```

```
His Glu Asp Val Lys Glu Ala Ile
1               5

<210> SEQ ID NO 87
<211> LENGTH: 9
<212> TYPE: PRT
<213> ORGANISM: Homo sapiens

<400> SEQUENCE: 87

Gly Pro Tyr Pro Phe Val Gln Ala Val
1               5

<210> SEQ ID NO 88
<211> LENGTH: 10
<212> TYPE: PRT
<213> ORGANISM: Homo sapiens

<400> SEQUENCE: 88

Tyr Glu His Glu Asp Val Lys Glu Ala Ile
1               5                   10

<210> SEQ ID NO 89
<211> LENGTH: 9
<212> TYPE: PRT
<213> ORGANISM: Homo sapiens

<400> SEQUENCE: 89

Glu Glu Ser Val Met Leu Leu Thr Val
1               5

<210> SEQ ID NO 90
<211> LENGTH: 9
<212> TYPE: PRT
<213> ORGANISM: Homo sapiens

<400> SEQUENCE: 90

Ile Glu Glu Asp Ser Ala Glu Lys Ile
1               5

<210> SEQ ID NO 91
<211> LENGTH: 9
<212> TYPE: PRT
<213> ORGANISM: Homo sapiens

<400> SEQUENCE: 91

Thr Glu Glu Asp Val Lys Ile Lys Phe
1               5

<210> SEQ ID NO 92
<211> LENGTH: 9
<212> TYPE: PRT
<213> ORGANISM: Homo sapiens

<400> SEQUENCE: 92

Asn Glu Gln Ser Lys Leu Leu Lys Val
1               5

<210> SEQ ID NO 93
<211> LENGTH: 9
<212> TYPE: PRT
<213> ORGANISM: Homo sapiens

<400> SEQUENCE: 93

Val Asp Asn Ile Ile Ile Gln Ser Ile
```

```
1               5

<210> SEQ ID NO 94
<211> LENGTH: 9
<212> TYPE: PRT
<213> ORGANISM: Homo sapiens

<400> SEQUENCE: 94

Tyr Val Ser Glu Val Pro Val Ser Val
1               5

<210> SEQ ID NO 95
<211> LENGTH: 9
<212> TYPE: PRT
<213> ORGANISM: Homo sapiens

<400> SEQUENCE: 95

Ser Glu Leu Thr Val His Gln Arg Ile
1               5

<210> SEQ ID NO 96
<211> LENGTH: 8
<212> TYPE: PRT
<213> ORGANISM: Homo sapiens

<400> SEQUENCE: 96

Val Gly Val Gly Lys Ser Ala Leu
1               5

<210> SEQ ID NO 97
<211> LENGTH: 9
<212> TYPE: PRT
<213> ORGANISM: Homo sapiens

<400> SEQUENCE: 97

Asp Met Asn Gln Val Leu His Ala Tyr
1               5

<210> SEQ ID NO 98
<211> LENGTH: 9
<212> TYPE: PRT
<213> ORGANISM: Homo sapiens

<400> SEQUENCE: 98

Asn Glu Lys Gly Lys Ala Leu Ile Tyr
1               5

<210> SEQ ID NO 99
<211> LENGTH: 11
<212> TYPE: PRT
<213> ORGANISM: Homo sapiens

<400> SEQUENCE: 99

Thr Glu Tyr Lys Leu Val Val Val Gly Ala Val
1               5                   10

<210> SEQ ID NO 100
<211> LENGTH: 10
<212> TYPE: PRT
<213> ORGANISM: Homo sapiens

<400> SEQUENCE: 100

Gln Glu Phe Ala Pro Leu Gly Thr Val Gly
1               5                   10
```

<210> SEQ ID NO 101
<211> LENGTH: 10
<212> TYPE: PRT
<213> ORGANISM: Homo sapiens

<400> SEQUENCE: 101

Gln Glu Val Arg Asn Thr Leu Leu Asn Val
1               5                   10

<210> SEQ ID NO 102
<211> LENGTH: 9
<212> TYPE: PRT
<213> ORGANISM: Homo sapiens

<400> SEQUENCE: 102

Val Glu Met Leu Gly Leu Ile Ser Cys
1               5

<210> SEQ ID NO 103
<211> LENGTH: 9
<212> TYPE: PRT
<213> ORGANISM: Homo sapiens

<400> SEQUENCE: 103

Leu Phe His Asp Met Asn Val Ser Tyr
1               5

<210> SEQ ID NO 104
<211> LENGTH: 9
<212> TYPE: PRT
<213> ORGANISM: Homo sapiens

<400> SEQUENCE: 104

Ile Ser Thr Phe Arg Gln Cys Ala Leu
1               5

<210> SEQ ID NO 105
<211> LENGTH: 9
<212> TYPE: PRT
<213> ORGANISM: Homo sapiens

<400> SEQUENCE: 105

Tyr Asn Thr Asp Asp Ile Glu Phe Tyr
1               5

<210> SEQ ID NO 106
<211> LENGTH: 9
<212> TYPE: PRT
<213> ORGANISM: Homo sapiens

<400> SEQUENCE: 106

Glu Glu Thr Pro Pro Phe Ser Asn Tyr
1               5

<210> SEQ ID NO 107
<211> LENGTH: 9
<212> TYPE: PRT
<213> ORGANISM: Homo sapiens

<400> SEQUENCE: 107

Gln Ala Ser Gly Asn His His Val Trp
1               5

<210> SEQ ID NO 108

```
<211> LENGTH: 9
<212> TYPE: PRT
<213> ORGANISM: Homo sapiens

<400> SEQUENCE: 108

Glu Glu Val Thr Pro Ile Leu Ala Ile
1               5

<210> SEQ ID NO 109
<211> LENGTH: 10
<212> TYPE: PRT
<213> ORGANISM: Homo sapiens

<400> SEQUENCE: 109

Ile Glu His Asn Ile Arg Asn Ala Lys Tyr
1               5                   10

<210> SEQ ID NO 110
<211> LENGTH: 9
<212> TYPE: PRT
<213> ORGANISM: Homo sapiens

<400> SEQUENCE: 110

Ala Glu Arg Leu Asp Val Lys Ala Ile
1               5

<210> SEQ ID NO 111
<211> LENGTH: 11
<212> TYPE: PRT
<213> ORGANISM: Homo sapiens

<400> SEQUENCE: 111

Leu Phe Gln Gln Gly Lys Asp Leu Gln Gln Tyr
1               5                   10

<210> SEQ ID NO 112
<211> LENGTH: 9
<212> TYPE: PRT
<213> ORGANISM: Homo sapiens

<400> SEQUENCE: 112

Asp Thr Ser Pro Val Ala Val Ala Leu
1               5

<210> SEQ ID NO 113
<211> LENGTH: 10
<212> TYPE: PRT
<213> ORGANISM: Homo sapiens

<400> SEQUENCE: 113

Ala Glu Glu Thr Pro Pro Phe Ser Asn Tyr
1               5                   10

<210> SEQ ID NO 114
<211> LENGTH: 9
<212> TYPE: PRT
<213> ORGANISM: Homo sapiens

<400> SEQUENCE: 114

Ala Ala Lys Ala Ala Leu Glu Asp Phe
1               5

<210> SEQ ID NO 115
<211> LENGTH: 9
<212> TYPE: PRT
```

```
<213> ORGANISM: Homo sapiens

<400> SEQUENCE: 115

Glu Val Thr Pro Ile Leu Ala Ile Arg
1               5

<210> SEQ ID NO 116
<211> LENGTH: 9
<212> TYPE: PRT
<213> ORGANISM: Homo sapiens

<400> SEQUENCE: 116

Asp Val Lys Ala Ile Gly Pro Leu Val
1               5

<210> SEQ ID NO 117
<211> LENGTH: 10
<212> TYPE: PRT
<213> ORGANISM: Homo sapiens

<400> SEQUENCE: 117

Asn Glu Thr Pro Val Ala Val Leu Thr Ile
1               5                   10

<210> SEQ ID NO 118
<211> LENGTH: 9
<212> TYPE: PRT
<213> ORGANISM: Homo sapiens

<400> SEQUENCE: 118

Leu Phe Val Val Phe Gln Thr Val Tyr
1               5

<210> SEQ ID NO 119
<211> LENGTH: 11
<212> TYPE: PRT
<213> ORGANISM: Homo sapiens

<400> SEQUENCE: 119

Ala Glu Ala Glu Arg Leu Asp Val Lys Ala Ile
1               5                   10

<210> SEQ ID NO 120
<211> LENGTH: 8
<212> TYPE: PRT
<213> ORGANISM: Homo sapiens

<400> SEQUENCE: 120

Ala Ser Gly Asn His His Val Trp
1               5

<210> SEQ ID NO 121
<211> LENGTH: 10
<212> TYPE: PRT
<213> ORGANISM: Homo sapiens

<400> SEQUENCE: 121

Lys Leu Phe His Asp Met Asn Val Ser Tyr
1               5                   10

<210> SEQ ID NO 122
<211> LENGTH: 11
<212> TYPE: PRT
<213> ORGANISM: Homo sapiens
```

```
<400> SEQUENCE: 122

Glu Thr Pro Pro Phe Ser Asn Tyr Asn Thr Leu
1               5                   10

<210> SEQ ID NO 123
<211> LENGTH: 8
<212> TYPE: PRT
<213> ORGANISM: Homo sapiens

<400> SEQUENCE: 123

Met Glu Leu Lys Val Glu Ser Phe
1               5

<210> SEQ ID NO 124
<211> LENGTH: 9
<212> TYPE: PRT
<213> ORGANISM: Homo sapiens

<400> SEQUENCE: 124

Glu His Ile Pro Glu Ser Ala Gly Phe
1               5

<210> SEQ ID NO 125
<211> LENGTH: 9
<212> TYPE: PRT
<213> ORGANISM: Homo sapiens

<400> SEQUENCE: 125

Tyr His Gly Asp Pro Met Pro Cys Leu
1               5

<210> SEQ ID NO 126
<211> LENGTH: 8
<212> TYPE: PRT
<213> ORGANISM: Homo sapiens

<400> SEQUENCE: 126

Asp Glu Glu Arg Ile Pro Val Leu
1               5

<210> SEQ ID NO 127
<211> LENGTH: 8
<212> TYPE: PRT
<213> ORGANISM: Homo sapiens

<400> SEQUENCE: 127

Ile Glu Val Glu Val Asn Glu Ile
1               5

<210> SEQ ID NO 128
<211> LENGTH: 8
<212> TYPE: PRT
<213> ORGANISM: Homo sapiens

<400> SEQUENCE: 128

Val Glu Ile Glu Gln Leu Thr Tyr
1               5

<210> SEQ ID NO 129
<211> LENGTH: 9
<212> TYPE: PRT
<213> ORGANISM: Homo sapiens

<400> SEQUENCE: 129
```

Leu Glu Leu Lys Ala Val His Ala Tyr
1               5

<210> SEQ ID NO 130
<211> LENGTH: 9
<212> TYPE: PRT
<213> ORGANISM: Homo sapiens

<400> SEQUENCE: 130

Glu Glu Ala Asp Phe Leu Leu Ala Tyr
1               5

<210> SEQ ID NO 131
<211> LENGTH: 9
<212> TYPE: PRT
<213> ORGANISM: Homo sapiens

<400> SEQUENCE: 131

Glu Asn Ile Thr Thr Ile Gln Phe Tyr
1               5

<210> SEQ ID NO 132
<211> LENGTH: 9
<212> TYPE: PRT
<213> ORGANISM: Homo sapiens

<400> SEQUENCE: 132

Phe His Ala Thr Asn Pro Leu Asn Leu
1               5

<210> SEQ ID NO 133
<211> LENGTH: 9
<212> TYPE: PRT
<213> ORGANISM: Homo sapiens

<400> SEQUENCE: 133

Val Phe Lys Asp Leu Ser Val Thr Leu
1               5

<210> SEQ ID NO 134
<211> LENGTH: 9
<212> TYPE: PRT
<213> ORGANISM: Homo sapiens

<400> SEQUENCE: 134

Gln Ala Val Ala Ala Val Gln Lys Leu
1               5

<210> SEQ ID NO 135
<211> LENGTH: 9
<212> TYPE: PRT
<213> ORGANISM: Homo sapiens

<400> SEQUENCE: 135

Ile Gln Asp Gln Ile Gln Asn Cys Ile
1               5

<210> SEQ ID NO 136
<211> LENGTH: 9
<212> TYPE: PRT
<213> ORGANISM: Homo sapiens

<400> SEQUENCE: 136

Val Ala Lys Gly Phe Ile Ser Arg Met
1               5

<210> SEQ ID NO 137
<211> LENGTH: 9
<212> TYPE: PRT
<213> ORGANISM: Homo sapiens

<400> SEQUENCE: 137

Gln Thr Lys Pro Ala Ser Leu Leu Tyr
1               5

<210> SEQ ID NO 138
<211> LENGTH: 9
<212> TYPE: PRT
<213> ORGANISM: Homo sapiens

<400> SEQUENCE: 138

Asp His Phe Glu Thr Ile Ile Lys Tyr
1               5

<210> SEQ ID NO 139
<211> LENGTH: 8
<212> TYPE: PRT
<213> ORGANISM: Homo sapiens

<400> SEQUENCE: 139

Val Glu Tyr Pro Tyr Thr Ser Phe
1               5

<210> SEQ ID NO 140
<211> LENGTH: 10
<212> TYPE: PRT
<213> ORGANISM: Homo sapiens

<400> SEQUENCE: 140

Ser Val Ser Asp Ile Ser Glu Tyr Arg Val
1               5                   10

<210> SEQ ID NO 141
<211> LENGTH: 11
<212> TYPE: PRT
<213> ORGANISM: Homo sapiens

<400> SEQUENCE: 141

Tyr Thr Phe Glu Ile Gln Gly Val Asn Gly Val
1               5                   10

<210> SEQ ID NO 142
<211> LENGTH: 11
<212> TYPE: PRT
<213> ORGANISM: Homo sapiens

<400> SEQUENCE: 142

Ile Tyr Thr Ser Ser Gly Gln Leu Gln Leu Phe
1               5                   10

<210> SEQ ID NO 143
<211> LENGTH: 10
<212> TYPE: PRT
<213> ORGANISM: Homo sapiens

<400> SEQUENCE: 143

Phe Ala Thr Pro Ser Leu His Thr Ser Val
1               5                   10

<210> SEQ ID NO 144
<211> LENGTH: 11
<212> TYPE: PRT
<213> ORGANISM: Homo sapiens

<400> SEQUENCE: 144

Ala Val Ser Lys Pro Gly Leu Asp Tyr Glu Leu
1               5                   10

<210> SEQ ID NO 145
<211> LENGTH: 9
<212> TYPE: PRT
<213> ORGANISM: Homo sapiens

<400> SEQUENCE: 145

Lys Tyr Ile Asn Lys Thr Ile Arg Val
1               5

<210> SEQ ID NO 146
<211> LENGTH: 10
<212> TYPE: PRT
<213> ORGANISM: Homo sapiens

<400> SEQUENCE: 146

Glu Thr Thr Glu Glu Met Lys Tyr Val Leu
1               5                   10

<210> SEQ ID NO 147
<211> LENGTH: 10
<212> TYPE: PRT
<213> ORGANISM: Homo sapiens

<400> SEQUENCE: 147

Val Val Ser His Pro His Leu Val Tyr Trp
1               5                   10

<210> SEQ ID NO 148
<211> LENGTH: 9
<212> TYPE: PRT
<213> ORGANISM: Homo sapiens

<400> SEQUENCE: 148

Asp Ile Phe Gln Val Val Lys Ala Ile
1               5

<210> SEQ ID NO 149
<211> LENGTH: 11
<212> TYPE: PRT
<213> ORGANISM: Homo sapiens

<400> SEQUENCE: 149

Phe Ala Phe Asp Ala Val Ser Lys Pro Gly Leu
1               5                   10

<210> SEQ ID NO 150
<211> LENGTH: 9
<212> TYPE: PRT
<213> ORGANISM: Homo sapiens

<400> SEQUENCE: 150

Ser Val Ser Asp Ile Ser Glu Tyr Arg
1               5

<210> SEQ ID NO 151
<211> LENGTH: 8

<212> TYPE: PRT
<213> ORGANISM: Homo sapiens

<400> SEQUENCE: 151

Tyr Thr Phe Glu Ile Gln Gly Val
1               5

<210> SEQ ID NO 152
<211> LENGTH: 9
<212> TYPE: PRT
<213> ORGANISM: Homo sapiens

<400> SEQUENCE: 152

Ala Thr Pro Ser Leu His Thr Ser Val
1               5

<210> SEQ ID NO 153
<211> LENGTH: 11
<212> TYPE: PRT
<213> ORGANISM: Homo sapiens

<400> SEQUENCE: 153

Asp Phe Ala Thr Pro Ser Leu His Thr Ser Val
1               5                   10

<210> SEQ ID NO 154
<211> LENGTH: 11
<212> TYPE: PRT
<213> ORGANISM: Homo sapiens

<400> SEQUENCE: 154

Lys Tyr Ile Asn Lys Thr Ile Arg Val Lys Phe
1               5                   10

<210> SEQ ID NO 155
<211> LENGTH: 9
<212> TYPE: PRT
<213> ORGANISM: Homo sapiens

<400> SEQUENCE: 155

Ser Val Lys Pro His Leu Cys Ser Leu
1               5

<210> SEQ ID NO 156
<211> LENGTH: 10
<212> TYPE: PRT
<213> ORGANISM: Homo sapiens

<400> SEQUENCE: 156

Asp Ile Ser Glu Tyr Arg Val Glu His Leu
1               5                   10

<210> SEQ ID NO 157
<211> LENGTH: 9
<212> TYPE: PRT
<213> ORGANISM: Homo sapiens

<400> SEQUENCE: 157

Trp Val Val Ser His Pro His Leu Val
1               5

<210> SEQ ID NO 158
<211> LENGTH: 9
<212> TYPE: PRT
<213> ORGANISM: Homo sapiens

```
<400> SEQUENCE: 158

Lys Val Phe Lys Leu Gly Asn Lys Val
1               5

<210> SEQ ID NO 159
<211> LENGTH: 10
<212> TYPE: PRT
<213> ORGANISM: Homo sapiens

<400> SEQUENCE: 159

Val Ser Lys Pro Gly Leu Asp Tyr Glu Leu
1               5                   10

<210> SEQ ID NO 160
<211> LENGTH: 9
<212> TYPE: PRT
<213> ORGANISM: Homo sapiens

<400> SEQUENCE: 160

Ser Pro Ser Lys Thr Ser Leu Thr Leu
1               5

<210> SEQ ID NO 161
<211> LENGTH: 10
<212> TYPE: PRT
<213> ORGANISM: Homo sapiens

<400> SEQUENCE: 161

Ala Ser Ala Asp Gly Thr Val Lys Leu Trp
1               5                   10

<210> SEQ ID NO 162
<211> LENGTH: 10
<212> TYPE: PRT
<213> ORGANISM: Homo sapiens

<400> SEQUENCE: 162

Leu Val Gly Pro Ala Gln Leu Ser His Trp
1               5                   10

<210> SEQ ID NO 163
<211> LENGTH: 10
<212> TYPE: PRT
<213> ORGANISM: Homo sapiens

<400> SEQUENCE: 163

Gln Thr Ala Ala Ala Val Gly Val Leu Lys
1               5                   10

<210> SEQ ID NO 164
<211> LENGTH: 11
<212> TYPE: PRT
<213> ORGANISM: Homo sapiens

<400> SEQUENCE: 164

Phe Pro Ser Pro Ser Lys Thr Ser Leu Thr Leu
1               5                   10

<210> SEQ ID NO 165
<211> LENGTH: 10
<212> TYPE: PRT
<213> ORGANISM: Homo sapiens

<400> SEQUENCE: 165
```

Ser Ser Thr Ser Asn Arg Ser Ser Thr Trp
1               5                   10

<210> SEQ ID NO 166
<211> LENGTH: 10
<212> TYPE: PRT
<213> ORGANISM: Homo sapiens

<400> SEQUENCE: 166

Leu Val Tyr Gly Pro Leu Gly Ala Gly Lys
1               5                   10

<210> SEQ ID NO 167
<211> LENGTH: 9
<212> TYPE: PRT
<213> ORGANISM: Homo sapiens

<400> SEQUENCE: 167

His Ser Tyr Ser Glu Leu Cys Thr Trp
1               5

<210> SEQ ID NO 168
<211> LENGTH: 9
<212> TYPE: PRT
<213> ORGANISM: Homo sapiens

<400> SEQUENCE: 168

Val Thr Leu Asp Val Ile Leu Glu Arg
1               5

<210> SEQ ID NO 169
<211> LENGTH: 10
<212> TYPE: PRT
<213> ORGANISM: Homo sapiens

<400> SEQUENCE: 169

His Ser Lys Pro Glu Asp Thr Asp Ala Trp
1               5                   10

<210> SEQ ID NO 170
<211> LENGTH: 9
<212> TYPE: PRT
<213> ORGANISM: Homo sapiens

<400> SEQUENCE: 170

Ile Ala Ala Ser Arg Ser Val Val Met
1               5

<210> SEQ ID NO 171
<211> LENGTH: 9
<212> TYPE: PRT
<213> ORGANISM: Homo sapiens

<400> SEQUENCE: 171

Ala Ala Ile Ala Ala Ser Arg Ser Val
1               5

<210> SEQ ID NO 172
<211> LENGTH: 8
<212> TYPE: PRT
<213> ORGANISM: Homo sapiens

<400> SEQUENCE: 172

Ala Ala Ser Arg Ser Val Val Met
1               5

```
1               5

<210> SEQ ID NO 173
<211> LENGTH: 9
<212> TYPE: PRT
<213> ORGANISM: Homo sapiens

<400> SEQUENCE: 173

Glu Met Asp Met His Leu Ser Asp Tyr
1               5

<210> SEQ ID NO 174
<211> LENGTH: 8
<212> TYPE: PRT
<213> ORGANISM: Homo sapiens

<400> SEQUENCE: 174

Val Glu Asn Gln Lys His Ser Leu
1               5

<210> SEQ ID NO 175
<211> LENGTH: 10
<212> TYPE: PRT
<213> ORGANISM: Homo sapiens

<400> SEQUENCE: 175

Gln Tyr Met Asp Ser Ser Leu Val Lys Ile
1               5                   10

<210> SEQ ID NO 176
<211> LENGTH: 9
<212> TYPE: PRT
<213> ORGANISM: Homo sapiens

<400> SEQUENCE: 176

Ser Ala Ser Leu His Pro Ala Thr Val
1               5

<210> SEQ ID NO 177
<211> LENGTH: 9
<212> TYPE: PRT
<213> ORGANISM: Homo sapiens

<400> SEQUENCE: 177

Val Pro Asp Gln Lys Ser Lys Gln Leu
1               5

<210> SEQ ID NO 178
<211> LENGTH: 9
<212> TYPE: PRT
<213> ORGANISM: Homo sapiens

<400> SEQUENCE: 178

Ile Val Phe Ile Ala Thr Ser Glu Phe
1               5

<210> SEQ ID NO 179
<211> LENGTH: 9
<212> TYPE: PRT
<213> ORGANISM: Homo sapiens

<400> SEQUENCE: 179

Tyr Pro Ala Pro Gln Pro Pro Val Leu
1               5
```

```
<210> SEQ ID NO 180
<211> LENGTH: 9
<212> TYPE: PRT
<213> ORGANISM: Homo sapiens

<400> SEQUENCE: 180

Ala Pro Lys Lys Lys Ser Ile Lys Leu
1               5

<210> SEQ ID NO 181
<211> LENGTH: 9
<212> TYPE: PRT
<213> ORGANISM: Homo sapiens

<400> SEQUENCE: 181

Leu Leu Leu Glu Val Val Trp His Leu
1               5

<210> SEQ ID NO 182
<211> LENGTH: 9
<212> TYPE: PRT
<213> ORGANISM: Homo sapiens

<400> SEQUENCE: 182

Phe Thr Asp Glu Lys Val Lys Ala Tyr
1               5

<210> SEQ ID NO 183
<211> LENGTH: 10
<212> TYPE: PRT
<213> ORGANISM: Homo sapiens

<400> SEQUENCE: 183

Arg Thr Ala Lys Gln Asn Pro Leu Thr Lys
1               5                   10

<210> SEQ ID NO 184
<211> LENGTH: 9
<212> TYPE: PRT
<213> ORGANISM: Homo sapiens

<400> SEQUENCE: 184

Phe Leu Ala Pro Thr Gly Val Pro Val
1               5

<210> SEQ ID NO 185
<211> LENGTH: 11
<212> TYPE: PRT
<213> ORGANISM: Homo sapiens

<400> SEQUENCE: 185

Arg Leu Ala Asp Ala Glu Lys Leu Phe Gln Leu
1               5                   10

<210> SEQ ID NO 186
<211> LENGTH: 11
<212> TYPE: PRT
<213> ORGANISM: Homo sapiens

<400> SEQUENCE: 186

Arg Thr Ala Lys Gln Asn Pro Leu Thr Lys Lys
1               5                   10

<210> SEQ ID NO 187
```

```
<211> LENGTH: 10
<212> TYPE: PRT
<213> ORGANISM: Homo sapiens

<400> SEQUENCE: 187

Ile Met Tyr Leu Thr Gly Met Val Asn Lys
1               5                   10

<210> SEQ ID NO 188
<211> LENGTH: 9
<212> TYPE: PRT
<213> ORGANISM: Homo sapiens

<400> SEQUENCE: 188

Thr Leu Gln Glu Leu Ser His Ala Leu
1               5

<210> SEQ ID NO 189
<211> LENGTH: 9
<212> TYPE: PRT
<213> ORGANISM: Homo sapiens

<400> SEQUENCE: 189

Val Ser Gln Pro Val Ala Pro Ser Tyr
1               5

<210> SEQ ID NO 190
<211> LENGTH: 10
<212> TYPE: PRT
<213> ORGANISM: Homo sapiens

<400> SEQUENCE: 190

Arg Leu Phe Thr Pro Ile Ser Ala Gly Tyr
1               5                   10

<210> SEQ ID NO 191
<211> LENGTH: 10
<212> TYPE: PRT
<213> ORGANISM: Homo sapiens

<400> SEQUENCE: 191

Ile Thr Glu Glu Pro Ile Leu Met Thr Tyr
1               5                   10

<210> SEQ ID NO 192
<211> LENGTH: 9
<212> TYPE: PRT
<213> ORGANISM: Homo sapiens

<400> SEQUENCE: 192

Lys Val Thr Gly His Arg Trp Leu Lys
1               5

<210> SEQ ID NO 193
<211> LENGTH: 9
<212> TYPE: PRT
<213> ORGANISM: Homo sapiens

<400> SEQUENCE: 193

Lys Leu Ser Glu Gln Ile Leu Lys Lys
1               5

<210> SEQ ID NO 194
<211> LENGTH: 9
<212> TYPE: PRT
```

-continued

<213> ORGANISM: Homo sapiens

<400> SEQUENCE: 194

Gly Thr Lys Pro Asn Pro His Val Tyr
1               5

<210> SEQ ID NO 195
<211> LENGTH: 9
<212> TYPE: PRT
<213> ORGANISM: Homo sapiens

<400> SEQUENCE: 195

Gln Gln Gln Gln Val Val Thr Asn Lys
1               5

<210> SEQ ID NO 196
<211> LENGTH: 10
<212> TYPE: PRT
<213> ORGANISM: Homo sapiens

<400> SEQUENCE: 196

Lys Val Leu Gly Lys Gly Ser Phe Ala Lys
1               5                   10

<210> SEQ ID NO 197
<211> LENGTH: 9
<212> TYPE: PRT
<213> ORGANISM: Homo sapiens

<400> SEQUENCE: 197

Ser Val Gln Ala Pro Val Pro Pro Lys
1               5

<210> SEQ ID NO 198
<211> LENGTH: 8
<212> TYPE: PRT
<213> ORGANISM: Epstein-Barr virus

<400> SEQUENCE: 198

Arg Ala Lys Phe Lys Gln Leu Leu
1               5

<210> SEQ ID NO 199
<211> LENGTH: 9
<212> TYPE: PRT
<213> ORGANISM: Influenza virus

<400> SEQUENCE: 199

Cys Thr Glu Leu Lys Leu Ser Asp Tyr
1               5

<210> SEQ ID NO 200
<211> LENGTH: 9
<212> TYPE: PRT
<213> ORGANISM: Influenza virus

<400> SEQUENCE: 200

Glu Leu Arg Ser Arg Tyr Trp Ala Ile
1               5

<210> SEQ ID NO 201
<211> LENGTH: 9
<212> TYPE: PRT
<213> ORGANISM: Human cytomegalovirus

```
<400> SEQUENCE: 201

Asn Leu Val Pro Met Val Ala Thr Val
1               5

<210> SEQ ID NO 202
<211> LENGTH: 9
<212> TYPE: PRT
<213> ORGANISM: Influenza virus

<400> SEQUENCE: 202

Gly Ile Leu Gly Phe Val Phe Thr Leu
1               5

<210> SEQ ID NO 203
<211> LENGTH: 10
<212> TYPE: PRT
<213> ORGANISM: Hepatitis C virus

<400> SEQUENCE: 203

Lys Leu Val Ala Leu Gly Ile Asn Ala Val
1               5                   10

<210> SEQ ID NO 204
<211> LENGTH: 9
<212> TYPE: PRT
<213> ORGANISM: Human immunodeficiency virus

<400> SEQUENCE: 204

Ile Leu Lys Glu Pro Val His Gly Val
1               5

<210> SEQ ID NO 205
<211> LENGTH: 9
<212> TYPE: PRT
<213> ORGANISM: Respiratory syncytial virus

<400> SEQUENCE: 205

Asn Pro Lys Ala Ser Leu Leu Ser Leu
1               5

<210> SEQ ID NO 206
<211> LENGTH: 13
<212> TYPE: PRT
<213> ORGANISM: Homo sapiens

<400> SEQUENCE: 206

Cys Ala Val Thr Val Thr Gly Arg Arg Ala Leu Thr Phe
1               5                   10

<210> SEQ ID NO 207
<211> LENGTH: 9
<212> TYPE: PRT
<213> ORGANISM: Homo sapiens

<400> SEQUENCE: 207

Cys Ala Leu Asn Ala Arg Leu Met Phe
1               5

<210> SEQ ID NO 208
<211> LENGTH: 13
<212> TYPE: PRT
<213> ORGANISM: Homo sapiens

<400> SEQUENCE: 208
```

Cys Ala Val Val Leu Asp Ser Asn Tyr Gln Leu Ile Trp
1               5                   10

<210> SEQ ID NO 209
<211> LENGTH: 15
<212> TYPE: PRT
<213> ORGANISM: Homo sapiens

<400> SEQUENCE: 209

Cys Ala Thr Ala Ser Arg Gln Gly Gly Ser Glu Lys Leu Val Phe
1               5                   10                  15

<210> SEQ ID NO 210
<211> LENGTH: 11
<212> TYPE: PRT
<213> ORGANISM: Homo sapiens

<400> SEQUENCE: 210

Cys Ala Ala Ser Ser Asn Tyr Gln Leu Ile Trp
1               5                   10

<210> SEQ ID NO 211
<211> LENGTH: 17
<212> TYPE: PRT
<213> ORGANISM: Homo sapiens

<400> SEQUENCE: 211

Cys Ala Ser Asn Pro Pro Asp Ala Ala Arg Gly Gln Glu Thr Gln Tyr
1               5                   10                  15
Phe

<210> SEQ ID NO 212
<211> LENGTH: 14
<212> TYPE: PRT
<213> ORGANISM: Homo sapiens

<400> SEQUENCE: 212

Cys Ala Ser Ser Tyr Arg Glu Tyr Asn Thr Glu Ala Phe Phe
1               5                   10

<210> SEQ ID NO 213
<211> LENGTH: 15
<212> TYPE: PRT
<213> ORGANISM: Homo sapiens

<400> SEQUENCE: 213

Cys Ser Ala Thr Arg Gly His Leu Ser Asn Gln Pro Gln His Phe
1               5                   10                  15

<210> SEQ ID NO 214
<211> LENGTH: 14
<212> TYPE: PRT
<213> ORGANISM: Homo sapiens

<400> SEQUENCE: 214

Cys Ala Ser Ser Arg Gly Gly Gly Thr Asp Thr Gln Tyr Phe
1               5                   10

<210> SEQ ID NO 215
<211> LENGTH: 13
<212> TYPE: PRT
<213> ORGANISM: Homo sapiens

<400> SEQUENCE: 215

```
Cys Ala Ser Ser Leu Gly Leu Ala Tyr Glu Gln Tyr Phe
1               5                   10
```

<210> SEQ ID NO 216
<211> LENGTH: 131
<212> TYPE: PRT
<213> ORGANISM: Homo sapiens

<400> SEQUENCE: 216

```
Met Leu Leu Leu Val Pro Val Leu Glu Val Ile Phe Thr Leu Gly
1               5                   10                  15

Gly Thr Arg Ala Gln Ser Val Thr Gln Leu Gly Ser His Val Ser Val
                20                  25                  30

Ser Glu Gly Ala Leu Val Leu Leu Arg Cys Asn Tyr Ser Ser Ser Val
                35                  40                  45

Pro Pro Tyr Leu Phe Trp Tyr Val Gln Tyr Pro Asn Gln Gly Leu Gln
            50                  55                  60

Leu Leu Leu Lys Tyr Thr Thr Gly Ala Thr Leu Val Lys Gly Ile Asn
65                  70                  75                  80

Gly Phe Glu Ala Glu Phe Lys Lys Ser Glu Thr Ser Phe His Leu Thr
                85                  90                  95

Lys Pro Ser Ala His Met Ser Asp Ala Ala Glu Tyr Phe Cys Ala Val
                100                 105                 110

Thr Val Thr Gly Arg Arg Ala Leu Thr Phe Gly Ser Gly Thr Arg Leu
            115                 120                 125

Gln Val Gln
    130
```

<210> SEQ ID NO 217
<211> LENGTH: 146
<212> TYPE: PRT
<213> ORGANISM: Homo sapiens

<400> SEQUENCE: 217

```
Met Ala Phe Trp Leu Arg Arg Leu Gly Leu His Phe Arg Pro His Leu
1               5                   10                  15

Gly Arg Arg Met Glu Ser Phe Leu Gly Gly Val Leu Leu Ile Leu Trp
                20                  25                  30

Leu Gln Val Asp Trp Val Lys Ser Gln Lys Ile Glu Gln Asn Ser Glu
            35                  40                  45

Ala Leu Asn Ile Gln Glu Gly Lys Thr Ala Thr Leu Thr Cys Asn Tyr
50                  55                  60

Thr Asn Tyr Ser Pro Ala Tyr Leu Gln Trp Tyr Arg Gln Asp Pro Gly
65                  70                  75                  80

Arg Gly Pro Val Phe Leu Leu Leu Ile Arg Glu Asn Glu Lys Glu Lys
                85                  90                  95

Arg Lys Glu Arg Leu Lys Val Thr Phe Asp Thr Thr Leu Lys Gln Ser
            100                 105                 110

Leu Phe His Ile Thr Ala Ser Gln Pro Ala Asp Ser Ala Thr Tyr Leu
            115                 120                 125

Cys Ala Leu Asn Ala Arg Leu Met Phe Gly Asp Gly Thr Gln Leu Val
        130                 135                 140

Val Lys
145
```

<210> SEQ ID NO 218
<211> LENGTH: 128

```
<212> TYPE: PRT
<213> ORGANISM: Homo sapiens

<400> SEQUENCE: 218

Met Lys Arg Ile Leu Gly Ala Leu Leu Gly Leu Leu Ser Ala Gln Val
1               5                   10                  15

Cys Cys Val Arg Gly Ile Gln Val Glu Gln Ser Pro Pro Asp Leu Ile
            20                  25                  30

Leu Gln Glu Gly Ala Asn Ser Thr Leu Arg Cys Asn Phe Ser Asp Ser
        35                  40                  45

Val Asn Asn Leu Gln Trp Phe His Gln Asn Pro Trp Gly Gln Leu Ile
50                  55                  60

Asn Leu Phe Tyr Ile Pro Ser Gly Thr Lys Gln Asn Gly Arg Leu Ser
65                  70                  75                  80

Ala Thr Thr Val Ala Thr Glu Arg Tyr Ser Leu Leu Tyr Ile Ser Ser
                85                  90                  95

Ser Gln Thr Thr Asp Ser Gly Val Tyr Phe Cys Ala Val Val Leu Asp
            100                 105                 110

Ser Asn Tyr Gln Leu Ile Trp Gly Ala Gly Thr Lys Leu Ile Ile Lys
        115                 120                 125

<210> SEQ ID NO 219
<211> LENGTH: 132
<212> TYPE: PRT
<213> ORGANISM: Homo sapiens

<400> SEQUENCE: 219

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Ser Leu Leu Ile
                85                  90                  95

Thr Ala Ser Arg Ala Ala Asp Thr Ala Ser Tyr Phe Cys Ala Thr Ala
            100                 105                 110

Ser Arg Gln Gly Gly Ser Glu Lys Leu Val Phe Gly Lys Gly Thr Lys
        115                 120                 125

Leu Thr Val Asn
    130

<210> SEQ ID NO 220
<211> LENGTH: 128
<212> TYPE: PRT
<213> ORGANISM: Homo sapiens

<400> SEQUENCE: 220

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
```

```
                35                  40                  45
Ser Asn Tyr Phe Pro Trp Tyr Lys Gln Glu Leu Gly Lys Gly Pro Gln
 50                  55                  60

Leu Ile Ile Asp Ile Arg Ser Asn Val Gly Glu Lys Lys Asp Gln Arg
 65                  70                  75                  80

Ile Ala Val Thr Leu Asn Lys Thr Ala Lys His Phe Ser Leu His Ile
                 85                  90                  95

Thr Glu Thr Gln Pro Glu Asp Ser Ala Val Tyr Phe Cys Ala Ala Ser
                100                 105                 110

Ser Asn Tyr Gln Leu Ile Trp Gly Ala Gly Thr Lys Leu Ile Ile Lys
                115                 120                 125

<210> SEQ ID NO 221
<211> LENGTH: 136
<212> TYPE: PRT
<213> ORGANISM: Homo sapiens

<400> SEQUENCE: 221

Met Asp Thr Trp Leu Val Cys Trp Ala Ile Phe Ser Leu Leu Lys Ala
 1               5                  10                  15

Gly Leu Thr Glu Pro Glu Val Thr Gln Thr Pro Ser His Gln Val Thr
                20                  25                  30

Gln Met Gly Gln Glu Val Ile Leu Arg Cys Val Pro Ile Ser Asn His
                35                  40                  45

Leu Tyr Phe Tyr Trp Tyr Arg Gln Ile Leu Gly Gln Lys Val Glu Phe
 50                  55                  60

Leu Val Ser Phe Tyr Asn Asn Glu Ile Ser Glu Lys Ser Glu Ile Phe
 65                  70                  75                  80

Asp Asp Gln Phe Ser Val Glu Arg Pro Asp Gly Ser Asn Phe Thr Leu
                 85                  90                  95

Lys Ile Arg Ser Thr Lys Leu Glu Asp Ser Ala Met Tyr Phe Cys Ala
                100                 105                 110

Ser Asn Pro Pro Asp Ala Ala Arg Gly Gln Glu Thr Gln Tyr Phe Gly
                115                 120                 125

Pro Gly Thr Arg Leu Leu Val Leu
                130                 135

<210> SEQ ID NO 222
<211> LENGTH: 132
<212> TYPE: PRT
<213> ORGANISM: Homo sapiens

<400> SEQUENCE: 222

Met Ser Ile Gly Leu Leu Cys Cys Val Ala Phe Ser Leu Leu Trp Ala
 1               5                  10                  15

Ser Pro Val Asn Ala Gly Val Thr Gln Thr Pro Lys Phe Gln Val Leu
                20                  25                  30

Lys Thr Gly Gln Ser Met Thr Leu Gln Cys Ala Gln Asp Met Asn His
                35                  40                  45

Asn Ser Met Tyr Trp Tyr Arg Gln Asp Pro Gly Met Gly Leu Arg Leu
 50                  55                  60

Ile Tyr Tyr Ser Ala Ser Glu Gly Thr Thr Asp Lys Gly Glu Val Pro
 65                  70                  75                  80

Asn Gly Tyr Asn Val Ser Arg Leu Asn Lys Arg Glu Phe Ser Leu Arg
                 85                  90                  95

Leu Glu Ser Ala Ala Pro Ser Gln Thr Ser Val Tyr Phe Cys Ala Ser
```

```
                100               105               110
Ser Tyr Arg Glu Tyr Asn Thr Glu Ala Phe Phe Gly Gln Gly Thr Arg
            115                 120                 125

Leu Thr Val Val
        130

<210> SEQ ID NO 223
<211> LENGTH: 131
<212> TYPE: PRT
<213> ORGANISM: Homo sapiens

<400> SEQUENCE: 223

Met Leu Leu Leu Leu Leu Leu Gly Pro Gly Ser Gly Leu Gly Ala
1               5                   10                  15

Val Val Ser Gln His Pro Ser Arg Val Ile Cys Lys Ser Gly Thr Ser
            20                  25                  30

Val Lys Ile Glu Cys Arg Ser Leu Asp Phe Gln Ala Thr Thr Met Phe
        35                  40                  45

Trp Tyr Arg Gln Phe Pro Lys Gln Ser Leu Met Leu Met Ala Thr Ser
    50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Thr Arg
            100                 105                 110

Gly His Leu Ser Asn Gln Pro Gln His Phe Gly Asp Gly Thr Arg Leu
        115                 120                 125

Ser Ile Leu
    130

<210> SEQ ID NO 224
<211> LENGTH: 133
<212> TYPE: PRT
<213> ORGANISM: Homo sapiens

<400> SEQUENCE: 224

Met Gly Thr Ser Leu Leu Cys Trp Val Val Leu Gly Phe Leu Gly Thr
1               5                   10                  15

Asp His Thr Gly Ala Gly Val Ser Gln Ser Pro Arg Tyr Lys Val Thr
            20                  25                  30

Lys Arg Gly Gln Asp Val Ala Leu Arg Cys Asp Pro Ile Ser Gly His
        35                  40                  45

Val Ser Leu Tyr Trp Tyr Arg Gln Ala Leu Gly Gln Gly Pro Glu Phe
    50                  55                  60

Leu Thr Tyr Phe Asn Tyr Glu Ala Gln Gln Asp Lys Ser Gly Leu Pro
65                  70                  75                  80

Asn Asp Arg Phe Ser Ala Glu Arg Pro Glu Gly Ser Ile Ser Thr Leu
                85                  90                  95

Thr Ile Gln Arg Thr Glu Gln Arg Asp Ser Ala Met Tyr Arg Cys Ala
            100                 105                 110

Ser Ser Arg Gly Gly Gly Thr Asp Thr Gln Tyr Phe Gly Pro Gly Thr
        115                 120                 125

Arg Leu Thr Val Leu
    130
```

```
<210> SEQ ID NO 225
<211> LENGTH: 131
<212> TYPE: PRT
<213> ORGANISM: Homo sapiens

<400> SEQUENCE: 225

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Leu Gly Leu Ala Tyr Glu Gln Tyr Phe Gly Pro Gly Thr Arg Leu
        115                 120                 125

Thr Val Thr
    130

<210> SEQ ID NO 226
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Tyr Glu Met Phe Asn Asp Lys Ser Phe Gln Arg Ala Pro Asp Asp Lys
1               5                   10                  15

Met Phe

<210> SEQ ID NO 227
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Selenocysteine
<220> FEATURE:
<221> NAME/KEY: MOD_RES
<222> LOCATION: (7)..(8)
<223> OTHER INFORMATION: Pyrrolysine

<400> SEQUENCE: 227

Phe Glu Gly Arg Lys Xaa Xaa Xaa Ile
1               5

<210> SEQ ID NO 228
<211> LENGTH: 14
<212> TYPE: PRT
<213> ORGANISM: Artificial Sequence
<220> FEATURE:
<223> OTHER INFORMATION: Description of Artificial Sequence: Synthetic
```

```
              peptide
<220> FEATURE:
<221> NAME/KEY: MOD_RES
<222> LOCATION: (2)..(2)
<223> OTHER INFORMATION: Ile or Leu
<220> FEATURE:
<221> NAME/KEY: MOD_RES
<222> LOCATION: (5)..(5)
<223> OTHER INFORMATION: Pyrrolysine
<220> FEATURE:
<221> NAME/KEY: MOD_RES
<222> LOCATION: (7)..(7)
<223> OTHER INFORMATION: Ile or Leu
<220> FEATURE:
<221> NAME/KEY: MOD_RES
<222> LOCATION: (8)..(8)
<223> OTHER INFORMATION: Pyrrolysine
<220> FEATURE:
<221> NAME/KEY: MOD_RES
<222> LOCATION: (10)..(10)
<223> OTHER INFORMATION: Ile or Leu
<220> FEATURE:
<221> NAME/KEY: MOD_RES
<222> LOCATION: (14)..(14)
<223> OTHER INFORMATION: Pyrrolysine

<400> SEQUENCE: 228

Pro Xaa Phe Ile Xaa Glu Xaa Xaa Ile Xaa Gly Glu Ile Xaa
1               5                   10

<210> SEQ ID NO 229
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
actgccatca ggtcggtata gtagc                                            25

<210> SEQ ID NO 230
<211> LENGTH: 2941
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (623)..(802)
<223> OTHER INFORMATION: a, c, t, g, unknown or other
<220> FEATURE:
<221> NAME/KEY: modified_base
<222> LOCATION: (1463)..(1687)
<223> OTHER INFORMATION: a, c, t, g, unknown or other

<400> SEQUENCE: 230
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa    120
actgggaaag tgatgtcgtg tactggctcc gccttttcc cgagggtggg ggagaaccgt     180
atataagtgc agtagtcgcc gtgaacgttc ttttcgcaa cgggtttgcc gccagaacac     240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
```

```
tctacgtctt tgtttcgttt tctgttctgc gccgttacag atccaagctg tgaccggcgc    540
ctactctaga gccgccacca tggccctgcc tgtgacagcc ctgctgctgc ctctggctct    600
gctgctgcat gccgctagac ccnnnnnnnn nnnnnnnnnn nnnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnnnnnn nngaggacct gaacaaggtg ttcccacccg aggtcgctgt    840
gtttgagcca tcagaagcag agatctccca cacccaaaag ccacactgg tgtgcctggc     900 cacaggcttc ttccccgacc acgtggagct gagctggtgg gtgaatggga aggaggtgca    960
cagtggggtc tgcacggacc cgcagcccct caaggagcag cccgccctca atgactccag   1020
atactgcctg agcagccgcc tgagggtctc ggccaccttc tggcagaacc cccgcaacca   1080
cttccgctgt caagtccagt tctacgggct ctcggagaat gacgagtgga cccaggatag   1140
ggccaaaccc gtcacccaga tcgtcagcgc cgaggcctgg ggtagagcag actgtggctt   1200
tacctcggtg tcctaccagc aagggtcct gtctgccacc atcctctatg agatcctgct    1260
agggaaggcc accctgtatg ctgtgctggt cagcgccctt gtgttgatgg ccatggtcaa   1320
gagaaaggat ttcggctccg gagccacgaa cttctctctg ttaaagcaag caggagacgt   1380
ggaagaaaac cccggtccca tggcattgcc tgtcacggca ctccttctcc cgctggccct   1440
gcttctccac gcggcgcgac ccnnnnnnnn nnnnnnnnnn nnnnnnnnnn nnnnnnnnnn   1500
nnnnnnnnnn nnnnnnnnnn nnnnnnnnnn nnnnnnnnnn nnnnnnnnnn nnnnnnnnnn   1560
nnnnnnnnnn nnnnnnnnnn nnnnnnnnnn nnnnnnnnnn nnnnnnnnnn nnnnnnnnnn   1620
nnnnnnnnnn nnnnnnnnnn nnnnnnnnnn nnnnnnnnnn nnnnnnnnnn nnnnnnnnnn   1680
nnnnnnncca aatatccaga accctgaccc tgccgtgtac cagctgagag actctaaatc   1740
cagtgacaag tctgtctgcc tattcaccga ttttgattct caaacaaatg tgtcacaaag   1800
taaggattct gatgtgtata tcacagacaa atgcgtgcta gacatgaggt ctatggactt   1860
caagagcaac agtgctgtgg cctggagcaa caaatctgac tttgcatgtg caaacgcctt   1920
caacaacagc attattccag aagacacctt cttccccagc ccagaaagtt cctgtgatgt   1980
caagctggtc gagaaaagct ttgaaacaga tacgaaccta aactttcaaa acctgtcagt   2040
gattgggttc cgaatcctcc tcctgaaagt ggccggggttt aatctgctca tgacgctgcg   2100
gctgtggtcc agcgcggccg ctgagggcag aggaagtctt ctaacatgcg gtgacgtgga   2160
ggagaatccc ggcccttccg gaatggagag cgacgagagc ggcctgcccg ccatggagat   2220
cgagtgccgc atcaccggca ccctgaacgg cgtggagttc gagctggtgg gcggcggaga   2280 gggcacccc aagcagggcc gcatgaccaa caagatgaag agcaccaaag cgcccctgac    2340
cttcagcccc tacctgctga gccacgtgat gggctacggc ttctaccact tcggcaccta   2400
ccccagcggc tacgagaacc ccttcctgca cgccatcaac acggcggct acaccaacac     2460 ccgcatcgag aagtacgagg acggcggcgt gctgcacgtg agcttcagct accgctacga   2520
ggccggccgc gtgatcggcg acttcaaggt ggtgggcacc ggcttccccg aggacagcgt   2580
gatcttcacc gacaagatca tccgcagcaa cgccaccgtg gagcacctgc acccatggg   2640 cgataacgtg ctggtgggca gcttcgcccg caccttcagc ctgcgcgacg gcggctacta   2700
cagcttcgtg gtggacagcc acatgcactt caagagcgcc atccacccca gcatcctgca   2760
gaacgggggc cccatgttcg ccttccgccg cgtggaggag ctgcacagca acaccgagct   2820
gggcatcgtg gagtaccagc acgccttcaa gacccccatc gccttcgcca gatcccgcgc   2880
```

| | |
|---|---:|
| tcagtcgtcc aattctgccg tggacggcac cgccggaccc ggctccaccg gatctcgcta | 2940 |
| g | 2941 |

<210> SEQ ID NO 231
<211> LENGTH: 3220
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 231

| | |
|---|---:|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gccttttttcc cgagggtggg ggagaaccgt | 180 |
| atataagtgc agtagtcgcc gtgaacgttc tttttcgcaa cgggtttgcc gccagaacac | 240 |
| agctgaagct tcgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg taccggcgc | 540 |
| ctactctaga gccgccacca tggccctgcc tgtgacagcc ctgctgctgc ctctggctct | 600 |
| gctgctgcat gccgctagac ccgaacctga agtcacccag actcccagcc atcaggtcac | 660 |
| acagatggga caggaagtga tcttgcgctg tgtccccatc tctaatcact tatacttcta | 720 |
| ttggtacaga caaatcttgg ggcagaaagt cgagtttctg gtttcctttt ataataatga | 780 |
| aatctcagag aagtctgaaa tattcgatga tcaattctca gttgaaaggc ctgatggatc | 840 |
| aaatttcact ctgaagatcc ggtccacaaa gctggaggac tcagccatgt acttctgtgc | 900 |
| cagcaacccc ccggacgctg cgagggggaca agagacccag tacttcgggc aggcacgcg | 960 |
| gctcctggtg ctcgaggacc tgaacaaggt gttcccaccc gaggtcgctg tgtttgagcc | 1020 |
| atcagaagca gagatctccc acacccaaaa ggccacactg gtgtgcctgg ccacaggctt | 1080 |
| cttcccccgac cacgtggagc tgagctggtg ggtgaatggg aaggaggtgc acagtggggt | 1140 |
| ctgcacggac ccgcagcccc tcaaggagca gcccgccctc aatgactcca gatactgcct | 1200 |
| gagcagccgc ctgagggtct cggccacctt ctggcagaac cccgcaacc acttccgctg | 1260 |
| tcaagtccag ttctacgggc tctcggagaa tgacgagtgg acccaggata gggccaaacc | 1320 |
| cgtcacccag atcgtcagcg ccgaggcctg gggtagagca gactgtggct ttacctcggt | 1380 |
| gtcctaccag caagggggtcc tgtctgccac catcctctat gagatcctgc tagggaaggc | 1440 |
| caccctgtat gctgtgctgg tcagcgccct tgtgttgatg gccatggtca agagaaagga | 1500 |
| tttcggctcc ggagccacga acttctctct gttaaagcaa gcaggagacg tggaagaaaa | 1560 |
| ccccggtccc atggcattgc ctgtcacggc actccttctc ccgctggccc tgcttctcca | 1620 |
| cgcggcgcga cccagtcgg tgacccagct tggcagccac gtctctgtct ctgagggagc | 1680 |
| cctggttctg ctgaggtgca actactcatc gtctgttcca ccatatctct tctggtatgt | 1740 |
| gcaataccc aaccaaggac tccagcttct cctgaagtac acaacagggg ccaccctggt | 1800 |
| taaaggcatc aacggttttg aggctgaatt taagaagagt gaaacctcct tccacctgac | 1860 |
| gaaaccctca gcccatatga gcgacgcggc tgagtacttc tgtgctgtga ccgtcacggg | 1920 |

| | |
|---|---|
| caggagagca cttacttttg ggagtggaac aagactccaa gtgcaaccaa atatccagaa | 1980 |
| ccctgaccct gccgtgtacc agctgagaga ctctaaatcc agtgacaagt ctgtctgcct | 2040 |
| attcaccgat tttgattctc aaacaaatgt gtcacaaagt aaggattctg atgtgtatat | 2100 |
| cacagacaaa tgcgtgctag acatgaggtc tatggacttc aagagcaaca gtgctgtggc | 2160 |
| ctggagcaac aaatctgact ttgcatgtgc aaacgccttc aacaacagca ttattccaga | 2220 |
| agacaccttc ttccccagcc cagaaagttc ctgtgatgtc aagctggtcg agaaaagctt | 2280 |
| tgaaacagat acgaacctaa actttcaaaa cctgtcagtg attgggttcc gaatcctcct | 2340 |
| cctgaaagtg gccgggttta atctgctcat gacgctgcgg ctgtggtcca gcgcggccgc | 2400 |
| tgagggcaga ggaagtcttc taacatgcgg tgacgtggag gagaatcccg gcccttccgg | 2460 |
| aatggagagc gacgagagcg gcctgcccgc catggagatc gagtgccgca tcaccggcac | 2520 |
| cctgaacggc gtggagttcg agctggtggg cggcggagag ggcaccccca gcagggccg | 2580 |
| catgaccaac aagatgaaga gcaccaaagg cgccctgacc ttcagcccct acctgctgag | 2640 |
| ccacgtgatg ggctacggct tctaccactt cggcacctac cccagcggct acgagaaccc | 2700 |
| cttcctgcac gccatcaaca acggcggcta caccaacacc cgcatcgaga gtacgagga | 2760 |
| cggcggcgtg ctgcacgtga gcttcagcta ccgctacgag gccggccgcg tgatcggcga | 2820 |
| cttcaaggtg gtgggcaccg gcttccccga ggacagcgtg atcttcaccg acaagatcat | 2880 |
| ccgcagcaac gccaccgtgg agcacctgca ccccatgggc gataacgtgc tggtgggcag | 2940 |
| cttcgcccgc accttcagcc tgcgcgacgg cggctactac agcttcgtgg tggacagcca | 3000 |
| catgcacttc aagagcgcca tccaccccag catcctgcag aacgggggcc ccatgttcgc | 3060 |
| cttccgccgc gtggaggagc tgcacagcaa caccgagctg ggcatcgtgg agtaccagca | 3120 |
| cgccttcaag accccatcg ccttcgccag atcccgcgct cagtcgtcca attctgccgt | 3180 |
| ggacggcacc gccggacccg gctccaccgg atctcgctag | 3220 |

<210> SEQ ID NO 232
<211> LENGTH: 3187
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 232

| | |
|---|---|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gccttttttcc cgagggtggg ggagaaccgt | 180 |
| atataagtgc agtagtcgcc gtgaacgttc tttttcgcaa cgggtttgcc gccagaacac | 240 |
| agctgaagct tcgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctactctaga gccgccacca tggccctgcc tgtgacagcc ctgctgctgc ctctggctct | 600 |
| gctgctgcat gccgctagac ccggtgtcac tcagacccca aaattccagg tcctgaagac | 660 |
| aggacagagc atgacactgc agtgtgccca ggatatgaac cataactcca tgtactggta | 720 |

```
tcgacaagac ccaggcatgg gactgaggct gatttattac tcagcttctg agggtaccac    780
tgacaaagga gaagtcccca atggctacaa tgtctccaga ttaaacaaac gggagttctc    840
gctcaggctg gagtcggctg ctccctccca gacatctgtg tacttctgtg ccagcagtta    900
ccgggagtac aacactgaag cttctttgg acaaggcacc agactcacag ttgtagagga    960
cctgaacaag gtgttcccac ccgaggtcgc tgtgtttgag ccatcagaag cagagatctc   1020
ccacacccaa aaggccacac tggtgtgcct ggccacaggc ttcttccccg accacgtgga   1080
gctgagctgg tgggtgaatg gaaggaggt gcacagtggg gtctgcacgg acccgcagcc   1140
cctcaaggag cagcccgccc tcaatgactc cagatactgc ctgagcagcc gcctgagggt   1200
ctcggccacc ttctggcaga accccgcaa ccacttccgc tgtcaagtcc agttctacgg   1260
gctctcggaa aatgacgagt ggaccccagga tagggccaaa cccgtcaccc agatcgtcag   1320
cgccgaggcc tggggtagag cagactgtgg ctttacctcg gtgtcctacc agcaagggt   1380
cctgtctgcc accatcctct atgagatcct gctaggaag gccacccgt atgctgtgct   1440
ggtcagcgcc cttgtgttga tggccatggt caagagaaag gatttcggct ccggagccac   1500
gaacttctct ctgttaaagc aagcaggaga cgtggaagaa accccgtc ccatggcatt   1560
gcctgtcacg gcactccttc tcccgctggc cctgcttctc cacgcggcgc gacccccaaa   1620
gatagaacag aattccgagg ccctgaacat tcaggagggt aaaacggcca ccctgacctg   1680
caactataca aactattctc cagcatactt acagtggtac cgacaagatc caggaagagg   1740
ccctgttttc ttgctactca tacgtgaaaa tgagaaagaa aaaggaaag aaagactgaa   1800
ggtcaccttt gataccaccc ttaaacagag tttgtttcat atcacagcct cccagcctgc   1860
agactcagct acctacctct gtgctctaaa tgccagactc atgtttggag atggaactca   1920
gctggtggtg aagccaaata tccagaaccc tgaccctgcc gtgtaccagc tgagagactc   1980
taaatccagt gacaagtctg tctgcctatt caccgatttt gattctcaaa caatgtgtc   2040
acaaagtaag gattctgatg tgtatatcac agacaaatgc gtgctagaca tgaggtctat   2100
ggacttcaag agcaacagtg ctgtggcctg gagcaacaaa tctgactttg catgtgcaaa   2160
cgccttcaac aacagcatta ttccagaaga caccttcttc cccagcccag aaagttcctg   2220
tgatgtcaag ctggtcgaga aaagctttga aacagatacg aacctaaact ttcaaaacct   2280
gtcagtgatt gggttccgaa tcctcctcct gaaagtggcc gggtttaatc tgctcatgac   2340
gctgcggctg tggtccagcg cggccgctga gggcagagga agtcttctaa catgcggtga   2400
cgtggaggag aatcccggcc cttccggaat ggagagcgac gagagcggcc tgcccgccat   2460
ggagatcgag tgccgcatca ccggcacccct gaacggcgtg gagttcgagc tggtgggcgg   2520
cggagagggc acccccaagc agggccgcat gaccaacaag atgaagagca ccaaggcgc   2580
cctgaccttc agcccctacc tgctgagcca cgtgatgggc tacggcttct accacttcgg   2640
cacctacccc agcggctacg agaaccccct cctgcacgcc atcaacaacg gcggctacac   2700
caacacccgc atcgagaagt acgaggacgg cggcgtgctg cacgtgagct tcagctaccg   2760
ctacgaggcc ggccgcgtga tcggcgactt caaggtggtg ggcaccggct tcccgagga   2820
cagcgtgatc ttcaccgaca agatcatccg cagcaacgcc accgtggagc acctgcaccc   2880
catgggcgat aacgtgctgg tgggcagctt cgcccgcacc ttcagcctgc gcgacggcgg   2940
ctactacagc ttcgtggtgg acagccacat gcacttcaag agcgccatcc accccagcat   3000
cctgcagaac gggggcccca tgttcgcctt ccgccgcgtg gaggagctgc acagcaacac   3060
```

-continued

```
cgagctgggc atcgtggagt accagcacgc cttcaagacc cccatcgcct tcgccagatc    3120
ccgcgctcag tcgtccaatt ctgccgtgga cggcaccgcc ggacccggct ccaccggatc    3180
tcgctag                                                              3187
```

NEOANTIGEN IDENTIFICATION USING HOTSPOTS

CROSS-REFERENCE TO RELATED APPLICATIONS

This application is the US Bypass Continuation Application of International Patent Application No. PCT/US18/55283, filed Oct. 18, 2018, which claims the benefit of and priority to U.S. Provisional Patent Application No. 62/570,569, filed on Oct. 10, 2017, the contents of which are incorporated by reference in their entirety.

SEQUENCE LISTING

The instant application contains a Sequence Listing which has been submitted electronically in ASCII format and is hereby incorporated by reference in its entirety. Said ASCII copy, created on Apr. 26, 2019, is named 32669-41078US_SL.txt and is 62,798 bytes in size.

BACKGROUND

Therapeutic vaccines and T-cell therapy based on tumor-specific neoantigens hold great promise as a next-generation of personalized cancer immunotherapy.[1-3] Cancers with a high mutational burden, such as non-small cell lung cancer (NSCLC) and melanoma, are particularly attractive targets of such therapy given the relatively greater likelihood of neoantigen generation.[4,5] Early evidence shows that neoantigen-based vaccination can elicit T-cell responses[6] and that neoantigen targeted T-cell therapy can cause tumor regression under certain circumstances in selected patients.[7] Both MHC class I and MHC class II have an impact on T-cell responses[70-71].

However identification of neoantigens and neoantigen-recognizing T-cells has become a central challenge in assessing tumor responses[77,110], examining tumor evolution[111] and designing the next generation of personalized therapies[112]. Current neoantigen identification techniques are either time-consuming and laborious[84,96], or insufficiently precise[87,91-93]. Although it has recently been demonstrated that neoantigen-recognizing T-cells are a major component of TIL[84,96,113,114] and circulate in the peripheral blood of cancer patients[107], current methods for identifying neoantigen-reactive T-cells have some combination of the following three limitations: (1) they rely on difficult-to-obtain clinical specimens such as TIL[97,98] or leukophereses[107] (2) they require screening impractically large libraries of peptides[95] or (3) they rely on MHC multimers, which may practically be available for only a small number of MHC alleles.

Furthermore, initial methods have been proposed incorporating mutation-based analysis using next-generation sequencing, RNA gene expression, and prediction of MHC binding affinity of candidate neoantigen peptides[8]. However, these proposed methods can fail to model the entirety of the epitope generation process, which contains many steps (e.g., TAP transport, proteasomal cleavage, MHC binding, transport of the peptide-MHC complex to the cell surface, and/or TCR recognition for MHC-I; endocytosis or autophagy, cleavage via extracellular or lysosomal proteases (e.g., cathepsins), competition with the CLIP peptide for HLA-DM-catalyzed HLA binding, transport of the peptide-MHC complex to the cell surface and/or TCR recognition for MHC-II) in addition to gene expression and MHC binding[9]. Consequently, existing methods are likely to suffer from reduced low positive predictive value (PPV). (FIG. 1A)

Indeed, analyses of peptides presented by tumor cells performed by multiple groups have shown that <5% of peptides that are predicted to be presented using gene expression and MHC binding affinity can be found on the tumor surface MHC[10,11] (FIG. 1B). This low correlation between binding prediction and MHC presentation was further reinforced by recent observations of the lack of predictive accuracy improvement of binding-restricted neoantigens for checkpoint inhibitor response over the number of mutations alone.[12]

This low positive predictive value (PPV) of existing methods for predicting presentation presents a problem for neoantigen-based vaccine design and for neoantigen-based T-cell therapy. If vaccines are designed using predictions with a low PPV, most patients are unlikely to receive a therapeutic neoantigen and fewer still are likely to receive more than one (even assuming all presented peptides are immunogenic). Similarly, if therapeutic T-cells are designed based on predictions with a low PPV, most patients are unlikely to receive T-cells that are reactive to tumor neoantigens and the time and physical resource cost of identifying predictive neoantigens using downstream laboratory techniques post-prediction may be unduly high. Thus, neoantigen vaccination and T-cell therapy with current methods is unlikely to succeed in a substantial number of subjects having tumors. (FIG. 1C)

Additionally, previous approaches generated candidate neoantigens using only cis-acting mutations, and largely neglected to consider additional sources of neo-ORFs, including mutations in splicing factors, which occur in multiple tumor types and lead to aberrant splicing of many genes[13], and mutations that create or remove protease cleavage sites.

Finally, standard approaches to tumor genome and transcriptome analysis can miss somatic mutations that give rise to candidate neoantigens due to suboptimal conditions in library construction, exome and transcriptome capture, sequencing, or data analysis. Likewise, standard tumor analysis approaches can inadvertently promote sequence artifacts or germline polymorphisms as neoantigens, leading to inefficient use of vaccine capacity or auto-immunity risk, respectively.

SUMMARY

Disclosed herein is an optimized approach for identifying and selecting neoantigens for personalized cancer vaccines, for T-cell therapy, or both. First, optimized tumor exome and transcriptome analysis approaches for neoantigen candidate identification using next-generation sequencing (NGS) are addressed. These methods build on standard approaches for NGS tumor analysis to ensure that the highest sensitivity and specificity neoantigen candidates are advanced, across all classes of genomic alteration. Second, novel approaches for high-PPV neoantigen selection are presented to overcome the specificity problem and ensure that neoantigens advanced for vaccine inclusion and/or as targets for T-cell therapy are more likely to elicit anti-tumor immunity. These approaches include, depending on the embodiment, trained statistical regression or nonlinear deep learning models that jointly model peptide-allele mappings as well as the per-allele motifs for peptides of multiple lengths, sharing statistical strength across peptides of different lengths. These deep learning models also utilize parameters describing the presence or absence of presentation hotspots in k-mer blocks associated with peptide sequences in determining presentation likelihood of the peptides. The nonlinear deep learning models particularly can be designed and trained to treat different MHC alleles in the same cell as independent, thereby addressing problems with linear models that would have them interfere with each other. Finally, additional considerations for personalized vaccine design and manufacturing based on neoantigens, and for production of personalized neoantigen-specific T-cells for T-cell therapy, are addressed.

The model disclosed herein outperforms state-of-the-art predictors trained on binding affinity and early predictors based on MS peptide data by up to an order of magnitude. By more reliably predicting presentation of peptides, the model enables more time- and cost-effective identification of neoantigen-specific or tumor antigen-specific T-cells for personlized therapy using a clinically practical process that uses limited volumes of patient peripheral blood, screens few peptides per patient, and does not necessarily rely on MHC multimers. However, in another embodiment, the model disclosed herein can be used to enable more time- and cost-effective identification of tumor antigen-specific T-cells using MHC multimers, by decreasing the number of peptides bound to MHC multimers that need to be screened in order to identify neoantigen- or tumor antigen-specific T-cells The predictive performance of the model disclosed herein on the TIL neoepitope dataset and the prospective neoantigen-reactive T-cell identification task demonstrate that it is now possible to obtain therapeutically-useful neoepitope predictions by modeling HLA processing and presentation. In summary, this work offers practical in silico antigen identification for antigen-targeted immunotherapy, thereby accelerating progress towards cures for patients.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 1F shows an example peptide spectrum generated from Promega's dynamic range standard. FIG. 1F discloses SEQ ID NO: 1.

FIGS. 2B and 2C illustrate a method of obtaining presentation information, in accordance with an embodiment. FIG. 2B discloses SEQ ID NO: 226. FIG. 2C discloses SEQ ID NOS 3-8, respectively, in order of appearance.

FIG. 4 illustrates an example set of training data, according to one embodiment. FIG. 4 discloses the "Peptide Sequences" as SEQ ID NOS 10-13 and the "C-Flanking Sequences" as SEQ ID NOS 15, 227, 228, and 228, respectively, in order of appearance.

FIG. 18B discloses SEQ ID NOS 27, 24, 21, 22, 163, 166, 74, 49, 68, 72, 21, 160, 164, 81, 161, 162, 165, 167, 168, and 169, respectively, in order of appearance.

FIG. 23 discloses SEQ ID NOS 229, 206, and 211, respectively, in order of appearance.

FIG. 25 discloses SEQ ID NO: 230.

FIG. 26 discloses SEQ ID NO: 231.

FIG. 27 discloses SEQ ID NO: 232.

DETAILED DESCRIPTION

I. Definitions

Figure 1A:
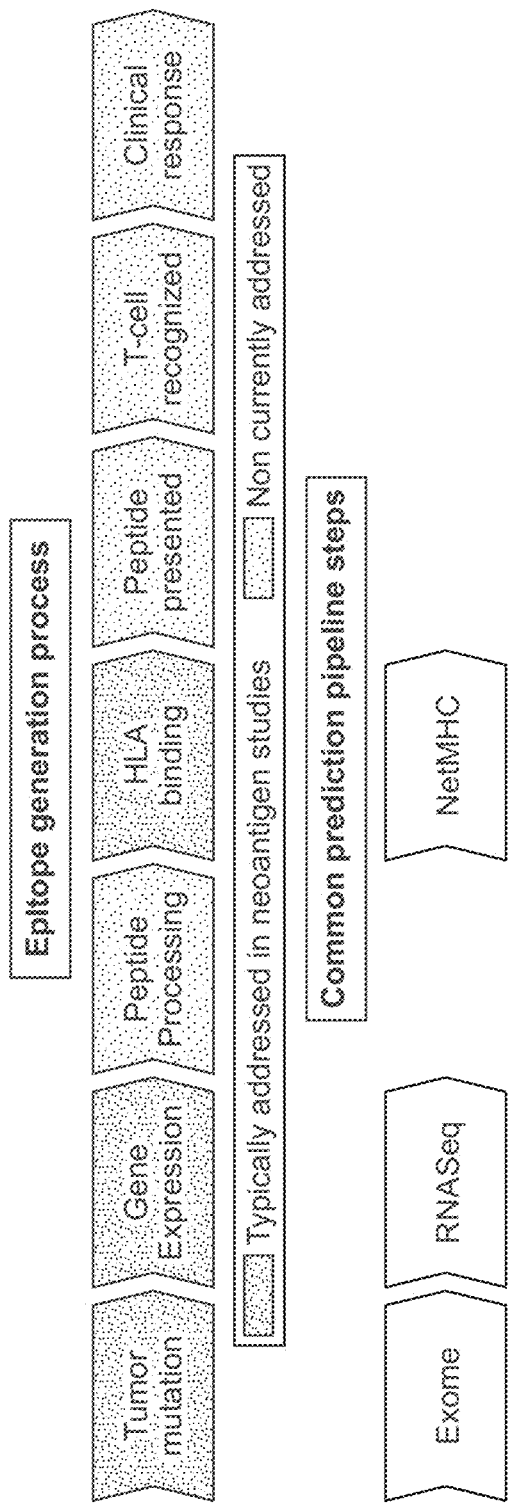
FIG. 1A shows current clinical approaches to neoantigen identification.
Figure 1B:
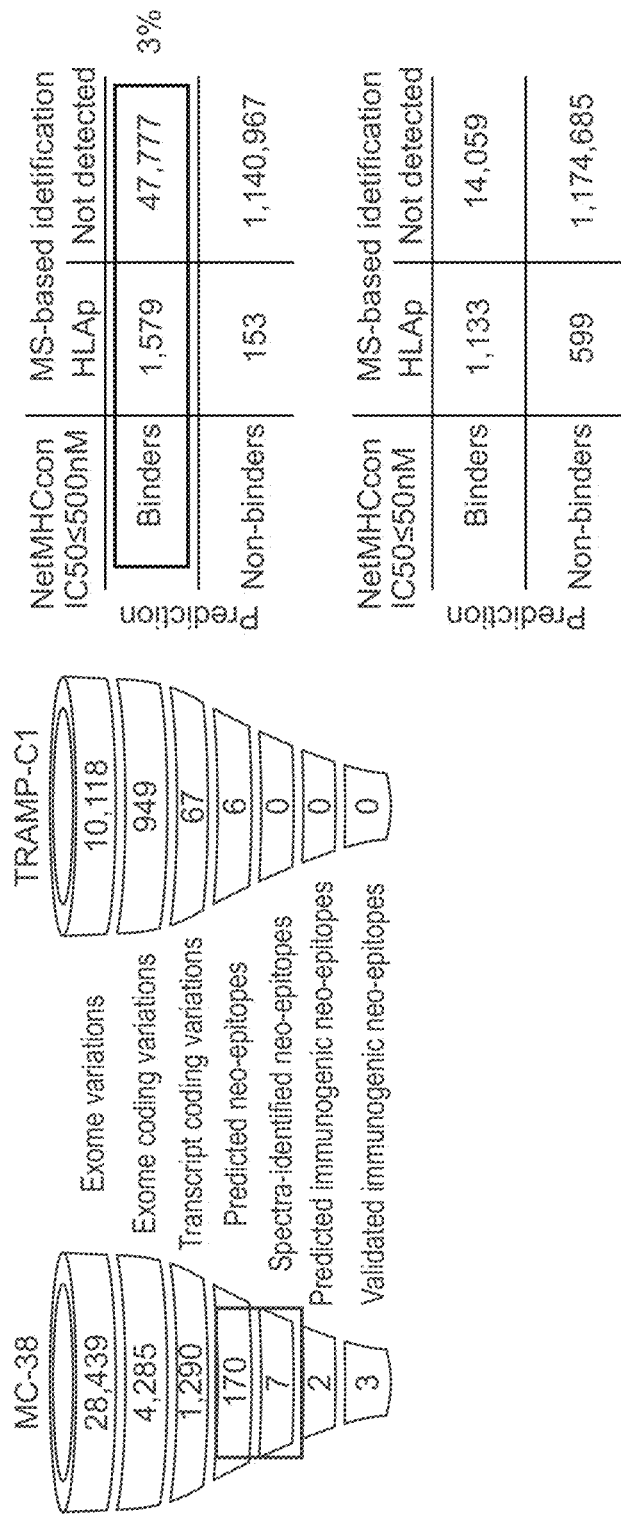
FIG. 1B shows that <5% of predicted bound peptides are presented on tumor cells.
Figure 1C:
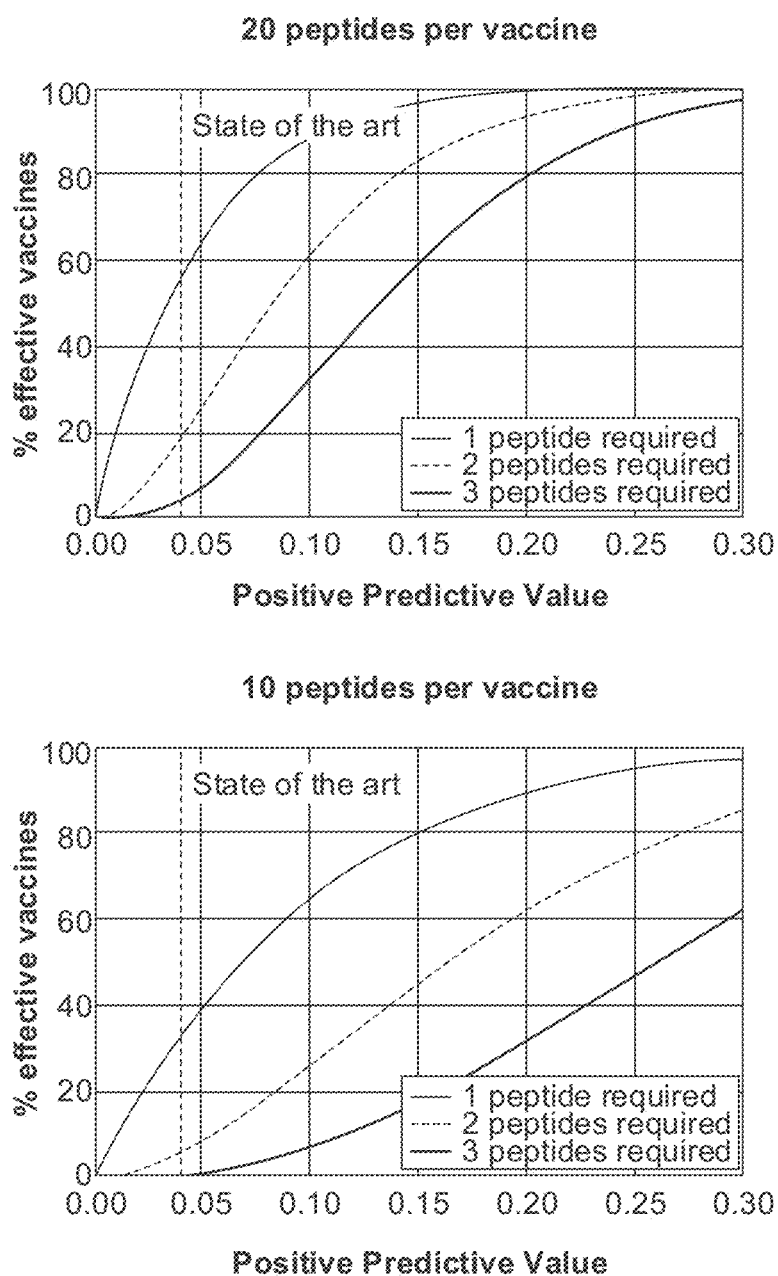
FIG. 1C shows the impact of the neoantigen prediction specificity problem.

In general, terms used in the claims and the specification are intended to be construed as having the plain meaning understood by a person of ordinary skill in the art. Certain terms are defined below to provide additional clarity. In case of conflict between the plain meaning and the provided definitions, the provided definitions are to be used.

As used herein the term "antigen" is a substance that induces an immune response.

As used herein the term "neoantigen" is an antigen that has at least one alteration that makes it distinct from the corresponding wild-type, parental antigen, e.g., via mutation in a tumor cell or post-translational modification specific to a tumor cell. A neoantigen can include a polypeptide sequence or a nucleotide sequence. A mutation can include a frameshift or nonframeshift indel, missense or nonsense substitution, splice site alteration, genomic rearrangement or gene fusion, or any genomic or expression alteration giving rise to a neoORF. A mutations can also include a splice variant. Post-translational modifications specific to a tumor cell can include aberrant phosphorylation. Post-translational modifications specific to a tumor cell can also include a proteasome-generated spliced antigen. See Liepe et al., A large fraction of HLA class I ligands are proteasome-generated spliced peptides; Science. 2016 Oct. 21; 354 (6310):354-358.

As used herein the term "tumor neoantigen" is a neoantigen present in a subject's tumor cell or tissue but not in the subject's corresponding normal cell or tissue.

As used herein the term "neoantigen-based vaccine" is a vaccine construct based on one or more neoantigens, e.g., a plurality of neoantigens.

As used herein the term "candidate neoantigen" is a mutation or other aberration giving rise to a new sequence that may represent a neoantigen.

As used herein the term "coding region" is the portion(s) of a gene that encode protein.

As used herein the term "coding mutation" is a mutation occurring in a coding region.

As used herein the term "ORF" means open reading frame.

As used herein the term "NEO-ORF" is a tumor-specific ORF arising from a mutation or other aberration such as splicing.

As used herein the term "missense mutation" is a mutation causing a substitution from one amino acid to another.

As used herein the term "nonsense mutation" is a mutation causing a substitution from an amino acid to a stop codon.

As used herein the term "frameshift mutation" is a mutation causing a change in the frame of the protein.

As used herein the term "indel" is an insertion or deletion of one or more nucleic acids.

As used herein, the term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Alternatively, sequence similarity or dissimilarity can be established by the combined presence or absence of particular nucleotides, or, for translated sequences, amino acids at selected sequence positions (e.g., sequence motifs).

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information.

As used herein the term "non-stop or read-through" is a mutation causing the removal of the natural stop codon.

As used herein the term "epitope" is the specific portion of an antigen typically bound by an antibody or T-cell receptor.

As used herein the term "immunogenic" is the ability to elicit an immune response, e.g., via T-cells, B cells, or both.

As used herein the term "HLA binding affinity" "MHC binding affinity" means affinity of binding between a specific antigen and a specific MHC allele.

As used herein the term "bait" is a nucleic acid probe used to enrich a specific sequence of DNA or RNA from a sample.

As used herein the term "variant" is a difference between a subject's nucleic acids and the reference human genome used as a control.

As used herein the term "variant call" is an algorithmic determination of the presence of a variant, typically from sequencing.

As used herein the term "polymorphism" is a germline variant, i.e., a variant found in all DNA-bearing cells of an individual.

As used herein the term "somatic variant" is a variant arising in non-germline cells of an individual.

As used herein the term "allele" is a version of a gene or a version of a genetic sequence or a version of a protein.

As used herein the term "HLA type" is the complement of HLA gene alleles.

As used herein the term "nonsense-mediated decay" or "NMD" is a degradation of an mRNA by a cell due to a premature stop codon.

As used herein the term "truncal mutation" is a mutation originating early in the development of a tumor and present in a substantial portion of the tumor's cells.

As used herein the term "subclonal mutation" is a mutation originating later in the development of a tumor and present in only a subset of the tumor's cells.

As used herein the term "exome" is a subset of the genome that codes for proteins. An exome can be the collective exons of a genome.

As used herein the term "logistic regression" is a regression model for binary data from statistics where the logit of the probability that the dependent variable is equal to one is modeled as a linear function of the dependent variables.

As used herein the term "neural network" is a machine learning model for classification or regression consisting of multiple layers of linear transformations followed by element-wise nonlinearities typically trained via stochastic gradient descent and back-propagation.

As used herein the term "proteome" is the set of all proteins expressed and/or translated by a cell, group of cells, or individual.

As used herein the term "peptidome" is the set of all peptides presented by MHC-I or MHC-II on the cell surface. The peptidome may refer to a property of a cell or a collection of cells (e.g., the tumor peptidome, meaning the union of the peptidomes of all cells that comprise the tumor).

As used herein the term "ELISPOT" means Enzyme-linked immunosorbent spot assay—which is a common method for monitoring immune responses in humans and animals.

As used herein the term "dextramers" is a dextran-based peptide-MHC multimers used for antigen-specific T-cell staining in flow cytometry.

As used herein the term "MHC multimers" is a peptide-MHC complex comprising multiple peptide-MHC monomer units.

As used herein the term "MHC tetramers" is a peptide-MHC complex comprising four peptide-MHC monomer units.

As used herein the term "tolerance or immune tolerance" is a state of immune non-responsiveness to one or more antigens, e.g. self-antigens.

As used herein the term "central tolerance" is a tolerance affected in the thymus, either by deleting self-reactive T-cell clones or by promoting self-reactive T-cell clones to differentiate into immunosuppressive regulatory T-cells (Tregs).

As used herein the term "peripheral tolerance" is a tolerance affected in the periphery by downregulating or anergizing self-reactive T-cells that survive central tolerance or promoting these T-cells to differentiate into Tregs.

The term "sample" can include a single cell or multiple cells or fragments of cells or an aliquot of body fluid, taken from a subject, by means including venipuncture, excretion, ejaculation, massage, biopsy, needle aspirate, lavage sample, scraping, surgical incision, or intervention or other means known in the art.

The term "subject" encompasses a cell, tissue, or organism, human or non-human, whether in vivo, ex vivo, or in vitro, male or female. The term subject is inclusive of mammals including humans.

The term "mammal" encompasses both humans and non-humans and includes but is not limited to humans, non-human primates, canines, felines, murines, bovines, equines, and porcines.

The term "clinical factor" refers to a measure of a condition of a subject, e.g., disease activity or severity. "Clinical factor" encompasses all markers of a subject's health status, including non-sample markers, and/or other characteristics of a subject, such as, without limitation, age and gender. A clinical factor can be a score, a value, or a set of values that can be obtained from evaluation of a sample (or population of samples) from a subject or a subject under a determined condition. A clinical factor can also be predicted by markers and/or other parameters such as gene expression surrogates. Clinical factors can include tumor type, tumor sub-type, and smoking history.

Abbreviations: MHC: major histocompatibility complex; HLA: human leukocyte antigen, or the human MHC gene locus; NGS: next-generation sequencing; PPV: positive predictive value; TSNA: tumor-specific neoantigen; FFPE: formalin-fixed, paraffin-embedded; NMD: nonsense-mediated decay; NSCLC: non-small-cell lung cancer; DC: dendritic cell.

It should be noted that, as used in the specification and the appended claims, the singular forms "a," "an," and "the" include plural referents unless the context clearly dictates otherwise.

Any terms not directly defined herein shall be understood to have the meanings commonly associated with them as understood within the art of the invention. Certain terms are discussed herein to provide additional guidance to the practitioner in describing the compositions, devices, methods and the like of aspects of the invention, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the invention herein.

All references, issued patents and patent applications cited within the body of the specification are hereby incorporated by reference in their entirety, for all purposes.

II. Methods of Identifying Neoantigens

Disclosed herein are methods for identifying neoantigens from tumor cells of a subject that are likely to be presented on a surface of the tumor cells. The method includes obtaining exome, transcriptome, and/or whole genome nucleotide sequencing data from the tumor cells as well as normal cells of the subject. This nucleotide sequencing data is used to obtain a peptide sequence of each neoantigen in a set of neoantigens. The set of neoantigens is identified by comparing the nucleotide sequencing data from the tumor cells and the nucleotide sequencing data from the normal cells. Specifically, the peptide sequence of each neoantigen in the set of neoantigens comprises at least one alteration that makes it distinct from the corresponding wild-type peptide sequence identified from the normal cells of the subject. The method further includes encoding the peptide sequence of each neoantigen in the set of neoantigens into a corresponding numerical vector. Each numerical vector includes information describing the amino acids that make up the peptide sequence and the positions of the amino acids in the peptide sequence. The method further comprises associating the peptide sequence of each of the neoantigens with one or more k-mer blocks of a plurality of k-mer blocks of the nucleotide sequencing data of the subject. The method further comprises inputting the numerical vectors and the associated k-mer blocks into a machine-learned presentation model to generate a presentation likelihood for each neoantigen in the set of neoantigens. Each presentation likelihood represents the likelihood that the corresponding neoantigen is presented by MHC alleles on the surface of the tumor cells of the subject. The machine-learned presentation model comprises a plurality of parameters and a function. The plurality of parameters are identified based on a training data set. The training data set comprises, for each sample in a plurality of samples, a label obtained by mass spectrometry measuring presence of peptides bound to at least one MHC allele in a set of MHC alleles identified as present in the sample, training peptide sequences encoded as numerical vectors that include information describing the amino acids that make up the peptides and the positions of the amino acids in the peptides, and, for each of the training peptide sequences of the sample, associations between the training peptide sequence and one or more k-mer blocks of a plurality of k-mer blocks of the nucleotide sequencing data of the training peptide sequences. The function represents a relation between the numerical vector and the associated k-mer blocks received as input by the machine-learned presentation model and the presentation likelihood generated as output by the machine-learned presentation model based on the numerical vector, the associated k-mer blocks, and the plurality of parameters. The method further includes selecting a subset of the set of neoantigens, based on the presentation likelihoods, to generate a set of selected neoantigens, and returning the set of selected neoantigens.

In some embodiments, inputting the numerical vector into the machine-learned presentation model comprises applying the machine-learned presentation model to the peptide sequence of the neoantigen to generate a dependency score for each of the MHC alleles. The dependency score for an MHC allele indicates whether the MHC allele will present the neoantigen, based on the particular amino acids at the particular positions of the peptide sequence. In further embodiments, inputting the numerical vector into the machine-learned presentation model further comprises transforming the dependency scores to generate a corresponding per-allele likelihood for each MHC allele indicating a likelihood that the corresponding WIC allele will present the corresponding neoantigen, and combining the per-allele likelihoods to generate the presentation likelihood of the neoantigen. In some embodiments, transforming the dependency scores models the presentation of the neoantigen as mutually exclusive across the MHC alleles. In alternative embodiments, inputting the numerical vector into the machine-learned presentation model further comprises transforming a combination of the dependency scores to generate the presentation likelihood. In such embodiments, transforming the combination of the dependency scores models the presentation of the neoantigen as interfering between the WIC alleles.

In some embodiments, the set of presentation likelihoods are further identified by one or more allele noninteracting features. In such embodiments, the method further comprises applying the machine-learned presentation model to the allele noninteracting features to generate a dependency score for the allele noninteracting features. The dependency score indicates whether the peptide sequence of the corresponding neoantigen will be presented based on the allele noninteracting features. In some embodiments, the one or more allele noninteracting features comprises the values indicating one of presence or absence of a presentation hotspot for each k-mer block of the peptide sequence of each neoantigen.

In some embodiments, the method further comprises combining the dependency score for each MHC allele with the dependency score for the allele noninteracting features, transforming the combined dependency score for each MHC allele to generate a per-allele likelihood for each MHC allele, and combining the per-allele likelihoods to generate the presentation likelihood. The per-allele likelihood for a MHC allele indicates a likelihood that the MHC allele will present the corresponding neoantigen. In alternative embodiments, the method further comprises combining the dependency scores for the WIC alleles and the dependency score for the allele noninteracting features, and transforming the combined dependency scores to generate the presentation likelihood.

In some embodiments, the WIC alleles include two or more different MHC alleles.

In some embodiments, the peptide sequences comprise peptide sequences having lengths other than 9 amino acids.

In some embodiments, encoding the peptide sequence comprises encoding the peptide sequence using a one-hot encoding scheme.

In some embodiments, the plurality of samples comprise at least one of cell lines engineered to express a single MHC allele, cell lines engineered to express a plurality of MHC alleles, human cell lines obtained or derived from a plurality of patients, fresh or frozen tumor samples obtained from a plurality of patients, and fresh or frozen tissue samples obtained from a plurality of patients.

In some embodiments, the training data set further comprises at least one of data associated with peptide-MHC binding affinity measurements for at least one of the peptides, and data associated with peptide-MHC binding stability measurements for at least one of the peptides.

In some embodiments, the set of presentation likelihoods are further identified by expression levels of the MHC alleles in the subject, as measured by RNA-seq or mass spectrometry.

In some embodiments, the set of presentation likelihoods are further identified by features comprising at least one of predicted affinity between a neoantigen in the set of neoantigens and the MHC alleles, and predicted stability of the neoantigen encoded peptide-MHC complex.

In some embodiments, the set of numerical likelihoods are further identified by features comprising at least one of the C-terminal sequences flanking the neoantigen encoded peptide sequence within its source protein sequence, and the N-terminal sequences flanking the neoantigen encoded peptide sequence within its source protein sequence.

In some embodiments, selecting the set of selected neoantigens comprises selecting neoantigens that have an increased likelihood of being presented on the tumor cell surface relative to unselected neoantigens, based on the machine-learned presentation model.

In some embodiments, selecting the set of selected neoantigens comprises selecting neoantigens that have an increased likelihood of being capable of inducing a tumor-specific immune response in the subject relative to unselected neoantigens, based on the machine-learned presentation model.

In some embodiments, selecting the set of selected neoantigens comprises selecting neoantigens that have an increased likelihood of being capable of being presented to naïve T-cells by professional antigen presenting cells (APCs) relative to unselected neoantigens, based on the presentation model. In such embodiments, the APC is optionally a dendritic cell (DC).

In some embodiments, selecting the set of selected neoantigens comprises selecting neoantigens that have a decreased likelihood of being subject to inhibition via central or peripheral tolerance relative to unselected neoantigens, based on the machine-learned presentation model.

In some embodiments, selecting the set of selected neoantigens comprises selecting neoantigens that have a decreased likelihood of being capable of inducing an autoimmune response to normal tissue in the subject relative to unselected neoantigens, based on the machine-learned presentation model.

In some embodiments, the one or more tumor cells are selected from the group consisting of: lung cancer, melanoma, breast cancer, ovarian cancer, prostate cancer, kidney cancer, gastric cancer, colon cancer, testicular cancer, head and neck cancer, pancreatic cancer, brain cancer, B-cell lymphoma, acute myelogenous leukemia, chronic myelogenous leukemia, chronic lymphocytic leukemia, and T-cell lymphocytic leukemia, non-small cell lung cancer, and small cell lung cancer.

In some embodiments, the method further comprises generating an output for constructing a personalized cancer vaccine from the set of selected neoantigens. In such embodiments, the output for the personalized cancer vaccine may comprise at least one peptide sequence or at least one nucleotide sequence encoding the set of selected neoantigens.

In some embodiments, the machine-learned presentation model is a neural network model. In such embodiments, the neural network model may include a plurality of network models for the MHC alleles, each network model assigned to a corresponding MHC allele of the MHC alleles and including a series of nodes arranged in one or more layers. In such embodiments, the neural network model may be trained by updating the parameters of the neural network model, the parameters of at least two network models being jointly updated for at least one training iteration. In some embodiments, the machine-learned presentation model may be a deep learning model that includes one or more layers of nodes.

In some embodiments, the MHC alleles are class I MHC alleles.

Also disclosed herein are computer systems comprising a computer processor and a memory storing computer program instructions. When the computer program instructions

III. Identification of Tumor Specific Mutations in Neoantigens

Also disclosed herein are methods for the identification of certain mutations (e.g., the variants or alleles that are present in cancer cells). In particular, these mutations can be present in the genome, transcriptome, proteome, or exome of cancer cells of a subject having cancer but not in normal tissue from the subject.

Genetic mutations in tumors can be considered useful for the immunological targeting of tumors if they lead to changes in the amino acid sequence of a protein exclusively in the tumor. Useful mutations include: (1) non-synonymous mutations leading to different amino acids in the protein; (2) read-through mutations in which a stop codon is modified or deleted, leading to translation of a longer protein with a novel tumor-specific sequence at the C-terminus; (3) splice site mutations that lead to the inclusion of an intron in the mature mRNA and thus a unique tumor-specific protein sequence; (4) chromosomal rearrangements that give rise to a chimeric protein with tumor-specific sequences at the junction of 2 proteins (i.e., gene fusion); (5) frameshift mutations or deletions that lead to a new open reading frame with a novel tumor-specific protein sequence. Mutations can also include one or more of nonframeshift indel, missense or nonsense substitution, splice site alteration, genomic rearrangement or gene fusion, or any genomic or expression alteration giving rise to a neoORF.

Peptides with mutations or mutated polypeptides arising from for example, splice-site, frameshift, readthrough, or gene fusion mutations in tumor cells can be identified by sequencing DNA, RNA or protein in tumor versus normal cells.

Also mutations can include previously identified tumor specific mutations. Known tumor mutations can be found at the Catalogue of Somatic Mutations in Cancer (COSMIC) database.

A variety of methods are available for detecting the presence of a particular mutation or allele in an individual's DNA or RNA. Advancements in this field have provided accurate, easy, and inexpensive large-scale SNP genotyping. For example, several techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods utilize amplification of a target genetic region, typically by PCR. Still other methods, based on the generation of small signal molecules by invasive cleavage followed by mass spectrometry or immobilized padlock probes and rolling-circle amplification. Several of the methods known in the art for detecting specific mutations are summarized below.

PCR based detection means can include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

Several methods have been developed to facilitate analysis of single nucleotide polymorphisms in genomic DNA or cellular RNA. For example, a single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide(s) present in the polymorphic site of the target molecule is complementary to that of the nucleotide derivative used in the reaction. This method has the advantage that it does not require the determination of large amounts of extraneous sequence data.

A solution-based method can be used for determining the identity of a nucleotide of a polymorphic site. Cohen, D. et al. (French Patent 2,650,840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer. An alternative method, known as Genetic Bit Analysis or GBA is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. can be a heterogeneous phase assay, in which the primer or the target molecule is immobilized to a solid phase.

Several primer-guided nucleotide incorporation procedures for assaying polymorphic sites in DNA have been described (Komher, J. S. et al., Nucl. Acids. Res. 17:7779-7784 (1989); Sokolov, B. P., Nucl. Acids Res. 18:3671 (1990); Syvanen, A.-C., et al., Genomics 8:684-692 (1990); Kuppuswamy, M. N. et al., Proc. Natl. Acad. Sci. (U.S.A.) 88:1143-1147 (1991); Prezant, T. R. et al., Hum. Mutat. 1:159-164 (1992); Ugozzoli, L. et al., GATA 9:107-112 (1992); Nyren, P. et al., Anal. Biochem. 208:171-175 (1993)). These methods differ from GBA in that they utilize incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al., Amer. J. Hum. Genet. 52:46-59 (1993)).

A number of initiatives obtain sequence information directly from millions of individual molecules of DNA or RNA in parallel. Real-time single molecule sequencing-by-synthesis technologies rely on the detection of fluorescent nucleotides as they are incorporated into a nascent strand of DNA that is complementary to the template being sequenced. In one method, oligonucleotides 30-50 bases in length are covalently anchored at the 5' end to glass cover slips. These anchored strands perform two functions. First, they act as capture sites for the target template strands if the templates are configured with capture tails complementary to the surface-bound oligonucleotides. They also act as primers for the template directed primer extension that forms the basis of the sequence reading. The capture primers function as a fixed position site for sequence determination using multiple cycles of synthesis, detection, and chemical cleavage of the dye-linker to remove the dye. Each cycle consists of adding the polymerase/labeled nucleotide mixture, rinsing, imaging and cleavage of dye. In an alternative method, polymerase is modified with a fluorescent donor molecule and immobilized on a glass slide, while each nucleotide is color-coded with an acceptor fluorescent moiety attached to a gamma-phosphate. The system detects the interaction between a fluorescently-tagged polymerase and a fluorescently modified nucleotide as the nucleotide becomes incorporated into the de novo chain. Other sequencing-by-synthesis technologies also exist.

Any suitable sequencing-by-synthesis platform can be used to identify mutations. As described above, four major sequencing-by-synthesis platforms are currently available: the Genome Sequencers from Roche/454 Life Sciences, the 1G Analyzer from Illumina/Solexa, the SOLiD system from Applied BioSystems, and the Heliscope system from Helicos Biosciences. Sequencing-by-synthesis platforms have also been described by Pacific BioSciences and VisiGen Biotechnologies. In some embodiments, a plurality of nucleic acid molecules being sequenced is bound to a support (e.g., solid support). To immobilize the nucleic acid on a support, a capture sequence/universal priming site can be added at the 3' and/or 5' end of the template. The nucleic acids can be bound to the support by hybridizing the capture sequence to a complementary sequence covalently attached to the support. The capture sequence (also referred to as a universal capture sequence) is a nucleic acid sequence complementary to a sequence attached to a support that may dually serve as a universal primer.

As an alternative to a capture sequence, a member of a coupling pair (such as, e.g., antibody/antigen, receptor/ligand, or the avidin-biotin pair as described in, e.g., US Patent Application No. 2006/0252077) can be linked to each fragment to be captured on a surface coated with a respective second member of that coupling pair.

Subsequent to the capture, the sequence can be analyzed, for example, by single molecule detection/sequencing, e.g., as described in the Examples and in U.S. Pat. No. 7,283,337, including template-dependent sequencing-by-synthesis. In sequencing-by-synthesis, the surface-bound molecule is exposed to a plurality of labeled nucleotide triphosphates in the presence of polymerase. The sequence of the template is determined by the order of labeled nucleotides incorporated into the 3' end of the growing chain. This can be done in real time or can be done in a step-and-repeat mode. For real-time analysis, different optical labels to each nucleotide can be incorporated and multiple lasers can be utilized for stimulation of incorporated nucleotides.

Sequencing can also include other massively parallel sequencing or next generation sequencing (NGS) techniques and platforms. Additional examples of massively parallel sequencing techniques and platforms are the Illumina HiSeq or MiSeq, Thermo PGM or Proton, the Pac Bio RS II or Sequel, Qiagen's Gene Reader, and the Oxford Nanopore MinION. Additional similar current massively parallel sequencing technologies can be used, as well as future generations of these technologies.

Any cell type or tissue can be utilized to obtain nucleic acid samples for use in methods described herein. For example, a DNA or RNA sample can be obtained from a tumor or a bodily fluid, e.g., blood, obtained by known techniques (e.g. venipuncture) or saliva. Alternatively, nucleic acid tests can be performed on dry samples (e.g. hair or skin). In addition, a sample can be obtained for sequencing from a tumor and another sample can be obtained from normal tissue for sequencing where the normal tissue is of the same tissue type as the tumor. A sample can be obtained for sequencing from a tumor and another sample can be obtained from normal tissue for sequencing where the normal tissue is of a distinct tissue type relative to the tumor.

Tumors can include one or more of lung cancer, melanoma, breast cancer, ovarian cancer, prostate cancer, kidney cancer, gastric cancer, colon cancer, testicular cancer, head and neck cancer, pancreatic cancer, brain cancer, B-cell lymphoma, acute myelogenous leukemia, chronic myelogenous leukemia, chronic lymphocytic leukemia, and T-cell lymphocytic leukemia, non-small cell lung cancer, and small cell lung cancer.

Alternatively, protein mass spectrometry can be used to identify or validate the presence of mutated peptides bound to MHC proteins on tumor cells. Peptides can be acid-eluted from tumor cells or from HLA molecules that are immunoprecipitated from tumor, and then identified using mass spectrometry.

IV. Neoantigens

Neoantigens can include nucleotides or polypeptides. For example, a neoantigen can be an RNA sequence that encodes for a polypeptide sequence. Neoantigens useful in vaccines can therefore include nucleotide sequences or polypeptide sequences.

Disclosed herein are isolated peptides that comprise tumor specific mutations identified by the methods disclosed herein, peptides that comprise known tumor specific mutations, and mutant polypeptides or fragments thereof identified by methods disclosed herein. Neoantigen peptides can be described in the context of their coding sequence where a neoantigen includes the nucleotide sequence (e.g., DNA or RNA) that codes for the related polypeptide sequence.

One or more polypeptides encoded by a neoantigen nucleotide sequence can comprise at least one of: a binding affinity with MHC with an IC50 value of less than 1000 nM, for MHC Class I peptides a length of 8-15, 8, 9, 10, 11, 12, 13, 14, or 15 amino acids, presence of sequence motifs within or near the peptide promoting proteasome cleavage, and presence or sequence motifs promoting TAP transport. For MHC Class II peptides a length 6-30, 6, 7, 8, 9, 10, 11, 12, 13, 14, 15, 16, 17, 18, 19, 20, 21, 22, 23, 24, 25, 26, 27, 28, 29, or 30 amino acids, presence of sequence motifs within or near the peptide promoting cleavage by extracellular or lysosomal proteases (e.g., cathepsins) or HLA-DM catalyzed HLA binding.

One or more neoantigens can be presented on the surface of a tumor.

One or more neoantigens can be is immunogenic in a subject having a tumor, e.g., capable of eliciting a T-cell response or a B cell response in the subject.

One or more neoantigens that induce an autoimmune response in a subject can be excluded from consideration in the context of vaccine generation for a subject having a tumor.

The size of at least one neoantigenic peptide molecule can comprise, but is not limited to, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 60, about 70, about 80, about 90, about 100, about 110, about 120 or greater amino molecule residues, and any range derivable therein. In specific embodiments the neoantigenic peptide molecules are equal to or less than 50 amino acids.

Neoantigenic peptides and polypeptides can be: for MHC Class I 15 residues or less in length and usually consist of between about 8 and about 11 residues, particularly 9 or 10 residues; for MHC Class II, 6-30 residues, inclusive.

If desirable, a longer peptide can be designed in several ways. In one case, when presentation likelihoods of peptides on HLA alleles are predicted or known, a longer peptide could consist of either: (1) individual presented peptides with an extensions of 2-5 amino acids toward the N- and C-terminus of each corresponding gene product; (2) a concatenation of some or all of the presented peptides with extended sequences for each. In another case, when sequencing reveals a long (>10 residues) neoepitope sequence present in the tumor (e.g. due to a frameshift, read-through or intron inclusion that leads to a novel peptide sequence), a longer peptide would consist of: (3) the entire stretch of novel tumor-specific amino acids—thus bypassing the need for computational or in vitro test-based selection of the strongest HLA-presented shorter peptide. In both cases, use of a longer peptide allows endogenous processing by patient-cells and may lead to more effective antigen presentation and induction of T-cell responses.

Neoantigenic peptides and polypeptides can be presented on an HLA protein. In some aspects neoantigenic peptides and polypeptides are presented on an HLA protein with greater affinity than a wild-type peptide. In some aspects, a neoantigenic peptide or polypeptide can have an IC50 of at least less than 5000 nM, at least less than 1000 nM, at least less than 500 nM, at least less than 250 nM, at least less than 200 nM, at least less than 150 nM, at least less than 100 nM, at least less than 50 nM or less.

In some aspects, neoantigenic peptides and polypeptides do not induce an autoimmune response and/or invoke immunological tolerance when administered to a subject.

Also provided are compositions comprising at least two or more neoantigenic peptides. In some embodiments the composition contains at least two distinct peptides. At least two distinct peptides can be derived from the same polypeptide. By distinct polypeptides is meant that the peptide vary by length, amino acid sequence, or both. The peptides are derived from any polypeptide known to or have been found to contain a tumor specific mutation. Suitable polypeptides from which the neoantigenic peptides can be derived can be found for example in the COSMIC database. COSMIC curates comprehensive information on somatic mutations in human cancer. The peptide contains the tumor specific mutation. In some aspects the tumor specific mutation is a driver mutation for a particular cancer type.

Neoantigenic peptides and polypeptides having a desired activity or property can be modified to provide certain desired attributes, e.g., improved pharmacological characteristics, while increasing or at least retaining substantially all of the biological activity of the unmodified peptide to bind the desired MHC molecule and activate the appropriate T-cell. For instance, neoantigenic peptide and polypeptides can be subject to various changes, such as substitutions, either conservative or non-conservative, where such changes might provide for certain advantages in their use, such as improved MHC binding, stability or presentation. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu, Met; Asp, Glu; Asn, Gln; Ser, Thr; Lys, Arg; and Phe, Tyr. The effect of single amino acid substitutions may also be probed using D-amino acids. Such modifications can be made using well known peptide synthesis procedures, as described in e.g., Merrifield, Science 232:341-347 (1986), Barany & Merrifield, The Peptides, Gross & Meienhofer, eds. (N.Y., Academic Press), pp. 1-284 (1979); and Stewart & Young, Solid Phase Peptide Synthesis, (Rockford, Ill., Pierce), 2d Ed. (1984).

Modifications of peptides and polypeptides with various amino acid mimetics or unnatural amino acids can be particularly useful in increasing the stability of the peptide and polypeptide in vivo. Stability can be assayed in a number of ways. For instance, peptidases and various biological media, such as human plasma and serum, have been used to test stability. See, e.g., Verhoef et al., Eur. J. Drug Metab Pharmacokin. 11:291-302 (1986). Half-life of the peptides can be conveniently determined using a 25% human serum (v/v) assay. The protocol is generally as follows. Pooled human serum (Type AB, non-heat inactivated) is delipidated by centrifugation before use. The serum is then diluted to 25% with RPMI tissue culture media and used to test peptide stability. At predetermined time intervals a small amount of reaction solution is removed and added to either 6% aqueous trichloracetic acid or ethanol. The cloudy reaction sample is cooled (4 degrees C.) for 15 minutes and then spun to pellet the precipitated serum proteins. The presence of the peptides is then determined by reversed-phase HPLC using stability-specific chromatography conditions.

The peptides and polypeptides can be modified to provide desired attributes other than improved serum half-life. For instance, the ability of the peptides to induce CTL activity can be enhanced by linkage to a sequence which contains at least one epitope that is capable of inducing a T helper cell response. Immunogenic peptides/T helper conjugates can be linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus can be a hetero- or homo-oligomer. When present, the spacer will usually be at least one or two residues, more usually three to six residues. Alternatively, the peptide can be linked to the T helper peptide without a spacer.

A neoantigenic peptide can be linked to the T helper peptide either directly or via a spacer either at the amino or carboxy terminus of the peptide. The amino terminus of either the neoantigenic peptide or the T helper peptide can be acylated. Exemplary T helper peptides include tetanus toxoid 830-843, influenza 307-319, malaria circumsporozoite 382-398 and 378-389.

Proteins or peptides can be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and can be found at computerized databases known to those of ordinary skill in the art. One such database is the National Center for Biotechnology Information's Genbank and GenPept databases located at the National Institutes of Health website. The coding regions for known genes can be amplified and/or expressed using the techniques disclosed herein or as would be known to those of ordinary skill in the art. Alternatively, various commercial preparations of proteins, polypeptides and peptides are known to those of skill in the art.

In a further aspect a neoantigen includes a nucleic acid (e.g. polynucleotide) that encodes a neoantigenic peptide or portion thereof. The polynucleotide can be, e.g., DNA, cDNA, PNA, CNA, RNA (e.g., mRNA), either single- and/or double-stranded, or native or stabilized forms of polynucleotides, such as, e.g., polynucleotides with a phosphorothiate backbone, or combinations thereof and it may or may not contain introns. A still further aspect provides an expression vector capable of expressing a polypeptide or portion thereof. Expression vectors for different-cell types are well known in the art and can be selected without undue experimentation. Generally, DNA is inserted into an expression vector, such as a plasmid, in proper orientation and correct reading frame for expression. If necessary, DNA can be linked to the appropriate transcriptional and translational regulatory control nucleotide sequences recognized by the desired host, although such controls are generally available in the expression vector. The vector is then introduced into the host through standard techniques. Guidance can be found e.g. in Sambrook et al. (1989) Molecular Cloning, A Laboratory Manual, Cold Spring Harbor Laboratory, Cold Spring Harbor, N.Y.

IV. Vaccine Compositions

Also disclosed herein is an immunogenic composition, e.g., a vaccine composition, capable of raising a specific immune response, e.g., a tumor-specific immune response. Vaccine compositions typically comprise a plurality of neoantigens, e.g., selected using a method described herein. Vaccine compositions can also be referred to as vaccines.

A vaccine can contain between 1 and 30 peptides, 2, 3, 4, 5, 6, 7, 8, 9, 10, 11, 12, 13, 14, 15, 16, 17, 18, 19, 20, 21, 22, 23, 24, 25, 26, 27, 28, 29, or 30 different peptides, 6, 7, 8, 9, 10 11, 12, 13, or 14 different peptides, or 12, 13 or 14 different peptides. Peptides can include post-translational modifications. A vaccine can contain between 1 and 100 or more nucleotide sequences, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more different nucleotide sequences, 6, 7, 8, 9, 10 11, 12, 13, or 14 different nucleotide sequences, or 12, 13 or 14 different nucleotide sequences. A vaccine can contain between 1 and 30 neoantigen sequences, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more different neoantigen sequences, 6, 7, 8, 9, 10 11, 12, 13, or 14 different neoantigen sequences, or 12, 13 or 14 different neoantigen sequences.

In one embodiment, different peptides and/or polypeptides or nucleotide sequences encoding them are selected so that the peptides and/or polypeptides capable of associating with different MHC molecules, such as different MHC class I molecules and/or different MHC class II molecules. In some aspects, one vaccine composition comprises coding sequence for peptides and/or polypeptides capable of associating with the most frequently occurring MHC class I molecules and/or MHC class II molecules. Hence, vaccine compositions can comprise different fragments capable of associating with at least 2 preferred, at least 3 preferred, or at least 4 preferred MHC class I molecules and/or MHC class II molecules.

The vaccine composition can be capable of raising a specific cytotoxic T-cells response and/or a specific helper T-cell response.

A vaccine composition can further comprise an adjuvant and/or a carrier. Examples of useful adjuvants and carriers are given herein below. A composition can be associated with a carrier such as e.g. a protein or an antigen-presenting cell such as e.g. a dendritic cell (DC) capable of presenting the peptide to a T-cell.

Adjuvants are any substance whose admixture into a vaccine composition increases or otherwise modifies the immune response to a neoantigen. Carriers can be scaffold structures, for example a polypeptide or a polysaccharide, to which a neoantigen, is capable of being associated. Optionally, adjuvants are conjugated covalently or non-covalently.

The ability of an adjuvant to increase an immune response to an antigen is typically manifested by a significant or substantial increase in an immune-mediated reaction, or reduction in disease symptoms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th response into a primarily cellular, or Th response.

Suitable adjuvants include, but are not limited to 1018 ISS, alum, aluminium salts, Amplivax, AS15, BCG, CP-870, 893, CpG7909, CyaA, dSLIM, GM-CSF, IC30, IC31, Imiquimod, ImuFact IMP321, IS Patch, ISS, ISCOMATRIX, JuvImmune, LipoVac, MF59, monophosphoryl lipid A, Montanide IMS 1312, Montanide ISA 206, Montanide ISA 50V, Montanide ISA-51, OK-432, OM-174, OM-197-NIP-EC, ONTAK, PepTel vector system, PLG microparticles, resiquimod, SRL172, Virosomes and other Virus-like particles, YF-17D, VEGF trap, R848, beta-glucan, Pam3Cys, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox. Quil or Superfos. Adjuvants such as incomplete Freund's or GM-CSF are useful. Several immunological adjuvants (e.g., MF59) specific for dendritic cells and their preparation have been described previously (Dupuis M, et al., Cell Immunol. 1998; 186(1):18-27; Allison A C; Dev Biol Stand. 1998; 92:3-11).

Also cytokines can be used. Several cytokines have been directly linked to influencing dendritic cell migration to lymphoid tissues (e.g., TNF-alpha), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12) (Gabrilovich D I, et al., J Immunother Emphasis Tumor Immunol. 1996 (6):414-418).

CpG immunostimulatory oligonucleotides have also been reported to enhance the effects of adjuvants in a vaccine setting. Other TLR binding molecules such as RNA binding TLR 7, TLR 8 and/or TLR 9 may also be used.

Other examples of useful adjuvants include, but are not limited to, chemically modified CpGs (e.g. CpR, Idera), Poly(I:C)(e.g. polyi:CI2U), non-CpG bacterial DNA or RNA as well as immunoactive small molecules and antibodies such as cyclophosphamide, sunitinib, bevacizumab, celebrex, NCX-4016, sildenafil, tadalafil, vardenafil, sorafinib, XL-999, CP-547632, pazopanib, ZD2171, AZD2171, ipilimumab, tremelimumab, and SC58175, which may act therapeutically and/or as an adjuvant. The amounts and concentrations of adjuvants and additives can readily be determined by the skilled artisan without undue experimentation. Additional adjuvants include colony-stimulating factors, such as Granulocyte Macrophage Colony Stimulating Factor (GM-CSF, sargramostim).

A vaccine composition can comprise more than one different adjuvant. Furthermore, a therapeutic composition can comprise any adjuvant substance including any of the above or combinations thereof. It is also contemplated that a vaccine and an adjuvant can be administered together or separately in any appropriate sequence.

A carrier (or excipient) can be present independently of an adjuvant. The function of a carrier can for example be to increase the molecular weight of in particular mutant to increase activity or immunogenicity, to confer stability, to increase the biological activity, or to increase serum half-life. Furthermore, a carrier can aid presenting peptides to T-cells. A carrier can be any suitable carrier known to the person skilled in the art, for example a protein or an antigen presenting cell. A carrier protein could be but is not limited to keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier is generally a physiologically acceptable carrier acceptable to humans and safe. However, tetanus toxoid and/or diptheria toxoid are suitable carriers. Alternatively, the carrier can be dextrans for example sepharose.

Cytotoxic T-cells (CTLs) recognize an antigen in the form of a peptide bound to an MHC molecule rather than the intact foreign antigen itself. The MHC molecule itself is located at the cell surface of an antigen presenting cell. Thus, an activation of CTLs is possible if a trimeric complex of peptide antigen, MHC molecule, and APC is present. Correspondingly, it may enhance the immune response if not only the peptide is used for activation of CTLs, but if additionally APCs with the respective MHC molecule are added. Therefore, in some embodiments a vaccine composition additionally contains at least one antigen presenting cell.

Neoantigens can also be included in viral vector-based vaccine platforms, such as vaccinia, fowlpox, self-replicating alphavirus, marabavirus, adenovirus (See, e.g., Tatsis et al., Adenoviruses, Molecular Therapy (2004) 10, 616-629), or lentivirus, including but not limited to second, third or hybrid second/third generation lentivirus and recombinant lentivirus of any generation designed to target specific cell types or receptors (See, e.g., Hu et al., Immunization Delivered by Lentiviral Vectors for Cancer and Infectious Diseases, Immunol Rev. (2011) 239(1): 45-61, Sakuma et al., Lentiviral vectors: basic to translational, Biochem J. (2012) 443(3):603-18, Cooper et al., Rescue of splicing-mediated intron loss maximizes expression in lentiviral vectors containing the human ubiquitin C promoter, Nucl. Acids Res. (2015) 43 (1): 682-690, Zufferey et al., Self-Inactivating Lentivirus Vector for Safe and Efficient In Vivo Gene Delivery, J. Virol. (1998) 72 (12): 9873-9880). Dependent on the packaging capacity of the above mentioned viral vector-based vaccine platforms, this approach can deliver one or more nucleotide sequences that encode one or more neoantigen peptides. The sequences may be flanked by non-mutated sequences, may be separated by linkers or may be preceded with one or more sequences targeting a subcellular compartment (See, e.g., Gros et al., Prospective identification of neoantigen-specific lymphocytes in the peripheral blood of melanoma patients, Nat Med. (2016) 22 (4):433-8, Stronen et al., Targeting of cancer neoantigens with donor-derived T-cell receptor repertoires, Science. (2016) 352 (6291):1337-41, Lu et al., Efficient identification of mutated cancer antigens recognized by T-cells associated with durable tumor regressions, Clin Cancer Res. (2014) 20(13):3401-10). Upon introduction into a host, infected cells express the neoantigens, and thereby elicit a host immune (e.g., CTL) response against the peptide(s). Vaccinia vectors and methods useful in immunization protocols are described in, e.g., U.S. Pat. No. 4,722,848. Another vector is BCG (Bacille Calmette Guerin). BCG vectors are described in Stover et al. (Nature 351:456-460 (1991)). A wide variety of other vaccine vectors useful for therapeutic administration or immunization of neoantigens, e.g., Salmonella typhi vectors, and the like will be apparent to those skilled in the art from the description herein.

IV.A. Additional Considerations for Vaccine Design and Manufacture Determination of a Set of Peptides that Cover all Tumor Subclones Truncal peptides, meaning those presented by all or most tumor subclones, will be prioritized for inclusion into the vaccine.[53] Optionally, if there are no truncal peptides predicted to be presented and immunogenic with high probability, or if the number of truncal peptides predicted to be presented and immunogenic with high probability is small enough that additional non-truncal peptides can be included in the vaccine, then further peptides can be prioritized by estimating the number and identity of tumor subclones and choosing peptides so as to maximize the number of tumor subclones covered by the vaccine.[54]

Neoantigen Prioritization

After all of the above neoantigen filters are applied, more candidate neoantigens may still be available for vaccine inclusion than the vaccine technology can support. Additionally, uncertainty about various aspects of the neoantigen analysis may remain and tradeoffs may exist between different properties of candidate vaccine neoantigens. Thus, in place of predetermined filters at each step of the selection process, an integrated multi-dimensional model can be considered that places candidate neoantigens in a space with at least the following axes and optimizes selection using an integrative approach.

1. Risk of auto-immunity or tolerance (risk of germline) (lower risk of auto-immunity is typically preferred)
2. Probability of sequencing artifact (lower probability of artifact is typically preferred)
3. Probability of immunogenicity (higher probability of immunogenicity is typically preferred)
4. Probability of presentation (higher probability of presentation is typically preferred)
5. Gene expression (higher expression is typically preferred)
6. Coverage of HLA genes (larger number of HLA molecules involved in the presentation of a set of neoantigens may lower the probability that a tumor will escape immune attack via downregulation or mutation of HLA molecules)
7. Coverage of HLA classes (covering both HLA-I and HLA-II may increase the probability of therapeutic response and decrease the probability of tumor escape)

V. Therapeutic and Manufacturing Methods

Also provided is a method of inducing a tumor specific immune response in a subject, vaccinating against a tumor, treating and or alleviating a symptom of cancer in a subject by administering to the subject one or more neoantigens such as a plurality of neoantigens identified using methods disclosed herein.

In some aspects, a subject has been diagnosed with cancer or is at risk of developing cancer. A subject can be a human, dog, cat, horse or any animal in which a tumor specific immune response is desired. A tumor can be any solid tumor such as breast, ovarian, prostate, lung, kidney, gastric, colon, testicular, head and neck, pancreas, brain, melanoma, and other tumors of tissue organs and hematological tumors, such as lymphomas and leukemias, including acute myelogenous leukemia, chronic myelogenous leukemia, chronic lymphocytic leukemia, T-cell lymphocytic leukemia, and B cell lymphomas.

A neoantigen can be administered in an amount sufficient to induce a CTL response.

A neoantigen can be administered alone or in combination with other therapeutic agents. The therapeutic agent is for example, a chemotherapeutic agent, radiation, or immunotherapy. Any suitable therapeutic treatment for a particular cancer can be administered.

In addition, a subject can be further administered an anti-immunosuppressive/immunostimulatory agent such as a checkpoint inhibitor. For example, the subject can be further administered an anti-CTLA antibody or anti-PD-1 or anti-PD-L1. Blockade of CTLA-4 or PD-L1 by antibodies can enhance the immune response to cancerous cells in the patient. In particular, CTLA-4 blockade has been shown effective when following a vaccination protocol.

The optimum amount of each neoantigen to be included in a vaccine composition and the optimum dosing regimen can be determined. For example, a neoantigen or its variant can be prepared for intravenous (i.v.) injection, sub-cutaneous (s.c.) injection, intradermal (i.d.) injection, intraperitoneal (i.p.) injection, intramuscular (i.m.) injection. Methods of injection include s.c., i.d., i.p., i.m., and i.v. Methods of DNA or RNA injection include i.d., i.m., s.c., i.p. and i.v. Other methods of administration of the vaccine composition are known to those skilled in the art.

A vaccine can be compiled so that the selection, number and/or amount of neoantigens present in the composition is/are tissue, cancer, and/or patient-specific. For instance, the exact selection of peptides can be guided by expression patterns of the parent proteins in a given tissue. The selection can be dependent on the specific type of cancer, the status of the disease, earlier treatment regimens, the immune status of the patient, and, of course, the HLA-haplotype of the patient. Furthermore, a vaccine can contain individualized components, according to personal needs of the particular patient. Examples include varying the selection of neoantigens according to the expression of the neoantigen in the particular patient or adjustments for secondary treatments following a first round or scheme of treatment.

For a composition to be used as a vaccine for cancer, neoantigens with similar normal self-peptides that are expressed in high amounts in normal tissues can be avoided or be present in low amounts in a composition described herein. On the other hand, if it is known that the tumor of a patient expresses high amounts of a certain neoantigen, the respective pharmaceutical composition for treatment of this cancer can be present in high amounts and/or more than one neoantigen specific for this particularly neoantigen or pathway of this neoantigen can be included.

Compositions comprising a neoantigen can be administered to an individual already suffering from cancer. In therapeutic applications, compositions are administered to a patient in an amount sufficient to elicit an effective CTL response to the tumor antigen and to cure or at least partially arrest symptoms and/or complications. An amount adequate to accomplish this is defined as "therapeutically effective dose." Amounts effective for this use will depend on, e.g., the composition, the manner of administration, the stage and severity of the disease being treated, the weight and general state of health of the patient, and the judgment of the prescribing physician. It should be kept in mind that compositions can generally be employed in serious disease states, that is, life-threatening or potentially life threatening situations, especially when the cancer has metastasized. In such cases, in view of the minimization of extraneous substances and the relative nontoxic nature of a neoantigen, it is possible and can be felt desirable by the treating physician to administer substantial excesses of these compositions.

For therapeutic use, administration can begin at the detection or surgical removal of tumors. This is followed by boosting doses until at least symptoms are substantially abated and for a period thereafter.

The pharmaceutical compositions (e.g., vaccine compositions) for therapeutic treatment are intended for parenteral, topical, nasal, oral or local administration. A pharmaceutical compositions can be administered parenterally, e.g., intravenously, subcutaneously, intradermally, or intramuscularly. The compositions can be administered at the site of surgical excision to induce a local immune response to the tumor. Disclosed herein are compositions for parenteral administration which comprise a solution of the neoantigen and vaccine compositions are dissolved or suspended in an acceptable carrier, e.g., an aqueous carrier. A variety of aqueous carriers can be used, e.g., water, buffered water, 0.9% saline, 0.3% glycine, hyaluronic acid and the like. These compositions can be sterilized by conventional, well known sterilization techniques, or can be sterile filtered. The resulting aqueous solutions can be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

Neoantigens can also be administered via liposomes, which target them to a particular cells tissue, such as lymphoid tissue. Liposomes are also useful in increasing half-life. Liposomes include emulsions, foams, micelles, insoluble monolayers, liquid crystals, phospholipid dispersions, lamellar layers and the like. In these preparations the neoantigen to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired neoantigen can be directed to the site of lymphoid cells, where the liposomes then deliver the selected therapeutic/immunogenic compositions. Liposomes can be formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., Ann. Rev. Biophys. Bioeng. 9; 467 (1980), U.S. Pat. Nos. 4,235,871, 4,501,728, 4,501,728, 4,837,028, and 5,019,369.

For targeting to the immune cells, a ligand to be incorporated into the liposome can include, e.g., antibodies or fragments thereof specific for cell surface determinants of the desired immune system cells. A liposome suspension can be administered intravenously, locally, topically, etc. in a dose which varies according to, inter alia, the manner of administration, the peptide being delivered, and the stage of the disease being treated.

For therapeutic or immunization purposes, nucleic acids encoding a peptide and optionally one or more of the peptides described herein can also be administered to the patient. A number of methods are conveniently used to deliver the nucleic acids to the patient. For instance, the nucleic acid can be delivered directly, as "naked DNA". This approach is described, for instance, in Wolff et al., Science 247: 1465-1468 (1990) as well as U.S. Pat. Nos. 5,580,859 and 5,589,466. The nucleic acids can also be administered using ballistic delivery as described, for instance, in U.S. Pat. No. 5,204,253. Particles comprised solely of DNA can be administered. Alternatively, DNA can be adhered to particles, such as gold particles. Approaches for delivering nucleic acid sequences can include viral vectors, mRNA vectors, and DNA vectors with or without electroporation.

The nucleic acids can also be delivered complexed to cationic compounds, such as cationic lipids. Lipid-mediated gene delivery methods are described, for instance, in 9618372WOAWO 96/18372; 9324640WOAWO 93/24640; Mannino & Gould-Fogerite, BioTechniques 6(7): 682-691 (1988); U.S. Pat. No. 5,279,833 Rose U.S. Pat. Nos. 5,279,833; 9,106,309WOAWO 91/06309; and Felgner et al., Proc. Natl. Acad. Sci. USA 84: 7413-7414 (1987).

Neoantigens can also be included in viral vector-based vaccine platforms, such as vaccinia, fowlpox, self-replicating alphavirus, marabavirus, adenovirus (See, e.g., Tatsis et al., Adenoviruses, *Molecular Therapy* (2004) 10, 616-629), or lentivirus, including but not limited to second, third or hybrid second/third generation lentivirus and recombinant lentivirus of any generation designed to target specific cell types or receptors (See, e.g., Hu et al., Immunization Delivered by Lentiviral Vectors for Cancer and Infectious Diseases, *Immunol Rev.* (2011) 239(1): 45-61, Sakuma et al., Lentiviral vectors: basic to translational, *Biochem J.* (2012) 443(3):603-18, Cooper et al., Rescue of splicing-mediated intron loss maximizes expression in lentiviral vectors containing the human ubiquitin C promoter, *Nucl. Acids Res.* (2015) 43 (1): 682-690, Zufferey et al., Self-Inactivating Lentivirus Vector for Safe and Efficient In Vivo Gene Delivery, *J. Virol.* (1998) 72 (12): 9873-9880). Dependent on the packaging capacity of the above mentioned viral vector-based vaccine platforms, this approach can deliver one or more nucleotide sequences that encode one or more neoantigen peptides. The sequences may be flanked by non-mutated sequences, may be separated by linkers or may be preceded with one or more sequences targeting a sub-cellular compartment (See, e.g., Gros et al., Prospective identification of neoantigen-specific lymphocytes in the peripheral blood of melanoma patients, *Nat Med.* (2016) 22 (4):433-8, Stronen et al., Targeting of cancer neoantigens with donor-derived T-cell receptor repertoires, *Science.* (2016) 352 (6291):1337-41, Lu et al., Efficient identification of mutated cancer antigens recognized by T-cells associated with durable tumor regressions, *Clin Cancer Res.* (2014) 20(13):3401-10). Upon introduction into a host, infected cells express the neoantigens, and thereby elicit a host immune (e.g., CTL) response against the peptide(s). Vaccinia vectors and methods useful in immunization protocols are described in, e.g., U.S. Pat. No. 4,722,848. Another vector is BCG (Bacille Calmette Guerin). BCG vectors are described in Stover et al. (Nature 351:456-460 (1991)). A wide variety of other vaccine vectors useful for therapeutic administration or immunization of neoantigens, e.g., *Salmonella typhi* vectors, and the like will be apparent to those skilled in the art from the description herein.

A means of administering nucleic acids uses minigene constructs encoding one or multiple epitopes. To create a DNA sequence encoding the selected CTL epitopes (minigene) for expression in human cells, the amino acid sequences of the epitopes are reverse translated. A human codon usage table is used to guide the codon choice for each amino acid. These epitope-encoding DNA sequences are directly adjoined, creating a continuous polypeptide sequence. To optimize expression and/or immunogenicity, additional elements can be incorporated into the minigene design. Examples of amino acid sequence that could be reverse translated and included in the minigene sequence include: helper T lymphocyte, epitopes, a leader (signal) sequence, and an endoplasmic reticulum retention signal. In addition, MHC presentation of CTL epitopes can be improved by including synthetic (e.g. poly-alanine) or naturally-occurring flanking sequences adjacent to the CTL epitopes. The minigene sequence is converted to DNA by assembling oligonucleotides that encode the plus and minus strands of the minigene. Overlapping oligonucleotides (30-100 bases long) are synthesized, phosphorylated, purified and annealed under appropriate conditions using well known techniques. The ends of the oligonucleotides are joined using T4 DNA ligase. This synthetic minigene, encoding the CTL epitope polypeptide, can then cloned into a desired expression vector.

Purified plasmid DNA can be prepared for injection using a variety of formulations. The simplest of these is reconstitution of lyophilized DNA in sterile phosphate-buffer saline (PBS). A variety of methods have been described, and new techniques can become available. As noted above, nucleic acids are conveniently formulated with cationic lipids. In addition, glycolipids, fusogenic liposomes, peptides and compounds referred to collectively as protective, interactive, non-condensing (PINC) could also be complexed to purified plasmid DNA to influence variables such as stability, intramuscular dispersion, or trafficking to specific organs or cell types.

Also disclosed is a method of manufacturing a tumor vaccine, comprising performing the steps of a method disclosed herein; and producing a tumor vaccine comprising a plurality of neoantigens or a subset of the plurality of neoantigens.

Neoantigens disclosed herein can be manufactured using methods known in the art. For example, a method of producing a neoantigen or a vector (e.g., a vector including at least one sequence encoding one or more neoantigens) disclosed herein can include culturing a host cell under conditions suitable for expressing the neoantigen or vector wherein the host cell comprises at least one polynucleotide encoding the neoantigen or vector, and purifying the neoantigen or vector. Standard purification methods include chromatographic techniques, electrophoretic, immunological, precipitation, dialysis, filtration, concentration, and chromatofocusing techniques.

Host cells can include a Chinese Hamster Ovary (CHO) cell, NS0 cell, yeast, or a HEK293 cell. Host cells can be transformed with one or more polynucleotides comprising at least one nucleic acid sequence that encodes a neoantigen or vector disclosed herein, optionally wherein the isolated polynucleotide further comprises a promoter sequence operably linked to the at least one nucleic acid sequence that encodes the neoantigen or vector. In certain embodiments the isolated polynucleotide can be cDNA.

VI. Neoantigen Identification

VI.A. Neoantigen Candidate Identification

Research methods for NGS analysis of tumor and normal exome and transcriptomes have been described and applied in the neoantigen identification space.[6,14,15] The example below considers certain optimizations for greater sensitivity and specificity for neoantigen identification in the clinical setting. These optimizations can be grouped into two areas, those related to laboratory processes and those related to the NGS data analysis.

VI.A.1. Laboratory Process Optimizations

The process improvements presented here address challenges in high-accuracy neoantigen discovery from clinical specimens with low tumor content and small volumes by extending concepts developed for reliable cancer driver gene assessment in targeted cancer panels[16] to the whole-exome and -transcriptome setting necessary for neoantigen identification. Specifically, these improvements include:
1. Targeting deep (>500x) unique average coverage across the tumor exome to detect mutations present at low mutant allele frequency due to either low tumor content or subclonal state.
2. Targeting uniform coverage across the tumor exome, with <5% of bases covered at <100x, so that the fewest possible neoantigens are missed, by, for instance:
   a. Employing DNA-based capture probes with individual probe QC[17]
   b. Including additional baits for poorly covered regions
3. Targeting uniform coverage across the normal exome, where <5% of bases are covered at <20x so that the fewest neoantigens possible remain unclassified for somatic/germline status (and thus not usable as TSNAs)
4. To minimize the total amount of sequencing required, sequence capture probes will be designed for coding regions of genes only, as non-coding RNA cannot give rise to neoantigens. Additional optimizations include:
   a. supplementary probes for HLA genes, which are GC-rich and poorly captured by standard exome sequencing[18]
   b. exclusion of genes predicted to generate few or no candidate neoantigens, due to factors such as insufficient expression, suboptimal digestion by the proteasome, or unusual sequence features.
5. Tumor RNA will likewise be sequenced at high depth (>100M reads) in order to enable variant detection, quantification of gene and splice-variant ("isoform") expression, and fusion detection. RNA from FFPE samples will be extracted using probe-based enrichment[19], with the same or similar probes used to capture exomes in DNA.

VI.A.2. NGS Data Analysis Optimizations

Improvements in analysis methods address the suboptimal sensitivity and specificity of common research mutation calling approaches, and specifically consider customizations relevant for neoantigen identification in the clinical setting. These include:
1. Using the HG38 reference human genome or a later version for alignment, as it contains multiple MHC regions assemblies better reflective of population polymorphism, in contrast to previous genome releases.
2. Overcoming the limitations of single variant callers[20] by merging results from different programs.[5]
   a. Single-nucleotide variants and indels will be detected from tumor DNA, tumor RNA and normal DNA with a suite of tools including: programs based on comparisons of tumor and normal DNA, such as Strelka[21] and Mutect[22]; and programs that incorporate tumor DNA, tumor RNA and normal DNA, such as UNCeqR, which is particularly advantageous in low-purity samples[23].
   b. Indels will be determined with programs that perform local re-assembly, such as Strelka and ABRA[24].
   c. Structural rearrangements will be determined using dedicated tools such as Pindel[25] or Breakseq[26].
3. In order to detect and prevent sample swaps, variant calls from samples for the same patient will be compared at a chosen number of polymorphic sites.
4. Extensive filtering of artefactual calls will be performed, for instance, by:
   a Removal of variants found in normal DNA, potentially with relaxed detection parameters in cases of low coverage, and with a permissive proximity criterion in case of indels
   b. Removal of variants due to low mapping quality or low base quality[27].
   c. Removal of variants stemming from recurrent sequencing artifacts, even if not observed in the corresponding normal[27]. Examples include variants primarily detected on one strand.
   d. Removal of variants detected in an unrelated set of controls[27]
5. Accurate HLA calling from normal exome using one of seq2HLA[28], ATHLATES[29] or Optitype and also combining exome and RNA sequencing data[28]. Additional potential optimizations include the adoption of a dedicated assay for HLA typing such as long-read DNA sequencing[30], or the adaptation of a method for joining RNA fragments to retain continuity[31].

6. Robust detection of neo-ORFs arising from tumor-specific splice variants will be performed by assembling transcripts from RNA-seq data using CLASS[32], Bayesembler[33], StringTie[34] or a similar program in its reference-guided mode (i.e., using known transcript structures rather than attempting to recreate transcripts in their entirety from each experiment). While Cufflinks[35] is commonly used for this purpose, it frequently produces implausibly large numbers of splice variants, many of them far shorter than the full-length gene, and can fail to recover simple positive controls. Coding sequences and nonsense-mediated decay potential will be determined with tools such as SpliceR[36] and MAMBA[37], with mutant sequences re-introduced. Gene expression will be determined with a tool such as Cufflinks[35] or Express (Roberts and Pachter, 2013). Wild-type and mutant-specific expression counts and/or relative levels will be determined with tools developed for these purposes, such as ASE[38] or HTSeq[39]. Potential filtering steps include:
   a Removal of candidate neo-ORFs deemed to be insufficiently expressed.
   b. Removal of candidate neo-ORFs predicted to trigger non-sense mediated decay (NMD).
7. Candidate neoantigens observed only in RNA (e.g., neoORFs) that cannot directly be verified as tumor-specific will be categorized as likely tumor-specific according to additional parameters, for instance by considering:
   a. Presence of supporting tumor DNA-only cis-acting frameshift or splice-site mutations
   b. Presence of corroborating tumor DNA-only trans-acting mutation in a splicing factor. For instance, in three independently published experiments with R625-mutant SF3B1, the genes exhibiting the most differentially splicing were concordant even though one experiment examined uveal melanoma patients[40], the second a uveal melanoma cell line[41], and the third breast cancer patients[42].
   c. For novel splicing isoforms, presence of corroborating "novel" splice junction reads in the RNASeq data.
   d. For novel re-arrangements, presence of corroborating juxta-exon reads in tumor DNA that are absent from normal DNA
   e. Absence from gene expression compendium such as GTEx[43] (i.e. making germline origin less likely)
8. Complementing the reference genome alignment-based analysis by comparing assembled DNA tumor and normal reads (or k-mers from such reads) directly to avoid alignment and annotation based errors and artifacts. (e.g. for somatic variants arising near germline variants or repeat-context indels)

In samples with poly-adenylated RNA, the presence of viral and microbial RNA in the RNA-seq data will be assessed using RNA CoMPASS[44] or a similar method, toward the identification of additional factors that may predict patient response.

VI.B. Isolation and Detection of HLA Peptides

Isolation of HLA-peptide molecules was performed using classic immunoprecipitation (IP) methods after lysis and solubilization of the tissue sample[55-58]. A clarified lysate was used for HLA specific IP.

Immunoprecipitation was performed using antibodies coupled to beads where the antibody is specific for HLA molecules. For a pan-Class I HLA immunoprecipitation, a pan-Class I CR antibody is used, for Class II HLA-DR, an HLA-DR antibody is used. Antibody is covalently attached to NHS-sepharose beads during overnight incubation. After covalent attachment, the beads were washed and aliquoted for IP.[59,60] Immunoprecipitations can also be performed with antibodies that are not covalently attached to beads. Typically this is done using sepharose or magnetic beads coated with Protein A and/or Protein G to hold the antibody to the column. Some antibodies that can be used to selectively enrich MHC/peptide complex are listed below.

| Antibody Name | Specificity |
|---|---|
| W6/32 | Class I HLA-A, B, C |
| L243 | Class II - HLA-DR |
| Tu36 | Class II - HLA-DR |
| LN3 | Class II - HLA-DR |
| Tu39 | Class II - HLA-DR, DP, DQ |

The clarified tissue lysate is added to the antibody beads for the immunoprecipitation. After immunoprecipitation, the beads are removed from the lysate and the lysate stored for additional experiments, including additional IPs. The IP beads are washed to remove non-specific binding and the HLA/peptide complex is eluted from the beads using standard techniques. The protein components are removed from the peptides using a molecular weight spin column or C18 fractionation. The resultant peptides are taken to dryness by SpeedVac evaporation and in some instances are stored at −20 C prior to MS analysis.

Dried peptides are reconstituted in an HPLC buffer suitable for reverse phase chromatography and loaded onto a C-18 microcapillary HPLC column for gradient elution in a Fusion Lumos mass spectrometer (Thermo). MS1 spectra of peptide mass/charge (m/z) were collected in the Orbitrap detector at high resolution followed by MS2 low resolution scans collected in the ion trap detector after HCD fragmentation of the selected ion. Additionally, MS2 spectra can be obtained using either CID or ETD fragmentation methods or any combination of the three techniques to attain greater amino acid coverage of the peptide. MS2 spectra can also be measured with high resolution mass accuracy in the Orbitrap detector.

MS2 spectra from each analysis are searched against a protein database using Comet[61,62] and the peptide identification are scored using Percolator[63-65]. Additional sequencing is performed using PEAKS studio (Bioinformatics Solutions Inc.) and other search engines or sequencing methods can be used including spectral matching and de novo sequencing[75].

VI.B.1. MS Limit of Detection Studies in Support of Comprehensive HLA Peptide Sequencing Using the peptide YVYVADVAAK (SEQ ID NO: 1) it was determined what the limits of detection are using different amounts of peptide loaded onto the LC column. The amounts of peptide tested were 1 pmol, 100 fmol, 10 fmol, 1 fmol, and 100 amol. (Table 1) The results are shown in FIG. 1F. These results indicate that the lowest limit of detection (LoD) is in the attomol range ($10^{-18}$), that the dynamic range spans five orders of magnitude, and that the signal to noise appears sufficient for sequencing at low femtomol ranges ($10^{-15}$).

| Peptide m/z | Loaded on Column | Copies/Cell in 1e9cells |
|---|---|---|
| 566.830 | 1 pmol | 600 |
| 562.823 | 100 fmol | 60 |
| 559.816 | 10 fmol | 6 |
| 556.810 | 1 fmol | 0.6 |
| 553.802 | 100 amol | 0.06 |

VII. Presentation Model

VII.A. System Overview

Figure 2A:
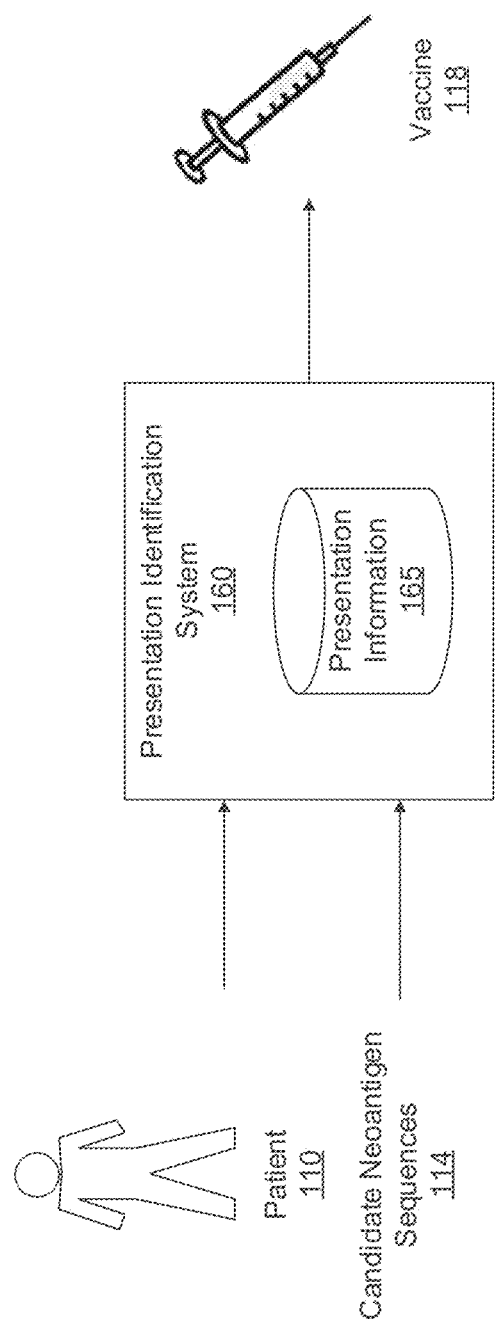
FIG. 2A is an overview of an environment for identifying likelihoods of peptide presentation in patients, in accordance with an embodiment.

FIG. 2A is an overview of an environment 100 for identifying likelihoods of peptide presentation in patients, in accordance with an embodiment. The environment 100 provides context in order to introduce a presentation identification system 160, itself including a presentation information store 165.

The presentation identification system 160 is one or computer models, embodied in a computing system as discussed below with respect to FIG. 29, that receives peptide sequences associated with a set of MHC alleles and determines likelihoods that the peptide sequences will be presented by one or more of the set of associated MHC alleles. The presentation identification system 160 may be applied to both class I and class II MHC alleles. This is useful in a variety of contexts. One specific use case for the presentation identification system 160 is that it is able to receive nucleotide sequences of candidate neoantigens associated with a set of MHC alleles from tumor cells of a patient 110 and determine likelihoods that the candidate neoantigens will be presented by one or more of the associated MHC alleles of the tumor and/or induce immunogenic responses in the immune system of the patient 110. Those candidate neoantigens with high likelihoods as determined by system 160 can be selected for inclusion in a vaccine 118, such an anti-tumor immune response can be elicited from the immune system of the patient 110 providing the tumor cells. Additionally, T-cells with TCRs that are responsive to candidate neoantigens with high presentation likelihoods can be produced for use in T-cell therapy, thereby also eliciting an anti-tumor immune response from the immune system of the patient 110.

The presentation identification system 160 determines presentation likelihoods through one or more presentation models. Specifically, the presentation models generate likelihoods of whether given peptide sequences will be presented for a set of associated MHC alleles, and are generated based on presentation information stored in store 165. For example, the presentation models may generate likelihoods of whether a peptide sequence "YVYVADVAAK" (SEQ ID NO: 1) will be presented for the set of alleles HLA-A*02:01, HLA-A*03:01, HLA-B*07:02, HLA-B*08:03, HLA-C*01:04 on the cell surface of the sample. The presentation information 165 contains information on whether peptides bind to different types of MHC alleles such that those peptides are presented by MHC alleles, which in the models is determined depending on positions of amino acids in the peptide sequences. The presentation model can predict whether an unrecognized peptide sequence will be presented in association with an associated set of MHC alleles based on the presentation information 165. As previously mentioned, the presentation models may be applied to both class I and class II MHC alleles.

VII.B. Presentation Information

FIG. 2 illustrates a method of obtaining presentation information, in accordance with an embodiment. The presentation information 165 includes two general categories of information: allele-interacting information and allele-noninteracting information. Allele-interacting information includes information that influence presentation of peptide sequences that are dependent on the type of MHC allele. Allele-noninteracting information includes information that influence presentation of peptide sequences that are independent on the type of MHC allele.

VII.B.1. Allele-Interacting Information

Allele-interacting information primarily includes identified peptide sequences that are known to have been presented by one or more identified MHC molecules from humans, mice, etc. Notably, this may or may not include data obtained from tumor samples. The presented peptide sequences may be identified from cells that express a single MHC allele. In this case the presented peptide sequences are generally collected from single-allele cell lines that are engineered to express a predetermined MHC allele and that are subsequently exposed to synthetic protein. Peptides presented on the MHC allele are isolated by techniques such as acid-elution and identified through mass spectrometry. FIG. 2B shows an example of this, where the example peptide YEMFNDKSQRAPDDKMF (SEQ ID NO: 2), presented on the predetermined MHC allele HLA-DRB1*12:01, is isolated and identified through mass spectrometry. Since in this situation peptides are identified through cells engineered to express a single predetermined MHC protein, the direct association between a presented peptide and the MHC protein to which it was bound to is definitively known.

The presented peptide sequences may also be collected from cells that express multiple MHC alleles. Typically in humans, 6 different types of MHC-I and up to 12 different types of MHC-II molecules are expressed for a cell. Such presented peptide sequences may be identified from multiple-allele cell lines that are engineered to express multiple predetermined MHC alleles. Such presented peptide sequences may also be identified from tissue samples, either from normal tissue samples or tumor tissue samples. In this case particularly, the MHC molecules can be immunoprecipitated from normal or tumor tissue. Peptides presented on the multiple MHC alleles can similarly be isolated by techniques such as acid-elution and identified through mass spectrometry. FIG. 2C shows an example of this, where the six example peptides, YEMFNDKSF (SEQ ID NO: 3), HROEIFSHDFJ (SEQ ID NO: 4), FJIEJFOESS (SEQ ID NO: 5), NEIOREIREI (SEQ ID NO: 6), JFKSIFEMMSJDSSUIFLKSJFIEIFJ (SEQ ID NO: 7), and KNFLENFIESOFI (SEQ ID NO: 8), are presented on identified class I MHC alleles HLA-A*01:01, HLA-A*02:01, HLA-B*07:02, HLA-B*08:01, and class II MHC alleles HLA-DRB1*10:01, HLA-DRB1:11:01 and are isolated and identified through mass spectrometry. In contrast to single-allele cell lines, the direct association between a presented peptide and the MHC protein to which it was bound to may be unknown since the bound peptides are isolated from the MHC molecules before being identified.

Allele-interacting information can also include mass spectrometry ion current which depends on both the concentration of peptide-MHC molecule complexes, and the ionization efficiency of peptides. The ionization efficiency varies from peptide to peptide in a sequence-dependent manner. Generally, ionization efficiency varies from peptide to peptide over approximately two orders of magnitude, while the concentration of peptide-MHC complexes varies over a larger range than that.

Figure 1D:
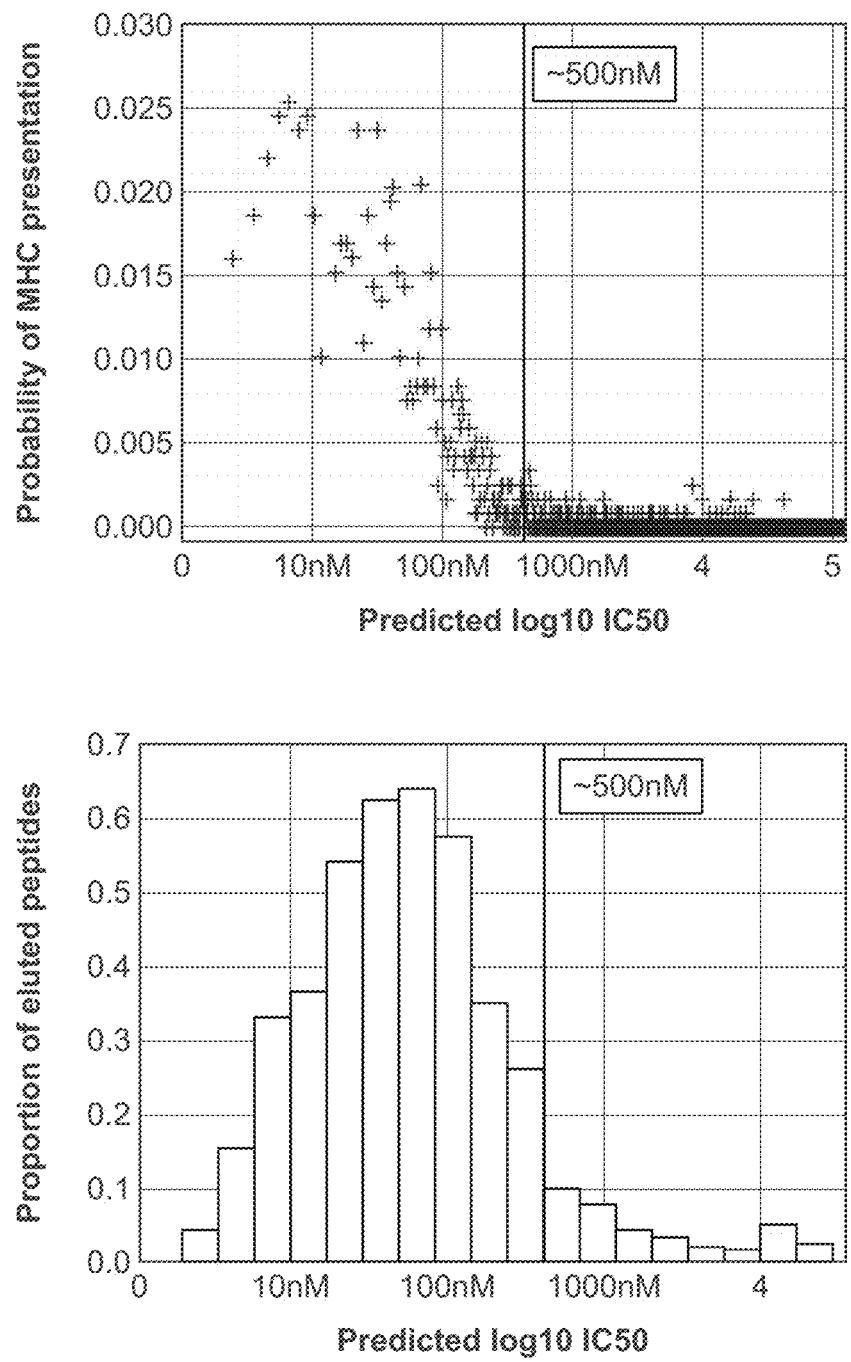
FIG. 1D shows that binding prediction is not sufficient for neoantigen identification.
Figure 1E:
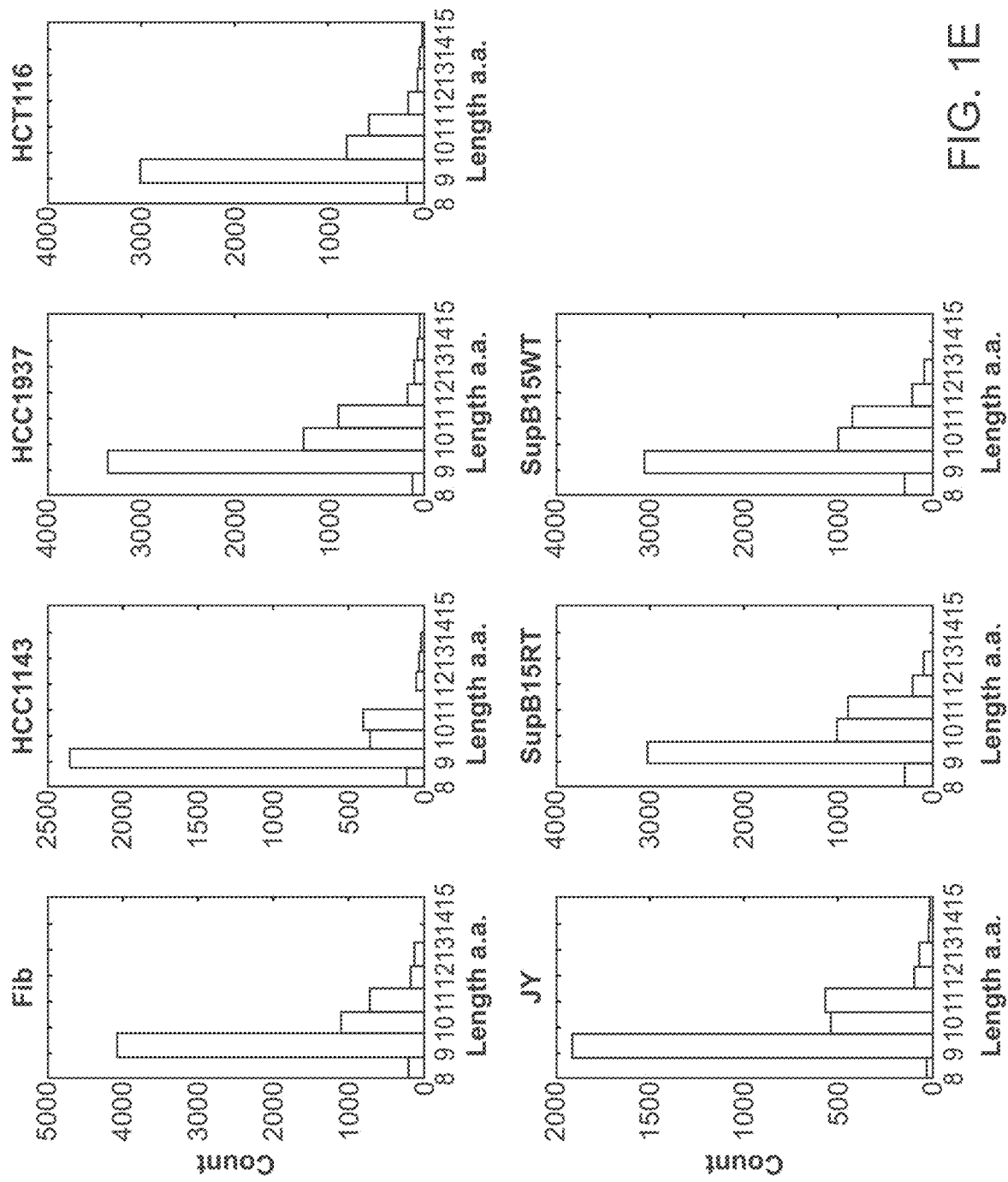
FIG. 1E shows probability of MHC-I presentation as a function of peptide length.
Figure 1G:
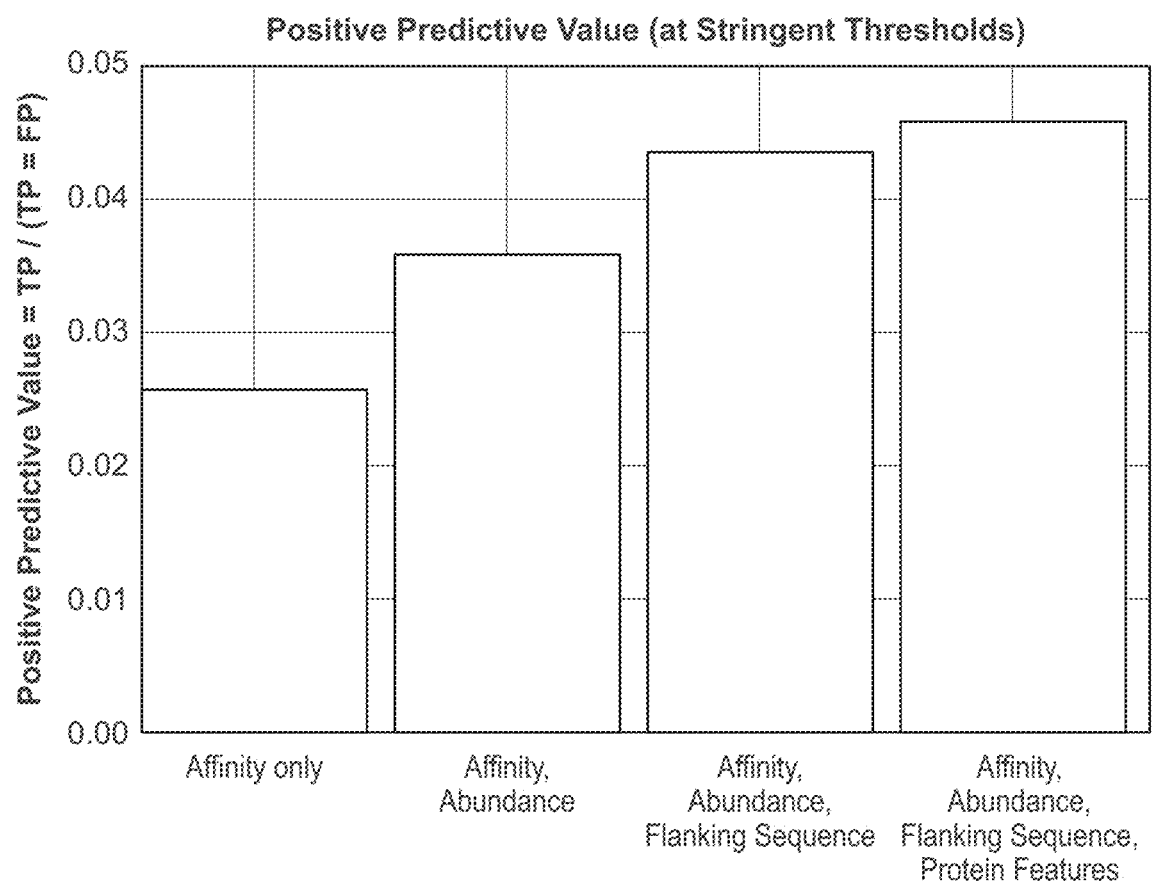
FIG. 1G shows how the addition of features increases the model positive predictive value.

Allele-interacting information can also include measurements or predictions of binding affinity between a given MHC allele and a given peptide. (72, 73, 74) One or more affinity models can generate such predictions. For example, going back to the example shown in FIG. 1D, presentation information 165 may include a binding affinity prediction of 1000 nM between the peptide YEMFNDKSF (SEQ ID NO: 3) and the class I allele HLA-A*01:01. Few peptides with IC50>1000 nm are presented by the MHC, and lower IC50 values increase the probability of presentation. Presentation information 165 may include a binding affinity prediction between the peptide KNFLENFIESOFI (SEQ ID NO: 8) and the class II allele HLA-DRB1:11:01.

Allele-interacting information can also include measurements or predictions of stability of the MHC complex. One or more stability models that can generate such predictions. More stable peptide-MHC complexes (i.e., complexes with longer half-lives) are more likely to be presented at high copy number on tumor cells and on antigen-presenting cells that encounter vaccine antigen. For example, going back to the example shown in FIG. 2C, presentation information 165 may include a stability prediction of a half-life of 1 h for the class I molecule HLA-A*01:01. Presentation information 165 may also include a stability prediction of a half-life for the class II molecule HLA-DRB1:11:01.

Allele-interacting information can also include the measured or predicted rate of the formation reaction for the peptide-MHC complex. Complexes that form at a higher rate are more likely to be presented on the cell surface at high concentration.

Allele-interacting information can also include the sequence and length of the peptide. MHC class I molecules typically prefer to present peptides with lengths between 8 and 15 peptides. 60-80% of presented peptides have length 9. MHC class II molecules typically prefer to present peptides with lengths between 6-30 peptides.

Allele-interacting information can also include the presence of kinase sequence motifs on the neoantigen encoded peptide, and the absence or presence of specific post-translational modifications on the neoantigen encoded peptide. The presence of kinase motifs affects the probability of post-translational modification, which may enhance or interfere with MHC binding.

Allele-interacting information can also include the expression or activity levels of proteins involved in the process of post-translational modification, e.g., kinases (as measured or predicted from RNA seq, mass spectrometry, or other methods).

Allele-interacting information can also include the probability of presentation of peptides with similar sequence in cells from other individuals expressing the particular MHC allele as assessed by mass-spectrometry proteomics or other means.

Allele-interacting information can also include the expression levels of the particular MHC allele in the individual in question (e.g. as measured by RNA-seq or mass spectrometry). Peptides that bind most strongly to an MHC allele that is expressed at high levels are more likely to be presented than peptides that bind most strongly to an MHC allele that is expressed at a low level.

Allele-interacting information can also include the overall neoantigen encoded peptide-sequence-independent probability of presentation by the particular MHC allele in other individuals who express the particular MHC allele.

Allele-interacting information can also include the overall peptide-sequence-independent probability of presentation by MHC alleles in the same family of molecules (e.g., HLA-A, HLA-B, HLA-C, HLA-DQ, HLA-DR, HLA-DP) in other individuals. For example, HLA-C molecules are typically expressed at lower levels than HLA-A or HLA-B molecules, and consequently, presentation of a peptide by HLA-C is a priori less probable than presentation by HLA-A or HLA-B. For another example, HLA-DP is typically expressed at lower levels than HLA-DR or HLA-DQ; consequently, presentation of a peptide by HLA-DP is a prior less probable than presentation by HLA-DR or HLA-DQ.

Allele-interacting information can also include the protein sequence of the particular MHC allele.

Any MHC allele-noninteracting information listed in the below section can also be modeled as an MHC allele-interacting information.

VII.B.2. Allele-Noninteracting Information

Allele-noninteracting information can include C-terminal sequences flanking the neoantigen encoded peptide within its source protein sequence. For MHC-I, C-terminal flanking sequences may impact proteasomal processing of peptides. However, the C-terminal flanking sequence is cleaved from the peptide by the proteasome before the peptide is transported to the endoplasmic reticulum and encounters MHC alleles on the surfaces of cells. Consequently, MHC molecules receive no information about the C-terminal flanking sequence, and thus, the effect of the C-terminal flanking sequence cannot vary depending on MHC allele type. For example, going back to the example shown in FIG. 2C, presentation information 165 may include the C-terminal flanking sequence FOEIFNDKSLDKFJI (SEQ ID NO: 9) of the presented peptide FJIEJFOESS (SEQ ID NO: 5) identified from the source protein of the peptide.

Allele-noninteracting information can also include mRNA quantification measurements. For example, mRNA quantification data can be obtained for the same samples that provide the mass spectrometry training data. As later described in reference to FIG. 13H, RNA expression was identified to be a strong predictor of peptide presentation. In one embodiment, the mRNA quantification measurements are identified from software tool RSEM. Detailed implementation of the RSEM software tool can be found at Bo Li and Colin N. Dewey. *RSEM: accurate transcript quantification from RNA-Seq data with or without a reference genome*. BMC Bioinformatics, 12:323, August 2011. In one embodiment, the mRNA quantification is measured in units of fragments per kilobase of transcript per Million mapped reads (FPKM).

Allele-noninteracting information can also include the N-terminal sequences flanking the peptide within its source protein sequence.

Allele-noninteracting information can also include the source gene of the peptide sequence. The source gene may be defined as the Ensembl protein family of the peptide sequence. In other examples, the source gene may be defined as the source DNA or the source RNA of the peptide sequence. The source gene can, for example, be represented as a string of nucleotides that encode for a protein, or alternatively be more categorically represented based on a named set of known DNA or RNA sequences that are known to encode specific proteins. In another example, allele-noninteracting information can also include the source transcript or isoform or set of potential source transcripts or isoforms of the peptide sequence drawn from a database such as Ensembl or RefSeq.

Allele-noninteracting information can also include the tissue type, cell type or tumor type of cells of origin of the peptide sequence.

Allele-noninteracting information can also include the presence of protease cleavage motifs in the peptide, optionally weighted according to the expression of corresponding proteases in the tumor cells (as measured by RNA-seq or mass spectrometry). Peptides that contain protease cleavage motifs are less likely to be presented, because they will be more readily degraded by proteases, and will therefore be less stable within the cell.

Allele-noninteracting information can also include the turnover rate of the source protein as measured in the appropriate cell type. Faster turnover rate (i.e., lower half-life) increases the probability of presentation; however, the predictive power of this feature is low if measured in a dissimilar cell type.

Allele-noninteracting information can also include the length of the source protein, optionally considering the specific splice variants ("isoforms") most highly expressed in the tumor cells as measured by RNA-seq or proteome mass spectrometry, or as predicted from the annotation of germline or somatic splicing mutations detected in DNA or RNA sequence data.

Allele-noninteracting information can also include the level of expression of the proteasome, immunoproteasome, thymoproteasome, or other proteases in the tumor cells (which may be measured by RNA-seq, proteome mass spectrometry, or immunohistochemistry). Different proteasomes have different cleavage site preferences. More weight will be given to the cleavage preferences of each type of proteasome in proportion to its expression level.

Allele-noninteracting information can also include the expression of the source gene of the peptide (e.g., as measured by RNA-seq or mass spectrometry). Possible optimizations include adjusting the measured expression to account for the presence of stromal cells and tumor-infiltrating lymphocytes within the tumor sample. Peptides from more highly expressed genes are more likely to be presented. Peptides from genes with undetectable levels of expression can be excluded from consideration.

Allele-noninteracting information can also include the probability that the source mRNA of the neoantigen encoded peptide will be subject to nonsense-mediated decay as predicted by a model of nonsense-mediated decay, for example, the model from Rivas et al, Science 2015.

Allele-noninteracting information can also include the typical tissue-specific expression of the source gene of the peptide during various stages of the cell cycle. Genes that are expressed at a low level overall (as measured by RNA-seq or mass spectrometry proteomics) but that are known to be expressed at a high level during specific stages of the cell cycle are likely to produce more presented peptides than genes that are stably expressed at very low levels.

Allele-noninteracting information can also include a comprehensive catalog of features of the source protein as given in e.g. uniProt or PDB http://www.rcsb.org/pdb/home/home.do. These features may include, among others: the secondary and tertiary structures of the protein, subcellular localization 11, Gene ontology (GO) terms. Specifically, this information may contain annotations that act at the level of the protein, e.g., 5' UTR length, and annotations that act at the level of specific residues, e.g., helix motif between residues 300 and 310. These features can also include turn motifs, sheet motifs, and disordered residues.

Allele-noninteracting information can also include features describing the properties of the domain of the source protein containing the peptide, for example: secondary or tertiary structure (e.g., alpha helix vs beta sheet); Alternative splicing.

Allele-noninteracting information can also include associations between a peptide sequence of the neoantigen and one or more k-mer blocks of a plurality of k-mer blocks of a source gene of the neoantigen (as present in the nucleotide sequencing data of the subject). During training of the presentation model, these associations between the peptide sequence of the neoantigen and the k-mer blocks of the nucleotide sequencing data of the neoantigen are input into the model, and are used in part by the model to learn model parameters that represent presence or absence of a presentation hotspot for the k-mer blocks associated with the training peptide sequences. Then, during use of the model subsequent to training, associations between a test peptide sequence and one or more k-mer blocks of a source gene of the test peptide sequence are input into the model, and the parameters learned by the model during training enable the presentation model to make more accurate predictions regarding the presentation likelihood of the test peptide sequence.

In general, the parameters of the model that represent presence or absence of a presentation hotspot for a k-mer block represent the residual propensity that the k-mer block will give rise to presented peptides, after controlling for all other variables (e.g., peptide sequence, RNA expression, amino acids commonly found in HLA-binding peptides, etc.). The parameters representing presence or absence of a presentation hotspot for a k-mer block may be a binary coefficient (e.g., 0 or 1), or an analog coefficient along a scale (e.g., between 0 and 1, inclusive). In either case, a greater coefficient (e.g., closer to 1 or 1) represents a greater likelihood that the k-mer block will give rise to presented peptides controlling for other factors, whereas lower coefficient (e.g., closer to 0 or 0) represents a lower likelihood that the k-mer block will give rise to presented peptides. For example, a k-mer block with a low hotspot coefficient might be a k-mer block from a gene with high RNA expression, with amino acids commonly found in HLA-binding peptides, where the source gene gives rise to lots of other presented peptides, but where presented peptides are rarely seen in the k-mer block. Since other sources of peptide presence may already be accounted for by other parameters (e.g., RNA expression on a k-mer block or larger basis, commonly found in HLA-binding peptides), these hotspot parameters provide new, separate information that does not "double count" information captured by other parameters.

Allele-noninteracting information can also include the probability of presentation of peptides from the source protein of the peptide in question in other individuals (after adjusting for the expression level of the source protein in those individuals and the influence of the different HLA types of those individuals).

Allele-noninteracting information can also include the probability that the peptide will not be detected or over-represented by mass spectrometry due to technical biases.

The expression of various gene modules/pathways as measured by a gene expression assay such as RNASeq, microarray(s), targeted panel(s) such as Nanostring, or single/multi-gene representatives of gene modules measured by assays such as RT-PCR (which need not contain the source protein of the peptide) that are informative about the state of the tumor cells, stroma, or tumor-infiltrating lymphocytes (TILs).

Allele-noninteracting information can also include the copy number of the source gene of the peptide in the tumor cells. For example, peptides from genes that are subject to homozygous deletion in tumor cells can be assigned a probability of presentation of zero.

Allele-noninteracting information can also include the probability that the peptide binds to the TAP or the measured or predicted binding affinity of the peptide to the TAP. Peptides that are more likely to bind to the TAP, or peptides that bind the TAP with higher affinity are more likely to be presented by MHC-I.

Allele-noninteracting information can also include the expression level of TAP in the tumor cells (which may be measured by RNA-seq, proteome mass spectrometry, immunohistochemistry). For MHC-I, higher TAP expression levels increase the probability of presentation of all peptides.

Allele-noninteracting information can also include the presence or absence of tumor mutations, including, but not limited to:
  i. Driver mutations in known cancer driver genes such as EGFR, KRAS, ALK, RET, ROS1, TP53, CDKN2A, CDKN2B, NTRK1, NTRK2, NTRK3
  ii. In genes encoding the proteins involved in the antigen presentation machinery (e.g., B2M, HLA-A, HLA-B, HLA-C, TAP-1, TAP-2, TAPBP, CALR, CNX, ERP57, HLA-DM, HLA-DMA, HLA-DMB, HLA-DO, HLA-DOA, HLA-DOBHLA-DP, HLA-DPA1, HLA-DPB1, HLA-DQ, HLA-DQA1, HLA-DQA2, HLA-DQB1, HLA-DQB2, HLA-DR, HLA-DRA, HLA-DRB1, HLA-DRB3, HLA-DRB4, HLA-DRB5 or any of the genes coding for components of the proteasome or immunoproteasome). Peptides whose presentation relies on a component of the antigen-presentation machinery that is subject to loss-of-function mutation in the tumor have reduced probability of presentation.

Presence or absence of functional germline polymorphisms, including, but not limited to:
  i. In genes encoding the proteins involved in the antigen presentation machinery (e.g., B2M, HLA-A, HLA-B, HLA-C, TAP-1, TAP-2, TAPBP, CALR, CNX, ERP57, HLA-DM, HLA-DMA, HLA-DMB, HLA-DO, HLA-DOA, HLA-DOBHLA-DP, HLA-DPA1, HLA-DPB1, HLA-DQ, HLA-DQA1, HLA-DQA2, HLA-DQB1, HLA-DQB2, HLA-DR, HLA-DRA, HLA-DRB1, HLA-DRB3, HLA-DRB4, HLA-DRB5 or any of the genes coding for components of the proteasome or immunoproteasome)

Allele-noninteracting information can also include tumor type (e.g., NSCLC, melanoma).

Allele-noninteracting information can also include known functionality of HLA alleles, as reflected by, for instance HLA allele suffixes. For example, the N suffix in the allele name HLA-A*24:09N indicates a null allele that is not expressed and is therefore unlikely to present epitopes; the full HLA allele suffix nomenclature is described at https://www.ebi.ac.uk/ipd/imgt/hla/nomenclature/suffixes.html.

Allele-noninteracting information can also include clinical tumor subtype (e.g., squamous lung cancer vs. non-squamous).

Allele-noninteracting information can also include smoking history.

Allele-noninteracting information can also include history of sunburn, sun exposure, or exposure to other mutagens.

Allele-noninteracting information can also include the typical expression of the source gene of the peptide in the relevant tumor type or clinical subtype, optionally stratified by driver mutation. Genes that are typically expressed at high levels in the relevant tumor type are more likely to be presented.

Allele-noninteracting information can also include the frequency of the mutation in all tumors, or in tumors of the same type, or in tumors from individuals with at least one shared MHC allele, or in tumors of the same type in individuals with at least one shared MHC allele.

In the case of a mutated tumor-specific peptide, the list of features used to predict a probability of presentation may also include the annotation of the mutation (e.g., missense, read-through, frameshift, fusion, etc.) or whether the mutation is predicted to result in nonsense-mediated decay (NMD). For example, peptides from protein segments that are not translated in tumor cells due to homozygous early-stop mutations can be assigned a probability of presentation of zero. NMD results in decreased mRNA translation, which decreases the probability of presentation.

VII.C. Presentation Identification System

Figure 3:
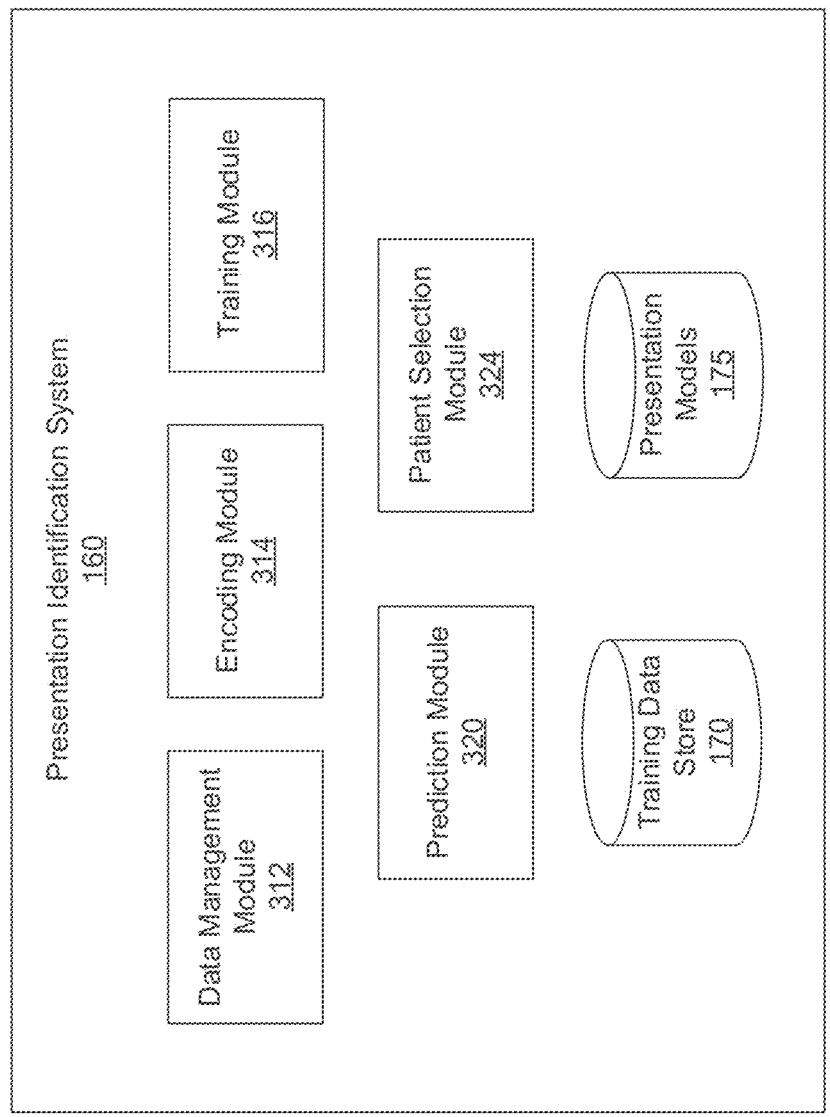
FIG. 3 is a high-level block diagram illustrating the computer logic components of the presentation identification system, according to one embodiment.

FIG. 3 is a high-level block diagram illustrating the computer logic components of the presentation identification system 160, according to one embodiment. In this example embodiment, the presentation identification system 160 includes a data management module 312, an encoding module 314, a training module 316, and a prediction module 320. The presentation identification system 160 is also comprised of a training data store 170 and a presentation models store 175. Some embodiments of the model management system 160 have different modules than those described here. Similarly, the functions can be distributed among the modules in a different manner than is described here.

VII.C.1. Data Management Module

The data management module 312 generates sets of training data 170 from the presentation information 165. Each set of training data contains a plurality of data instances, in which each data instance i contains a set of independent variables $z^i$ that include at least a presented or non-presented peptide sequence $p^i$, one or more associated MHC alleles $a^i$ associated with the peptide sequence $p^i$, and a dependent variable $y^i$ that represents information that the presentation identification system 160 is interested in predicting for new values of independent variables.

In one particular implementation referred throughout the remainder of the specification, the dependent variable $y^i$ is a binary label indicating whether peptide $p^i$ was presented by the one or more associated MHC alleles $a^i$. However, it is appreciated that in other implementations, the dependent variable $y^i$ can represent any other kind of information that the presentation identification system 160 is interested in predicting dependent on the independent variables $z^i$. For example, in another implementation, the dependent variable $y^i$ may also be a numerical value indicating the mass spectrometry ion current identified for the data instance.

The peptide sequence $p^i$ for data instance i is a sequence of k amino acids, in which k may vary between data instances i within a range. For example, that range may be 8-15 for MHC class I or 6-30 for MHC class II. In one specific implementation of system 160, all peptide sequences $p^i$ in a training data set may have the same length, e.g. 9. The number of amino acids in a peptide sequence may vary depending on the type of MHC alleles (e.g., MHC alleles in humans, etc.). The MHC alleles $a^i$ for data instance i indicate which MHC alleles were present in association with the corresponding peptide sequence $p^i$.

The data management module 312 may also include additional allele-interacting variables, such as binding affinity $b^i$ and stability $s^i$ predictions in conjunction with the peptide sequences $p^i$ and associated MHC alleles $a^i$ contained in the training data 170. For example, the training data 170 may contain binding affinity predictions $b^i$ between a peptide $p^i$ and each of the associated MHC molecules indicated in $a^i$. As another example, the training data 170 may contain stability predictions $s^i$ for each of the MHC alleles indicated in $a^i$.

The data management module 312 may also include allele-noninteracting variables $w^i$, such as C-terminal flanking sequences and mRNA quantification measurements in conjunction with the peptide sequences $p^i$.

The data management module 312 also identifies peptide sequences that are not presented by MHC alleles to generate the training data 170. Generally, this involves identifying the "longer" sequences of source protein that include presented peptide sequences prior to presentation. When the presentation information contains engineered cell lines, the data management module 312 identifies a series of peptide sequences in the synthetic protein to which the cells were exposed to that were not presented on MHC alleles of the cells. When the presentation information contains tissue samples, the data management module 312 identifies source proteins from which presented peptide sequences originated from, and identifies a series of peptide sequences in the source protein that were not presented on MHC alleles of the tissue sample cells.

The data management module 312 may also artificially generate peptides with random sequences of amino acids and identify the generated sequences as peptides not presented on MHC alleles. This can be accomplished by randomly generating peptide sequences allows the data management module 312 to easily generate large amounts of synthetic data for peptides not presented on MHC alleles. Since in reality, a small percentage of peptide sequences are presented by MHC alleles, the synthetically generated peptide sequences are highly likely not to have been presented by MHC alleles even if they were included in proteins processed by cells.

FIG. 4 illustrates an example set of training data 170A, according to one embodiment. Specifically, the first 3 data instances in the training data 170A indicate peptide presentation information from a single-allele cell line involving the allele HLA-C*01:03 and 3 peptide sequences QCEIO-WAREFLKEIGJ (SEQ ID NO: 10), FIEUHFWI (SEQ ID NO: 11), and FEWRHRJTRUJR (SEQ ID NO: 12). The fourth data instance in the training data 170A indicates peptide information from a multiple-allele cell line involving the alleles HLA-B*07:02, HLA-C*01:03, HLA-A*01:01 and a peptide sequence QIEJOEIJE (SEQ ID NO: 13). The first data instance indicates that peptide sequence QCEIOWARE (SEQ ID NO: 14) was not presented by the allele HLA-DRB3:01:01. As discussed in the prior two paragraphs, the negatively-labeled peptide sequences may be randomly generated by the data management module 312 or identified from source protein of presented peptides. The training data 170A also includes a binding affinity prediction of 1000 nM and a stability prediction of a half-life of 1 h for the peptide sequence-allele pair. The training data 170A also includes allele-noninteracting variables, such as the C-terminal flanking sequence of the peptide FJELFISBOSJFIE (SEQ ID NO: 15), and a mRNA quantification measurement of $10^2$ TPM. The fourth data instance indicates that peptide sequence QIEJOEIJE (SEQ ID NO: 13) was presented by one of the alleles HLA-B*07:02, HLA-C*01:03, or HLA-A*01:01. The training data 170A also includes binding affinity predictions and stability predictions for each of the alleles, as well as the C-terminal flanking sequence of the peptide and the mRNA quantification measurement for the peptide.

VII.C.2. Encoding Module

The encoding module 314 encodes information contained in the training data 170 into a numerical representation that can be used to generate the one or more presentation models. In one implementation, the encoding module 314 one-hot encodes sequences (e.g., peptide sequences or C-terminal flanking sequences) over a predetermined 20-letter amino acid alphabet. Specifically, a peptide sequence $p^i$ with $k_i$ amino acids is represented as a row vector of $20 \cdot k_i$ elements, where a single element among $p^i_{20 \cdot (j-1)+1}, p^i_{20 \cdot (j-1)+2}, \ldots, p^i_{20 \cdot j}$ that corresponds to the alphabet of the amino acid at the j-th position of the peptide sequence has a value of 1. Otherwise, the remaining elements have a value of 0. As an example, for a given alphabet {A, C, D, E, F, G, H, I, K, L, M, N, P, Q, R, S, T, V, W, Y}, the peptide sequence EAF of 3 amino acids for data instance i may be represented by the row vector of 60 elements $p^i$=[0 0 0 1 0 0 0 0 0 0 0 0 0 0 0 0 0 0 0 0 1 0 0 0 0 0 0 0 0 0 0 0 0 0 0 0 0 0 0 0 1 0 0 0 0 0 0 0 0 0 0 0 0 0 0 0 0 0 0 0]. The C-terminal flanking sequence $c^i$ can be similarly encoded as described above, as well as the protein sequence $d_h$ for MHC alleles, and other sequence data in the presentation information.

When the training data 170 contains sequences of differing lengths of amino acids, the encoding module 314 may further encode the peptides into equal-length vectors by adding a PAD character to extend the predetermined alphabet. For example, this may be performed by left-padding the peptide sequences with the PAD character until the length of the peptide sequence reaches the peptide sequence with the greatest length in the training data 170. Thus, when the peptide sequence with the greatest length has $k_{max}$ amino acids, the encoding module 314 numerically represents each sequence as a row vector of $(20+1) \cdot k_{max}$ elements. As an example, for the extended alphabet {PAD, A, C, D, E, F, G, H, I, K, L, M, N, P, Q, R, S, T, V, W, Y} and a maximum amino acid length of $k_{max}$=5, the same example peptide sequence EAF of 3 amino acids may be represented by the row vector of 105 elements $p^i$=[1 0 0 0 0 0 0 0 0 0 0 0 0 0 0 0 0 0 0 0 0 1 0 0 0 0 0 0 0 0 0 0 0 0 0 0 0 0 0 0 0 0 0 1 0 0 0 0 0 0 0 0 0 0 0 0 0 0 0 0 0 1 0 0 0 0 0 0 0 0 0 0 0 0 0 0 0 0 0 0 0 0 0 0 1 0 0 0 0 0 0 0 0 0 0 0 0 0 0 0 0 0 0 0 0]. The C-terminal flanking sequence $c^i$ or other sequence data can be similarly encoded as described above. Thus, each independent variable or column in the peptide sequence $p^i$ or $c^i$ represents presence of a particular amino acid at a particular position of the sequence.

Although the above method of encoding sequence data was described in reference to sequences having amino acid sequences, the method can similarly be extended to other types of sequence data, such as DNA or RNA sequence data, and the like.

The encoding module 314 also encodes the one or more MHC alleles $a^i$ for data instance i as a row vector of m elements, in which each element h=1, 2, . . . , m corresponds to a unique identified MHC allele. The elements corresponding to the MHC alleles identified for the data instance i have a value of 1. Otherwise, the remaining elements have a value of 0. As an example, the alleles HLA-B*07:02 and HLA-DRB1*10:01 for a data instance i corresponding to a multiple-allele cell line among m=4 unique identified MHC allele types {HLA-A*01:01, HLA-C*01:08, HLA-B*07:02, HLA-DRB1*10:01} may be represented by the row vector of 4 elements $a^i$=[0 0 1 1], in which $a_3^i$=1 and $a_4^i$=1. Although the example is described herein with 4 identified MHC allele types, the number of MHC allele types can be hundreds or thousands in practice. As previously discussed, each data instance i typically contains at most 6 different MHC allele types in association with the peptide sequence $p_i$.

The encoding module 314 also encodes the label $y_i$ for each data instance i as a binary variable having values from the set of {0, 1}, in which a value of 1 indicates that peptide $x^i$ was presented by one of the associated MHC alleles $a^i$, and a value of 0 indicates that peptide $x^i$ was not presented by any of the associated MHC alleles $a^i$. When the dependent variable $y^i$ represents the mass spectrometry ion current, the encoding module 314 may additionally scale the values using various functions, such as the log function having a range of $(-\infty, \infty)$ for ion current values between $[0, \infty)$.

The encoding module 314 may represent a pair of allele-interacting variables $x_h^i$ for peptide $p_i$ and an associated MHC allele h as a row vector in which numerical representations of allele-interacting variables are concatenated one after the other. For example, the encoding module 314 may represent $x_h^i$ as a row vector equal to $[p^i]$, $[p^i b_h^i]$, $[p^i s_h^i]$, or $[p^i b_h^i s_h^i]$, where $b_h^i$ is the binding affinity prediction for peptide $p_i$ and associated MHC allele h, and similarly for $s_h^i$ for stability. Alternatively, one or more combination of allele-interacting variables may be stored individually (e.g., as individual vectors or matrices).

In one instance, the encoding module 314 represents binding affinity information by incorporating measured or predicted values for binding affinity in the allele-interacting variables $x_h^i$.

In one instance, the encoding module 314 represents binding stability information by incorporating measured or predicted values for binding stability in the allele-interacting variables $x_h^i$, In one instance, the encoding module 314 represents binding on-rate information by incorporating measured or predicted values for binding on-rate in the allele-interacting variables $x_h^i$.

In one instance, for peptides presented by class I MHC molecules, the encoding module 314 represents peptide length as a vector $T_k=[\mathbb{1}(L_k=8)\mathbb{1}(L_k=9)\mathbb{1}(L_k=10)\mathbb{1}(L_k=11)\ \mathbb{1}(L_k=12)\mathbb{1}(L_k=13)\mathbb{1}(L_k=14)\mathbb{1}(L_k=15)]$ where $\mathbb{1}$ is the indicator function, and $L_k$ denotes the length of peptide $p_k$. The vector $T_k$ can be included in the allele-interacting variables $x_h^i$. In another instance, for peptides presented by class II MHC molecules, the encoding module 314 represents peptide length as a vector $T_k=[\mathbb{1}(L_k=6)\mathbb{1}(L_k=7)$ $\mathbb{1}(L_k=8)\mathbb{1}(L_k=9)\mathbb{1}(L_k=10)\mathbb{1}(L_k=11)\ \mathbb{1}(L_k=12)\mathbb{1}(L_k=13)$ $\mathbb{1}(L_k=14)\mathbb{1}(L_k=15)\mathbb{1}(L_k=16)\mathbb{1}(L_k=17)\mathbb{1}(L_k=18)\mathbb{1}(L_k=19)$ $\mathbb{1}(L_k=20)\mathbb{1}(L_k=21)\ \mathbb{1}(L_k=22)\mathbb{1}(L_k=23)\mathbb{1}(L_k=24)\mathbb{1}(L_k=25)$ $\mathbb{1}(L_k=26)\mathbb{1}(L_k=27)\mathbb{1}(L_k=28)\mathbb{1}(L_k=29)\mathbb{1}(L_k=30)]$ where $\mathbb{1}$ is the indicator function, and $L_k$ denotes the length of peptide $p_k$. The vector $T_k$ can be included in the allele-interacting variables $x_h^i$.

In one instance, the encoding module 314 represents RNA expression information of MHC alleles by incorporating RNA-seq based expression levels of MHC alleles in the allele-interacting variables $x_h^i$.

Similarly, the encoding module 314 may represent the allele-noninteracting variables $w^i$ as a row vector in which numerical representations of allele-noninteracting variables are concatenated one after the other. For example, $w^i$ may be a row vector equal to $[c^i]$ or $[c^i m^i w^i]$ in which $w^i$ is a row vector representing any other allele-noninteracting variables in addition to the C-terminal flanking sequence of peptide $p^i$ and the mRNA quantification measurement $m^i$ associated with the peptide. Alternatively, one or more combination of allele-noninteracting variables may be stored individually (e.g., as individual vectors or matrices).

In one instance, the encoding module 314 represents turnover rate of source protein for a peptide sequence by incorporating the turnover rate or half-life in the allele-noninteracting variables $w^i$.

In one instance, the encoding module 314 represents length of source protein or isoform by incorporating the protein length in the allele-noninteracting variables $w^i$.

In one instance, the encoding module 314 represents activation of immunoproteasome by incorporating the mean expression of the immunoproteasome-specific proteasome subunits including the $\beta 1_i$, $\beta 2_i$, $\beta 5_i$ subunits in the allele-noninteracting variables $w^i$.

In one instance, the encoding module 314 represents the RNA-seq abundance of the source protein of the peptide or gene or transcript of a peptide (quantified in units of FPKM, TPM by techniques such as RSEM) can be incorporating the abundance of the source protein in the allele-noninteracting variables $w^i$.

In one instance, the encoding module 314 represents the probability that the transcript of origin of a peptide will undergo nonsense-mediated decay (NMD) as estimated by the model in, for example, Rivas et. al. *Science*, 2015 by incorporating this probability in the allele-noninteracting variables $w^i$.

In one instance, the encoding module 314 represents the activation status of a gene module or pathway assessed via RNA-seq by, for example, quantifying expression of the genes in the pathway in units of TPM using e.g., RSEM for each of the genes in the pathway then computing a summary statistics, e.g., the mean, across genes in the pathway. The mean can be incorporated in the allele-noninteracting variables $w^i$.

In one instance, the encoding module 314 represents the copy number of the source gene by incorporating the copy number in the allele-noninteracting variables $w^i$.

In one instance, the encoding module 314 represents the TAP binding affinity by including the measured or predicted TAP binding affinity (e.g., in nanomolar units) in the allele-noninteracting variables $w^i$.

In one instance, the encoding module 314 represents TAP expression levels by including TAP expression levels measured by RNA-seq (and quantified in units of TPM by e.g., RSEM) in the allele-noninteracting variables $w^i$.

In one instance, the encoding module 314 represents tumor mutations as a vector of indicator variables (i.e., $d^k=1$ if peptide $p^k$ comes from a sample with a KRAS G12D mutation and 0 otherwise) in the allele-noninteracting variables $w^i$.

In one instance, the encoding module 314 represents germline polymorphisms in antigen presentation genes as a vector of indicator variables (i.e., $d^k=1$ if peptide $p^k$ comes from a sample with a specific germline polymorphism in the TAP). These indicator variables can be included in the allele-noninteracting variables $w^i$.

In one instance, the encoding module 314 represents tumor type as a length-one one-hot encoded vector over the alphabet of tumor types (e.g., NSCLC, melanoma, colorectal cancer, etc). These one-hot-encoded variables can be included in the allele-noninteracting variables $w^i$.

In one instance, the encoding module 314 represents MHC allele suffixes by treating 4-digit HLA alleles with different suffixes. For example, HLA-A*24:09N is considered a different allele from HLA-A*24:09 for the purpose of the model. Alternatively, the probability of presentation by an N-suffixed MHC allele can be set to zero for all peptides, because HLA alleles ending in the N suffix are not expressed.

In one instance, the encoding module 314 represents tumor subtype as a length-one one-hot encoded vector over the alphabet of tumor subtypes (e.g., lung adenocarcinoma, lung squamous cell carcinoma, etc). These one-hot encoded variables can be included in the allele-noninteracting variables $w^i$.

In one instance, the encoding module 314 represents smoking history as a binary indicator variable ($d^k=1$ if the patient has a smoking history, and 0 otherwise), that can be included in the allele-noninteracting variables $w^i$. Alternatively, smoking history can be encoded as a length-one one-hot encoded variable over an alphabet of smoking severity. For example, smoking status can be rated on a 1-5 scale, where 1 indicates nonsmokers, and 5 indicates current heavy smokers. Because smoking history is primarily relevant to lung tumors, when training a model on multiple tumor types, this variable can also be defined to be equal to 1 if the patient has a history of smoking and the tumor type is lung tumors and zero otherwise.

In one instance, the encoding module 314 represents sunburn history as a binary indicator variable ($d^k=1$ if the patient has a history of severe sunburn, and 0 otherwise), which can be included in the allele-noninteracting variables $w^i$. Because severe sunburn is primarily relevant to melanomas, when training a model on multiple tumor types, this variable can also be defined to be equal to 1 if the patient has a history of severe sunburn and the tumor type is melanoma and zero otherwise.

In one instance, the encoding module 314 represents distribution of expression levels of a particular gene or transcript for each gene or transcript in the human genome as summary statistics (e.g., mean, median) of distribution of expression levels by using reference databases such as TCGA. Specifically, for a peptide $p^k$ in a sample with tumor type melanoma, not only the measured gene or transcript expression level of the gene or transcript of origin of peptide $p^k$ in the allele-noninteracting variables $w^i$, but also the mean and/or median gene or transcript expression of the gene or transcript of origin of peptide $p^k$ in melanomas as measured by TCGA can be included.

In one instance, the encoding module 314 represents mutation type as a length-one one-hot-encoded variable over the alphabet of mutation types (e.g., missense, frameshift, NMD-inducing, etc). These onehot-encoded variables can be included in the allele-noninteracting variables $w^i$.

In one instance, the encoding module 314 represents protein-level features of protein as the value of the annotation (e.g., 5' UTR length) of the source protein in the allele-noninteracting variables $w^i$. In another instance, the encoding module 314 represents residue-level annotations of the source protein for peptide $p^i$ by including an indicator variable, that is equal to 1 if peptide $p^i$ overlaps with a helix motif and 0 otherwise, or that is equal to 1 if peptide $p^i$ is completely contained with within a helix motif in the allele-noninteracting variables $w^i$. In another instance, a feature representing proportion of residues in peptide $p^i$ that are contained within a helix motif annotation can be included in the allele-noninteracting variables $w^i$.

In one instance, the encoding module 314 represents type of proteins or isoforms in the human proteome as an indicator vector $o^k$ that has a length equal to the number of proteins or isoforms in the human proteome, and the corresponding element $o^k_i$ is 1 if peptide $p^k$ comes from protein i and 0 otherwise.

In one instance, the encoding module 314 represents the source gene $G=\text{gene}(p^i)$ of peptide $p^i$ as a categorical variable with L possible categories, where L denotes the upper limit of the number of indexed source genes 1, 2, . . . , L.

In one instance, the encoding module 314 represents tissue type, cell type, tumor type, or tumor histology type $T=\text{tissue}(p^i)$ of peptide $p^i$ as a categorical variable with M possible categories, where M denotes the upper limit of the number of indexed types 1, 2, . . . , M. Types of tissue can include, for example, lung tissue, cardiac tissue, intestine tissue, nerve tissue, and the like. Types of cells can include dendritic cells, macrophages, CD4 T cells, and the like. Types of tumors can include lung adenocarcinoma, lung squamous cell carcinoma, melanoma, non-Hodgkin lymphoma, and the like.

The encoding module 314 may also represent the overall set of variables $z^i$ for peptide $p^i$ and an associated MHC allele h as a row vector in which numerical representations of the allele-interacting variables $x^i$ and the allele-noninteracting variables $w^i$ are concatenated one after the other. For example, the encoding module 314 may represent $z_h^i$ as a row vector equal to $[x_h^i \ w^i]$ or $[w_i x_h^i]$.

VIII. Training Module

The training module 316 constructs one or more presentation models that generate likelihoods of whether peptide sequences will be presented by MHC alleles associated with the peptide sequences. Specifically, given a peptide sequence $p^k$ and a set of MHC alleles $a^k$ associated with the peptide sequence $p^k$, each presentation model generates an estimate $u_k$ indicating a likelihood that the peptide sequence $p^k$ will be presented by one or more of the associated MHC alleles $a^k$.

VIII.A. Overview

The training module 316 constructs the one more presentation models based on the training data sets stored in store 170 generated from the presentation information stored in 165. Generally, regardless of the specific type of presentation model, all of the presentation models capture the dependence between independent variables and dependent variables in the training data 170 such that a loss function is minimized. Specifically, the loss function $l(y_{i \in S}, u_{i \in S}, \theta)$ represents discrepancies between values of dependent variables $y_{i \in S}$ for one or more data instances S in the training data 170 and the estimated likelihoods $u_{i \in S}$ for the data instances S generated by the presentation model. In one particular implementation referred throughout the remainder of the specification, the loss function ($y_{i \in S}$, $u_{i \in S}$, $\theta$) is the negative log likelihood function given by equation (1a) as follows:

$$\ell(y_{i \in S}, u_{i \in S}; \theta) = \sum_{i \in S} (y_i \log u_i + (1 - y_i) \log(1 - u_i)). \quad (1a)$$

However, in practice, another loss function may be used. For example, when predictions are made for the mass spectrometry ion current, the loss function is the mean squared loss given by equation 1b as follows:

$$\ell(y_{i \in S}, u_{i \in S}; \theta) = \sum_{i \in S} (\|y_i - u_i\|^2)_2. \quad (1b)$$

The presentation model may be a parametric model in which one or more parameters $\theta$ mathematically specify the dependence between the independent variables and dependent variables. Typically, various parameters of parametric-type presentation models that minimize the loss function ($y_{i \in S}$, $u_{i \in S}$, $\theta$) are determined through gradient-based numerical optimization algorithms, such as batch gradient algorithms, stochastic gradient algorithms, and the like. Alternatively, the presentation model may be a non-parametric model in which the model structure is determined from the training data 170 and is not strictly based on a fixed set of parameters.

VIII.B. Per-Allele Models

The training module 316 may construct the presentation models to predict presentation likelihoods of peptides on a per-allele basis. In this case, the training module 316 may train the presentation models based on data instances S in the training data 170 generated from cells expressing single MHC alleles.

In one implementation, the training module 316 models the estimated presentation likelihood $u_k$ for peptide $p^k$ for a specific allele h by:

$$u_k^h = Pr(p^k \text{ presented}; MHC \text{ allele } h) = f(g_h(x_h^k; \theta_h)), \quad (2)$$

where peptide sequence $x_h^k$ denotes the encoded allele-interacting variables for peptide $p^k$ and corresponding MHC allele h, $f(\cdot)$ is any function, and is herein throughout is referred to as a transformation function for convenience of description. Further, $g_h(\cdot)$ is any function, is herein throughout referred to as a dependency function for convenience of description, and generates dependency scores for the allele-interacting variables $x_h^k$ based on a set of parameters $\theta_h$ determined for MHC allele h. The values for the set of parameters $\theta_h$ for each MHC allele h can be determined by minimizing the loss function with respect to $\theta_h$, where i is each instance in the subset S of training data 170 generated from cells expressing the single MHC allele h.

The output of the dependency function $g_h(x_h^k; \theta_h)$ represents a dependency score for the MHC allele h indicating whether the MHC allele h will present the corresponding neoantigen based on at least the allele interacting features $x_h^k$, and in particular, based on positions of amino acids of the peptide sequence of peptide $p^k$. For example, the dependency score for the MHC allele h may have a high value if the MHC allele h is likely to present the peptide $p^k$, and may have a low value if presentation is not likely. The transformation function $f(\cdot)$ transforms the input, and more specifically, transforms the dependency score generated by $g_h(x_h^k; \theta_h)$ in this case, to an appropriate value to indicate the likelihood that the peptide $p^k$ will be presented by an MHC allele.

In one particular implementation referred throughout the remainder of the specification, $f(\cdot)$ is a function having the range within [0, 1] for an appropriate domain range. In one example, $f(\cdot)$ is the expit function given by:

$$f(z) = \frac{\exp(z)}{1 + \exp(z)}. \quad (4)$$

As another example, $f(\cdot)$ can also be the hyperbolic tangent function given by:

$$f(z) = \tan h(z) \quad (5)$$

when the values for the domain z is equal to or greater than 0. Alternatively, when predictions are made for the mass spectrometry ion current that have values outside the range [0, 1], $f(\cdot)$ can be any function such as the identity function, the exponential function, the log function, and the like.

Thus, the per-allele likelihood that a peptide sequence $p^k$ will be presented by a MHC allele h can be generated by applying the dependency function $g_h(\cdot)$ for the MHC allele h to the encoded version of the peptide sequence $p^k$ to generate the corresponding dependency score. The dependency score may be transformed by the transformation function $f(\cdot)$ to generate a per-allele likelihood that the peptide sequence $p^k$ will be presented by the MHC allele h.

VIII.B.1 Dependency Functions for Allele Interacting Variables

In one particular implementation referred throughout the specification, the dependency function $g_h(\cdot)$ is an affine function given by:

$$g_h(x_h^i; \theta_h) = x_h^i \cdot \theta_h. \quad (6)$$

that linearly combines each allele-interacting variable in $x_h^k$ with a corresponding parameter in the set of parameters $\theta_h$ determined for the associated MHC allele h.

In another particular implementation referred throughout the specification, the dependency function $g_h(\cdot)$ is a network function given by:

$$g_h(x_h^i; \theta_h) = NN_h(x_h^i; \theta_h). \quad (7)$$

represented by a network model $NN_h(\cdot)$ having a series of nodes arranged in one or more layers. A node may be connected to other nodes through connections each having an associated parameter in the set of parameters $\theta_h$. A value at one particular node may be represented as a sum of the values of nodes connected to the particular node weighted by the associated parameter mapped by an activation function associated with the particular node. In contrast to the affine function, network models are advantageous because the presentation model can incorporate non-linearity and process data having different lengths of amino acid sequences. Specifically, through non-linear modeling, network models can capture interaction between amino acids at different positions in a peptide sequence and how this interaction affects peptide presentation.

In general, network models $NN_h(\cdot)$ may be structured as feed-forward networks, such as artificial neural networks (ANN), convolutional neural networks (CNN), deep neural networks (DNN), and/or recurrent networks, such as long short-term memory networks (LSTM), bi-directional recurrent networks, deep bi-directional recurrent networks, and the like.

In one instance referred throughout the remainder of the specification, each MHC allele in h=1,2, ..., m is associated with a separate network model, and $NN_h(\cdot)$ denotes the output(s) from a network model associated with MHC allele h.

Figure 5:
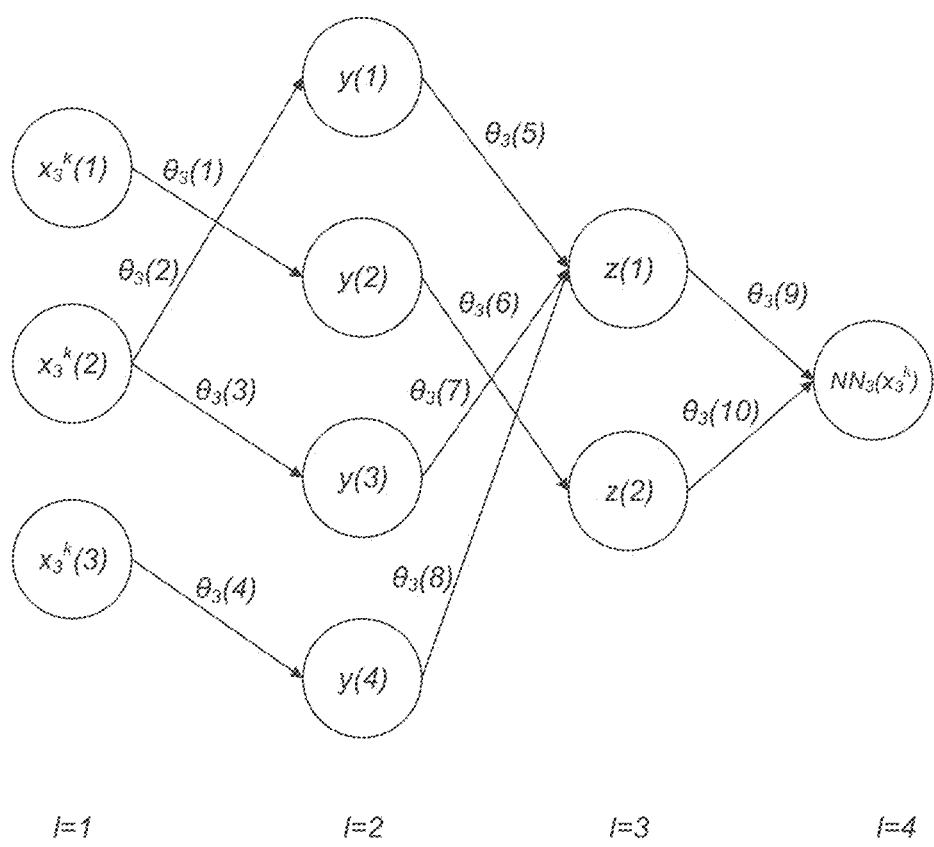
FIG. 5 illustrates an example network model in association with an MHC allele.

FIG. 5 illustrates an example network model $NN_3(\cdot)$ in association with an arbitrary MHC allele h=3. As shown in FIG. 5, the network model $NN_3(\cdot)$ for MHC allele h=3 includes three input nodes at layer l=1, four nodes at layer l=2, two nodes at layer l=3, and one output node at layer l=4. The network model $NN_3(\cdot)$ is associated with a set of ten parameters $\theta_3(1)$, $\theta_3(2)$, ..., $\theta_3(10)$. The network model $NN_3(\cdot)$ receives input values (individual data instances including encoded polypeptide sequence data and any other training data used) for three allele-interacting variables $x_3^k(1)$, $x_3^k(2)$, and $x_3^k(3)$ for MHC allele h=3 and outputs the value $NN_3(x_3^k)$. The network function may also include one or more network models each taking different allele interacting variables as input.

In another instance, the identified MHC alleles h=1, 2, ..., m are associated with a single network model $NN_H(\cdot)$, and $NN_h(\cdot)$ denotes one or more outputs of the single network model associated with MHC allele h. In such an instance, the set of parameters $\theta_h$ may correspond to a set of parameters for the single network model, and thus, the set of parameters $\theta_h$ may be shared by all MHC alleles.

Figure 6A:
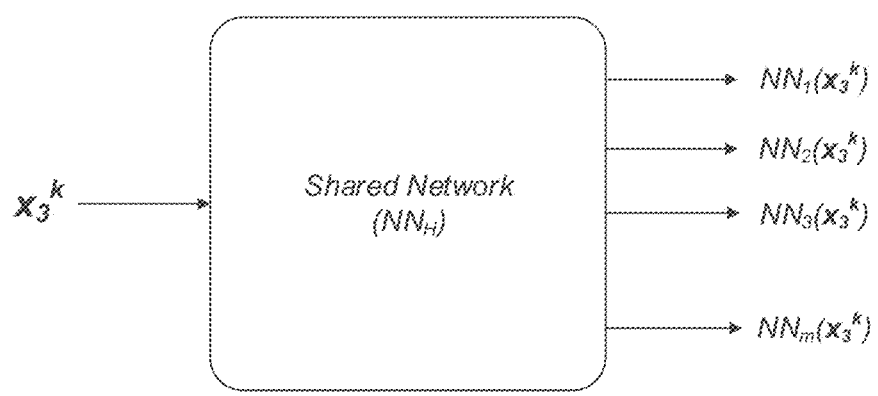
FIG. 6A illustrates an example network model $NN_H(\cdot)$ shared by MHC alleles, according to one embodiment.

FIG. 6A illustrates an example network model $NN_H(\cdot)$ shared by MHC alleles h=1, 2, ..., m. As shown in FIG. 6A, the network model $NN_H(\cdot)$ includes m output nodes each corresponding to an MHC allele. The network model $NN_3(\cdot)$ receives the allele-interacting variables $x_3^k$ for MHC allele h=3 and outputs m values including the value $NN_3(x_3^k)$ corresponding to the MHC allele h=3.

In yet another instance, the single network model $NN_H(\cdot)$ may be a network model that outputs a dependency score given the allele interacting variables $x_h^k$ and the encoded protein sequence $d_h$ of an MHC allele h. In such an instance, the set of parameters $\theta_h$ may again correspond to a set of parameters for the single network model, and thus, the set of parameters $\theta_h$ may be shared by all MHC alleles. Thus, in such an instance, $NN_h(\cdot)$ may denote the output of the single network model $NN_H(\cdot)$ given inputs $[x_h^k \ d_h]$ to the single network model. Such a network model is advantageous because peptide presentation probabilities for MHC alleles that were unknown in the training data can be predicted just by identification of their protein sequence.

Figure 6B:
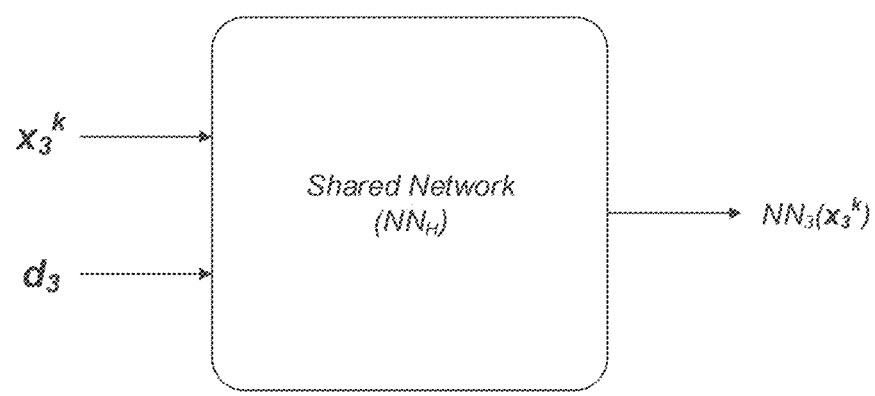
FIG. 6B illustrates an example network model $NN_H(\cdot)$ shared by MHC alleles, according to another embodiment.

FIG. 6B illustrates an example network model $NN_H(\cdot)$ shared by MHC alleles. As shown in FIG. 6B, the network model $NN_H(\cdot)$ receives the allele interacting variables and protein sequence of MHC allele h=3 as input, and outputs a dependency score $NN_3(x_3^k)$ corresponding to the MHC allele h=3.

In yet another instance, the dependency function $g_h(\cdot)$ can be expressed as:

$$g_h(x_h^k; \theta_h) = g'_h(x_h^k; \theta'_h) + \theta_h^0$$

where $g'_h(x_h^k; \theta'_h)$ is the affine function with a set of parameters $\theta'_h$, the network function, or the like, with a bias parameter $\theta_h^0$ in the set of parameters for allele interacting variables for the MHC allele that represents a baseline probability of presentation for the MHC allele h.

In another implementation, the bias parameter $\theta_h^0$ may be shared according to the gene family of the MHC allele h. That is, the bias parameter $\theta_h^0$ for MHC allele h may be equal to $\theta_{gene(h)}^0$, where gene(h) is the gene family of MHC allele h. For example, class I MHC alleles HLA-A*02:01, HLA-A*02:02, and HLA-A*02:03 may be assigned to the gene family of "HLA-A," and the bias parameter $\theta_h^0$ for each of these MHC alleles may be shared. As another example, class II MHC alleles HLA-DRB1:10:01, HLA-DRB1:11:01, and HLA-DRB3:01:01 may be assigned to the gene family of "HLA-DRB," and the bias parameter $\theta_h^0$ for each of these MHC alleles may be shared.

Returning to equation (2), as an example, the likelihood that peptide $p^k$ will be presented by MHC allele h=3, among m=4 different identified MHC alleles using the affine dependency function $g_h(\cdot)$ can be generated by:

$$u_k^3 = f(x_3^k \cdot \theta_3),$$

where $x_3^k$ are the identified allele-interacting variables for MHC allele h=3, and $\theta_3$ are the set of parameters determined for MHC allele h=3 through loss function minimization.

As another example, the likelihood that peptide $p_k$ will be presented by MHC allele h=3, among m=4 different identified MHC alleles using separate network transformation functions $g_h(\cdot)$, can be generated by:

$$u_k^3 = f(NN_3(x_3^k; \theta_3)),$$

where $x_3^k$ are the identified allele-interacting variables for MHC allele h=3, and $\theta_3$ are the set of parameters determined for the network model $NN_3(\cdot)$ associated with MHC allele h=3.

Figure 7:
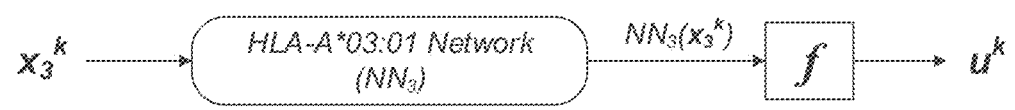
FIG. 7 illustrates generating a presentation likelihood for a peptide in association with an MHC allele using an example network model.

FIG. 7 illustrates generating a presentation likelihood for peptide $p^k$ in association with MHC allele h=3 using an example network model $NN_3(\cdot)$. As shown in FIG. 7, the network model $NN_3(\cdot)$ receives the allele-interacting variables $x_3^k$ for MHC allele h=3 and generates the output $NN_3(x_3^k)$. The output is mapped by function $f(\cdot)$ to generate the estimated presentation likelihood $u_k$.

VIII.B.3 Dependency Functions for Allele-Noninteracting Variables

Similarly to the dependency function $g_h(\cdot)$ for allele-interacting variables, the dependency function $g_w(\cdot)$ for allele noninteracting variables may be an affine function or a network function in which a separate network model is associated with allele-noninteracting variables $w^k$.

Specifically, the dependency function $g_w(\cdot)$ is an affine function given by:

$$g_w(w^k; \theta_w) = w^k \cdot \theta_w.$$

that linearly combines the allele-noninteracting variables in $w^k$ with a corresponding parameter in the set of parameters $\theta_w$.

The dependency function $g_w(\cdot)$ may also be a network function given by:

$$g_w(w^k; \theta_w) = NN_w(w^k; \theta_w).$$

represented by a network model $NN_w(\cdot)$ having an associated parameter in the set of parameters $\theta_w$. The network function may also include one or more network models each taking different allele noninteracting variables as input.

In another instance, the dependency function $g_w(\cdot)$ for the allele-noninteracting variables can be given by:

$$g_w(w^k; \theta_w) = g'_w(w^k; \theta'_w) + h(m^k; \theta_w^m), \quad (10)$$

where $g'_w(w^k; \theta'_w)$ is the affine function, the network function with the set of allele noninteracting parameters $\theta'_w$, or the like, $m^k$ is the mRNA quantification measurement for peptide $p^k$, $h(\cdot)$ is a function transforming the quantification measurement, and $\theta_w^m$ is a parameter in the set of parameters for allele noninteracting variables that is combined with the mRNA quantification measurement to generate a dependency score for the mRNA quantification measurement. In one particular embodiment referred throughout the remainder of the specification, h(•) is the log function, however in practice h(•) may be any one of a variety of different functions.

In yet another instance, the dependency function $g_w(\bullet)$ for the allele-noninteracting variables can be given by:

$$g_w(w^k;\theta_w) = g'_w(w^k;\theta_w) + \theta^o_w \cdot o^k, \quad (11)$$

where $g'_w(w^k; \theta'_w)$ is the affine function, the network function with the set of allele noninteracting parameters $\theta'_w$, or the like, $o^k$ is the indicator vector described in Section VII.C.2 representing proteins and isoforms in the human proteome for peptide $p^k$, and $\theta_w^o$ is a set of parameters in the set of parameters for allele noninteracting variables that is combined with the indicator vector. In one variation, when the dimensionality of $o^k$ and the set of parameters $\theta_w^o$ are significantly high, a parameter regularization term, such as $\lambda \cdot \|\theta_w^o\|$, where $\|\bullet\|$ represents L1 norm, L2 norm, a combination, or the like, can be added to the loss function when determining the value of the parameters. The optimal value of the hyperparameter λ can be determined through appropriate methods.

In yet another instance, the dependency function $g_w(\bullet)$ for the allele-noninteracting variables can be given by:

$$g_w(w^k;\theta_w) = g'_w(w^k;\theta'_w) + \sum_{l=1}^{L} \mathbb{1}(\text{gene}(p^k) = l) \cdot \theta_w^l, \quad (12)$$

where $g'_w(w^k; \theta'_w)$ is the affine function, the network function with the set of allele noninteracting parameters $\theta'_w$, or the like, $o^k$ (gene($p^k$=l)) is the indicator function that equals to 1 if peptide $p^k$ is from source gene l as described above in reference to allele noninteracting variables, and $\theta_w^l$ is a parameter indicating "antigenicity" of source gene l. In one variation, when L is significantly high, and thus, the number of parameters $\theta_w^{l=1, 2, \ldots, L}$ are significantly high, a parameter regularization term, such as $\lambda \cdot \|\theta_w^l\|$, where $\|\bullet\|$ represents L1 norm, L2 norm, a combination, or the like, can be added to the loss function when determining the value of the parameters. The optimal value of the hyperparameter λ can be determined through appropriate methods.

In yet another instance, the dependency function $g_w(\bullet)$ for the allele-noninteracting variables can be given by:

$$g_w(w^k;\theta_w) = g'_w(w^k;\theta'_w) + \sum_{m=1}^{M}\sum_{l=1}^{L}\mathbb{1}(\text{gene}(p^k)=l, \text{tissue}(p^k)=m) \cdot \theta_w^{lm} \quad (12b)$$

where $g'_w(w^k; \theta'_w)$ is the affine function, the network function with the set of allele noninteracting parameters $\theta'_w$, or the like, $\mathbb{1}(\text{gene}(p^k)=l, \text{tissue}(p^k)=m)$ is the indicator function that equals to 1 if peptide $p^k$ is from source gene l and if peptide $p^k$ is from tissue type m as described above in reference to allele noninteracting variables, and $\theta_w^{lm}$ is a parameter indicating antigenicity of the combination of source gene l and tissue type m. Specifically, the antigenicity of gene l for tissue type m may denote the residual propensity for cells of tissue type m to present peptides from gene l after controlling for RNA expression and peptide sequence context.

In one variation, when L or M is significantly high, and thus, the number of parameters $\theta_w^{lm=1, 2, \ldots, LM}$ are significantly high, a parameter regularization term, such as $\lambda \cdot \|\theta_w^{lm}\|$, where $\|\bullet\|$ represents L1 norm, L2 norm, a combination, or the like, can be added to the loss function when determining the value of the parameters. The optimal value of the hyperparameter λ, can be determined through appropriate methods. In another variation, a parameter regularization term can be added to the loss function when determining the value of the parameters, such that the parameters for the same source gene do not significantly differ between tissue types. For example, a penalization term such as:

$$\lambda \cdot \sum_{l=1}^{L} \sqrt{\sum_{m=1}^{M}\left(\theta_w^{lm} - \overline{\theta_w^l}\right)^2}$$

where $$\overline{\theta_w^l}$$

is the average antigenicity across tissue types for source gene l, may penalize the standard deviation of antigenicity across different tissue types in the loss function.

In yet another instance, the dependency function $g_w(\bullet)$ for the allele-noninteracting variables can be given by:

$$g_w(w^k;\theta_w) = \quad (12c)$$
$$g'_w(w^k;\theta'_w) + \sum_{l=1}^{L}\mathbb{1}(\text{gene}(p^k)=l) \cdot \theta_w^l + \sum_{m=1}^{M}\mathbb{1}(\text{loc}(p^k)=m) \cdot \theta_w^m$$

where $g'_w(w^k; \theta'_w)$ is the affine function, the network function with the set of allele noninteracting parameters $\theta'_w$, or the like, $\mathbb{1}(\text{gene}(p^k)=l)$ is the indicator function that equals to 1 if peptide $p^k$ is from source gene l as described above in reference to allele noninteracting variables, and $\theta_w^l$ is a parameter indicating "antigenicity" of source gene l, and $\mathbb{1}(\text{loc}(p^k)=m)$ is the indicator function that equals to 1 if peptide $p^k$ is from proteomic location m, and $\theta_w^m$ is a parameter indicating the extent to which proteomic location m is a presentation "hotspot". In one embodiment, a proteomic location can comprise a block of n adjacent peptides from the same protein, where n is a hyperparameter of the model determined via appropriate methods such as grid-search cross-validation.

In practice, the additional terms of any of equations (10), (11), (12a), (12b) and (12c) may be combined to generate the dependency function $g_w(\bullet)$ for allele noninteracting variables. For example, the term h(•) indicating mRNA quantification measurement in equation (10) and the term indicating source gene antigenicity in equation (12) may be summed together along with any other affine or network function to generate the dependency function for allele noninteracting variables.

Returning to equation (8), as an example, the likelihood that peptide $p^k$ will be presented by MHC allele h=3, among m=4 different identified MHC alleles using the affine transformation functions $g_h(\cdot)$, $g_w(\cdot)$, can be generated by:

$$u_k^3 = f(w^k \cdot \theta_w + x_3^k \cdot \theta_3),$$

where $w^k$ are the identified allele-noninteracting variables for peptide $p^k$, and $\theta_w$ are the set of parameters determined for the allele-noninteracting variables.

As another example, the likelihood that peptide $p^k$ will be presented by MHC allele h=3, among m=4 different identified MHC alleles using the network transformation functions $g_h(\cdot)$ $g_w(\cdot)$ can be generated by:

$$u_k^3 = f(NN_w(w^k; \theta_w) + NN_3(x_3^k; \theta_3))$$

where $w^k$ are the identified allele-interacting variables for peptide $p^k$, and $\theta_w$ are the set of parameters determined for allele-noninteracting variables.

Figure 8:
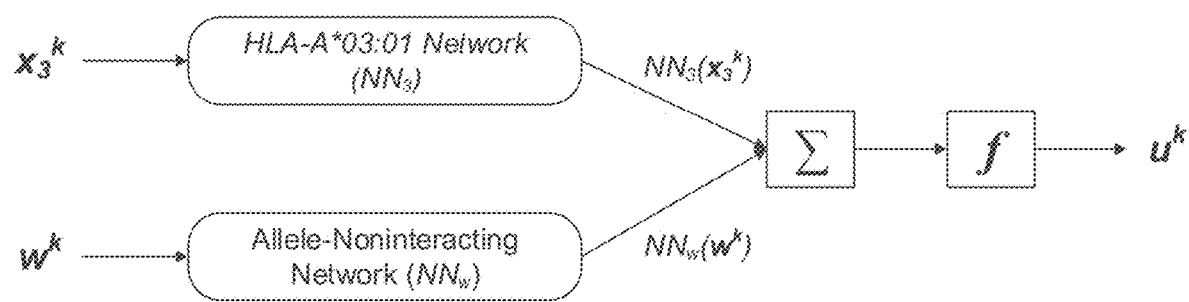
FIG. 8 illustrates generating a presentation likelihood for a peptide in association with a WIC allele using example network models.

FIG. 8 illustrates generating a presentation likelihood for peptide $p^k$ in association with MHC allele h=3 using example network models $NN_3(\cdot)$ and $NN_w(\cdot)$. As shown in FIG. 8, the network model $NN_3(\cdot)$ receives the allele-interacting variables $x_3^k$ for MHC allele h=3 and generates the output $NN_3(x_3^k)$. The network model $NN_w(\cdot)$ receives the allele-noninteracting variables $w^k$ for peptide $p^k$ and generates the output $NN_w(w^k)$. The outputs are combined and mapped by function $f(\cdot)$ to generate the estimated presentation likelihood $u_k$.

VIII.B.2. Per-Allele with Allele-Noninteracting Variables

In one implementation, the training module 316 incorporates allele-noninteracting variables and models the estimated presentation likelihood $u_k$ for peptide $p^k$ by:

$$u_k^h = Pr(p^k \text{ presented}) = f(g_w(w^k; \theta_w) + g_h(x_h^i; \theta_h)), \quad (8)$$

where $w^k$ denotes the encoded allele-noninteracting variables for peptide $p^k$, $g_w(\cdot)$ is a function for the allele-noninteracting variables $w^k$ based on a set of parameters $\theta_w$ determined for the allele-noninteracting variables. Specifically, the values for the set of parameters $\theta_h$ for each MHC allele h and the set of parameters $\theta_w$ for allele-noninteracting variables can be determined by minimizing the loss function with respect to $\theta_h$ and $\theta_w$, where i is each instance in the subset S of training data 170 generated from cells expressing single MHC alleles.

The output of the dependency function $g_w(w^k; \theta_w)$ represents a dependency score for the allele noninteracting variables indicating whether the peptide $p^k$ will be presented by one or more MHC alleles based on the impact of allele noninteracting variables. For example, the dependency score for the allele noninteracting variables may have a high value if the peptide $p^k$ is associated with a C-terminal flanking sequence that is known to positively impact presentation of the peptide $p^k$, and may have a low value if the peptide $p^k$ is associated with a C-terminal flanking sequence that is known to negatively impact presentation of the peptide $p_k$.

According to equation (8), the per-allele likelihood that a peptide sequence $p^k$ will be presented by a MHC allele h can be generated by applying the function $g_h(\cdot)$ for the MHC allele h to the encoded version of the peptide sequence $p^k$ to generate the corresponding dependency score for allele interacting variables. The function $g_w(\cdot)$ for the allele non-interacting variables are also applied to the encoded version of the allele noninteracting variables to generate the dependency score for the allele noninteracting variables. Both scores are combined, and the combined score is transformed by the transformation function $f(\cdot)$ to generate a per-allele likelihood that the peptide sequence $p^k$ will be presented by the MHC allele h.

Alternatively, the training module 316 may include allele-noninteracting variables $w^k$ in the prediction by adding the allele-noninteracting variables $w^k$ to the allele-interacting variables $x_h^k$ in equation (2). Thus, the presentation likelihood can be given by:

$$u_k^h = Pr(p^k \text{ presented;allele } h) = f(g_h([x_h^k, w^k]; \theta_h)). \quad (9)$$

VIII.C. Multiple-Allele Models

The training module 316 may also construct the presentation models to predict presentation likelihoods of peptides in a multiple-allele setting where two or more MHC alleles are present. In this case, the training module 316 may train the presentation models based on data instances S in the training data 170 generated from cells expressing single MHC alleles, cells expressing multiple MHC alleles, or a combination thereof.

VIII.C.1. Example 1: Maximum of Per-Allele Models

In one implementation, the training module 316 models the estimated presentation likelihood $u_k$ for peptide $p_k$ in association with a set of multiple MHC alleles H as a function of the presentation likelihoods $u_k^{h \in H}$ determined for each of the MHC alleles h in the set H determined based on cells expressing single-alleles, as described above in conjunction with equations (2)-(11). Specifically, the presentation likelihood $u_k$ can be any function of $u_k^{h \in H}$. In one implementation, as shown in equation (12), the function is the maximum function, and the presentation likelihood $u_k$ can be determined as the maximum of the presentation likelihoods for each MHC allele h in the set H.

$$u_k = Pr(p^k \text{ presented; alleles } H) = \max(u^{h \in H}_k).$$

VIII.C.2. Example 2.1: Function-of-Sums Models

In one implementation, the training module 316 models the estimated presentation likelihood $u_k$ for peptide $p^k$ by:

$$u_k = Pr(p^k \text{ presented}) = f\left(\sum_{h=1}^{m} a_h^k \cdot g_h(x_h^k; \theta_h)\right), \quad (13)$$

where elements $a_h^k$ are 1 for the multiple MHC alleles H associated with peptide sequence $p^k$ and $x_h^k$ denotes the encoded allele-interacting variables for peptide $p^k$ and the corresponding MHC alleles. The values for the set of parameters $\theta_h$ for each MHC allele h can be determined by minimizing the loss function with respect to $\theta_h$, where i is each instance in the subset S of training data 170 generated from cells expressing single MHC alleles and/or cells expressing multiple MHC alleles. The dependency function $g_h$ may be in the form of any of the dependency functions $g_h$ introduced above in sections VIII.B.1.

According to equation (13), the presentation likelihood that a peptide sequence $p^k$ will be presented by one or more MHC alleles h can be generated by applying the dependency function $g_h(\cdot)$ to the encoded version of the peptide sequence $p^k$ for each of the MHC alleles H to generate the corresponding score for the allele interacting variables. The scores for each MHC allele h are combined, and transformed by the transformation function $f(\cdot)$ to generate the presentation likelihood that peptide sequence $p^k$ will be presented by the set of WIC alleles H.

The presentation model of equation (13) is different from the per-allele model of equation (2), in that the number of associated alleles for each peptide $p^k$ can be greater than 1. In other words, more than one element in $a_h^k$ can have values of 1 for the multiple MHC alleles H associated with peptide sequence $p^k$.

As an example, the likelihood that peptide $p^k$ will be presented by MHC alleles h=2, h=3, among m=4 different identified MHC alleles using the affine transformation functions $g_h(\cdot)$, can be generated by:

$$u_k = f(x_2^k \cdot \theta_2 + x_3^k \cdot \theta_3),$$

where $x_2^k$, $x_3^k$ are the identified allele-interacting variables for MHC alleles h=2, h=3, and $\theta_2$, $\theta_3$ are the set of parameters determined for MHC alleles h=2, h=3.

As another example, the likelihood that peptide $p^k$ will be presented by MHC alleles h=2, h=3, among m=4 different identified MHC alleles using the network transformation functions $g_h(\cdot)$, $g_w(\cdot)$, can be generated by:

$$u_k = f(NN_2(x_2^k;\theta_2) + NN_3(x_3^k;\theta_3)),$$

where $NN_2(\cdot)$, $NN_3(\cdot)$ are the identified network models for MHC alleles h=2, h=3, and $\theta_2$, $\theta_3$ are the set of parameters determined for MHC alleles h=2, h=3.

Figure 9:
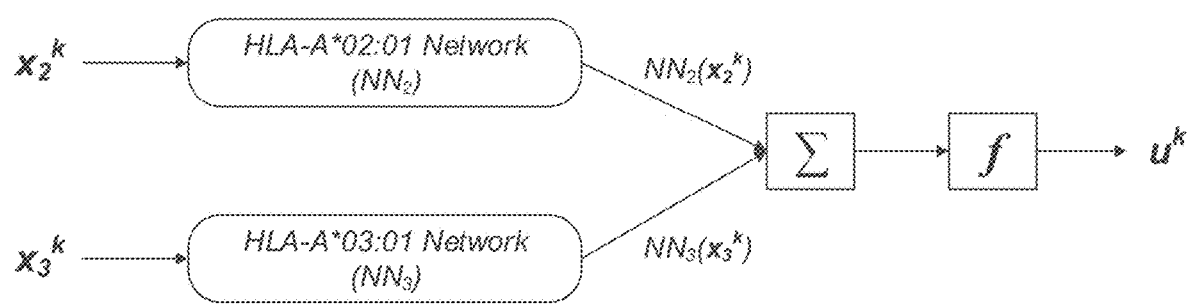
FIG. 9 illustrates generating a presentation likelihood for a peptide in association with MHC alleles using example network models.

FIG. 9 illustrates generating a presentation likelihood for peptide $p^k$ in association with MHC alleles h=2, h=3 using example network models $NN_2(\cdot)$ and $NN_3(\cdot)$. As shown in FIG. 9, the network model $NN_2(\cdot)$ receives the allele-interacting variables $x_2^k$ for MHC allele h=2 and generates the output $NN_2(x_2^k)$ and the network model $NN_3(\cdot)$ receives the allele-interacting variables $x_3^k$ for MHC allele h=3 and generates the output $NN_3(x_3^k)$. The outputs are combined and mapped by function $f(\cdot)$ to generate the estimated presentation likelihood $u_k$.

VIII.C.3. Example 2.2: Function-of-Sums Models with Allele-Noninteracting Variables In one implementation, the training module 316 incorporates allele-noninteracting variables and models the estimated presentation likelihood $u_k$ for peptide $p^k$ by:

$$u_k = Pr(p^k \text{ presented}) = f\left(g_w(w^k;\theta_w) + \sum_{h=1}^{m} a_h^k \cdot g_h(x_h^k;\theta_h)\right), \quad (14)$$

where $w^k$ denotes the encoded allele-noninteracting variables for peptide $p^k$. Specifically, the values for the set of parameters $\theta_h$ for each MHC allele h and the set of parameters $\theta_w$ for allele-noninteracting variables can be determined by minimizing the loss function with respect to $\theta_h$ and $\theta_w$, where i is each instance in the subset S of training data 170 generated from cells expressing single MHC alleles and/or cells expressing multiple MHC alleles. The dependency function $g_w$ may be in the form of any of the dependency functions $g_w$ introduced above in sections VIII.B.3.

Thus, according to equation (14), the presentation likelihood that a peptide sequence $p^k$ will be presented by one or more MHC alleles H can be generated by applying the function $g_h(\cdot)$ to the encoded version of the peptide sequence $p^k$ for each of the MHC alleles H to generate the corresponding dependency score for allele interacting variables for each MHC allele h. The function $g_w(\cdot)$ for the allele noninteracting variables is also applied to the encoded version of the allele noninteracting variables to generate the dependency score for the allele noninteracting variables. The scores are combined, and the combined score is transformed by the transformation function $f(\cdot)$ to generate the presentation likelihood that peptide sequence $p^k$ will be presented by the MHC alleles H.

In the presentation model of equation (14), the number of associated alleles for each peptide $p^k$ can be greater than 1. In other words, more than one element in $a_h^k$ can have values of 1 for the multiple MHC alleles H associated with peptide sequence $p^k$.

As an example, the likelihood that peptide $p^k$ will be presented by MHC alleles h=2, h=3, among m=4 different identified MHC alleles using the affine transformation functions $g_h(\cdot)$ $g_w(\cdot)$ can be generated by:

$$u_k = f(w^k \cdot \theta_w + x_2^k \cdot \theta_2 + x_3^k \cdot \theta_3),$$

where $w^k$ are the identified allele-noninteracting variables for peptide $p^k$, and $\theta_w$ are the set of parameters determined for the allele-noninteracting variables.

As another example, the likelihood that peptide $p^k$ will be presented by MHC alleles h=2, h=3, among m=4 different identified MHC alleles using the network transformation functions $g_h(\cdot)$, $g_w(\cdot)$, can be generated by:

$$u_k = f(NN_w(w^k;\theta_w) + NN_2(x_2^k;\theta_2) + NN_3(x_3^k;\theta_3))$$

where $w^k$ are the identified allele-interacting variables for peptide $p^k$, and $\theta_w$ are the set of parameters determined for allele-noninteracting variables.

Figure 10:
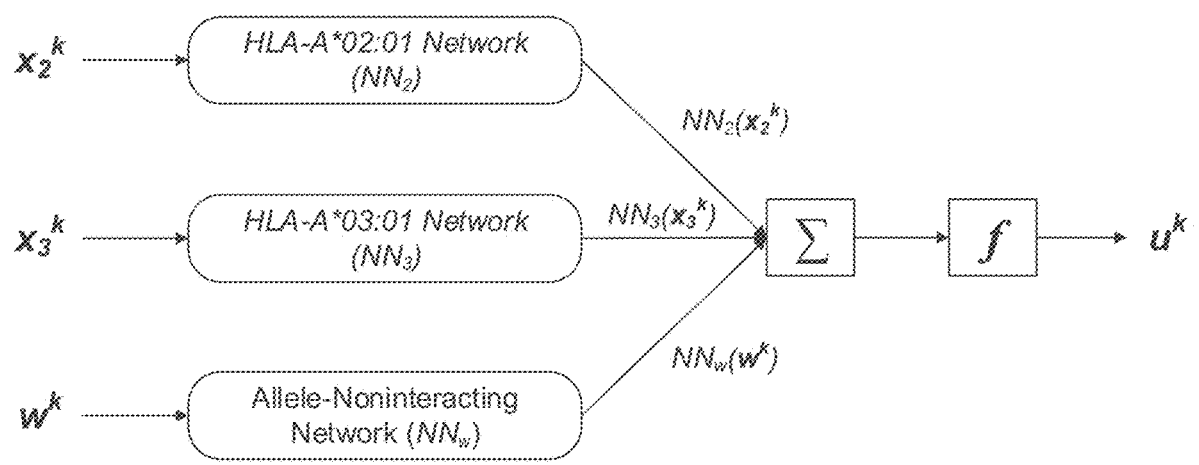
FIG. 10 illustrates generating a presentation likelihood for a peptide in association with MHC alleles using example network models.

FIG. 10 illustrates generating a presentation likelihood for peptide $p^k$ in association with MHC alleles h=2, h=3 using example network models $NN_2(\cdot)$, $NN_3(\cdot)$, and $NN_w(\cdot)$. As shown in FIG. 10, the network model $NN_2(\cdot)$ receives the allele-interacting variables $x_2^k$ for MHC allele h=2 and generates the output $NN_2(x_2^k)$. The network model $NN_3(\cdot)$ receives the allele-interacting variables $x_3^k$ for MHC allele h=3 and generates the output $NN_3(x_3^k)$. The network model $NN_w(\cdot)$ receives the allele-noninteracting variables $w^k$ for peptide $p^k$ and generates the output $NN_w(w^k)$. The outputs are combined and mapped by function $f(\cdot)$ to generate the estimated presentation likelihood $u_k$.

Alternatively, the training module 316 may include allele-noninteracting variables $w^k$ in the prediction by adding the allele-noninteracting variables $w^k$ to the allele-interacting variables $x_h^k$ in equation (15). Thus, the presentation likelihood can be given by:

$$u_k = Pr(p^k \text{ presented}) = f\left(\sum_{h=1}^{m} a_h^k \cdot g_h([x_h^k w^k];\theta_h)\right). \quad (15)$$

VIII.C.4. Example 3.1: Models Using Implicit Per-Allele Likelihoods

In another implementation, the training module 316 models the estimated presentation likelihood $u_k$ for peptide by:

$$u_k = Pr(p_k \text{ presented}) = r(s(v=[a_1^k \cdot u'^1_k(\theta) \ldots a_m^k \cdot u'^m_k(\theta)])), \quad (16)$$

where elements $a_h^k$ are 1 for the multiple MHC alleles h∈H associated with peptide sequence $p^k$, $u'_k^h$ is an implicit per-allele presentation likelihood for MHC allele h, vector v is a vector in which element $v_h$ corresponds to $a_h^k \cdot u'_k{}^h$, $s(\bullet)$ is a function mapping the elements of v, and $r(\bullet)$ is a clipping function that clips the value of the input into a given range. As described below in more detail, $s(\bullet)$ may be the summation function or the second-order function, but it is appreciated that in other embodiments, $s(\bullet)$ can be any function such as the maximum function. The values for the set of parameters θ for the implicit per-allele likelihoods can be determined by minimizing the loss function with respect to θ, where i is each instance in the subset S of training data 170 generated from cells expressing single MHC alleles and/or cells expressing multiple MHC alleles.

The presentation likelihood in the presentation model of equation (17) is modeled as a function of implicit per-allele presentation likelihoods $u'_k{}^h$ that each correspond to the likelihood peptide $p^k$ will be presented by an individual MHC allele h. The implicit per-allele likelihood is distinct from the per-allele presentation likelihood of section VIII.B in that the parameters for implicit per-allele likelihoods can be learned from multiple allele settings, in which direct association between a presented peptide and the corresponding MHC allele is unknown, in addition to single-allele settings. Thus, in a multiple-allele setting, the presentation model can estimate not only whether peptide $p^k$ will be presented by a set of MHC alleles H as a whole, but can also provide individual likelihoods $u'_k{}^{h \in H}$ that indicate which MHC allele h most likely presented peptide $p^k$. An advantage of this is that the presentation model can generate the implicit likelihoods without training data for cells expressing single MHC alleles.

In one particular implementation referred throughout the remainder of the specification, $r(\bullet)$ is a function having the range [0, 1]. For example, $r(\bullet)$ may be the clip function:

$$r(z)=\min(\max(z,0),1),$$

where the minimum value between z and 1 is chosen as the presentation likelihood $u_k$. In another implementation, $r(\bullet)$ is the hyperbolic tangent function given by:

$$r(z)=\tan h(z)$$

when the values for the domain z is equal to or greater than 0.

VIII.C.5. Example 3.2: Sum-of-Functions Model

In one particular implementation, $s(\bullet)$ is a summation function, and the presentation likelihood is given by summing the implicit per-allele presentation likelihoods:

$$u_k = Pr(p^k \text{ presented}) = r\left(\sum_{h=1}^{m} a_h^k \cdot u'_k{}^h(\theta)\right). \quad (17)$$

In one implementation, the implicit per-allele presentation likelihood for MHC allele h is generated by:

$$u'_k{}^h = f(g_h(x^k_h; \theta_h)), \quad (18)$$

such that the presentation likelihood is estimated by:

$$u_k = Pr(p^k \text{ presented}) = r\left(\sum_{h=1}^{m} a_h^k \cdot f(g_h(x^k_h; \theta_h))\right) \quad (19)$$

According to equation (19), the presentation likelihood that a peptide sequence $p^k$ will be presented by one or more MHC alleles H can be generated by applying the function $g_h(\bullet)$ to the encoded version of the peptide sequence $p^k$ for each of the MHC alleles H to generate the corresponding dependency score for allele interacting variables. Each dependency score is first transformed by the function $f(\bullet)$ to generate implicit per-allele presentation likelihoods $u'_k{}^h$. The per-allele likelihoods $u'_k{}^h$ are combined, and the clipping function may be applied to the combined likelihoods to clip the values into a range [0, 1] to generate the presentation likelihood that peptide sequence $p^k$ will be presented by the set of MHC alleles H. The dependency function $g_h$ may be in the form of any of the dependency functions $g_h$ introduced above in sections VIII.B.1.

As an example, the likelihood that peptide $p^k$ will be presented by MHC alleles h=2, h=3, among m=4 different identified MHC alleles using the affine transformation functions $g_h(\bullet)$, can be generated by:

$$u_k = r(f(x^k_2 \cdot \theta_2) + f(x^k_3 \cdot \theta_3)),$$

where $x_2^k$, $x_3^k$ are the identified allele-interacting variables for MHC alleles h=2, h=3, and $\theta_2$, $\theta_3$ are the set of parameters determined for MHC alleles h=2, h=3.

As another example, the likelihood that peptide $p^k$ will be presented by MHC alleles h=2, h=3, among m=4 different identified MHC alleles using the network transformation functions $g_h(\bullet)$, $g_w(\bullet)$, can be generated by:

$$u_k = r(f(NN_2(x^k_2; \theta_2)) + f(NN^3(x^k_3; \theta_3))),$$

where $NN_2(\bullet)$, $NN_3(\bullet)$ are the identified network models for MHC alleles h=2, h=3, and $\theta_2$, $\theta_3$ are the set of parameters determined for MHC alleles h=2, h=3.

Figure 11:
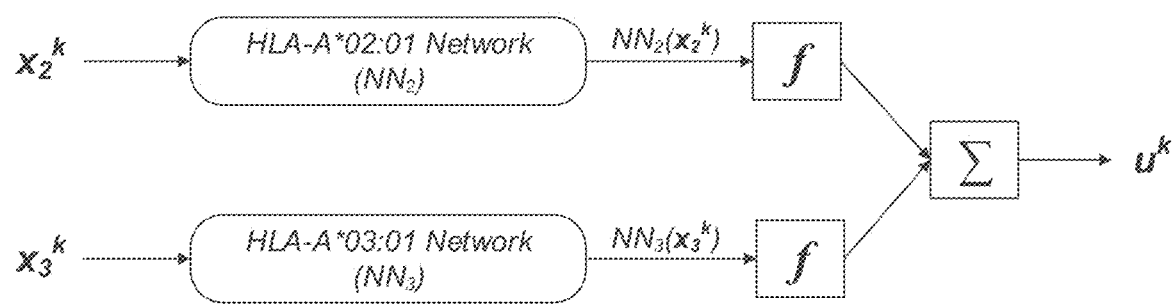
FIG. 11 illustrates generating a presentation likelihood for a peptide in association with MHC alleles using example network models.

FIG. 11 illustrates generating a presentation likelihood for peptide $p^k$ in association with MHC alleles h=2, h=3 using example network models $NN_2(\bullet)$ and $NN_3(\bullet)$. As shown in FIG. 9, the network model $NN_2(\bullet)$ receives the allele-interacting variables $x_2^k$ for MHC allele h=2 and generates the output $NN_2(x_2^k)$ and the network model $NN_3(\bullet)$ receives the allele-interacting variables $x_3^k$ for MHC allele h=3 and generates the output $NN_3(x_3^k)$. Each output is mapped by function $f(\bullet)$ and combined to generate the estimated presentation likelihood $u_k$.

In another implementation, when the predictions are made for the log of mass spectrometry ion currents, $r(\bullet)$ is the log function and $f(\bullet)$ is the exponential function.

VIII.C.6. Example 3.3: Sum-of-Functions Models
with Allele-Noninteracting Variables In one implementation, the implicit per-allele presentation likelihood for MHC allele h is generated by:

$$u_k{}'^h = f(g_h(x^k_h; \theta_h) + g_w(w^k; \theta_w)), \quad (20)$$

such that the presentation likelihood is generated by:

$$u_k = Pr(p^k \text{ presented}) = r\left(\sum_{h=1}^{m} a_h^k \cdot f(g_w(w^k; \theta_w) + g_h(x^k_h; \theta_h))\right), \quad (21)$$

to incorporate the impact of allele noninteracting variables on peptide presentation.

According to equation (21), the presentation likelihood that a peptide sequence $p^k$ will be presented by one or more MHC alleles H can be generated by applying the function $g_h(\bullet)$ to the encoded version of the peptide sequence $p^k$ for each of the MHC alleles H to generate the corresponding dependency score for allele interacting variables for each MHC allele h. The function $g_w(\bullet)$ for the allele noninteracting variables is also applied to the encoded version of the allele noninteracting variables to generate the dependency score for the allele noninteracting variables. The score for the allele noninteracting variables are combined to each of the dependency scores for the allele interacting variables. Each of the combined scores are transformed by the function $f(\bullet)$ to generate the implicit per-allele presentation likelihoods. The implicit likelihoods are combined, and the clipping function may be applied to the combined outputs to clip the values into a range [0,1] to generate the presentation likelihood that peptide sequence $p^k$ will be presented by the MHC alleles H. The dependency function $g_w$ may be in the form of any of the dependency functions $g_w$ introduced above in sections VIII.B.3.

As an example, the likelihood that peptide $p_k$ will be presented by MHC alleles h=2, h=3, among m=4 different identified MHC alleles using the affine transformation functions $g_h(\bullet)$, $g_w(\bullet)$ can be generated by:

$$u_k = r(f(w^k \cdot \theta_w + x^k_2 \cdot \theta_2) + f(w^k \cdot \theta_w + x^k_3 \cdot \theta_3)),$$

where $w^k$ are the identified allele-noninteracting variables for peptide $p^k$, and $\theta_w$ are the set of parameters determined for the allele-noninteracting variables.

As another example, the likelihood that peptide $p^k$ will be presented by MHC alleles h=2, h=3, among m=4 different identified MHC alleles using the network transformation functions $g_h(\bullet)$, $g_w(\bullet)$, can be generated by:

$$u_k = r(f(NN_w(w^k;\theta_w) + NN_2(x^k_2;\theta_2)) + f(NN_w(w^k;\theta_w) + NN_3(x^k_3;\theta_3)))$$

where $w^k$ are the identified allele-interacting variables for peptide $p^k$, and $\theta_w$ are the set of parameters determined for allele-noninteracting variables.

Figure 12:
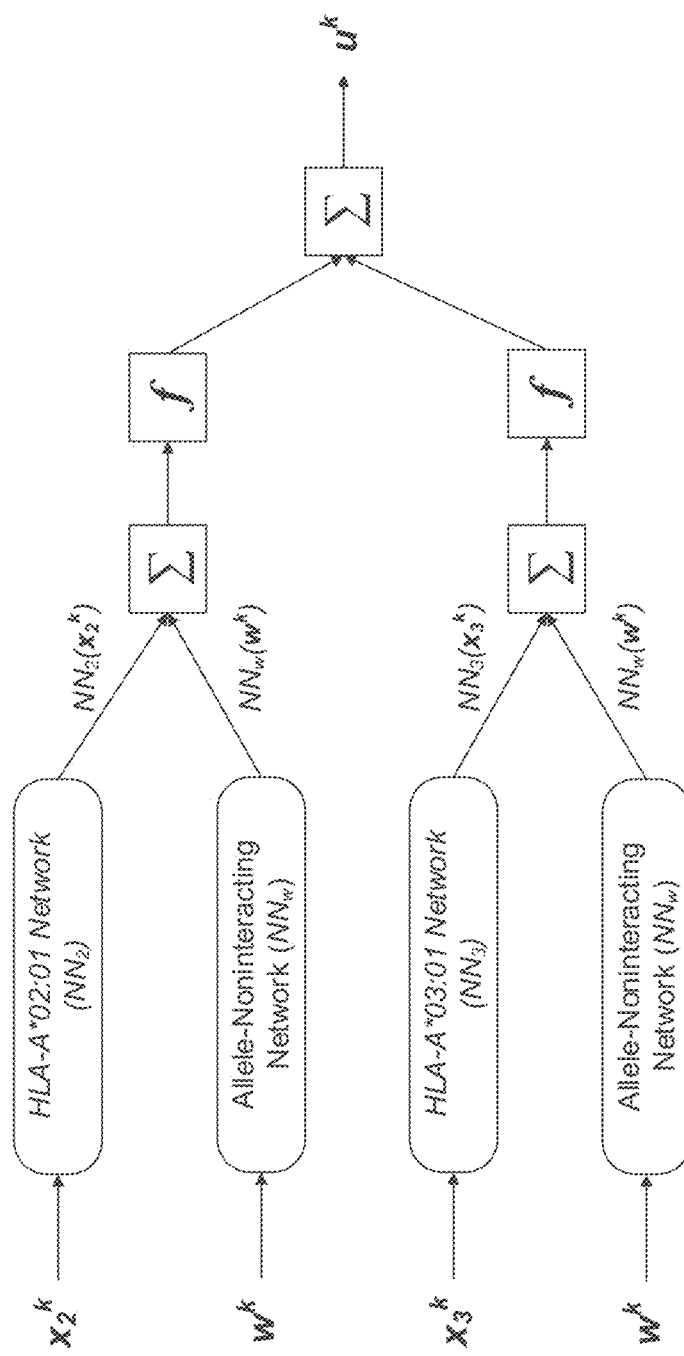
FIG. 12 illustrates generating a presentation likelihood for a peptide in association with MHC alleles using example network models.

FIG. 12 illustrates generating a presentation likelihood for peptide $p^k$ in association with MHC alleles h=2, h=3 using example network models $NN_2(\bullet)$, $NN_3(\bullet)$, and $NN_w(\bullet)$. As shown in FIG. 12, the network model $NN_2(\bullet)$ receives the allele-interacting variables $x_2^k$ for MHC allele h=2 and generates the output $NN_2(x_2^k)$. The network model $NN_w(\bullet)$ receives the allele-noninteracting variables $w^k$ for peptide $p^k$ and generates the output $NN_w(w^k)$. The outputs are combined and mapped by function $f(\bullet)$. The network model $NN_3(\bullet)$ receives the allele-interacting variables $x_3^k$ for MHC allele h=3 and generates the output $NN_3(x_3^k)$, which is again combined with the output $NN_w(w^k)$ of the same network model $NN_w(\bullet)$ and mapped by function $f(\bullet)$. Both outputs are combined to generate the estimated presentation likelihood $u_k$.

In another implementation, the implicit per-allele presentation likelihood for MHC allele h is generated by:

$$u_k'^h = f(g_h([x^k_h w^k];\theta_h)). \quad (22)$$

such that the presentation likelihood is generated by:

$$u_k = Pr(p^k \text{ presented}) = r\left(\sum_{h=1}^{m} a_h^k \cdot f(g_h([x^k_h w^k]; \theta_h))\right).$$

VIII.C.7. Example 4: Second Order Models

In one implementation, $s(\bullet)$ is a second-order function, and the estimated presentation likelihood $u_k$ for peptide $p^k$ is given by:

$$u_k = Pr(p^k \text{ presented}) = \sum_{h=1}^{m} a_h^k \cdot u_k'^h(\theta) - \sum_{h=1}^{m}\sum_{j<h} a_h^k \cdot a_j^k \cdot u_k'^h(\theta) \cdot u_k'^j(\theta) \quad (23)$$

where elements $u'^h_k$ are the implicit per-allele presentation likelihood for MHC allele h. The values for the set of parameters $\theta$ for the implicit per-allele likelihoods can be determined by minimizing the loss function with respect to $\theta$, where i is each instance in the subset S of training data 170 generated from cells expressing single MHC alleles and/or cells expressing multiple MHC alleles. The implicit per-allele presentation likelihoods may be in any form shown in equations (18), (20), and (22) described above.

In one aspect, the model of equation (23) may imply that there exists a possibility peptide $p^k$ will be presented by two MHC alleles simultaneously, in which the presentation by two HLA alleles is statistically independent.

According to equation (23), the presentation likelihood that a peptide sequence $p^k$ will be presented by one or more MHC alleles H can be generated by combining the implicit per-allele presentation likelihoods and subtracting the likelihood that each pair of MHC alleles will simultaneously present the peptide $p^k$ from the summation to generate the presentation likelihood that peptide sequence $p^k$ will be presented by the MHC alleles H.

As an example, the likelihood that peptide $p^k$ will be presented by HLA alleles h=2, h=3, among m=4 different identified HLA alleles using the affine transformation functions $g_h(\bullet)$, can be generated by:

$$u_k = f(x^k_w \cdot \theta_2) + \theta(x^k_3 \cdot \theta_3) - f(x^k_w \cdot \theta_2) \cdot \theta(x^k_3 \cdot \theta_3),$$

where $x_2^k$, $x_3^k$ are the identified allele-interacting variables for HLA alleles h=2, h=3, and $\theta_2$, $\theta_3$ are the set of parameters determined for HLA alleles h=2, h=3.

As another example, the likelihood that peptide $p^k$ will be presented by HLA alleles h=2, h=3, among m=4 different identified HLA alleles using the network transformation functions $g_h(\bullet)$, $g_w(\bullet)$, can be generated by:

$$u_k = f(NN_2(x^k_2;\theta_2)) + f(NN_3(x^k_3;\theta_3)) - f(NN_2(x^k_2;\theta_2)) \cdot f(NN_3(x^k_3;\theta_3)),$$

where $NN_2(\bullet)$, $NN_3(\bullet)$ are the identified network models for HLA alleles h=2, h=3, and $\theta_2$, $\theta_3$ are the set of parameters determined for HLA alleles h=2, h=3.

IX. Example 5: Prediction Module

The prediction module 320 receives sequence data and selects candidate neoantigens in the sequence data using the presentation models. Specifically, the sequence data may be DNA sequences, RNA sequences, and/or protein sequences extracted from tumor tissue cells of patients. The prediction module 320 processes the sequence data into a plurality of peptide sequences $p^k$ having 8-15 amino acids for MHC-I or 6-30 amino acids for MHC-II. For example, the prediction module 320 may process the given sequence "IEFROE-IFJEF (SEQ ID NO: 16)" into three peptide sequences having 9 amino acids "IEFROEIFJ (SEQ ID NO: 17)," "EFROEIFJE (SEQ ID NO: 18)," and "FROEIFJEF (SEQ ID NO: 19)." In one embodiment, the prediction module 320 may identify candidate neoantigens that are mutated peptide sequences by comparing sequence data extracted from normal tissue cells of a patient with the sequence data extracted from tumor tissue cells of the patient to identify portions containing one or more mutations.

The prediction module 320 applies one or more of the presentation models to the processed peptide sequences to estimate presentation likelihoods of the peptide sequences. Specifically, the prediction module 320 may select one or more candidate neoantigen peptide sequences that are likely to be presented on tumor HLA molecules by applying the presentation models to the candidate neoantigens. In one implementation, the prediction module 320 selects candidate neoantigen sequences that have estimated presentation likelihoods above a predetermined threshold. In another implementation, the presentation model selects the v candidate neoantigen sequences that have the highest estimated presentation likelihoods (where v is generally the maximum number of epitopes that can be delivered in a vaccine). A vaccine including the selected candidate neoantigens for a given patient can be injected into the patient to induce immune responses.

X. Example 6: Patient Selection Module

The patient selection module 324 selects a subset of patients for vaccine treatment and/or T-cell therapy based on whether the patients satisfy inclusion criteria. In one embodiment, the inclusion criteria is determined based on the presentation likelihoods of patient neoantigen candidates as generated by the presentation models. By adjusting the inclusion criteria, the patient selection module 324 can adjust the number of patients that will receive the vaccine and/or T-cell therapy based on his or her presentation likelihoods of neoantigen candidates. Specifically, a stringent inclusion criteria results in a fewer number of patients that will be treated with the vaccine and/or T-cell therapy, but may result in a higher proportion of vaccine and/or T-cell therapy-treated patients that receive effective treatment (e.g., 1 or more tumor-specific neoantigens (TSNA) and/or 1 or more neoantigen-responsive T-cells). On the other hand, a lenient inclusion criteria results in a higher number of patients that will be treated with the vaccine and/or with T-cell therapy, but may result in a lower proportion of vaccine and/or T-cell therapy-treated patients that receive effective treatment. The patient selection module 324 modifies the inclusion criteria based on the desired balance between target proportion of patients that will receive treatment and proportion of patients that receive effective treatment.

In some embodiments, inclusion criteria for selection of patients to receive vaccine treatment are the same as inclusion criteria for selection of patients to receive T-cell therapy. However, in alternative embodiments, inclusion criteria for selection of patients to receive vaccine treatment may differ from inclusion criteria for selection of patients to receive T-cell therapy. The following Sections X.A and X.B discuss inclusion criteria for selection of patients to receive vaccine treatment and inclusion criteria for selection of patients to receive T-cell therapy, respectively.

X.A. Patient Selection for Vaccine Treatment

In one embodiment, patients are associated with a corresponding treatment subset of v neoantigen candidates that can potentially be included in customized vaccines for the patients with vaccine capacity v. In one embodiment, the treatment subset for a patient are the neoantigen candidates with the highest presentation likelihoods as determined by the presentation models. For example, if a vaccine can include v=20 epitopes, the vaccine can include the treatment subset of each patient that have the highest presentation likelihoods as determined by the presentation model. However, it is appreciated that in other embodiments, the treatment subset for a patient can be determined based on other methods. For example, the treatment subset for a patient may be randomly selected from the set of neoantigen candidates for the patient, or may be determined in part based on current state-of-the-art models that model binding affinity or stability of peptide sequences, or some combination of factors that include presentation likelihoods from the presentation models and affinity or stability information regarding those peptide sequences.

In one embodiment, the patient selection module 324 determines that a patient satisfies the inclusion criteria if the tumor mutation burden of the patient is equal to or above a minimum mutation burden. The tumor mutation burden (TMB) of a patient indicates the total number of nonsynonymous mutations in the tumor exome. In one implementation, the patient selection module 324 may select a patient for vaccine treatment if the absolute number of TMB of the patient is equal to or above a predetermined threshold. In another implementation, the patient selection module 324 may select a patient for vaccine treatment if the TMB of the patient is within a threshold percentile among the TMB's determined for the set of patients.

In another embodiment, the patient selection module 324 determines that a patient satisfies the inclusion criteria if a utility score of the patient based on the treatment subset of the patient is equal to or above a minimum utility score. In one implementation, the utility score is a measure of the estimated number of presented neoantigens from the treatment subset.

The estimated number of presented neoantigens may be predicted by modeling neoantigen presentation as a random variable of one or more probability distributions. In one implementation, the utility score for patient i is the expected number of presented neoantigen candidates from the treatment subset, or some function thereof. As an example, the presentation of each neoantigen can be modeled as a Bernoulli random variable, in which the probability of presentation (success) is given by the presentation likelihood of the neoantigen candidate. Specifically, for a treatment subset $S_i$ of v neoantigen candidates $p^{i1}, p^{i2}, \ldots, p^{iv}$ each having the highest presentation likelihoods $u_{i1}, u_{i2}, \ldots, u_{iv}$, presentation of neoantigen candidate $p_{ij}$ is given by random variable $A_{ij}$, in which:

$$P(A_{ij}=1)=u_{ij}, P(A_{ij}=0)=1-u_{ij}. \qquad (24)$$

The expected number of presented neoantigens is given by the summation of the presentation likelihoods for each neoantigen candidate. In other words, the utility score for patient i can be expressed as:

$$util_i(S_i) = \mathbb{E}\left[\sum_{j=1}^{v} A_{ij}\right] = \sum_{j=1}^{v} u_{ij}. \qquad (25)$$

The patient selection module 324 selects a subset of patients having utility scores equal to or above a minimum utility for vaccine treatment.

In another implementation, the utility score for patient i is the probability that at least a threshold number of neoantigens k will be presented. In one instance, the number of presented neoantigens in the treatment subset $S_i$ of neoantigen candidates is modeled as a Poisson Binomial random variable, in which the probabilities of presentation (successes) are given by the presentation likelihoods of each of the epitopes. Specifically, the number of presented neoantigens for patient i can be given by random variable $N_i$, in which:

$$N_i = \sum_{j=1}^{v} A_{ij} \sim PBD(u_{i1}, u_{i2}, \ldots, u_{iv}). \tag{26}$$

where $PBD(\cdot)$ denotes the Poisson Binomial distribution. The probability that at least a threshold number of neoantigens k will be presented is given by the summation of the probabilities that the number of presented neoantigens $N_i$ will be equal to or above k. In other words, the utility score for patient i can be expressed as:

$$util_i(Si) = \mathbb{P}[N_i \geq k] = \sum_{m=1}^{k} \mathbb{P}[N_i = m]. \tag{27}$$

The patient selection module 324 selects a subset of patients having the utility score equal to or above a minimum utility for vaccine treatment.

In another implementation, the utility score for patient i is the number of neoantigens in the treatment subset $S_i$ of neoantigen candidates having binding affinity or predicted binding affinity below a fixed threshold (e.g., 500 nM) to one or more of the patient's HLA alleles. In one instance, the fixed threshold is a range from 1000 nM to 10 nM. Optionally, the utility score may count only those neoantigens detected as expressed via RNA-seq.

In another implementation, the utility score for patient i is the number of neoantigens in the treatment subset $S_i$ of neoantigen candidates having binding affinity to one or more of that patient's HLA alleles at or below a threshold percentile of binding affinities for random peptides to that HLA allele. In one instance, the threshold percentile is a range from the $10^{th}$ percentile to the $0.1^{th}$ percentile. Optionally, the utility score may count only those neoantigens detected as expressed via RNA-seq.

It is appreciated that the examples of generating utility scores illustrated with respect to equations (25) and (27) are merely illustrative, and the patient selection module 324 may use other statistics or probability distributions to generate the utility scores.

X.B. Patient Selection for T-Cell Therapy

In another embodiment, instead of or in addition to receiving vaccine treatment, patients can receive T-cell therapy. Like vaccine treatment, in embodiments in which a patient receives T-cell therapy, the patient may be associated with a corresponding treatment subset of v neoantigen candidates as described above. This treatment subset of v neoantigen candidates can be used for in vitro identification of T cells from the patient that are responsive to one or more of the v neoantigen candidates. These identified T cells can then be expanded and infused into the patient for customized T-cell therapy.

Patients may be selected to receive T-cell therapy at two different time points. The first point is after the treatment subset of v neoantigen candidates have been predicted for a patient using the models, but before in vitro screening for T cells that are specific to the predicted treatment subset of v neoantigen candidates. The second point is after in vitro screening for T cells that are specific to the predicted treatment subset of v neoantigen candidates.

First, patients may be selected to receive T-cell therapy after the treatment subset of v neoantigen candidates have been predicted for the patient, but before in vitro identification of T-cells from the patient that are specific to the predicted subset of v neoantigen candidates. Specifically, because in vitro screening for neoantigen-specific T-cells from the patient can be expensive, it may be desirable to only select patients to screen for neoantigen-specific T-cells if the patients are likely to have neoantigen-specific T-cells. To select patients before the in vitro T-cell screening step, the same criteria that are used to select patients for vaccine treatment may be used. Specifically, in some embodiments, the patient selection module 324 may select a patient to receive T-cell therapy if the tumor mutation burden of the patient is equal to or above a minimum mutation burden as described above. In another embodiment, the patient selection module 324 may select a patient to receive T-cell therapy if a utility score of the patient based on the treatment subset of v neoantigen candidates for the patient is equal to or above a minimum utility score, as described above.

Second, in addition to or instead of selecting patients to receive T-cell therapy before in vitro identification of T-cells from the patient that are specific to the predicted subset of v neoantigen candidates, patients may also be selected to receive T-cell therapy after in vitro identification of T-cells that are specific to the predicted treatment subset of v neoantigen candidates. Specifically, a patient may be selected to receive T-cell therapy if at least a threshold quantity of neoantigen-specific TCRs are identified for the patient during the in vitro screening of the patient's T-cells for neoantigen recognition. For example, a patient may be selected to receive T-cell therapy only if at least two neoantigen-specific TCRs are identified for the patient, or only if neoantigen-specific TCRs are identified for two distinct neoantigens.

In another embodiment, a patient may be selected to receive T-cell therapy only if at least a threshold quantity of neoantigens of the treatment subset of v neoantigen candidates for the patient are recognized by the patient's TCRs. For example, a patient may be selected to receive T-cell therapy only if at least one neoantigen of the treatment subset of v neoantigen candidates for the patient are recognized by the patient's TCRs. In further embodiments, a patient may be selected to receive T-cell therapy only if at least a threshold quantity of TCRs for the patient are identified as neoantigen-specific to neoantigen peptides of a particular HLA restriction class. For example, a patient may be selected to receive T-cell therapy only if at least one TCR for the patient is identified as neoantigen-specific HLA class I restricted neoantigen peptides.

In even further embodiments, a patient may be selected to receive T-cell therapy only if at least a threshold quantity of neoantigen peptides of a particular HLA restriction class are recognized by the patient's TCRs. For example, a patient may be selected to receive T-cell therapy only if at least one HLA class I restricted neoantigen peptide is recognized by the patient's TCRs. As another example, a patient may be selected to receive T-cell therapy only if at least two HLA class II restricted neoantigen peptides are recognized by the patient's TCRs. Any combination of the above criteria may also be used for selecting patients to receive T-cell therapy after in vitro identification of T-cells that are specific to the predicted treatment subset of v neoantigen candidates for the patient.

XI. Example 7: Experimentation Results Showing Example Patient Selection Performance The validity of patient selection methods described in Section X are tested by performing patient selection on a set of simulated patients each associated with a test set of simulated neoantigen candidates, in which a subset of simulated neoantigens is known to be presented in mass spectrometry data. Specifically, each simulated neoantigen candidate in the test set is associated with a label indicating whether the neoantigen was presented in a multiple-allele JY cell line HLA-A*02:01 and HLA-B*07:02 mass spectrometry data set from the Bassani-Sternberg data set (data set "D1") (data can be found at www.ebi.ac.uk/pride/archive/projects/PXD0000394). As described in more detail below in conjunction with FIG. 13A, a number of neoantigen candidates for the simulated patients are sampled from the human proteome based on the known frequency distribution of mutation burden in non-small cell lung cancer (NSCLC) patients.

Per-allele presentation models for the same HLA alleles are trained using a training set that is a subset of the single-allele HLA-A*02:01 and HLA-B*07:02 mass spectrometry data from the IEDB data set (data set "D2") (data can be found at http://www.iedb.org/doc/mhc_ligand_full.zip). Specifically, the presentation model for each allele was the per-allele model shown in equation (8) that incorporated N-terminal and C-terminal flanking sequences as allele-noninteracting variables, with network dependency functions $g_h(\cdot)$ and $g_w(\cdot)$ and the expit function $f(\cdot)$. The presentation model for allele HLA-A*02:01 generates a presentation likelihood that a given peptide will be presented on allele HLA-A*02:01, given the peptide sequence as an allele-interacting variable, and the N-terminal and C-terminal flanking sequences as allele-noninteracting variables. The presentation model for allele HLA-B*07:02 generates a presentation likelihood that a given peptide will be presented on allele HLA-B*07:02, given the peptide sequence as an allele-interacting variable, and the N-terminal and C-terminal flanking sequences as allele-noninteracting variables.

As laid out in the following examples and with reference to FIGS. 13A-13E, various models, such as the trained presentation models and current state-of-the-art models for peptide binding prediction, are applied to the test set of neoantigen candidates for each simulated patient to identify different treatment subsets for patients based on the predictions. Patients that satisfy inclusion criteria are selected for vaccine treatment, and are associated with customized vaccines that include epitopes in the treatment subsets of the patients. The size of the treatment subsets are varied according to different vaccine capacities. No overlap is introduced between the training set used to train the presentation model and the test set of simulated neoantigen candidates.

In the following examples, the proportion of selected patients having at least a certain number of presented neoantigens among the epitopes included in the vaccines are analyzed. This statistic indicates the effectiveness of the simulated vaccines to deliver potential neoantigens that will elicit immune responses in patients. Specifically, a simulated neoantigen in a test set is presented if the neoantigen is presented in the mass spectrometry data set D2. A high proportion of patients with presented neoantigens indicate potential for successful treatment via neoantigen vaccines by inducing immune responses.

Figure 13A:
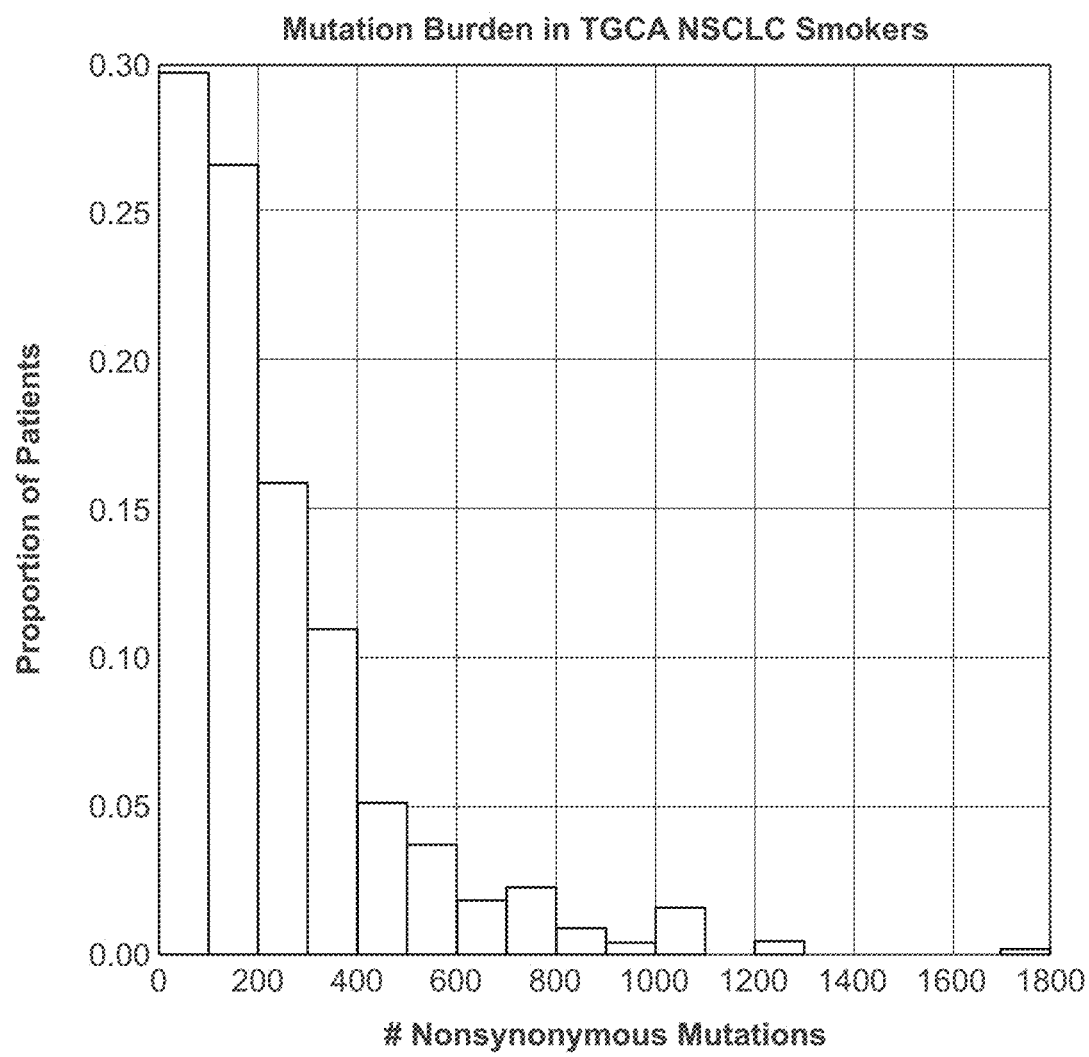
FIG. 13A illustrates a sample frequency distribution of mutation burden in NSCLC patients.

XI.A. Example 7A: Frequency Distribution of Mutation Burden for NSCLC Cancer Patients FIG. 13A illustrates a sample frequency distribution of mutation burden in NSCLC patients. Mutation burden and mutations in different tumor types, including NSCLC, can be found, for example, at the cancer genome atlas (TCGA) (https://cancergenome.nih.gov). The x-axis represents the number of non-synonymous mutations in each patient, and the y-axis represents the proportion of sample patients that have the given number of non-synonymous mutations. The sample frequency distribution in FIG. 13A shows a range of 3-1786 mutations, in which 30% of the patients have fewer than 100 mutations. Although not shown in FIG. 13A, research indicates that mutation burden is higher in smokers compared to that of non-smokers, and that mutation burden may be a strong indicator of neoantigen load in patients.

As introduced at the beginning of Section XI above, each of a number of simulated patients are associated with a test set of neoantigen candidates. The test set for each patient is generated by sampling a mutation burden $m_i$ from the frequency distribution shown in FIG. 13A for each patient. For each mutation, a 21-mer peptide sequence from the human proteome is randomly selected to represent a simulated mutated sequence. A test set of neoantigen candidate sequences are generated for patient i by identifying each (8, 9, 10, 11)-mer peptide sequence spanning the mutation in the 21-mer. Each neoantigen candidate is associated with a label indicating whether the neoantigen candidate sequence was present in the mass spectrometry D1 data set. For example, neoantigen candidate sequences present in data set D1 may be associated with a label "1," while sequences not present in data set D1 may be associated with a label "0." As described in more detail below, FIGS. 13B through 13E illustrate experimental results on patient selection based on presented neoantigens of the patients in the test set.

Figure 13B:
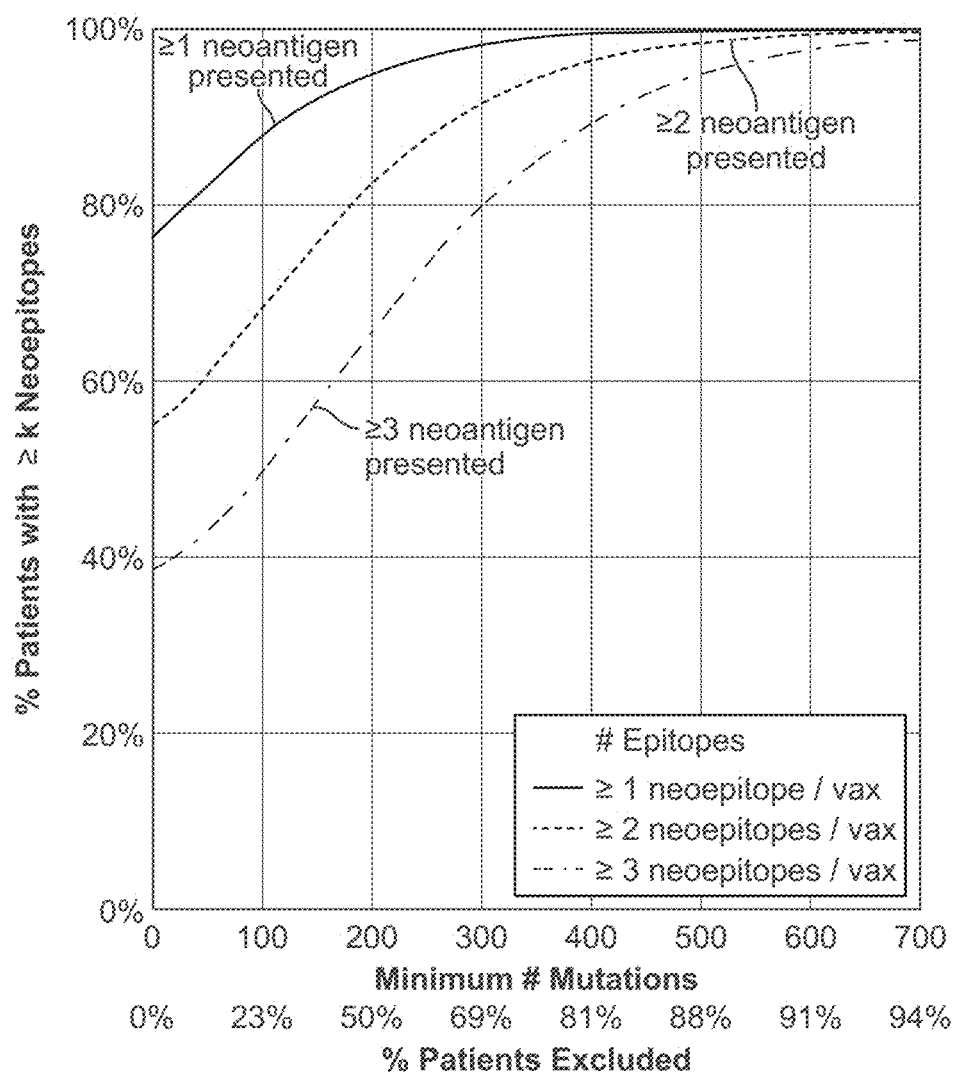
FIG. 13B illustrates the number of presented neoantigens in simulated vaccines for patients selected based on an inclusion criteria of whether the patients satisfy a minimum mutation burden, in accordance with an embodiment.

XI.B. Example 7B: Proportion of Selected Patients with Neoantigen Presentation Based on Mutation Burden Inclusion Criteria FIG. 13B illustrates the number of presented neoantigens in simulated vaccines for patients selected based on an inclusion criteria of whether the patients satisfy a minimum mutation burden. The proportion of selected patients that have at least a certain number of presented neoantigens in the corresponding test is identified.

In FIG. 13B, the x-axis indicates the proportion of patients excluded from vaccine treatment based on the minimum mutation burden, as indicated by the label "minimum # of mutations." For example, a data point at 200 "minimum # of mutations" indicates that the patient selection module 324 selected only the subset of simulated patients having a mutation burden of at least 200 mutations. As another example, a data point at 300 "minimum # of mutations" indicates that the patient selection module 324 selected a lower proportion of simulated patients having at least 300 mutations. The y-axis indicates the proportion of selected patients that are associated with at least a certain number of presented neoantigens in the test set without any vaccine capacity v. Specifically, the top plot shows the proportion of selected patients that present at least 1 neoantigen, the middle plot shows the proportion of selected patients that present at least 2 neoantigens, and the bottom plot shows the proportion of selected patients that present at least 3 neoantigens.

As indicated in FIG. 13B, the proportion of selected patients with presented neoantigens increases significantly with higher mutation burden. This indicates that mutation burden as an inclusion criteria can be effective in selecting patients for whom neoantigen vaccines are more likely to induce successful immune responses.

Figure 13C:
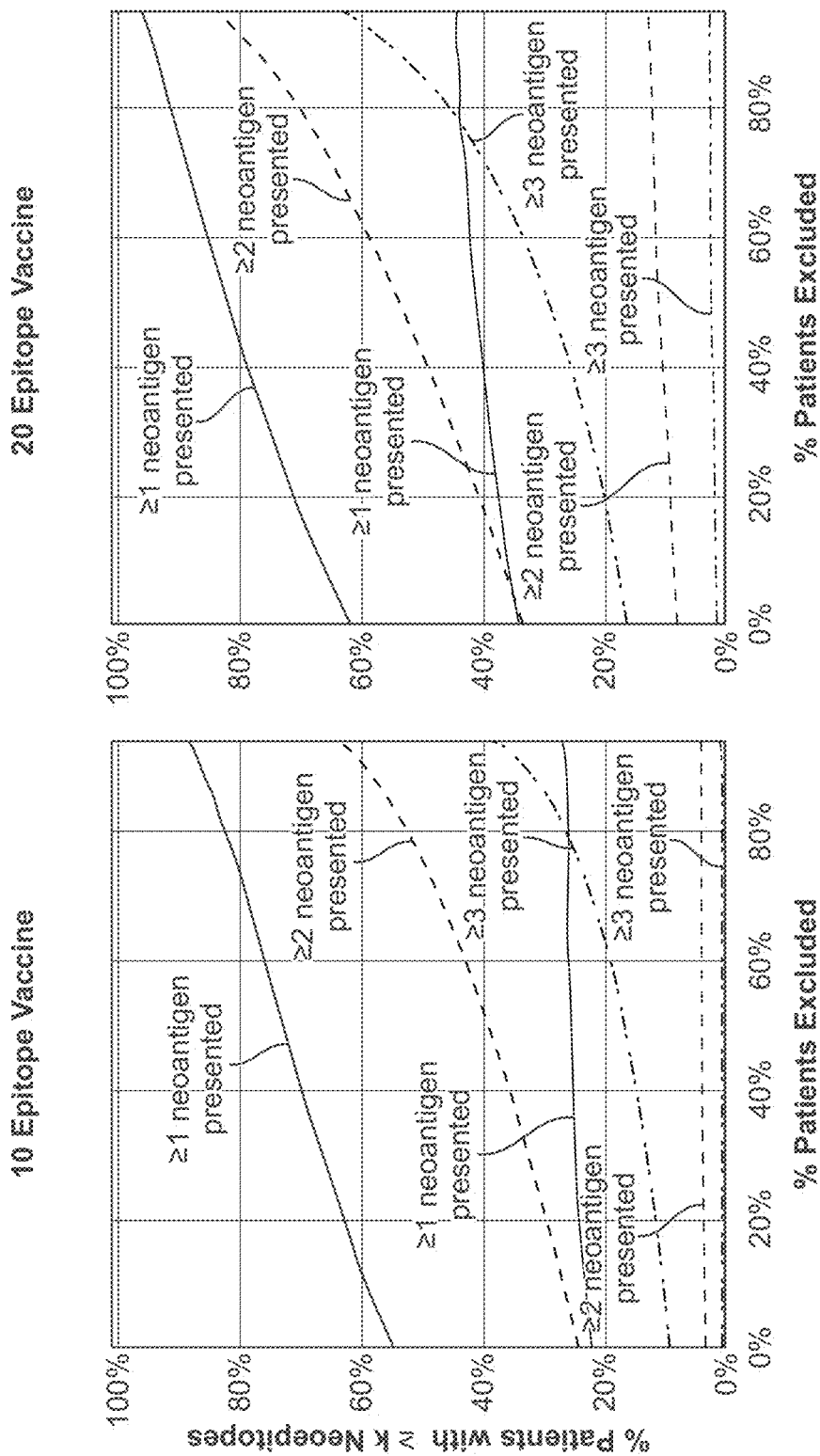
FIG. 13C compares the number of presented neoantigens in simulated vaccines between selected patients associated with vaccines including treatment subsets identified based on presentation models and selected patients associated with vaccines including treatment subsets identified through current state-of-the-art models, in accordance with an embodiment.

XI.C. Example 7C: Comparison of Neoantigen Presentation for Vaccines Identified by Presentation Models Vs. State-of-the-Art Models FIG. 13C compares the number of presented neoantigens in simulated vaccines between selected patients associated with vaccines including treatment subsets identified based on presentation models and selected patients associated with vaccines including treatment subsets identified through current state-of-the-art models. The left plot assumes limited vaccine capacity v=10, and the right plot assumes limited vaccine capacity v=20. The patients are selected based on utility scores indicating expected number of presented neoantigens.

In FIG. 13C, the solid lines indicate patients associated with vaccines including treatment subsets identified based on presentation models for alleles HLA-A*02:01 and HLA-B*07:02. The treatment subset for each patient is identified by applying each of the presentation models to the sequences in the test set, and identifying the v neoantigen candidates that have the highest presentation likelihoods. The dotted lines indicate patients associated with vaccines including treatment subsets identified based on current state-of-the-art models NETMHCpan for the single allele HLA-A*02:01. Implementation details for NETMHCpan is provided in detail at http://www.cbs.dtu.dk/services/NetMHCpan. The treatment subset for each patient is identified by applying the NETMHCpan model to the sequences in the test set, and identifying the v neoantigen candidates that have the highest estimated binding affinities. The x-axis of both plots indicates the proportion of patients excluded from vaccine treatment based on expectation utility scores indicating the expected number of presented neoantigens in treatment subsets identified based on presentation models. The expectation utility score is determined as described in reference to equation (25) in Section X. The y-axis indicates the proportion of selected patients that present at least a certain number of neoantigens (1, 2, or 3 neoantigens) included in the vaccine.

As indicated in FIG. 13C, patients associated with vaccines including treatment subsets based on presentation models receive vaccines containing presented neoantigens at a significantly higher rate than patients associated with vaccines including treatment subsets based on state-of-the-art models. For example, as shown in the right plot, 80% of selected patients associated with vaccines based on presentation models receive at least one presented neoantigen in the vaccine, compared to only 40% of selected patients associated with vaccines based on current state-of-the-art models. The results indicate that presentation models as described herein are effective for selecting neoantigen candidates for vaccines that are likely to elicit immune responses for treating tumors.

Figure 13D:
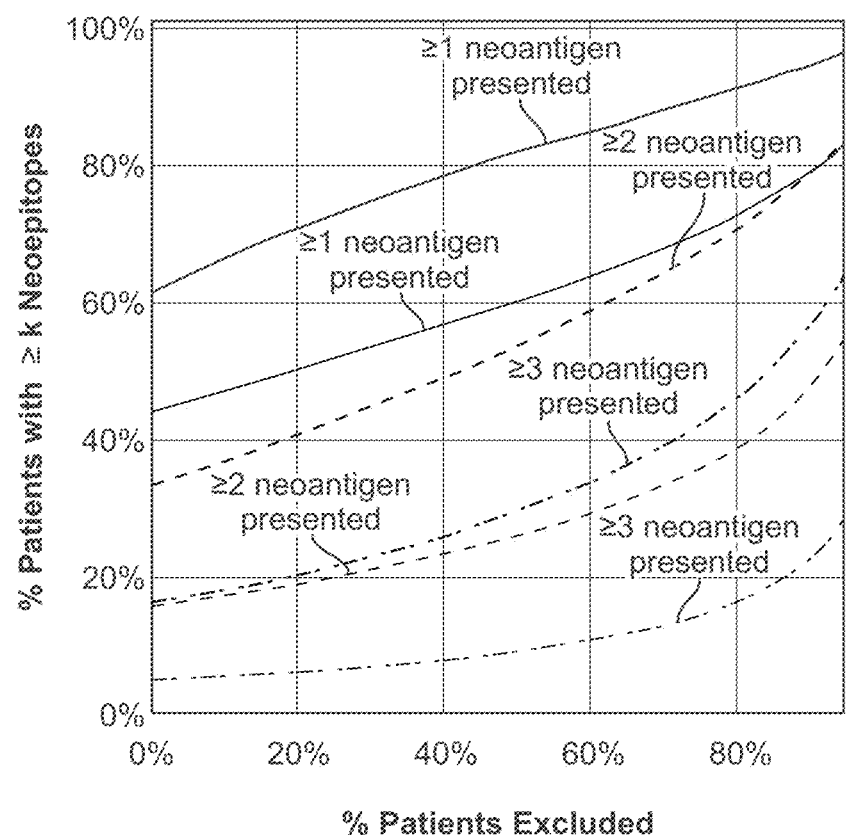
FIG. 13D compares the number of presented neoantigens in simulated vaccines between selected patients associated with vaccines including treatment subsets identified based on a single per-allele presentation model for HLA-A*02:01 and selected patients associated with vaccines including treatment subsets identified based on both per-allele presentation models for HLA-A*02:01 and HLA-B*07:02. The vaccine capacity is set as v=20 epitopes, in accordance with an embodiment.

XI.D. Example 7D: Effect of HLA Coverage on Neoantigen Presentation for Vaccines Identified Through Presentation Models FIG. 13D compares the number of presented neoantigens in simulated vaccines between selected patients associated with vaccines including treatment subsets identified based on a single per-allele presentation model for HLA-A*02:01 and selected patients associated with vaccines including treatment subsets identified based on both per-allele presentation models for HLA-A*02:01 and HLA-B*07:02. The vaccine capacity is set as v=20 epitopes. For each experiment, the patients are selected based on expectation utility scores determined based on the different treatment subsets.

In FIG. 13D, the solid lines indicate patients associated with vaccines including treatment subsets based on both presentation models for HLA alleles HLA-A*02:01 and HLA-B*07:02. The treatment subset for each patient is identified by applying each of the presentation models to the sequences in the test set, and identifying the v neoantigen candidates that have the highest presentation likelihoods. The dotted lines indicate patients associated with vaccines including treatment subsets based on a single presentation model for HLA allele HLA-A*02:01. The treatment subset for each patient is identified by applying the presentation model for only the single HLA allele to the sequences in the test set, and identifying the v neoantigen candidates that have the highest presentation likelihoods. For solid line plots, the x-axis indicates the proportion of patients excluded from vaccine treatment based on expectation utility scores for treatment subsets identified by both presentation models. For dotted line plots, the x-axis indicates the proportion of patients excluded from vaccine treatment based on expectation utility scores for treatment subsets identified by the single presentation model. The y-axis indicates the proportion of selected patients that present at least a certain number of neoantigens (1, 2, or 3 neoantigens).

As indicated in FIG. 13D, patients associated with vaccines including treatment subsets identified by presentation models for both HLA alleles present neoantigens at a significantly higher rate than patients associated with vaccines including treatment subsets identified by a single presentation model. The results indicate the importance of establishing presentation models with high HLA allele coverage.

Figure 13E:
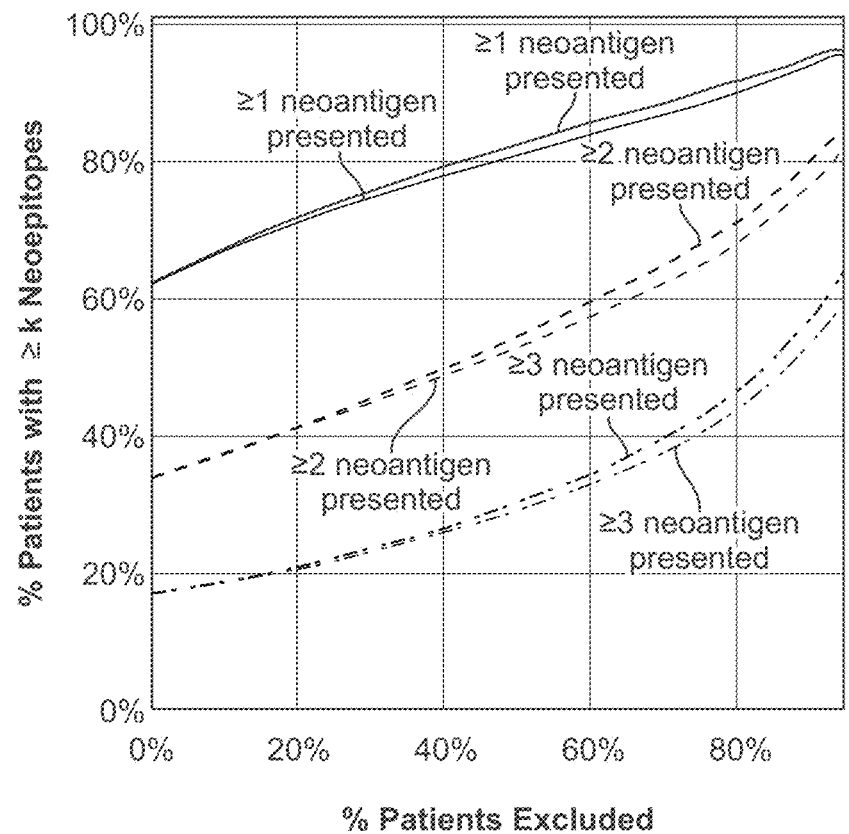
FIG. 13E compares the number of presented neoantigens in simulated vaccines between patients selected based on mutation burden and patients selected by expectation utility score, in accordance with an embodiment.

XI.E. Example 7E: Comparison of Neoantigen Presentation for Patients Selected by Mutation Burden vs. Expected Number of Presented Neoantigens FIG. 13E compares the number of presented neoantigens in simulated vaccines between patients selected based on mutation burden and patients selected by expectation utility score. The expectation utility scores are determined based on treatment subsets identified by presentation models having a size of v=20 epitopes.

In FIG. 13E, the solid lines indicate patients selected based on expectation utility score associated with vaccines including treatment subsets identified by presentation models. The treatment subset for each patient is identified by applying the presentation models to sequences in the test set, and identifying the v=20 neoantigen candidates that have the highest presentation likelihoods. The expectation utility score is determined based on the presentation likelihoods of the identified treatment subset based on equation (25) in section X. The dotted lines indicate patients selected based on mutation burden associated with vaccines also including treatment subsets identified by presentation models. The x-axis indicates the proportion of patients excluded from vaccine treatment based on expectation utility scores for solid line plots, and proportion of patients excluded based on mutation burden for dotted line plots. The y-axis indicates the proportion of selected patients who receive a vaccine containing at least a certain number of presented neoantigens (1, 2, or 3 neoantigens). As indicated in FIG. 13E, patients selected based on expectation utility scores receive a vaccine containing presented neoantigens at a higher rate than patients selected based on mutation burden. However, patients selected based on mutation burden receive a vaccine containing presented neoantigens at a higher rate than unselected patients. Thus, mutation burden is an effective patient selection criteria for successful neoantigen vaccine treatment, though expectation utility scores are more effective.

XII. Example 8: Evaluation of Mass Spectrometry-Trained Model on Held-Out Mass Spectrometry Data As HLA peptide presentation by tumor cells is a key requirement for anti-tumor immunity[91,96,97], a large (N=74 patients) integrated dataset of human tumor and normal tissue samples with paired class I HLA peptide sequences, HLA types and transcriptome RNA-seq (Methods) was generated with the aim of using these and publicly available data[92,98,99] to train a novel deep learning model[100] to predict antigen presentation in human cancer. Samples were chosen among several tumor types of interest for immunotherapy development and based on tissue availability. Mass spectrometry identified an average of 3,704 peptides per sample at peptide-level FDR<0.1 (range 344-11,301). The peptides followed the characteristic class I HLA length distribution: lengths 8-15aa, with a modal length of 9 (56% of peptides). Consistent with previous reports, a majority of peptides (median 79%) were predicted to bind at least one patient HLA allele at the standard 500 nM affinity threshold by MHCflurry[90], but with substantial variability across samples (e.g., 33% of peptides in one sample had predicted affinities >500 nM). The commonly used[101] "strong binder" threshold of 50 nM captured a median of only 42% of presented peptides. Transcriptome sequencing yielded an average of 131M unique reads per sample and 68% of genes were expressed at a level of at least 1 transcript per million (TPM) in at least one sample, highlighting the value of a large and diverse sample set to observe expression of a maximal number of genes. Peptide presentation by the HLA was strongly correlated with mRNA expression. Striking and reproducible gene-to-gene differences in the rate of peptide presentation, beyond what could be explained by differences in RNA expression or sequence alone, were observed. The observed HLA types matched expectations for specimens from a predominantly European-ancestry group of patients.

Using these and publicly available HLA peptide data[92,98,99], a neural network (NN) model was trained to predict HLA antigen presentation. To learn allele-specific models from tumor mass spectrometry data where each peptide could have been presented by any one of six HLA alleles, a novel network architecture capable of jointly learning the allele-peptide mappings and allele-specific presentation motifs (Methods) was developed. For each patient, the positive-labeled data points were peptides detected via mass spectrometry, and the negative-labeled data points were peptides from the reference proteome (SwissProt) that were not detected via mass spectrometry in that sample. The data was split into training, validation and testing sets (Methods). The training set consisted of 142,844 HLA presented peptides (FDR<~0.02) from 101 samples (69 newly described in this study and 32 previously published). The validation set (used for early stopping) consisted of 18,004 presented peptides from the same 101 samples. Two mass spectrometry datasets were used for testing: (1) A tumor sample test set consisting of 571 presented peptides from 5 additional tumor samples (2 lung, 2 colon, 1 ovarian) that were held out of the training data, and (2) a single-allele cell line test set consisting of 2,128 presented peptides from genomic location windows (blocks) adjacent to, but distinct from, the locations of single-allele peptides included in the training data (see Methods for additional details on the train/test splits).

The training data identified predictive models for 53 HLA alleles. In contrast to prior work[92,104], these models captured the dependence of HLA presentation on each sequence position for peptides of multiple lengths. The model also correctly learned the critical dependencies on gene RNA expression and gene-specific presentation propensity, with the mRNA abundance and learned per-gene propensity of presentation combining independently to yield up to a ~60-fold difference in rate of presentation between the lowest-expressed, least presentation-prone and the highest expressed, most presentation-prone genes. It was further observed that the model predicted the measured stability of HLA/peptide complexes in IEDB[88] ($p<1e-10$ for 10 alleles), even after controlling for predicted binding affinity ($p<0.05$ for 8/10 alleles tested). Collectively, these features form the basis for improved prediction of immunogenic HLA class I peptides.

Figure 14:
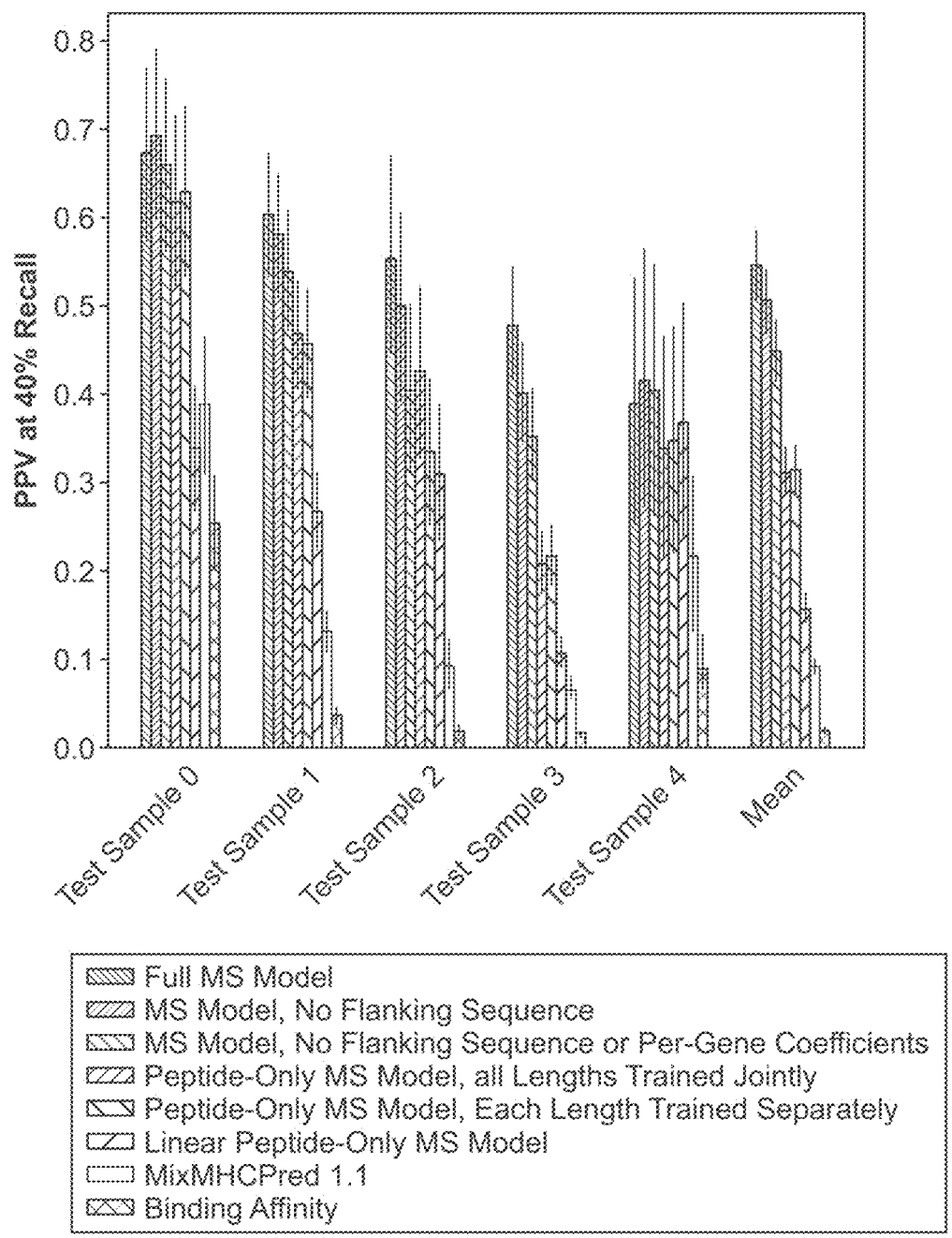
FIG. 14 compares the positive predictive values (PPV) at 40% recall of different versions of the MS Model and earlier approaches to modeling HLA presented peptides[29] in human tumors, when each model is tested on the test set comprising five different held-out test samples, each test sample comprising a held-out tumor sample with a 1:2500 ratio of presented to non-presented peptides.

Performance of this NN model as a predictor of HLA presentation on the held-out mass spectrometry test sets was evaluated. Specifically, FIG. 14 compares the positive predictive values (PPV) at 40% recall of different versions of the MS Model and a recently published approach to modeling eluted peptides from mass spectrometry (MixMHCPred), when each model is tested on the five different held-out test samples. FIG. 14 also depicts the average PPV at 40% recall of the models for the five test samples.

The models tested in FIG. 14 are (from left to right): "Full MS Model": the full NN model described in the Methods; "MS Model, No Flanking Sequence": identical to the full NN model, except with the flanking sequence feature removed; "MS Model, No Flanking Sequence or Per-Gene Parameters": identical to the full NN model, except with the flanking sequence and per-gene parameter features removed; "Peptide-Only MS Model, all Lengths Trained Jointly": identical to the full NN model, except the only features used are peptide sequence and HLA type; "Peptide-Only MS Model, Each Length Trained Separately": for this model, the model structure was the same as the peptide-only MS model, except separate models for 9 and 10mers were trained; "Linear Peptide-Only MS Model (with Ensembling)": identical to the peptide-only MS model with each peptide length trained separately; except instead of modeling peptide sequence using neural networks, an ensemble of linear models trained using the same optimization procedure used for the full model and described in the Methods was used; "MixMHCPred 1.1" is MixMHCPred with default settings; "Binding affinity" is MHCflurry 1.2.0.

The "Full MS Model," the "MS Model, No Flanking Sequence," the "MS Model, No Flanking Sequence or Per-Gene Parameter," the "Peptide-Only MS Model, all Lengths Trained Jointly," the "Peptide-Only MS Model, all Lengths Trained Separately," and the "Linear Peptide-Only MS Model" are all neural network models trained on mass spectrometry data as described above. However, each model is trained and tested using different features of a sample. The "MixMHCPred 1.1" model and the "Binding Affinity"

model are earlier approaches to modeling HLA presented peptides[104]. Only 9 and 10mers were used in the comparison because MixMHCPred does not currently model peptides of lengths other than 9 and 10. The last 5 models ("Peptide-Only MS Model, all Lengths Trained Jointly" through "Binding Affinity") have the same inputs: peptide sequence and HLA types, only. In particular, none of the last 5 models uses RNA abundance to make predictions.

The best performing peptide-only model ("Peptide-Only MS Model, all Lengths Trained Jointly") achieves an average PPV of 0.41 at 40% recall, while the worst-performing peptide-only model trained on the mass spectrometry data ("Linear Peptide-Only MS Model") achieves an average PPV of only 28% (only slightly higher than to the average PPV of MixMHCPred 1.1 at 18%), highlighting the value of improved NN modeling of peptide sequences. Note that MixMHCPred 1.1 is trained on different data than the linear peptide-only MS model, but has many of the same modeling characteristics (e.g., it is a linear model, where the models for each peptide length are trained separately).

Overall, the NN model achieved significantly improved prediction of HLA peptide presentation, with a PPV up to 9-fold higher than standard binding affinity+gene expression on the tumor test set. The large PPV advantage of the MS-based NN model persisted across various recall thresholds and was statistically significant ($p<10^{-6}$ for all tumor samples). The positive predictive value of standard binding affinity+gene expression for HLA peptide presentation reached as low as 6%, in line with previous estimates[87,93]. Notably, however, this ~6% PPV still represents a >100-fold enrichment over baseline prevalence, because only a small proportion of peptides are detected as presented (e.g., ~1 in 2500 in the tumor MS test dataset).

By comparing a reduced model trained on mass spectrometry data that uses only HLA type and peptide sequence as inputs to the full MS model, it was determined that ~30% of the gain in PPV over binding affinity prediction came from modeling peptide-extrinsic features (RNA abundance, flanking sequence, per-gene parameters) that can be captured with mass spectrometry but not binding affinity assays. The other ~70% of the gain came from improved modeling of peptide sequence. It was not just the nature of the training dataset (HLA presented peptides), but the overall model architecture that contributed to the improved performance, as it also outperformed earlier approaches to modeling HLA presented peptides[104] in human tumors. The new model architecture enabled learning of allele-specific models via an end-to-end training process that does not require ex ante assignment of peptides to purported presenting alleles using binding affinity predictions or hard-clustering approaches[104-106]. Importantly, it also avoided imposing accuracy-reducing restrictions on the allele-specific submodels as a prerequisite to deconvolution, such as linearity, or separate consideration of each peptide length[104]. The full model outperforms several simplified models and previously published approaches that impose these restrictions.

XIII. Example 9: Experimentation Results Including Presentation Hotspot Modeling To specifically evaluate the benefit of using presentation hotspot parameters in modeling HLA presentation, the performance of a neural network presentation model that incorporates presentation hotspot parameters was compared with the performance of a neural network presentation model that does not incorporate presentation hotspot parameters. The base neural network architecture was the same for both models and was identical to the presentation model described above in Section VII. In brief, the models included peptide and flanking amino acid sequence parameters, RNA-sequencing transcription data (TPM), protein family data, per-sample identification, and HLA-A, B, C types. Ensembles of 5 networks were used for each model. The model that included the presentation hotspot parameters used Equation 12c described above in Section VIII.B.3., with a per-gene proteomic block size of 10, and peptide lengths 8-12.

The two models were compared by performing experiments using the mass spectrometry dataset described above in Section XII. Specifically, five samples were held-out from model training and validation for the purpose of fairly evaluating the competing models. The remaining samples were randomly divided 90% for model training and 10% for validating the training.

Figure 15A:
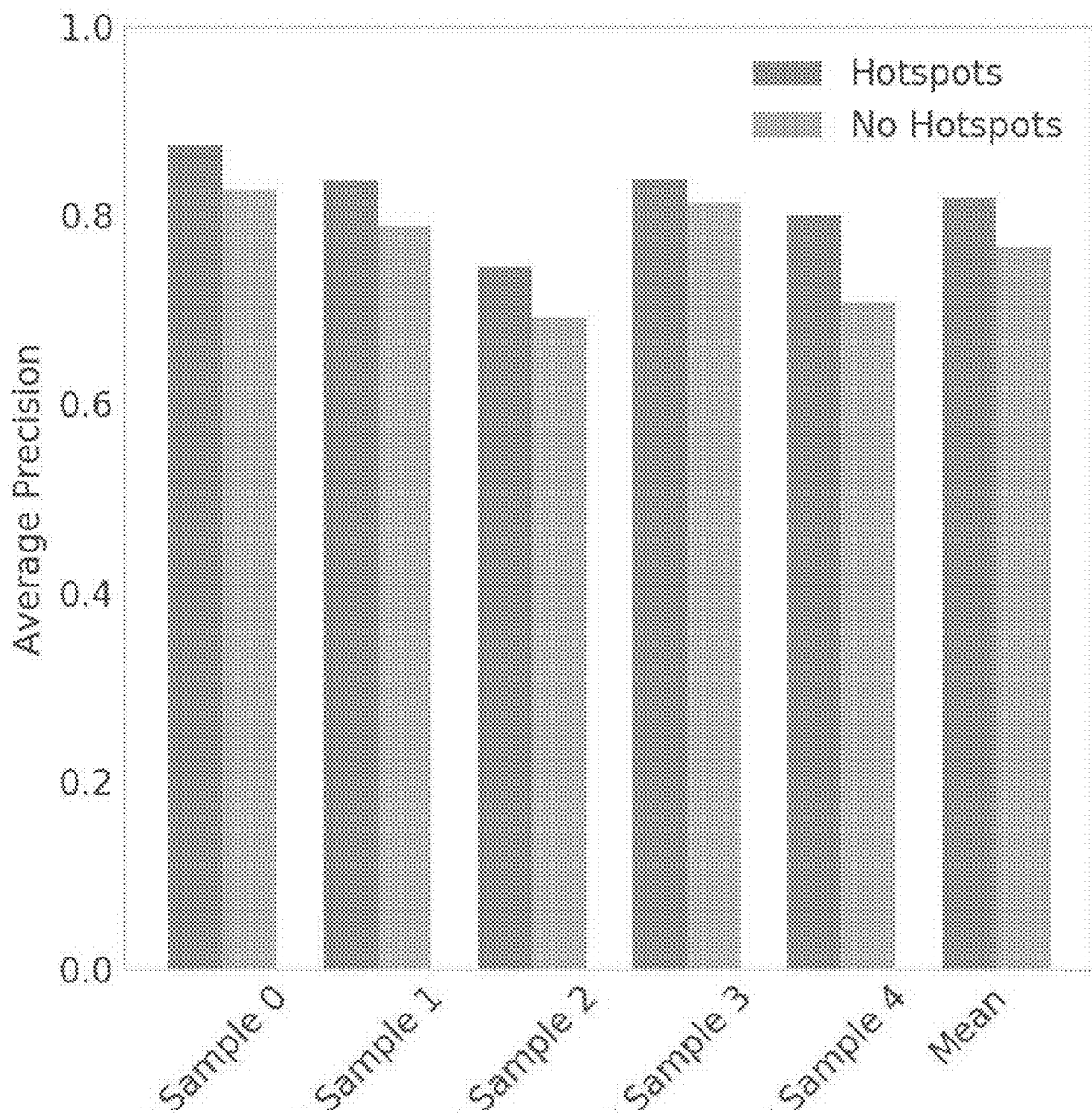
FIG. 15A compares the average positive predictive values (PPVs) across recall of a presentation model that uses presentation hotspot parameters and a presentation model that does not use presentation hotspot parameters, when the models are tested on five held-out test samples.
Figure 15B:
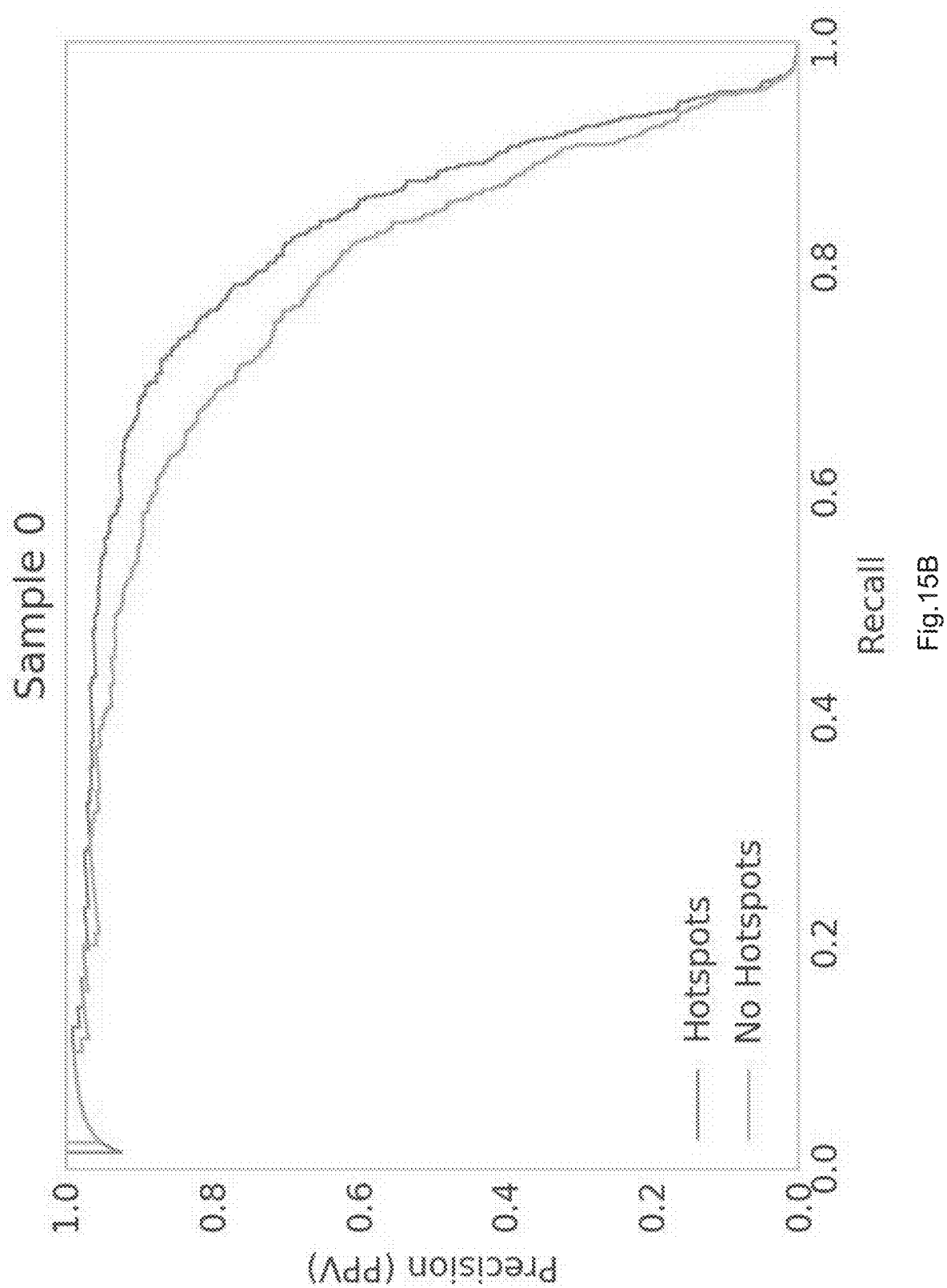
FIG. 15B compares precision and recall curves for a presentation model that uses presentation hotspot parameters and a presentation model that does not use presentation hotspot parameters, when the models are tested on a held-out test sample 0.
Figure 15C:
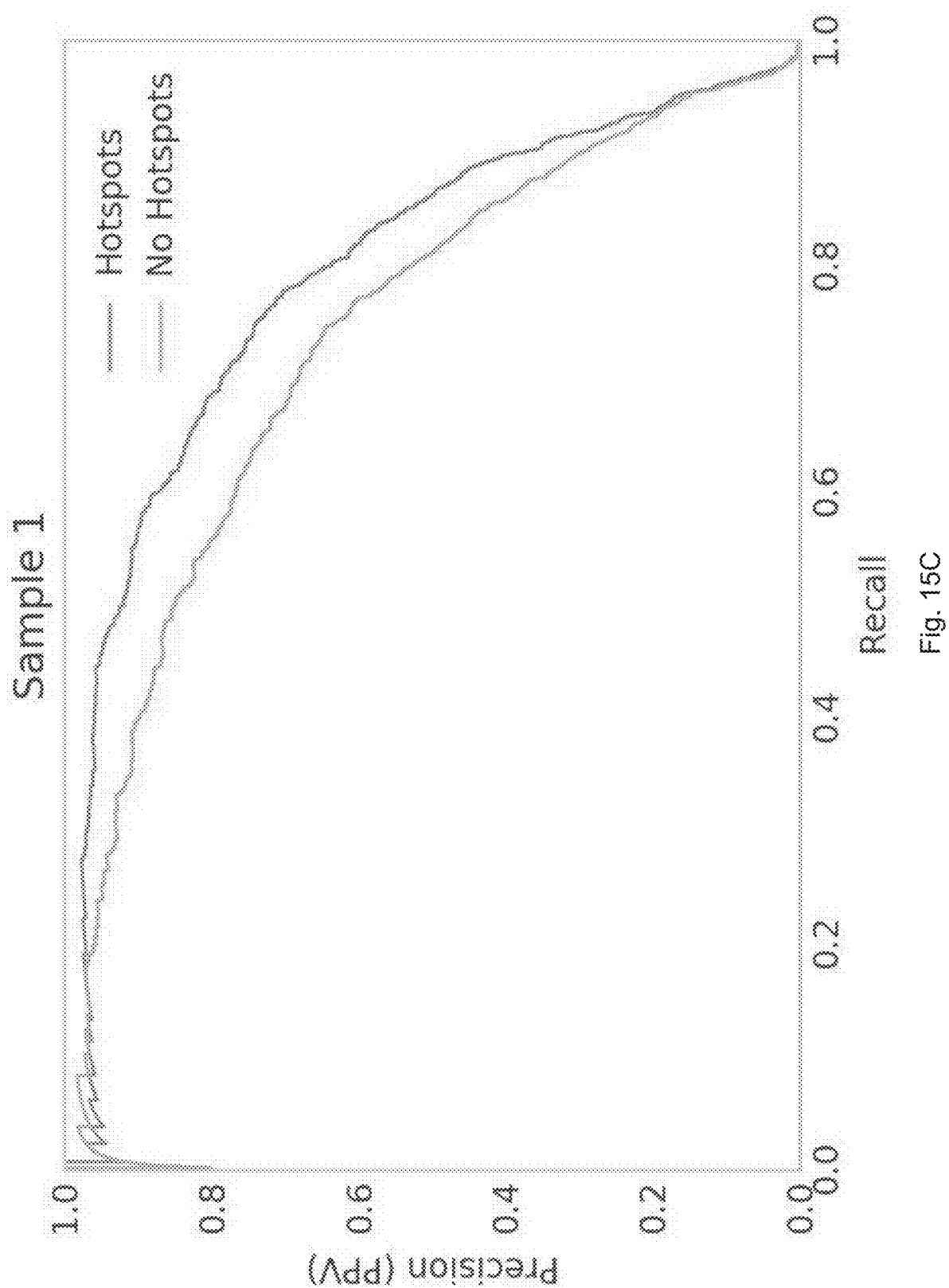
FIG. 15C compares precision and recall curves for a presentation model that uses presentation hotspot parameters and a presentation model that does not use presentation hotspot parameters, when the models are tested on a held-out test sample 1.
Figure 15D:
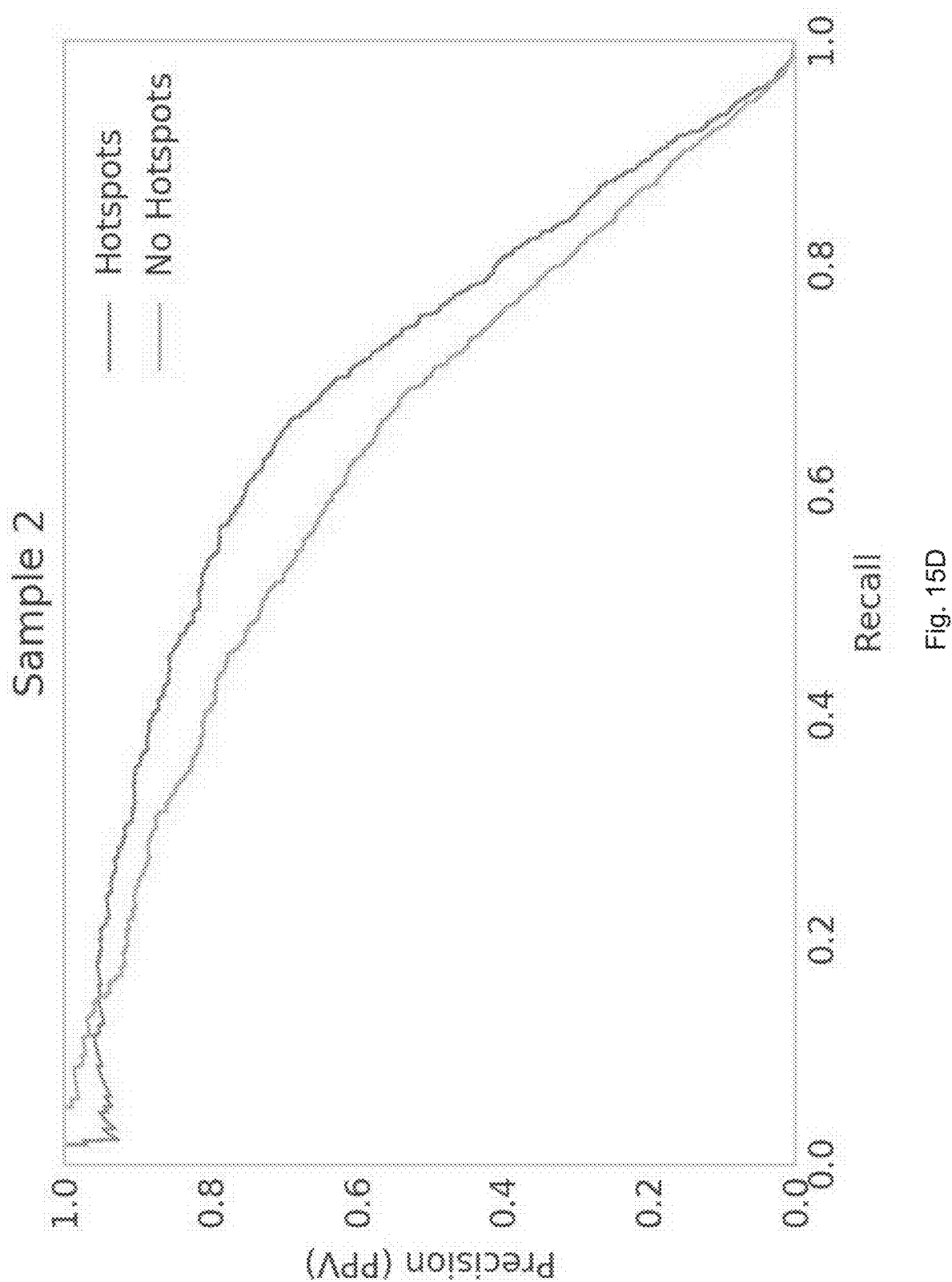
FIG. 15D compares precision and recall curves for a presentation model that uses presentation hotspot parameters and a presentation model that does not use presentation hotspot parameters, when the models are tested on a held-out test sample 2.
Figure 15E:
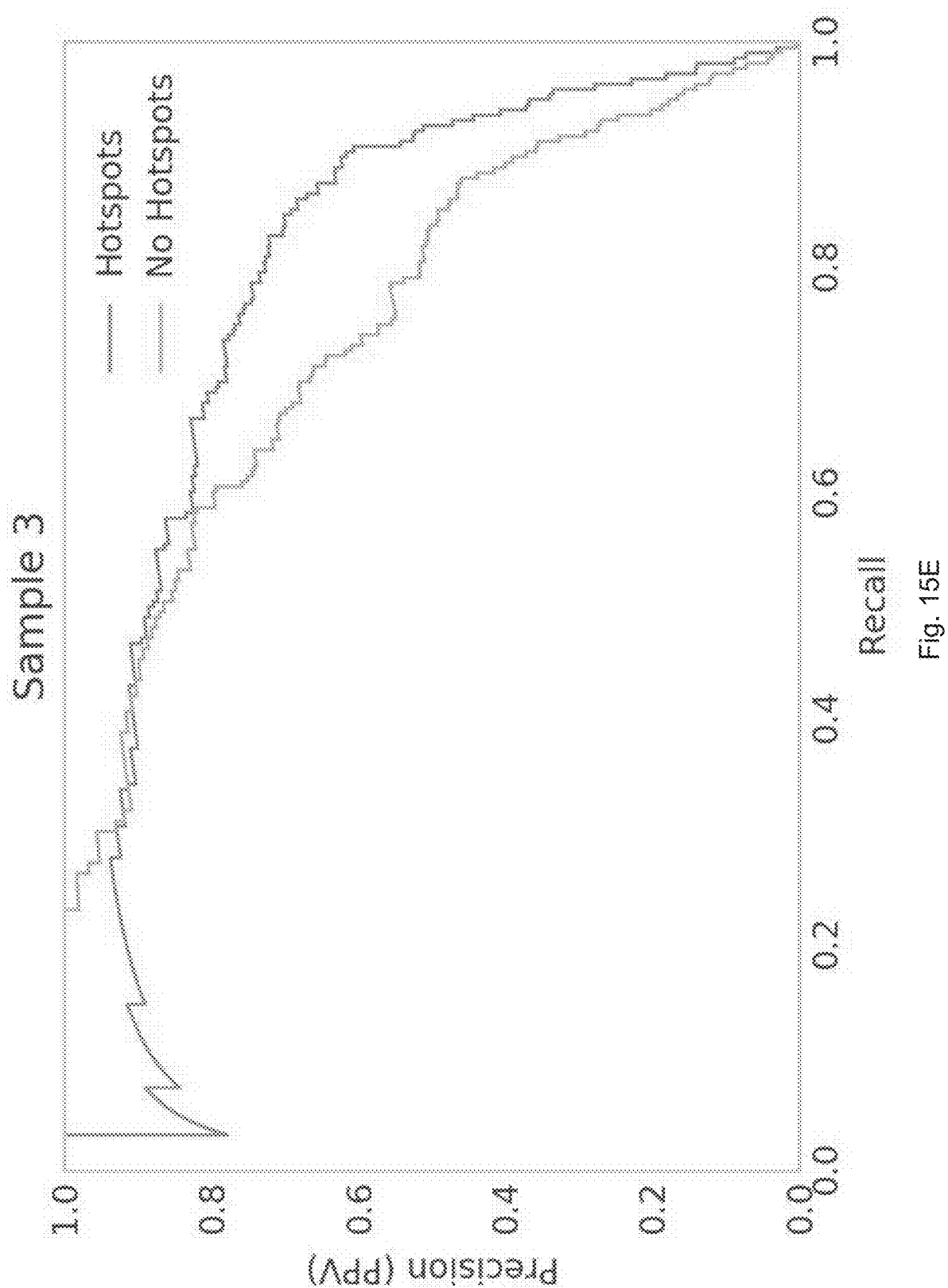
FIG. 15E compares precision and recall curves for a presentation model that uses presentation hotspot parameters and a presentation model that does not use presentation hotspot parameters, when the models are tested on a held-out test sample 3.
Figure 15F:
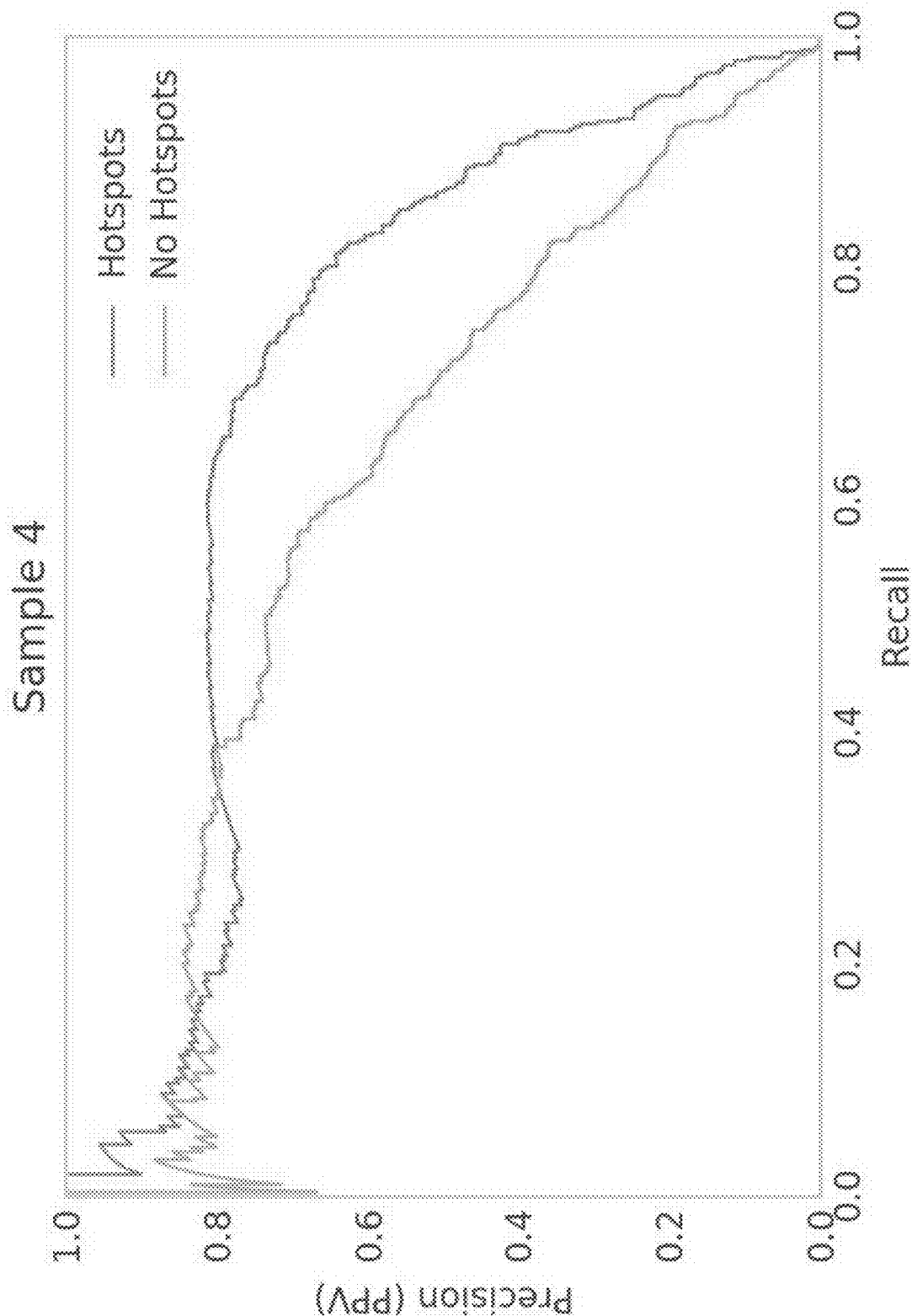
FIG. 15F compares precision and recall curves for a presentation model that uses presentation hotspot parameters and a presentation model that does not use presentation hotspot parameters, when the models are tested on a held-out test sample 4.

FIG. 15A compares the average positive predictive values (PPVs) across recall of the presentation model that used presentation hotspot parameters and the presentation model that did not use presentation hotspot parameters, when the models were tested on the five held-out test samples. The model that incorporated presentation hotspot parameters outperformed the model that did not incorporate presentation hotspot parameters on each of the samples individually, with a mean average precision of 0.82 with presentation hotspot parameters and 0.77 without presentation hotspot parameters.

FIGS. 15B-F compare precision and recall curves for the presentation model that used presentation hotspot parameters and the presentation model that did not use presentation hotspot parameters, when the models were tested on each of the five held-out test samples.

XIV. Example 10: Evaluation of Presentation Hotspot Parameters for Identifying T-Cell Epitopes The benefit of using presentation hotspot parameters to model HLA presentation to identify human tumor CD8 T-cell epitopes (i.e., immunotherapy targets) was also directly tested. Defining an appropriate test dataset for this evaluation is challenging, as the test dataset should contain peptides that are both recognized by T-cells and presented by the HLA on the tumor cell surface. In addition, formal performance assessment calls for not only positive-labeled (i.e., T-cell recognized) peptides, but also a sufficient number of negative-labeled (i.e., tested but not recognized) peptides. Mass spectrometry datasets address tumor presentation but not T-cell recognition; oppositely, priming or T-cell assays post-vaccination address T-cell recognition but not tumor presentation.

To obtain an appropriate dataset, we collected published CD8 T-cell epitopes from 5 recent studies that met the required criteria: study A[96] examined TIL in 9 patients with gastrointestinal tumors and reported T-cell recognition of 12/1,053 somatic SNV mutations tested by IFN-y ELISPOT using the tandem minigene (TMG) method in autologous DCs. Study B[84] also used TMGs and reported T-cell recognition of 6/574 SNVs by CD8+PD-1+ circulating lymphocytes from 5 melanoma patients. Study C[97] assessed TIL from 3 melanoma patients using pulsed peptide stimulation and found responses to 5/381 tested SNV mutations. Study D[108] assessed TIL from one breast cancer patient using a combination of TMG assays and pulsing with minimal epitope peptides and reported recognition of 2/62 SNVs. Study E[160] assessed TIL in 17 patients from the National Cancer Institute with 52 TSNA. The combined dataset included 4,843 assayed SNVs from 33 patients, including 75 TSNA with pre-existing T-cell responses. Importantly, because the dataset was comprised largely of neoantigen recognition by tumor-infiltrating lymphocytes, successful prediction on this data set demonstrates that the model has the ability to identify not just neoantigens that are able to prime T-cells as in the previous section, but also neoantigens presented to T cells by tumors.

To simulate the selection of antigens for personalized immunotherapy, somatic mutations were ranked in order of probability of presentation using two methods: (1) the MS model including the hotspot feature (as described in equation 12c with block size n=10), and (2) the traditional MS model without the hotspot feature. As capacities of antigen-specific immunotherapies are limited in the number of specificities targeted (e.g., current personalized vaccines encode ~10-20 mutations[6, 81-82]), predictive methods were compared by counting the number of pre-existing T-cell responses in the top 5, 10, 20, or 30-ranked peptides for each patient. The results are depicted in FIG. 16.

Figure 16:
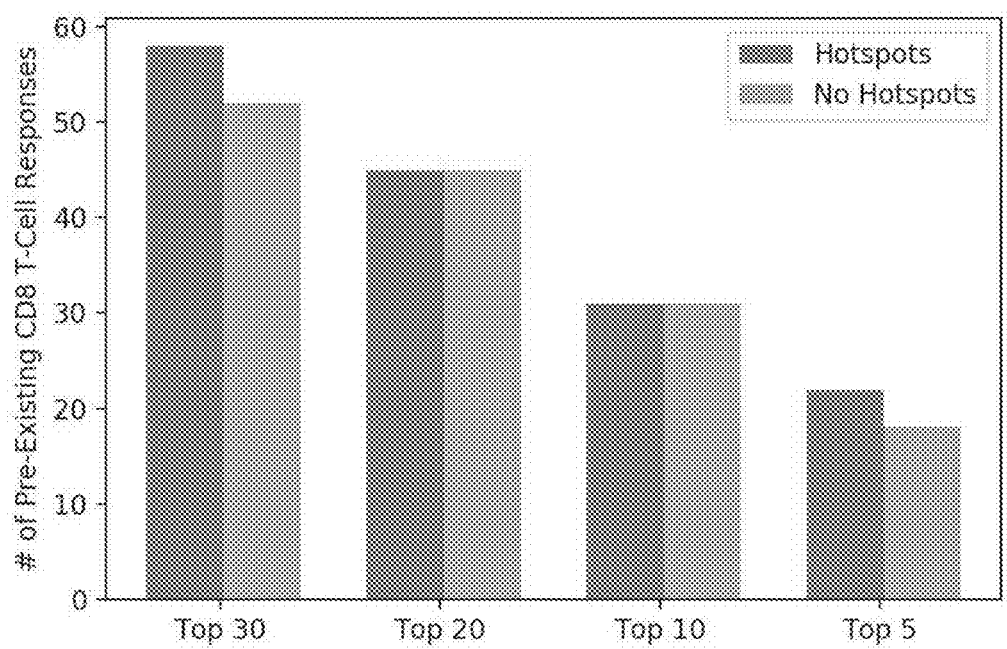
FIG. 16 compares the proportion of peptides that span somatic mutations recognized by T-cells for the top 5, 10, 20, and 30-ranked peptides identified by a presentation model that uses presentation hotspot parameters and by a presentation model that does not use presentation hotspot parameters, for a test set comprising test samples taken from patients with at least one pre-existing T-cell response.

Specifically, FIG. 16 compares the proportion of peptides that span somatic mutations recognized by T-cells for the top 5, 10, 20, and 30-ranked peptides identified by a presentation model that uses presentation hotspot parameters and by a presentation model that does not use presentation hotspot parameters, for a test set comprising test samples taken from patients with at least one pre-existing T-cell response. As illustrated in FIG. 16, the model with the hotspot feature performed comparably to the model without the feature, where both models predicted 45 and 31 T-cell responses in the top 20 and 10 ranked peptides, respectively. However, the hotspot model showed improvement when predicting the top 30 and top 5 peptides, where the hotspot model included 6 and 4 more T-cell responses, respectively.

XIII.A. Data

We obtained mutation calls, HLA types and T-cell recognition data from the supplementary information of Gros et al.[84], Tran et al.[140], Stronen et al.[141], Zacharakis et al., and Koşaloğlu-Yalçin et al.[160].

For the mutation-level analysis (FIG. 16), the positive-labeled datapoints for Gros et al., Tran et al., Zacharakis et al.[108], and Koşaloğlu-Yalçin et al.[160] were mutations recognized by patient T-cells in both the TMG assay or the minimal epitope peptide-pulsing assays. The negative-labeled datapoints were all other mutations tested in TMG assays. For Stronen et al, the positive labeled mutations were mutations spanned by at least one recognized peptide, and the negative datapoints were all mutations tested but not recognized in the tetramer assays. For the Gros, Tran and Zacharakis data, mutations were ranked either by summing probabilities of presentation or taking the minimum binding affinity across all mutation-spanning peptides, as the mutated-25mer TMG assay tests the T-cell recognition of all peptides spanning the mutation. For the Stronen data, mutations were ranked either by summing probabilities of presentation or taking the minimum binding affinity across all mutation-spanning peptides tested in the tetramer assays. The full list of mutations and features is available in Supplementary Table 1.

For the epitope-level analysis, the positive-labeled datapoints were all minimal epitopes recognized by patient T-cells in peptide-pulsing or tetramer assays, and the negative datapoints were all minimal epitopes not recognized by T-cells in peptide-pulsing or tetramer assays and all mutation-spanning peptides from tested TMGs that were not recognized by patient T-cells. In the case of Gros et al, Tran et al and Zacharakis et al minimal epitope peptides spanning mutations recognized in the TMG analysis that were not tested via peptide-pulsing assays were removed from the analysis, as the T-cell recognition status of these peptides was not determined experimentally.

XV. Example 11: Identification of Neoantigen-Reactive T-Cells in Cancer Patients This example demonstrates that improved prediction can enable neoantigen identification from routine patient samples. To do so, archival FFPE tumor biopsies and 5-30 ml of peripheral blood were analyzed from 9 patients with metastatic NSCLC undergoing anti-PD(L)1 therapy (Supplementary Table 2: Patient demographics and treatment information for N=9 patients studied in FIGS. 17A-C. Key fields include tumor stage and subtype, anti-PD1 therapy received, and summary of NGS results.). Tumor whole exome sequencing, tumor transcriptome sequencing, and matched normal exome sequencing resulted in an average of 198 somatic mutations per patient (SNVs and short indel), of which an average of 118 were expressed (Methods, Supplementary Table 2). The full MS model was applied to prioritize 20 neoepitopes per patient for testing against pre-existing anti-tumor T-cell responses. To focus the analysis on likely CD8 responses, the prioritized peptides were synthesized as 8-11mer minimal epitopes (Methods), and then peripheral blood mononuclear cells (PBMCs) were cultured with the synthesized peptides in short in vitro stimulation (IVS) cultures to expand neoantigen-reactive T-cells (Supplementary Table 3). After two weeks the presence of antigen-specific T-cells was assessed using IFN-gamma ELISpot against the prioritized neoepitopes. In seven patients for whom sufficient PBMCs were available, separate experiments were also performed to fully or partially deconvolve the specific antigens recognized. The results are depicted in FIGS. 17A-C and 18A-21.

Figure 17A:
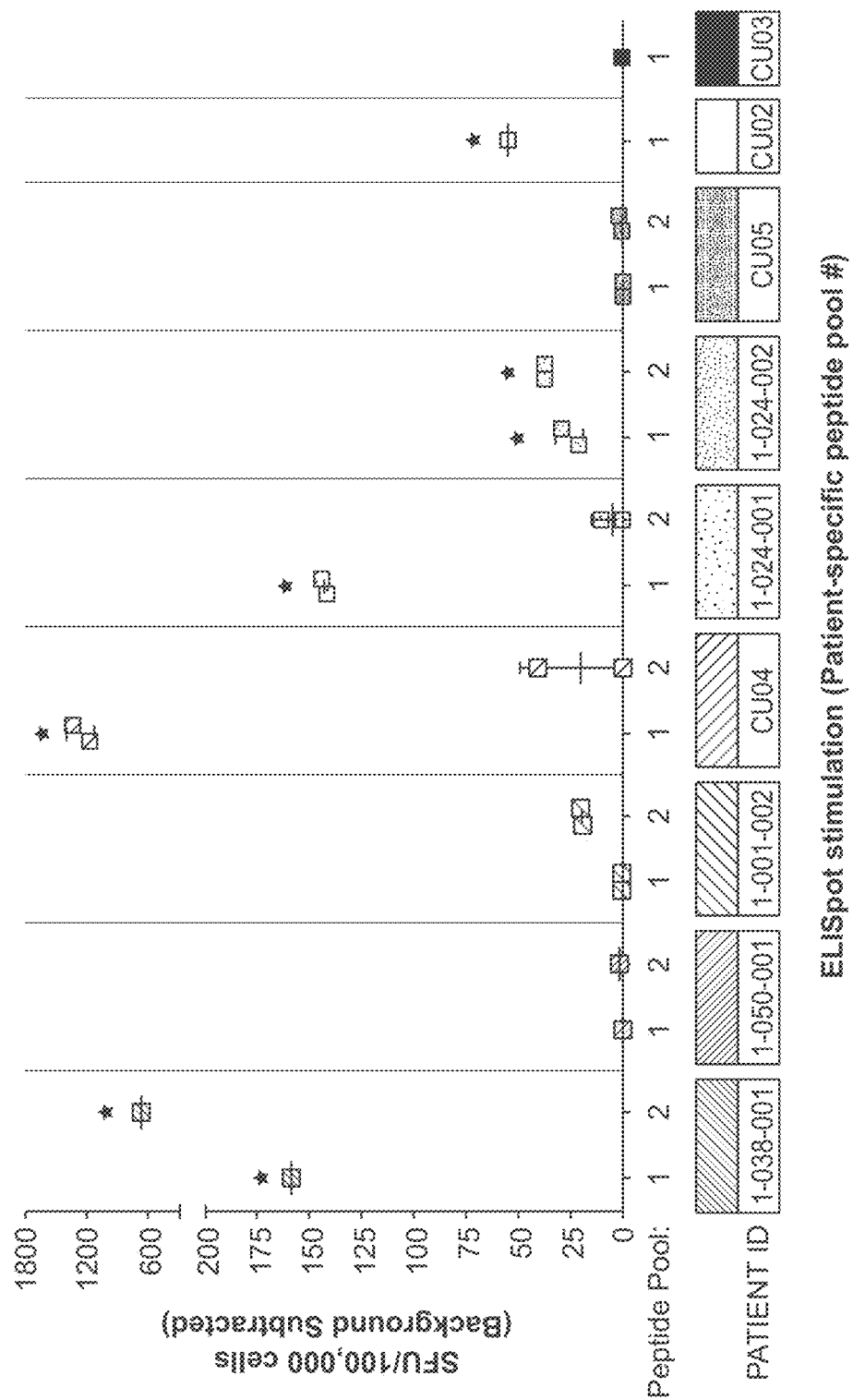
FIG. 17A depicts detection of T-cell responses to patient-specific neoantigen peptide pools for nine patients.
Figure 17B:
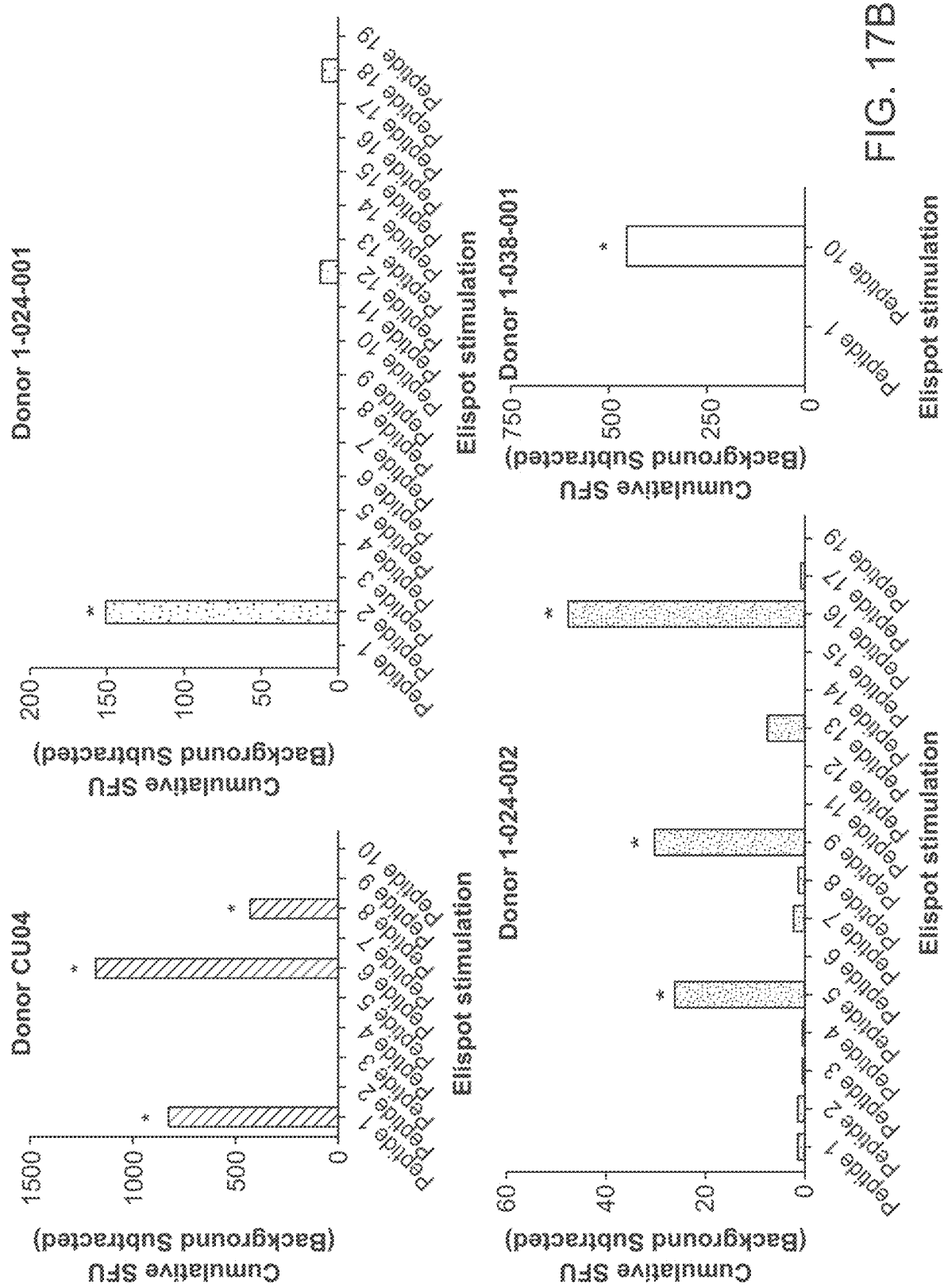
FIG. 17B depicts detection of T-cell responses to individual patient-specific neoantigen peptides for four patients.
Figure 17C:
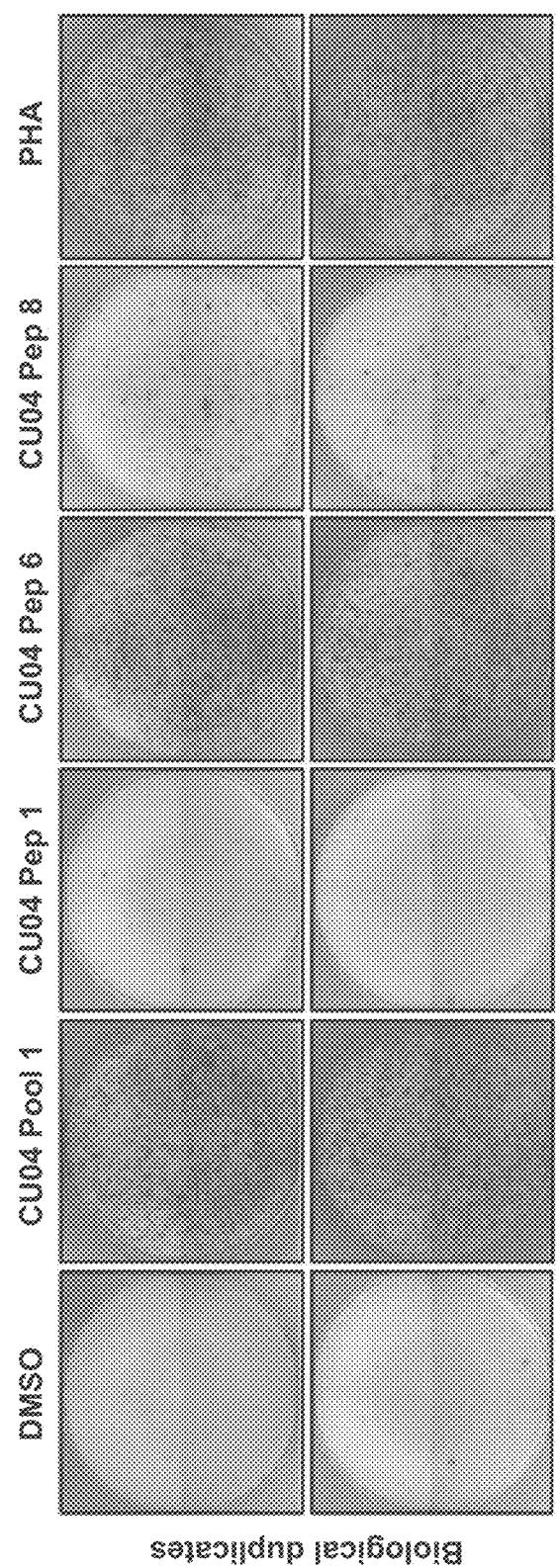
FIG. 17C depicts example images of ELISpot wells for patient CU04.
Figure 21:
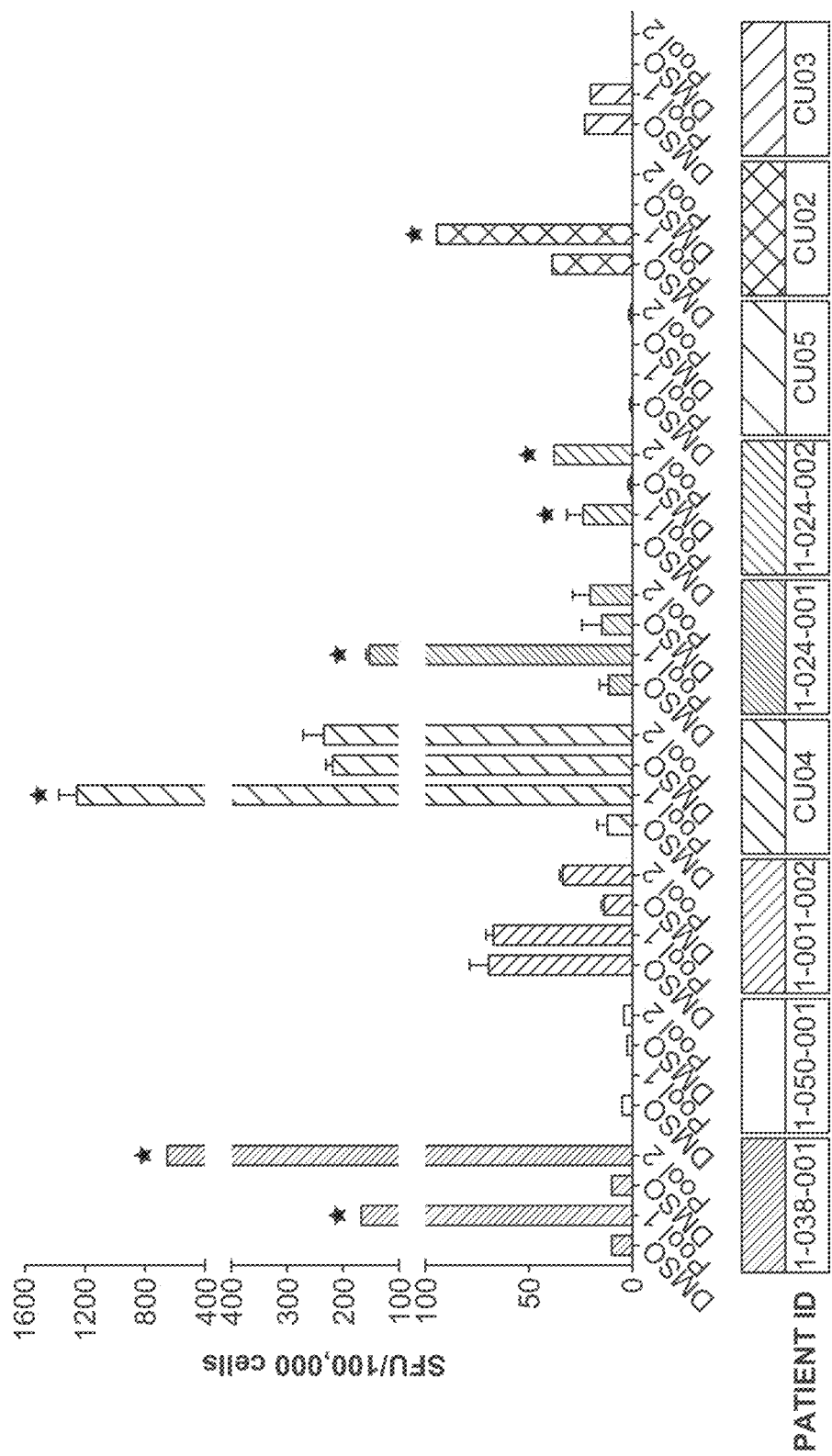
FIG. 21 depicts detection of T-cell responses to the two patient-specific neoantigen peptide pools and to DMSO negative controls for the patients of FIG. 17A.

FIG. 17A depicts detection of T-cell responses to patient-specific neoantigen peptide pools for nine patients. For each patient, predicted neoantigens were combined into 2 pools of 10 peptides each according to model ranking and any sequence homologies (homologous peptides were separated into different pools). Then, for each patient, the in vitro expanded PBMCs for the patient were stimulated with the 2 patient-specific neoantigen peptide pools in IFN-gamma ELISpot. Data in FIG. 17A are presented as spot forming units (SFU) per $10^5$ plated cells with background (corresponding DMSO negative controls) subtracted. Background measurements (DMSO negative controls) are shown in FIG. 21. Responses of single wells (patients 1-038-001, CU02, CU03 and 1-050-001) or replicates with mean and standard deviation (all other patients) against cognate peptide pools #1 and #2 are shown for patients 1-038-001, 1-050-001, 1-001-002, CU04, 1-024-001, 1-024-002 and CU05. For patients CU02 and CU03, cell numbers allowed testing against specific peptide pool #1 only. Samples with values >2-fold increase above background were considered positive and are designated with a star (responsive donors include patients 1-038-001, CU04, 1-024-001, 1-024-002, and CU02). Unresponsive donors include patients 1-050-001, 1-001-002, CU05, and CU03. FIG. 17C depicts photographs of ELISpot wells with in vitro expanded PBMCs from patient CU04, stimulated in IFN-gamma ELISpot with DMSO negative control, PHA positive control, CU04-specific neoantigen peptide pool #1, CU04-specific peptide 1, CU04-specific peptide 6, and CU04-specific peptide 8.

Figure 18A:
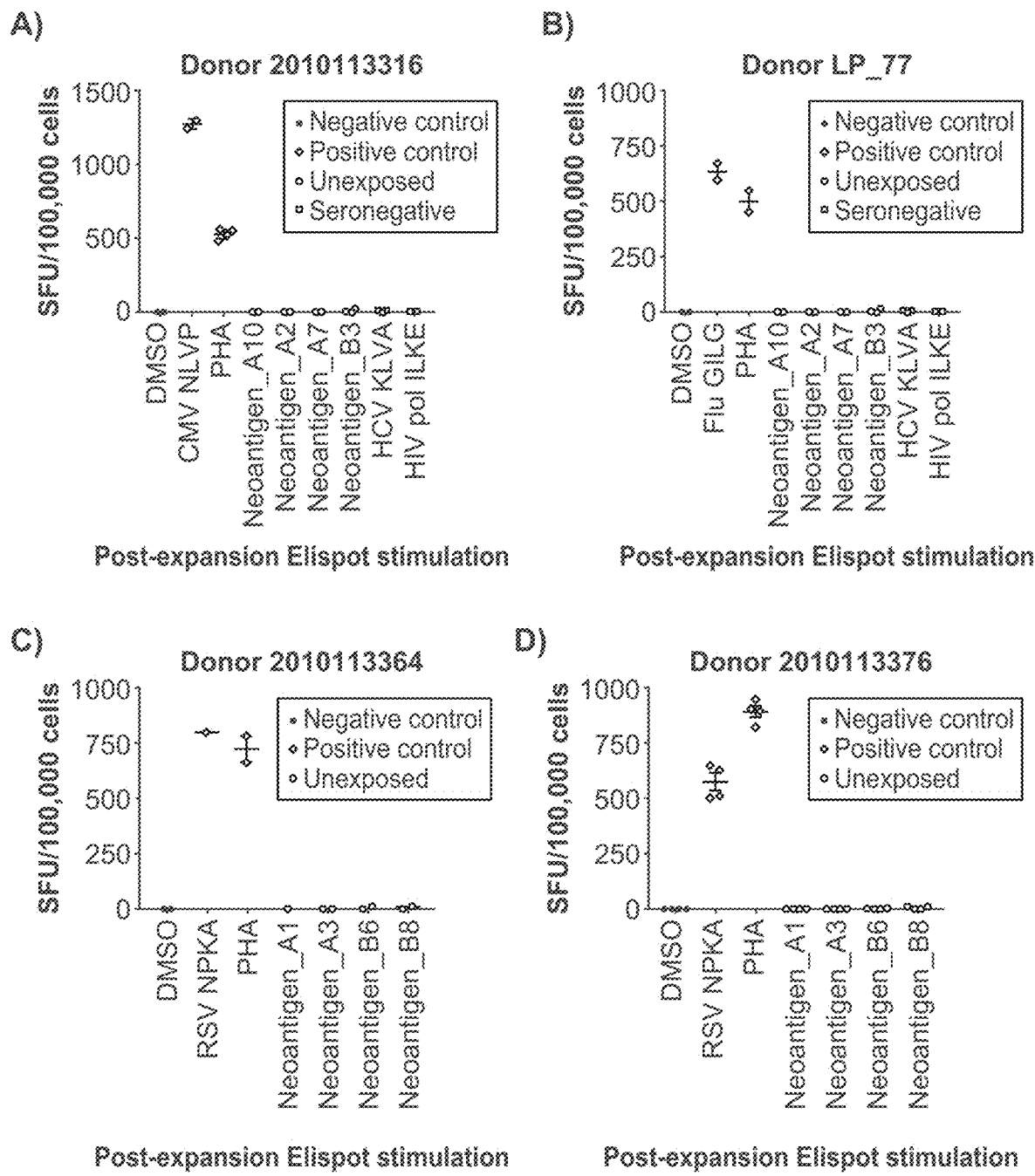
FIG. 18A depicts results from control experiments with neoantigens in HLA-matched healthy donors.
Figure 18A:
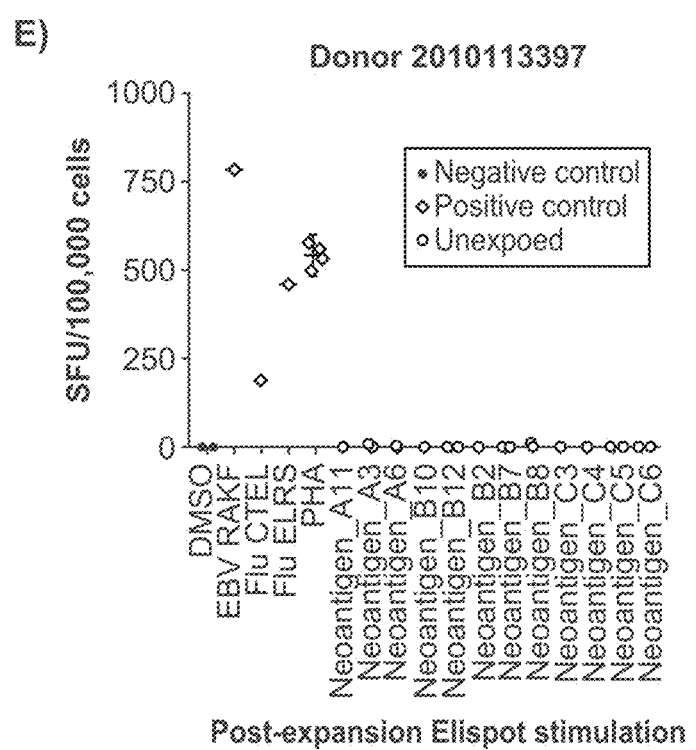
Figure 18B:
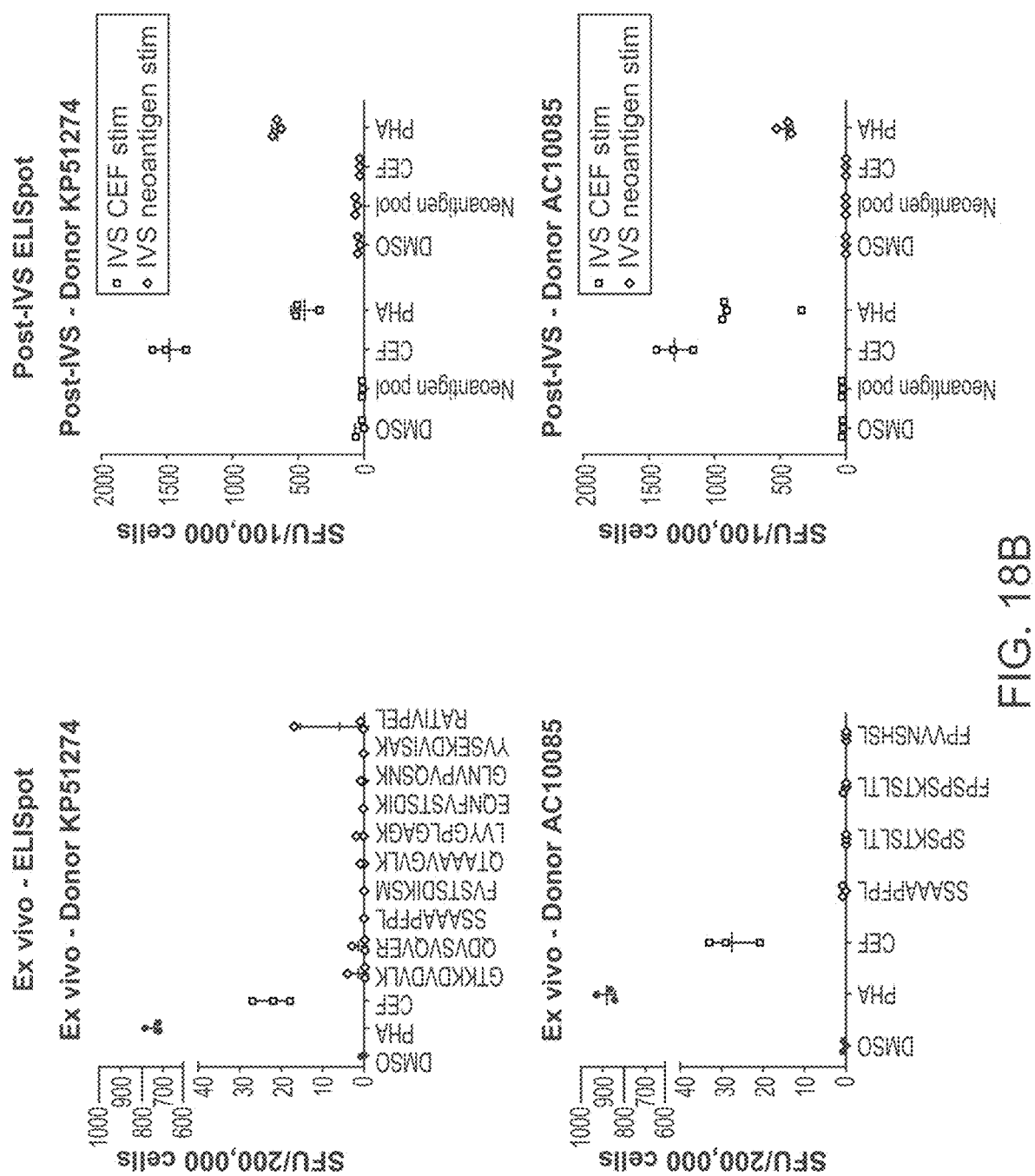
FIG. 18B depicts results from control experiments with neoantigens in HLA-matched healthy donors.
Figure 18B:
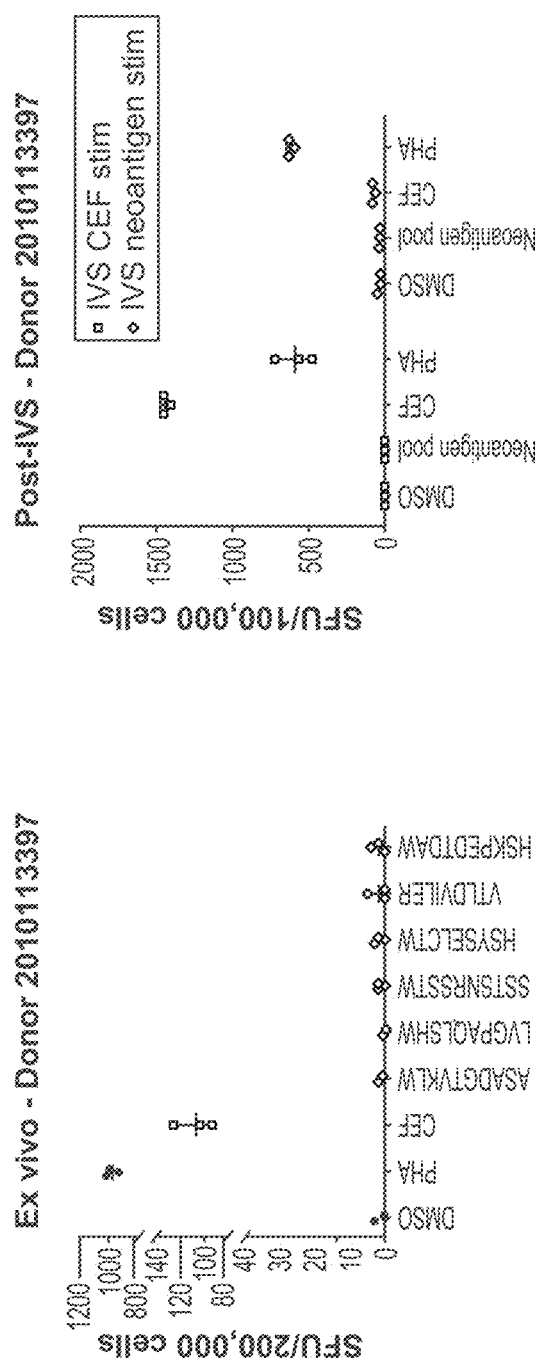

FIGS. 18A-B depict results from control experiments with patient neoantigens in HLA-matched healthy donors. The results of these experiments verify that in vitro culture conditions expanded only pre-existing in vivo primed memory T-cells, rather than enabling de novo priming in vitro.

Figure 19:
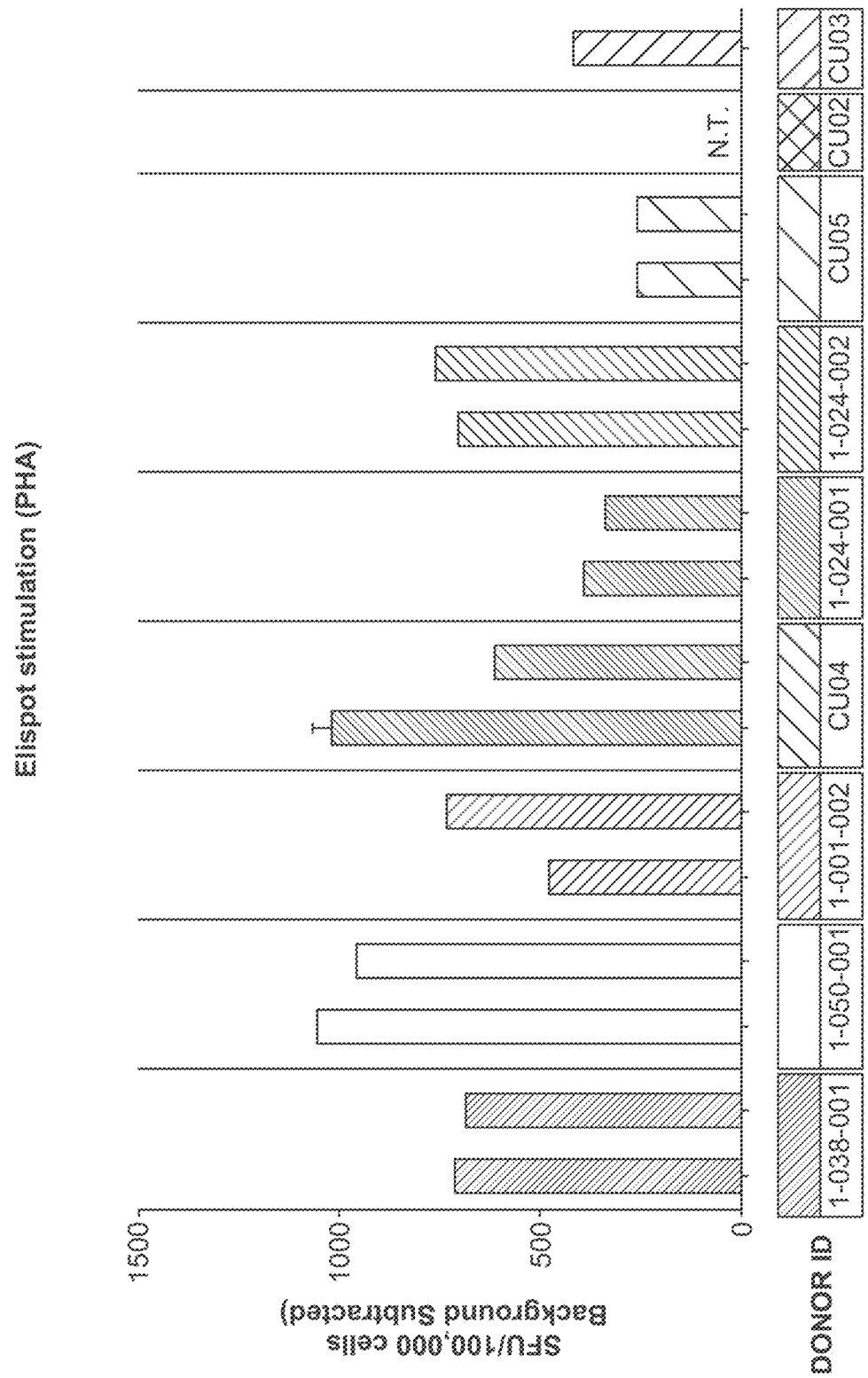
FIG. 19 depicts detection of T-cell responses to PHA positive control for each donor and each in vitro expansion depicted in FIG. 17A.

FIG. 19 depicts detection of T-cell responses to PHA positive control for each donor and each in vitro expansion depicted in FIG. 17A. For each donor and each in vitro expansion in FIG. 17A, the in vitro expanded patient PBMCs were stimulated with PHA for maximal T-cell activation. Data in FIG. 19 are presented as spot forming units (SFU) per $10^5$ plated cells with background (corresponding DMSO negative controls) subtracted. Responses of single wells or biological replicates are shown for patients 1-038-001, 1-050-001, 1-001-002, CU04, 1-24-01, 1-024-002, CU05 and CU03. Testing with PHA was not conducted for patient CU02. Cells from patient CU02 were included into analyses, as a positive response against peptide pool #1 (FIG. 17A) indicated viable and functional T-cells. As shown in FIG. 17A, donors that were responsive to peptide pools include patients 1-038-001, CU04, 1-024-001, and 1-024-002. As also shown in FIG. 17A, donors that were unresponsive to peptide pools include patients 1-050-001, 1-001-002, CU05, and CU03.

Figure 20A:
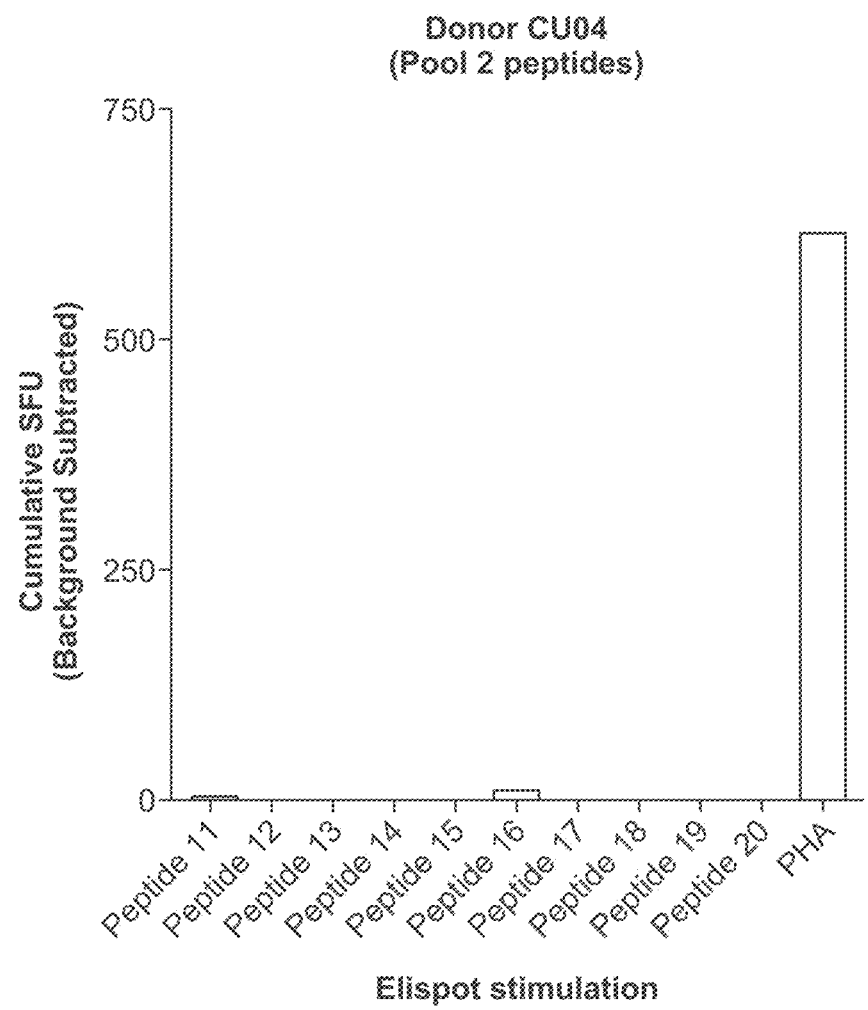
FIG. 20A depicts detection of T-cell responses to each individual patient-specific neoantigen peptide in pool #2 for patient CU04.

FIG. 20A depicts detection of T-cell responses to each individual patient-specific neoantigen peptide in pool #2 for patient CU04. FIG. 20A also depicts detection of T-cell responses to PHA positive control for patient CU04. (This is positive control data is also shown in FIG. 19.) For patient CU04, the in vitro expanded PBMCs for the patient were stimulated in IFN-gamma ELISpot with patient-specific individual neoantigen peptides from pool #2 for patient CU04. The in vitro expanded PBMCs for the patient were also stimulated in IFN-gamma ELISpot with PHA as a positive control. Data are presented as spot forming units (SFU) per $10^5$ plated cells with background (corresponding DMSO negative controls) subtracted.

Figure 20B:
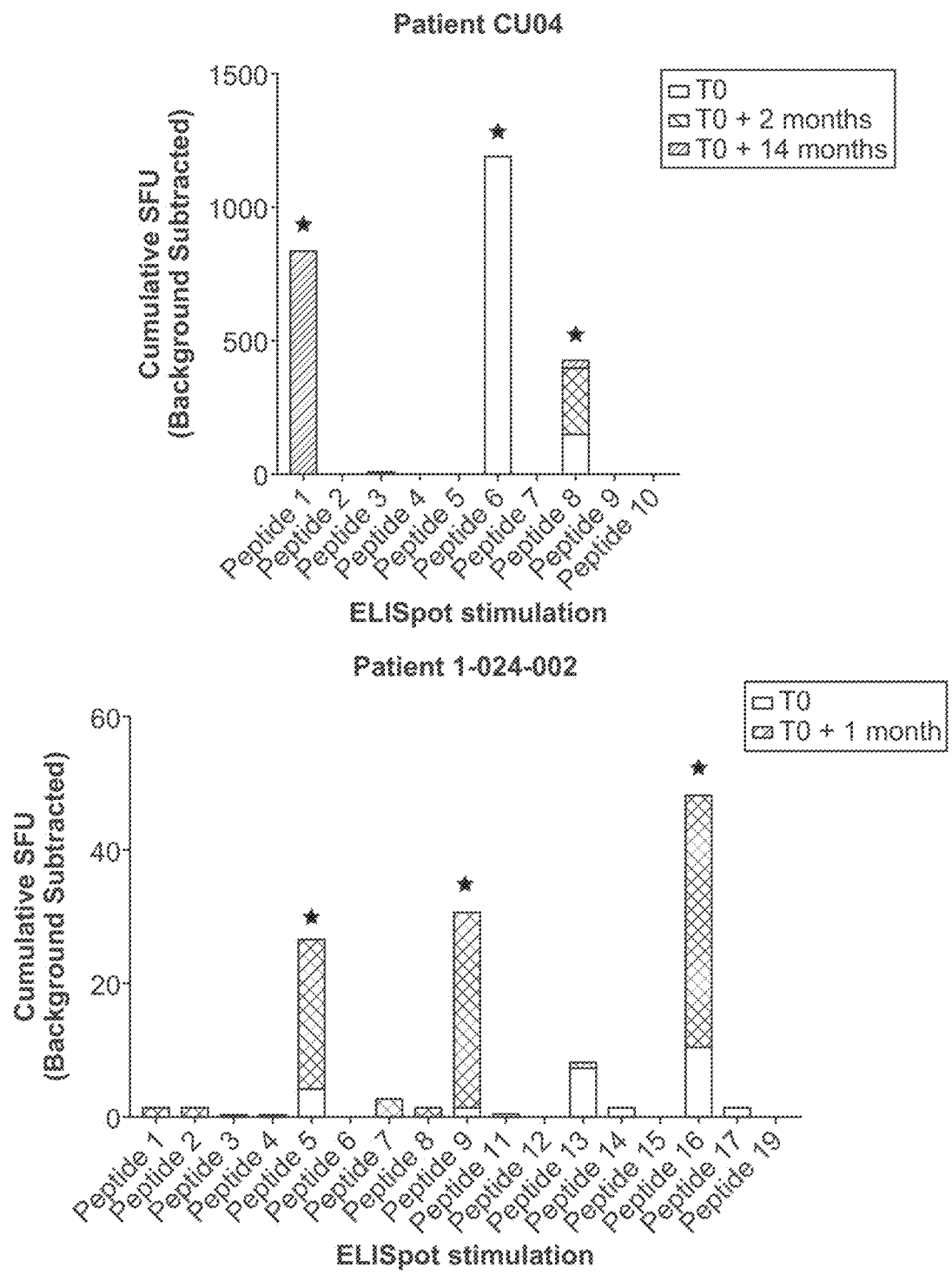
FIG. 20B depicts detection of T-cell responses to individual patient-specific neoantigen peptides for each of three visits of patient CU04 and for each of two visits of patient 1-024-002, each visit occurring at a different time point.

FIG. 20B depicts detection of T-cell responses to individual patient-specific neoantigen peptides for each of three visits of patient CU04 and for each of two visits of patient 1-024-002, each visit occurring at a different time point. For both patients, the in vitro expanded PBMCs for the patient were stimulated in IFN-gamma ELISpot with patient-specific individual neoantigen peptides. For each patient, data for each visit are presented as cumulative (added) spot forming units (SFU) per $10^5$ plated cells with background (corresponding DMSO controls) subtracted. Data for patient CU04 are shown as background subtracted cumulative SFU from 3 visits. For patient CU04, background subtracted SFU are shown for the initial visit (T0) and subsequent visits 2 months (T0+2 months) and 14 months (T0+14 months) after the initial visit (T0). Data for patient 1-024-002 are shown as background subtracted cumulative SFU from 2 visits. For patient 1-024-002, background subtracted SFU are shown for the initial visit (T0) and a subsequent visit 1 month (T0+1 month) after the initial visit (T0). Samples with values >2-fold increase above background were considered positive and are designated with a star.

Figure 20C:
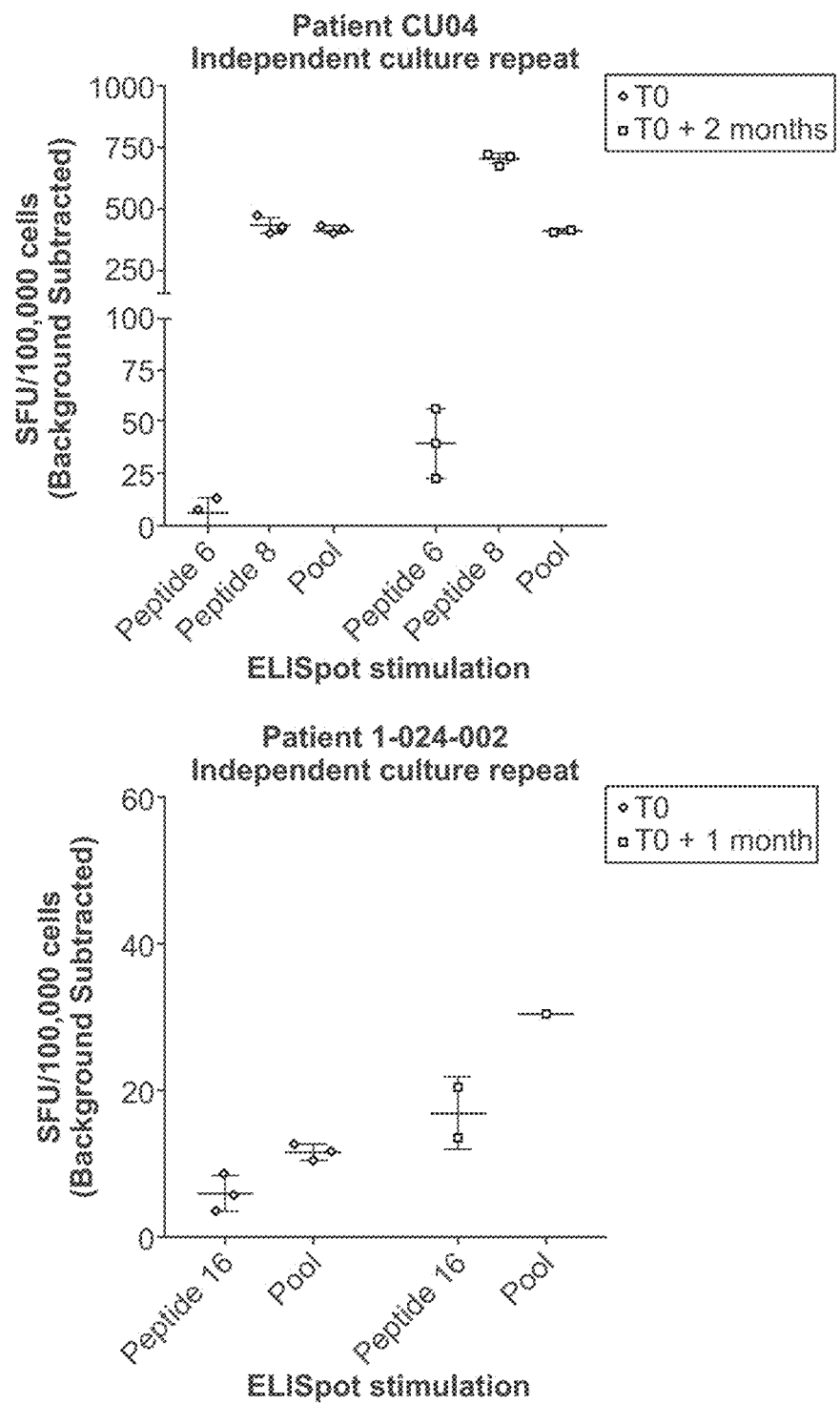
FIG. 20C depicts detection of T-cell responses to individual patient-specific neoantigen peptides and to patient-specific neoagntigen peptide pools for each of two visits of patient CU04 and for each of two visits of patient 1-024-002, each visit occurring at a different time point.

FIG. 20C depicts detection of T-cell responses to individual patient-specific neoantigen peptides and to patient-specific neoantigen peptide pools for each of two visits of patient CU04 and for each of two visits of patient 1-024-002, each visit occurring at a different time point. For both patients, the in vitro expanded PBMCs for the patient were stimulated in IFN-gamma ELISpot with patient-specific individual neoantigen peptides as well as with patient-specific neoantigen peptide pools. Specifically, for patient CU04, the in vitro expanded PBMCs for patient CU04 were stimulated in IFN-gamma ELISpot with CU04-specific individual neoantigen peptides 6 and 8 as well as with CU04-specific neoantigen peptide pools, and for patient 1-024-002, the in vitro expanded PBMCs for patient 1-024-002 were stimulated in IFN-gamma ELISpot with 1-024-002-specific individual neoantigen peptide 16 as well as with 1-024-002-specific neoantigen peptide pools. The data of FIG. 20C are presented as spot forming units (SFU) per $10^5$ plated cells with background (corresponding DMSO controls) subtracted for each technical replicate with mean and range. Data for patient CU04 are shown as background subtracted SFU from 2 visits. For patient CU04, background subtracted SFU are shown for the initial visit (T0; technical triplicates) and a subsequent visit at 2 months (T0+2 months; technical triplicates) after the initial visit (T0). Data for patient 1-024-002 are shown as background subtracted SFU from 2 visits. For patient 1-024-002, background subtracted SFU are shown for the initial visit (T0; technical triplicates) and a subsequent visit 1 month (T0+1 month; technical duplicates, except for the sample stimulated with patient 1-024-002-specific neoantigen peptide pools) after the initial visit (T0).

FIG. 21 depicts detection of T-cell responses to the two patient-specific neoantigen peptide pools and to DMSO negative controls for the patients of FIG. 17A. For each patient, the in vitro expanded PBMCs for the patient were stimulated with the two patient-specific neoantigen peptide pools in IFN-gamma ELISpot. For each donor and each in vitro expansion, the in vitro expanded patient PBMCs were also stimulated in IFN-gamma ELISpot with DMSO as a negative control. Data in FIG. 21 are presented as spot forming units (SFU) per $10^5$ plated cells with background (corresponding DMSO negative controls) included for patient-specific neoantigen peptide pools and corresponding DMSO controls. Responses of single wells (1-038-001, CU02, CU03 and 1-050-001) or average with standard deviation of biological duplicates (all other samples) against cognate peptide pools #1 and #2 are shown for patients 1-038-001, 1-050-001, 1-001-002, CU04, 1-024-001, 1-024-002 and CU05. For patients CU02 and CU03, cell numbers allowed testing against specific peptide pool #1 only. Samples with values >2-fold increase above background were considered positive and are designated with a star (responsive donors include patients 1-038-001, CU04, 1-024-001, 1-024-002, and CU02). Unresponsive donors include patients 1-050-001, 1-001-002, CU05, and CU03.

As discussed briefly above with regard to FIGS. 18A-B, to verify that the in vitro culture conditions expanded only pre-existing in vivo primed memory T-cells, rather than enabling de novo priming in vitro, a series of control experiments were performed with neoantigens in HLA-matched healthy donors. The results of these experiments are depicted in FIGS. 18A-B and in Supplementary Table 5. The results of these experiments confirmed the absence of de novo priming and absence of a detectable neoantigen-specific T-cell response in healthy donors using IVS culture technique.

By contrast, pre-existing neoantigen-reactive T-cells were identified in the majority (5/9, 56%) of patients tested with patient-specific peptide pools (FIGS. 17A and 19-21) using IFN-gamma ELISpot. Of the 7 patients for whom cell numbers permitted complete or partial testing of individual neoantigen cognate peptides, 4 patients responded to at least one of the tested neoantigen peptides, and all of these patients had a corresponding pool response (FIG. 17B). The remaining 3 patients tested with individual neoantigens (patients 1-001-002, 1-050-001 and CU05) had no detectable responses against single peptides (data not shown), confirming the lack of response seen for these patients against neoantigen pools (FIG. 17A). Among the 4 responsive patients, samples from a single visit were available for 2 patients with a response (patients 1-024-001 and 1-038-001), while samples from multiple visits were available for the other 2 patients with a response (CU04 and 1-024-002). For the 2 patients with samples from multiple visits, the cumulative (added) spot forming units (SFU) from 3 visits (patient CU04) or 2 visits (patient 1-024-002) are shown in FIG. 17B and broken down by visit in FIG. 20B. Additional PBMC samples from the same visits were also available for patients 1-024-002 and CU04, and repeat IVS culture and ELISpot confirmed responses to patient-specific neoantigens (FIG. 20C).

Overall, among patients for whom at least one T-cell recognized neoepitope was identified as shown by a response to a pool of 10 peptides in FIG. 17A, the number of recognized neoepitopes averaged at least 2 per patient (minimum of 10 epitopes identified in 5 patients, counting a recognized pool that could not be deconvolved as 1 recognized peptide). In addition to testing for IFN-gamma response by ELISpot, culture supernatants were also tested for granzyme B by ELISA and for TNF-alpha, IL-2 and IL-5 by MSD cytokine multiplex assay. Cells from 4 of the 5 patients with positive ELISpots secreted 3 or more analytes, including granzyme B (Supplementary Table 4), indicating polyfunctionality of neoantigen-specific T-cells. Importantly, because the combined prediction and IVS method did not rely on a limited set of available MHC multimers, responses were tested broadly across restricting HLA alleles. Furthermore, this approach directly identifies the minimal epitope, in contrast to tandem minigene screening, which identifies recognized mutations, and requires a separate deconvolution step to identify minimal epitopes. Overall, the neoantigen identification yield was comparable to previous best methods[96] testing TIL against all mutations with apheresis samples, while screening only 20 synthetic peptides with a routine 5-30 mL of whole blood.

XV.A. Peptides

Custom-made, recombinant lyophilized peptides were purchased from JPT Peptide Technologies (Berlin, Germany) or Genscript (Piscataway, N.J., USA) and reconstituted at 10-50 mM in sterile DMSO (VWR International, Pittsburgh, Pa., USA), aliquoted and stored at −80° C.

XV.B. Human Peripheral Blood Mononuclear Cells (PBMCs)

Cryopreserved HLA-typed PBMCs from healthy donors (confirmed HIV, HCV and HBV seronegative) were purchased from Precision for Medicine (Gladstone, N.J., USA) or Cellular Technology, Ltd. (Cleveland, Ohio, USA) and stored in liquid nitrogen until use. Fresh blood samples were purchased from Research Blood Components (Boston, Mass., USA), leukopaks from AllCells (Boston, Mass., USA) and PBMCs were isolated by Ficoll-Paque density gradient (GE Healthcare Bio, Marlborough, Mass., USA) prior to cryopreservation. Patient PBMCs were processed at local clinical processing centers according to local clinical standard operating procedures (SOPs) and IRB approved protocols. Approving IRBs were Quorum Review IRB, Comitato Etico Interaziendale A.O.U. San Luigi Gonzaga di Orbassano, and Comité Ético de la Investigación del Grupo Hospitalario Quirón en Barcelona.

Briefly, PBMCs were isolated through density gradient centrifugation, washed, counted, and cryopreserved in CryoStor CS10 (STEMCELL Technologies, Vancouver, BC, V6A 1B6, Canada) at $5 \times 10^6$ cells/ml. Cryopreserved cells were shipped in cryoports and transferred to storage in $LN_2$ upon arrival. Patient demographics are listed in Supplementary Table 2. Cryopreserved cells were thawed and washed twice in OpTmizer T-cell Expansion Basal Medium (Gibco, Gaithersburg, Md., USA) with Benzonase (EMD Millipore, Billerica, Mass., USA) and once without Benzonase. Cell counts and viability were assessed using the Guava ViaCount reagents and module on the Guava easyCyte HT cytometer (EMD Millipore). Cells were subsequently resuspended at concentrations and in media appropriate for proceeding assays (see next sections).

XV.C. In Vitro Stimulation (IVS) Cultures

Pre-existing T-cells from healthy donor or patient samples were expanded in the presence of cognate peptides and IL-2 in a similar approach to that applied by Ott et al.[81] Briefly, thawed PBMCs were rested overnight and stimulated in the presence of peptide pools (10 µM per peptide, 10 peptides per pool) in ImmunoCult™-XF T-cell Expansion Medium (STEMCELL Technologies) with 10 IU/ml rhIL-2 (R&D Systems Inc., Minneapolis, Minn.) for 14 days in 24-well tissue culture plates. Cells were seeded at $2 \times 10^6$ cells/well and fed every 2-3 days by replacing 2/3 of the culture media. One patient sample showed a deviation from the protocol and should be considered as a potential false negative: Patient CU03 did not yield sufficient numbers of cells post thawing and cells were seeded at $2 \times 10^5$ cells per peptide pool (10-fold fewer than per protocol).

XV.D. IFNγ Enzyme Linked Immunospot (ELISpot) Assay

Detection of IFNγ-producing T-cells was performed by ELISpot assay[142]. Briefly, PBMCs (ex vivo or post in vitro expansion) were harvested, washed in serum free RPMI (VWR International) and cultured in the presence of controls or cognate peptides in OpTmizer T-cell Expansion Basal Medium (ex vivo) or in ImmunoCult™-XF T-cell Expansion Medium (expanded cultures) in ELISpot Multiscreen plates (EMD Millipore) coated with anti-human IFNγ capture antibody (Mabtech, Cincinatti, Ohio, USA). Following 18 h incubation in a 5% $CO_2$, 37° C., humidified incubator, cells were removed from the plate and membrane-bound IFNγ was detected using anti-human IFNγ detection antibody (Mabtech), Vectastain Avidin peroxidase complex (Vector Labs, Burlingame, Calif., USA) and AEC Substrate (BD Biosciences, San Jose, Calif., USA). ELISpot plates were allowed to dry, stored protected from light and sent to Zellnet Consulting, Inc., Fort Lee, N.J., USA) for standardized evaluation[143]. Data are presented as spot forming units (SFU) per plated number of cells.

XV.E. Granzyme B ELISA and MSD Multiplex Assay

Detection of secreted IL-2, IL-5 and TNF-alpha in ELISpot supernatants was performed using a 3-plex assay MSD U-PLEX Biomarker assay (catalog number K15067L-2). Assays were performed according to the manufacturer's instructions. Analyte concentrations (pg/ml) were calculated using serial dilutions of known standards for each cytokine. For graphical data representation, values below the minimum range of the standard curve were represented equals zero. Detection of Granzyme B in ELISpot supernatants was performed using the Granzyme B DuoSet® ELISA (R & D Systems, Minneapolis, Minn.) according to the manufacturer's instructions. Briefly, ELISpot supernatants were diluted 1:4 in sample diluent and run alongside serial dilutions of Granzyme B standards to calculate concentrations (pg/ml). For graphical data representation, values below the minimum range of the standard curve were represented equals zero.

XV.F. Negative Control Experiments for IVS Assay—Neoantigens from Tumor Cell Lines Tested in Healthy Donors FIG. 18A illustrates negative control experiments for IVS assay for neoantigens from tumor cell lines tested in healthy donors. Healthy donor PBMCs were stimulated in IVS culture with peptide pools containing positive control peptides (previous exposure to infectious diseases), HLA-matched neoantigens originating from tumor cell lines (unexposed), and peptides derived from pathogens for which the donors were seronegative. Expanded cells were subsequently analyzed by IFNγ ELISpot ($10^5$ cells/well) following stimulation with DMSO (negative controls, black circles), PHA and common infectious diseases peptides (positive controls, red circles), neoantigens (unexposed, light blue circles), or HIV and HCV peptides (donors were confirmed to be seronegative, navy blue, A and B). Data are shown as spot forming units (SFU) per $10^5$ seeded cells. Biological replicates with mean and SEM are shown. No responses were observed to neoantigens or to peptides deriving from pathogens to which the donors have not been exposed (seronegative).

XV.G. Negative Control Experiments for IVS Assay—Neoantigens from Patients Tested in Healthy Donors FIG. 18A illustrates negative control experiments for IVS assay for neoantigens from patients tested for reactivity in healthy donors. Assessment of T-cell responses in healthy donors to HLA-matched neoantigen peptide pools. Left panel: Healthy donor PBMCs were stimulated with controls (DMSO, CEF and PHA) or HLA-matched patient-derived neoantigen peptides in ex vivo IFN-gamma ELISpot. Data are presented as spot forming units (SFU) per $2 \times 10^5$ plated cells for triplicate wells. Right panel: Healthy donor PBMCs post IVS culture, expanded in the presence of either neoantigen pool or CEF pool were stimulated in IFN-gamma ELISpot either with controls (DMSO, CEF and PHA) or HLA-matched patient-derived neoantigen peptide pool. Data are presented as SFU per $1 \times 10^5$ plated cells for triplicate wells. No responses to neoantigens in healthy donors are seen.

XV.H. Supplementary Table 3: Peptides Tested for T-Cell Recognition in NSCLC Patients Details on neoantigen peptides tested for the N=9 patients studied in FIGS. 17A-C (Identification of Neoantigen-Reactive T-cells from NSCLC Patients). Key fields include source mutation, peptide sequence, and pool and individual peptide responses observed. The "most probable restriction" column indicates which allele the model predicted was most likely to present each peptide. The ranks of these peptides among all mutated peptides for each patient as computed with binding affinity prediction (Methods) are also included.

There were four peptides highly ranked by the full MS model and recognized by CD8 T-cells that had low predicted binding affinities or were ranked low by binding affinity prediction.

For three of these peptides, this is caused by differences in HLA coverage between the model and MHCflurry 1.2.0. Peptide YEHEDVKEA (SEQ ID NO: 20) is predicted to be presented by HLA-B*49:01, which is not covered by MHCflurry 1.2.0. Similarly, peptides SSAAAPFPL (SEQ ID NO: 21) and FVSTSDIKSM (SEQ ID NO: 22) are predicted to be presented by HLA-C*03:04, which is also not covered by MHCflurry 1.2.0. The online NetMHCpan 4.0 (BA) predictor, a pan-specific binding affinity predictor that in principle covers all alleles, ranks SSAAAPFPL (SEQ ID NO: 21) as a strong binder to HLA-C*03:04 (23.2 nM, ranked 2nd for patient 1-024-002), predicts weak binding of FVSTSDIKSM (SEQ ID NO: 22) to HLA-C*03:04 (943.4 nM, ranked 39th for patient 1-024-002) and weak binding of YEHEDVKEA (SEQ ID NO: 20) to HLA-B*49:01 (3387.8 nM), but stronger binding to HLA-B*41:01 (208.9 nM, ranked 11th for patient 1-038-001), which is also present in this patient but is not covered by the model. Thus, of these three peptides, FVSTSDIKSM (SEQ ID NO: 22) would have been missed by binding affinity prediction, SSAAAPFPL (SEQ ID NO: 21) would have been captured, and the HLA restriction of YEHEDVKEA (SEQ ID NO: 20) is uncertain.

The remaining five peptides for which a peptide-specific T-cell response was deconvolved came from patients where the most probable presenting allele as determined by the model was also covered by MHCflurry 1.2.0. Of these five peptides, 4/5 had predicted binding affinities stronger than the standard 500 nM threshold and ranked in the top 20, though with somewhat lower ranks than the ranks from the model (peptides DENITTIQF (SEQ ID NO: 23), QDVSVQVER (SEQ ID NO: 24), EVADAATLTM (SEQ ID NO: 25), DTVEYPYTSF (SEQ ID NO: 26) were ranked 0, 4, 5, 7 by the model respectively vs 2, 14, 7, and 9 by MHCflurry). Peptide GTKKDVDVLK (SEQ ID NO: 27) was recognized by CD8 T-cells and ranked 1 by the model, but had rank 70 and predicted binding affinity 2169 nM by MHCflurry.

Overall, 6/8 of the individually-recognized peptides that were ranked highly by the full MS model also ranked highly using binding affinity prediction and had predicted binding affinity <500 nM, while 2/8 of the individually-recognized peptides would have been missed if binding affinity prediction had been used instead of the full MS model.

XV.I. Supplementary Table 4: MSD Cytokine Multiplex and ELISA Assays on ELISpot Supernatants from NSCLC Neoantigen Peptides Analytes detected in supernatants from positive ELISpot (IFNgamma) wells are shown for granzyme B (ELISA), TNFalpha, IL-2 and IL-5 (MSD). Values are shown as average pg/ml from technical replicates. Positive values are shown in italics. Granzyme B ELISA: Values ≥1.5-fold over DMSO background were considered positive. U-Plex MSD assay: Values ≥1.5-fold over DMSO background were considered positive.

XV.J. Supplementary Table 5: Neoantigen and Infectious Disease Epitopes in IVS Control Experiments Details on tumor cell line neoantigen and viral peptides tested in IVS control experiments shown in FIGS. 18A-B.

Key fields include source cell line or virus, peptide sequence, and predicted presenting HLA allele.

XV.K. Data

The MS peptide dataset used to train and test the prediction model (FIG. 16) is available at the MassIVE Archive (massive.ucsd.edu), accession number MSV000082648. Neoantigen peptides tested by ELISpot (FIGS. 17A-C and 18A-B) are included with the manuscript (Supplementary Tables 3 and 5).

XVI. Methods of Examples 8-11

XVI.A. Mass Spectrometry

XVI.A.1. Specimens

Archived frozen tissue specimens for mass spectrometry analysis were obtained from commercial sources, including BioServe (Beltsville, Md.), ProteoGenex (Culver City, Calif.), iSpecimen (Lexington, Mass.), and Indivumed (Hamburg, Germany). A subset of specimens was also collected prospectively from patients at Hopital Marie Lannelongue (Le Plessis-Robinson, France) under a research protocol approved by the Comité de Protection des Personnes, Ile-de-France VII.

XVI.A.2. HLA Immunoprecipitation

Isolation of HLA-peptide molecules was performed using established immunoprecipitation (IP) methods after lysis and solubilization of the tissue sample[87,124-126]. Fresh frozen tissue was pulverized (CryoPrep; Covaris, Woburn, Mass.), lysis buffer (1% CHAPS, 20 mM Tris-HCl, 150 mM NaCl, protease and phosphatase inhibitors, pH=8) was added to solubilize the tissue and the resultant solution was centrifuged at 4 C for 2 hrs to pellet debris. The clarified lysate is used for the HLA specific IP. Immunoprecipitation was performed as previously described using the antibody W6/32[127]. The lysate is added to the antibody beads and rotated at 4 C overnight for the immunoprecipitation. After immunoprecipitation, the beads were removed from the lysate. The IP beads were washed to remove non-specific binding and the HLA/peptide complex was eluted from the beads with 2N acetic acid. The protein components were removed from the peptides using a molecular weight spin column. The resultant peptides were taken to dryness by SpeedVac evaporation and stored at −20 C prior to MS analysis.

XVI.A.3. Peptide Sequencing

Dried peptides were reconstituted in HPLC buffer A and loaded onto a C-18 microcapillary HPLC column for gradient elution in to the mass spectrometer. A gradient of 0-40% B (solvent A—0.1% formic acid, solvent B— 0.1% formic acid in 80% acetonitrile) in 180 minutes was used to elute the peptides into the Fusion Lumos mass spectrometer (Thermo). MS1 spectra of peptide mass/charge (m/z) were collected in the Orbitrap detector with 120,000 resolution followed by 20 MS2 low resolution scans collected in the either the Orbitrap or ion trap detector after HCD fragmentation of the selected ion. Selection of MS2 ions was performed using data dependent acquisition mode and dynamic exclusion of 30 seconds after MS2 selection of an ion. Automatic gain control (AGC) for MS1 scans was set to 4×105 and for MS2 scans was set to 1×104. For sequencing HLA peptides, +1, +2 and +3 charge states can be selected for MS2 fragmentation.

MS2 spectra from each analysis were searched against a protein database using Comet[128,129] and the peptide identification were scored using Percolator[130-132].

XVI.B. Machine Learning

XVI.B.1. Data Encoding

For each sample, the training data points were all 8-11mer (inclusive) peptides from the reference proteome that mapped to exactly one gene expressed in the sample. The overall training dataset was formed by concatenating the training datasets from each training sample. Lengths 8-11 were chosen as this length range captures ~95% of all HLA class I presented peptides; however, adding lengths 12-15 to the model could be accomplished using the same methodology, at the cost of a modest increase in computational demands. Peptides and flanking sequence were vectorized using a one-hot encoding scheme. Peptides of multiple lengths (8-11) were represented as fixed-length vectors by augmenting the amino acid alphabet with a pad character and padding all peptides to the maximum length of 11. RNA abundance of the source protein of the training peptides was represented as the logarithm of the isoform-level transcripts per million (TPM) estimate obtained from RSEM[133]. For each peptide, the per-peptide TPM was computed as the sum of the per-isoform TPM estimates for each of the isoforms that contain the peptide. Peptides from genes expressed at 0 TPM were excluded from the training data, and at test time, peptides from non-expressed genes are assigned a probability of presentation of 0. Lastly, each peptide was assigned to an Ensembl protein family ID, and each unique Ensembl protein family ID corresponded to a per-gene presentation propensity intercept (see next section).

XVI.B.2 Specification of the Model Architecture

The full presentation model has the following functional form:

$$Pr(\text{peptide } i \text{ presented}) = \Sigma_{k=1}^{m} a_k^i \cdot Pr(\text{peptide } i \text{ presented by allele } a), \quad \text{(Equation 1)}$$

where k indexes HLA alleles in the dataset, which run from 1 to m, and $a_k^i$ is an indicator variable whose value is 1 if allele k is present in the sample from which peptide i is derived and 0 otherwise. Note that for a given peptide i, all but at most 6 of the $a_k^i$ (the 6 corresponding to the HLA type of the sample of origin of peptide i) will be zero. The sum of probabilities is clipped at $1-\epsilon$, with $\epsilon=10^{-6}$ for instance.

The per-allele probabilities of presentation are modeled as below:

$$Pr(\text{peptide } i \text{ presented by allele } a) = \text{sigmoid}\{NN_a(\text{peptide}_i) + NN_{flanking}(\text{flanking}_i) + NN_{RNA}(\log(TPM_i)) + a_{sample(i)} + \beta_{protein(i)}\},$$

where the variables have the following meanings: sigmoid is the sigmoid (aka expit) function, $\text{peptide}_i$ is the onehot-encoded middle-padded amino acid sequence of peptide i, $NN_a$ is a neural network with linear last-layer activation modeling the contribution of the peptide sequence to the probability of presentation, $\text{flanking}_i$ is the onehot-encoded flanking sequence of peptide i in its source protein, $NN_{flanking}$ is a neural network with linear last-layer activation modeling the contribution of the flanking sequence to the probability of presentation, $TPM_i$ is the expression of the source mRNAs of peptide i in TPM units, sample(i) is the sample (i.e., patient) of origin of peptide i, $a_{sample(i)}$ is a per-sample intercept, protein(i) is the source protein of peptide i, and $\beta_{protein(i)}$ is a per-protein intercept (aka the per-gene propensity of presentation).

For the models described in the results section, the component neural networks have the following architectures:

Each of the $NN_a$ is one output node of a one-hidden-layer multi-layer-perceptron (MLP) with input dimension 231 (11 residues×21 possible characters per residue, including the pad character), width 256, rectified linear unit (ReLU) activations in the hidden layer, linear activation in the output layer, and one output node per HLA allele a in the training dataset.

$NN_{flanking}$ is a one-hidden-layer MLP with input dimension 210 (5 residues of N-terminal flanking sequence+5 residues of C-terminal flanking sequence×21 possible characters per residue, including the pad character), width 32, rectified linear unit (ReLU) activations in the hidden layer and linear activation in the output layer.

$NN_{RNA}$ is a one-hidden-layer MLP with input dimension 1, width 16, rectified linear unit (ReLU) activations in the hidden layer and linear activation in the output layer.

Note that some components of the model (e.g., $NN_a$) depend on a particular HLA allele, but many components ($NN_{flanking}$, $NN_{RNA}$, $a_{sample(i)}$, $\beta_{protein(i)}$) do not. The former is referred to as "allele-interacting" and the latter as "allele-noninteracting". Features to model as allele-interacting or noninteracting were chosen on the basis of biological prior knowledge: the HLA allele sees the peptide, so the peptide sequence should be modeled as allele-interacting, but no information about the source protein, RNA expression or flanking sequence is conveyed to the HLA molecule (as the peptide has been separated from its source protein by the time it encounters the HLA in the endoplasmic reticulum), so these features should be modeled as allele-noninteracting. The model was implemented in Keras v2.0.4[134] and Theano v0.9.0[135].

The peptide MS model used the same deconvolution procedure as the full MS model (Equation 1), but the per-allele probabilities of presentation were generated using reduced per-allele models that consider only peptide sequence and HLA allele a:

$Pr$(peptide i presented by allele a)=sigmoid{$NN_a$ (peptide$_i$)}.

The peptide MS model uses the same features as binding affinity prediction, but the weights of the model are trained on a different data type (i.e., mass spectrometry data vs HLA-peptide binding affinity data). Therefore, comparing the predictive performance of the peptide MS model to the full MS model reveals the contribution of non-peptide features (i.e., RNA abundance, flanking sequence, gene ID) to the overall predictive performance, and comparing the predictive performance of the peptide MS model to the binding affinity models reveals the importance of improved modeling of the peptide sequence to the overall predictive performance.

XVI.B.3. Train/Validate/Test Splits

We ensured that no peptides appeared in more than one of the training/validation/testing sets using the following procedure: first by removing all peptides from the reference proteome that appear in more than one protein, then by partitioning the proteome into blocks of 10 adjacent peptides. Each block was assigned uniquely to the training, validation or testing sets. In this way, no peptide appears in more than one of the training, validation on testing sets. The validation set was used only for early stopping. The tumor sample test data in FIGS. 14-16 represent test set peptides (i.e., peptides from the blocks of adjacent peptides assigned uniquely to the test set) from five tumor samples that were held out of the training and validation sets entirely.

XVI.B.4. Model Training

For model training, all peptides were modeled as independent where the per-peptides loss is the negative Bernoulli log-likelihood loss function (aka log loss). Formally, the contribution of peptide i to the overall loss is $$Loss(i) = -\log(Bernoulli(y_i | Pr(\text{peptide } i \text{ presented})))$$, where $y_i$ is the label of peptide i; i.e., $y^i=1$ if peptide i is presented and 0 otherwise, and Bernoulli(y|p) denotes the Bernoulli likelihood of parameter $p \in [0, 1]$ given i.i.d. binary observation vector y. The model was trained by minimizing the loss function.

In order to reduce training time, the class balance was adjusted by removing 90% of the negative-labeled training data at random, yielding an overall training set class balance of one presented peptide per ~2000 non-presented peptides. Model weights were initialized using the Glorot uniform procedure61 and trained using the ADAM62 stochastic optimizer with standard parameters on Nvidia Maxwell TITAN X GPUs. A validation set consisting of 10% of the total data was used for early stopping. The model was evaluated on the validation set every quarter-epoch and model training was stopped after the first quarter-epoch where the validation loss (i.e., the negative Bernoulli log-likelihood on the validation set) failed to decrease.

The full presentation model was an ensemble of 10 model replicates, with each replicate trained independently on a shuffled copy of the same training data with a different random initialization of the model weights for every model within the ensemble. At test time, predictions were generated by taking the mean of the probabilities output by the model replicates.

XVI.B.5. Motif Logos

Motif logos were generated using the weblogolib Python API v3.5.0[138]. To generate binding affinity logos, the mhc_ligand_full.csv file was downloaded from the Immune Epitope Database (IEDB[88]) in July, 2017 and peptides meeting the following criteria were retained: measurement in nanomolar (nM) units, reference date after 2000, object type equal to "linear peptide" and all residues in the peptide drawn from the canonical 20-letter amino acid alphabet. Logos were generated using the subset of the filtered peptides with measured binding affinity below the conventional binding threshold of 500 nM. For alleles pair with too few binders in IEDB, logos were not generated. To generate logos representing the learned presentation model, model predictions for 2,000,000 random peptides were predicted for each allele and each peptide length. For each allele and each length, the logos were generated using the peptides ranked in the top 1% (i.e., the top 20,000) by the learned presentation model. Importantly, this binding affinity data from IEDB was not used in model training or testing, but rather used only for the comparison of motifs learned.

XVI.B.6. Binding Affinity Prediction

We predicted peptide-MHC binding affinities using the binding affinity-only predictor from MHCflurry v1.2.0[139], an open-source, GPU-compatible HLA class I binding affinity predictor with performance comparable to the NetMHC family of models. To combine binding affinity predictions for a single peptide across multiple HLA alleles, the minimum binding affinity was selected. To combine binding affinities across multiple peptides (i.e., in order to rank mutations spanned by multiple mutated peptides as in FIG. 16), the minimum binding affinity across the peptides was selected. For RNA expression thresholding on the T-cell dataset, tumor-type matched RNA-seq data from TCGA to threshold at TPM>1 was used. All of the original T-cell datasets were filtered on TPM>0 in the original publications, so the TCGA RNA-seq data to filter on TPM>0 was not used.

XVI.B.7. Presentation Prediction

To combine probabilities of presentation for a single peptide across multiple HLA alleles, the sum of the probabilities was identified, as in Equation 1. To combine probabilities of presentation across multiple peptides (i.e., in order to rank mutations spanned by multiple peptides as in FIG. 16), the sum of the probabilities of presentation was identified. Probabilistically, if presentation of the peptides is viewed as i.i.d. Bernoulli random variables, the sum of the probabilities corresponds to the expected number of presented mutated peptides:

$$E[\text{\# presented neoantigens spanning mutation } i] = \sum_{j=1}^{n_i} Pr[\text{epitope } j \text{ presented}],$$

where Pr[epitope j presented] is obtained by applying the trained presentation model to epitope j, and $n_i$ denotes the number of mutated epitopes spanning mutation i. For example, for an SNV i distant from the termini of its source gene, there are 8 spanning 8-mers, 9-spanning 9-mers, 10 spanning 10-mers and 11 spanning 11-mers, for a total of $n_i$=38 spanning mutated epitopes.

XVI.C. Next Generation Sequencing

XVI.C.1. Specimens

For transcriptome analysis of the frozen resected tumors, RNA was obtained from same tissue specimens (tumor or adjacent normal) as used for MS analyses. For neoantigen exome and transcriptome analysis in patients on anti-PD1 therapy, DNA and RNA was obtained from archival FFPE tumor biopsies. Adjacent normal, matched blood or PBMCs were used to obtain normal DNA for normal exome and HLA typing.

XVI.C.2. Nucleic Acid Extraction and Library Construction

Normal/germline DNA derived from blood were isolated using Qiagen DNeasy columns (Hilden, Germany) following manufacturer recommended procedures. DNA and RNA from tissue specimens were isolated using Qiagen Allprep DNA/RNA isolation kits following manufacturer recommended procedures. The DNA and RNA were quantitated by Picogreen and Ribogreen Fluorescence (Molecular Probes), respectively specimens with >50 ng yield were advanced to library construction. DNA sequencing libraries were generated by acoustic shearing (Covaris, Woburn, Mass.) followed by DNA Ultra II (NEB, Beverly, Mass.) library preparation kit following the manufacturers recommended protocols. Tumor RNA sequencing libraries were generated by heat fragmentation and library construction with RNA Ultra II (NEB). The resulting libraries were quantitated by Picogreen (Molecular Probes).

XVI.C.3. Whole Exome Capture

Exon enrichment for both DNA and RNA sequencing libraries was performed using xGEN Whole Exome Panel (Integrated DNA Technologies). One to 1.5 μg of normal DNA or tumor DNA or RNA-derived libraries were used as input and allowed to hybridize for greater than 12 hours followed by streptavidin purification. The captured libraries were minimally amplified by PCR and quantitated by NEB-Next Library Quant Kit (NEB). Captured libraries were pooled at equimolar concentrations and clustered using the c-bot (Illumina) and sequenced at 75 base paired-end on a HiSeq4000 (Illumina) to a target unique average coverage of >500× tumor exome, >100× normal exome, and >100M reads tumor transcriptome.

XVI.C.4. Analysis

Exome reads (FFPE tumor and matched normals) were aligned to the reference human genome (hg38) using BWA-MEM[144] (v. 0.7.13-r1126). RNA-seq reads (FFPE and frozen tumor tissue samples) were aligned to the genome and GENCODE transcripts (v. 25) using STAR (v. 2.5.1b). RNA expression was quantified using RSEM[133] (v. 1.2.31) with the same reference transcripts. Picard (v. 2.7.1) was used to mark duplicate alignments and calculate alignment metrics. For FFPE tumor samples following base quality score recalibration with GATK[145] (v. 3.5-0), substitution and short indel variants were determined using paired tumor-normal exomes with FreeBayes[146] (1.0.2). Filters included allele frequency >4%; median base quality >25, minimum mapping quality of supporting reads 30, and alternate read count in normal <=2 with sufficient coverage obtained. Variants must also be detected on both strands. Somatic variants occurring in repetitive regions were excluded. Translation and annotation were performed with snpEff[147] (v. 4.2) using RefSeq transcripts. Non-synonymous, non-stop variants verified in tumor RNA alignments were advanced to neoantigen prediction. Optitype[148] 1.3.1 was used to generate HLA types.

XVI.C.5. FIGS. 18A-B: Tumor Cell Lines and Matched Normals for IVS Control Experiments Tumor cell lines H128, H122, H2009, H2126, Colo829 and their normal donor matched control cell lines BL128, BL2122, BL2009, BL2126 and Colo829BL were all purchased from ATCC (Manassas, Va.) were grown to $10^{83}$-$10^{84}$ cells per seller's instructions then snap frozen for nucleic acid extraction and sequencing. NGS processing was performed generally as described above, except that MuTect[149] (3.1-0) was used for substitution mutation detection only. Peptides used in the IVS control assays are listed in Supplementary Table 5.

XVI.D. Presentation Hotspot Modeling for MHC Class II Molecules

We also evaluated performance of the model disclosed herein for class II HLA peptide presentation when using presentation hotspot parameters and when not using presentation hotspot parameters. While class I complexes present cytosolic proteins and are found on the surface of all nucleated cells in humans, class II complexes are found mostly on antigen-presenting cells and are primarily responsible for presenting extracelluar (exogenous) proteins. There are also differences between classes I and II in their binding mechanisms and peptide lengths.

To evaluate performance of the model disclosed herein for class II HLA peptide presentation when using the presentation hotspot feature and when not using the presentation hotspot feature, published class II mass spectrometry data was obtained for two cell lines, each of which expressed a single HLA class I allele. One cell line expressed HLA-DRB1*15:01 and the other expressed HLA-DRB5*01:01*01:01[150]. These two cell lines were used for training data. For test data, class II mass spectrometry data was obtained from a separate cell line expressing both HLA-DRB1*15:01 and HLA-DRB5*01:01.[151] RNA sequencing data was not available either the training or testing cell lines, therefore RNA-sequencing data from a different B-cell line, B721.221[92], was substituted.

The peptide sets were split into training, validation and testing sets using the same procedure as for the HLA class I data, except that for the class II data peptides with lengths between 9 and 20 were included. The training data included 330 peptides presented by HLA-DRB1*15:01, and 103 peptides presented by HLA-DRB5*01:01. The test dataset included 223 peptides presented by either HLA-DRB1*15:01 or HLA-DRB5*01:01 along with 4708 non-presented peptides.

Figure 22:
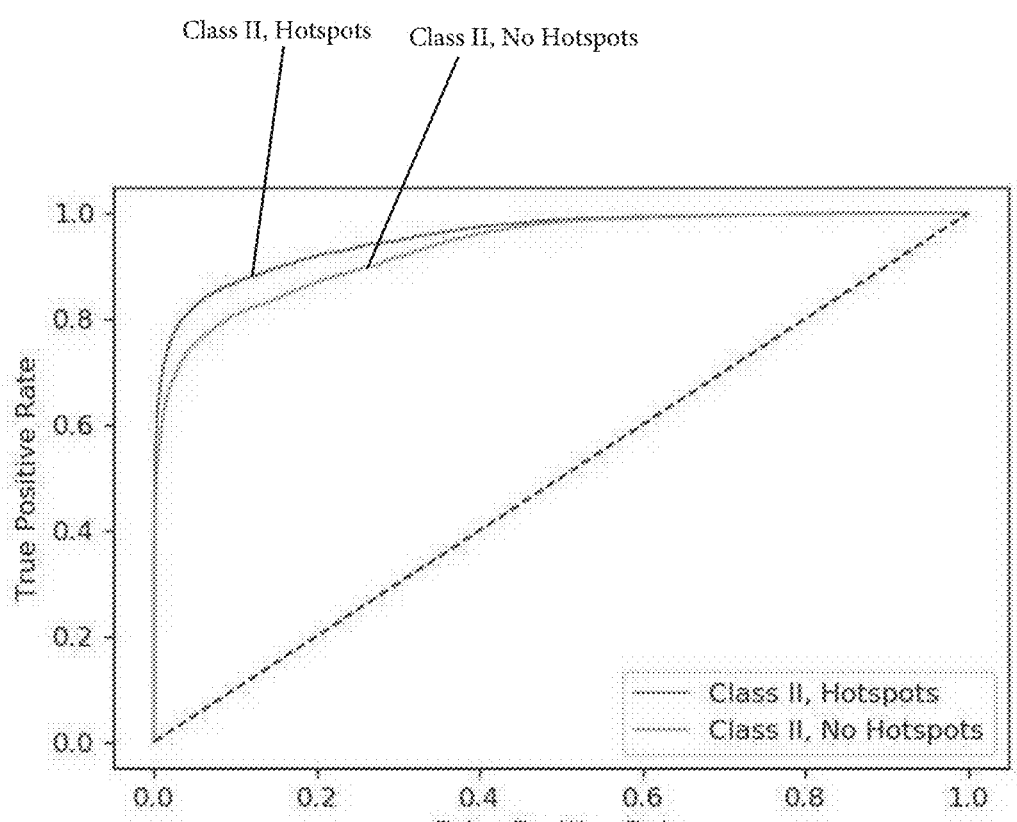
FIG. 22 compares the predictive performance of a presentation model that uses presentation hotspot parameters with a presentation model that does not use presentation hotspot parameters, when predicting presentation of neoepitopes by MHC class II molecules.

The presentation model used to generate the results depicted in FIG. 22 is the MHC class II presentation prediction model disclosed herein. The presentation model was an ensemble of 10 models trained on the training dataset to predict HLA class II peptide presentation. The architecture and training procedures for these models were identical to those used to predict class I presentation, with the exception that class II models took as input peptides sequences one hot-encoded and zero-padded to length 20 rather than 11. FIG. 22 compares the predictive performance of the presentation model that used presentation hotspot parameters with the presentation model that did not use presentation hotspot parameters, when predicting presentation of neoepitopes by MHC class II molecules. Specifically, FIG. 22 depicts receiver operating characteristic (ROC) curves for these two version of the presentation model. The hotspots model yielded improved performance, attaining an the area under the ROC curve (ROC AUC) of 0.96, while the model without hotspots yielded a ROC AUC of just 0.93.

Figure 23:
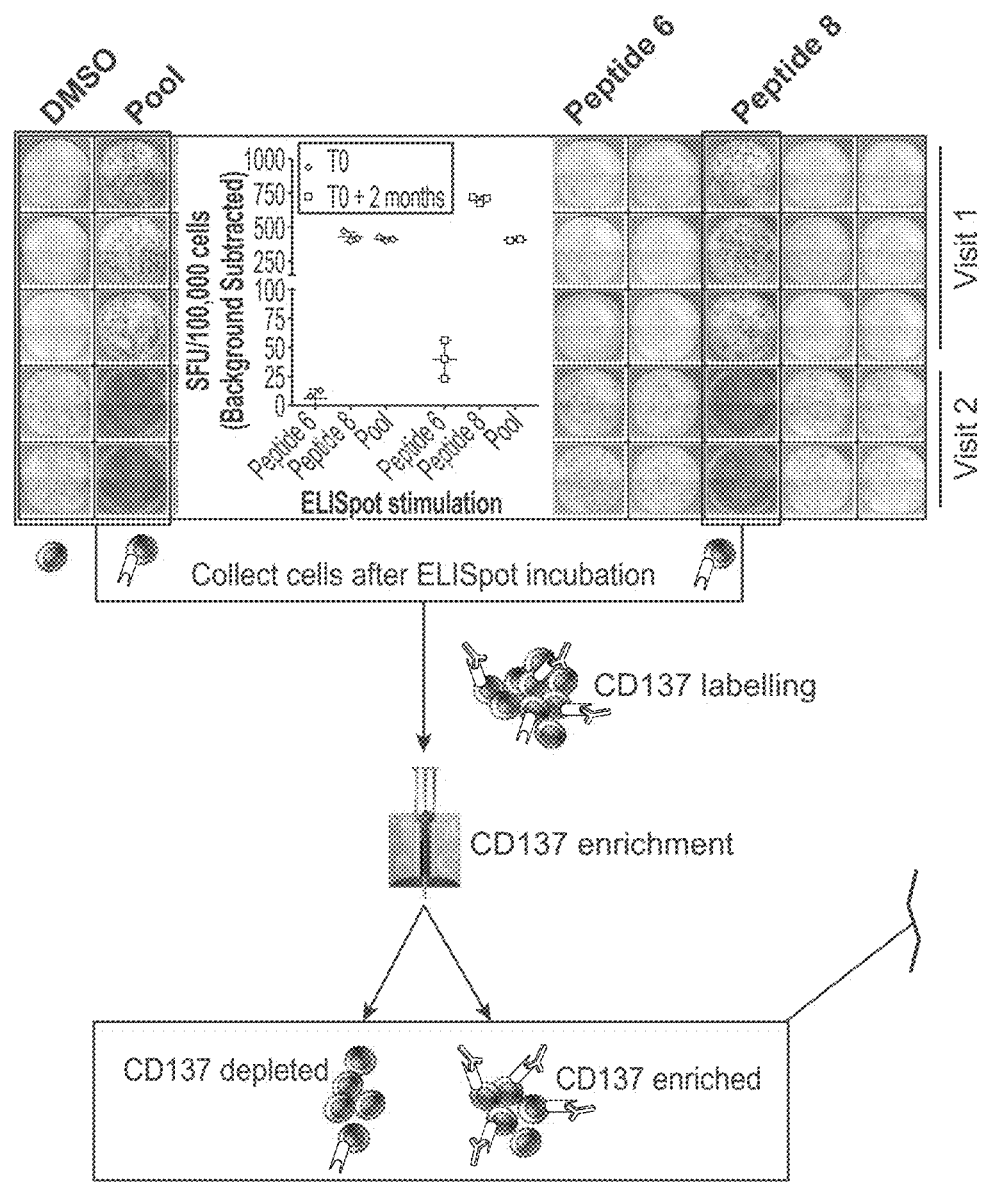
FIG. 23 depicts a method for sequencing TCRs of neoantigen-specific memory T-cells from the peripheral blood of a NSCLC patient.
Figure 23:
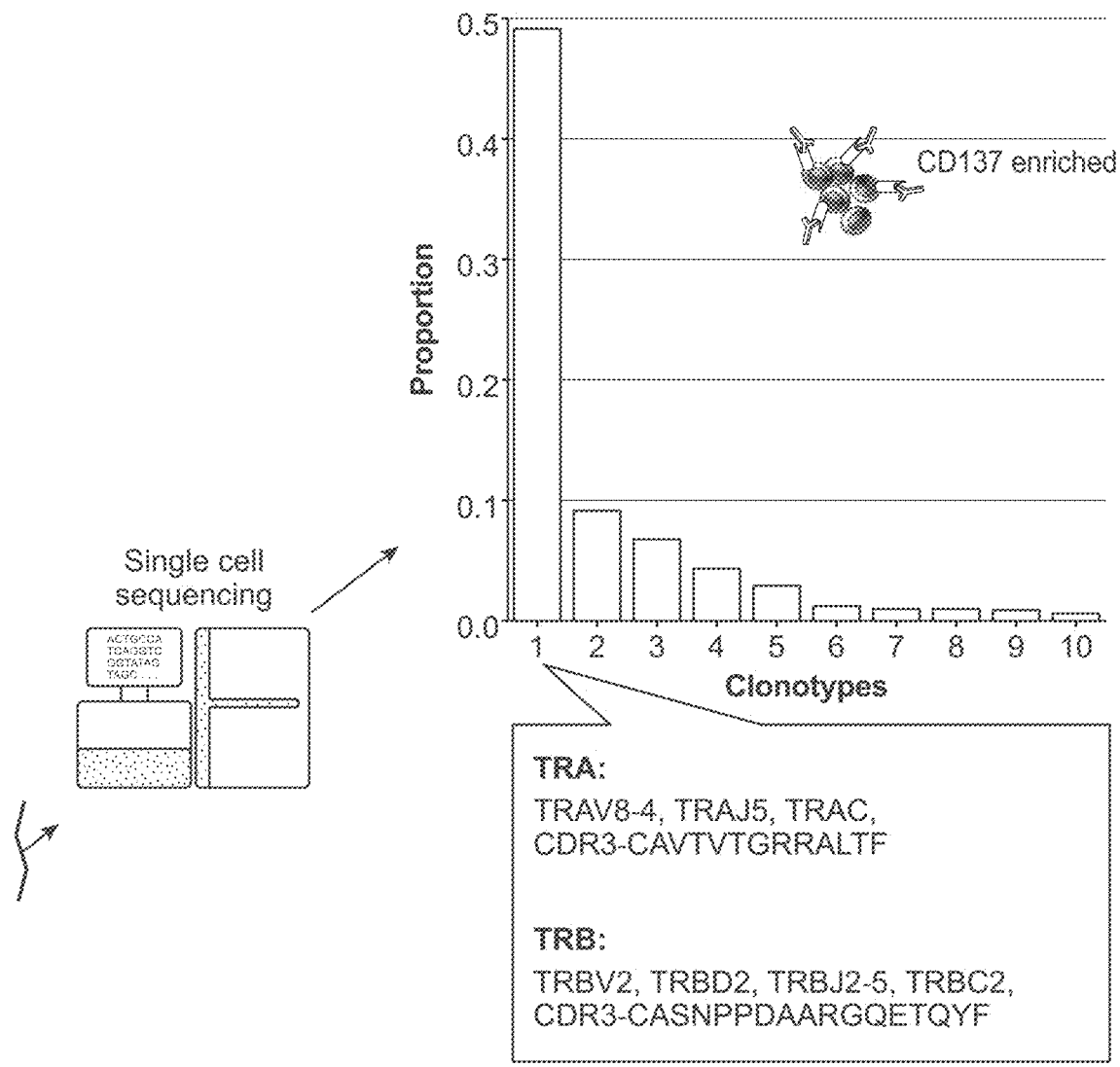

XVII. Example 12: Sequencing TCRs of Neoantigen-Specific Memory T-Cells from Peripheral Blood of a NSCLC Patient FIG. 23 depicts a method for sequencing TCRs of neoantigen-specific memory T-cells from the peripheral blood of a NSCLC patient. Peripheral blood mononuclear cells (PBMCs) from NSCLC patient CU04 (described above with regard to FIGS. 17A-21) were collected after ELISpot incubation. Specifically, as discussed above, the in vitro expanded PBMCs from 2 visits of patient CU04 were stimulated in IFN-gamma ELISpot with the CU04-specific individual neoantigen peptides (FIG. 20C), with the CU04-specific neoantigen peptide pool (FIG. 20C), and with DMSO negative control (FIG. 21). Following incubation and prior to addition of detection antibody, the PBMCs were transferred to a new culture plate and maintained in an incubator during completion of the ELISpot assay. Positive (responsive) wells were identified based on ELISpot results. As shown in FIG. 20, the positive wells identified include the wells stimulated with CU04-specific individual neoantigen peptide 8 and the wells simulated with the CU04-specific neoantigen peptide pool. Cells from these positive wells and negative control (DMSO) wells were combined and stained for CD137 with magnetically-labelled antibodies for enrichment using Miltenyi magnetic isolation columns.

CD137-enriched and -depleted T-cell fractions isolated and expanded as described above were sequenced using 10× Genomics single cell resolution paired immune TCR profiling approach. Specifically, live T cells were partitioned into single cell emulsions for subsequent single cell cDNA generation and full-length TCR profiling (5' UTR through constant region—ensuring alpha and beta pairing). One approach utilizes a molecularly barcoded template switching oligo at the 5' end of the transcript, a second approach utilizes a molecularly barcoded constant region oligo at the 3' end, and a third approach couples an RNA polymerase promoter to either the 5' or 3' end of a TCR. All of these approaches enable the identification and deconvolution of alpha and beta TCR pairs at the single-cell level. The resulting barcoded cDNA transcripts underwent an optimized enzymatic and library construction workflow to reduce bias and ensure accurate representation of clonotypes within the pool of cells. Libraries were sequenced on Illumina's MiSeq or HiSeq4000 instruments (paired-end 150 cycles) for a target sequencing depth of about five to fifty thousand reads per cell. The resulting TCR nucleic acid sequences are depicted in Supplementary Table 6. The presence of the TCRa and TCRb chains described in Supplementary Table 6 were confirmed by an orthogonal anchor-PCR based TCR sequencing approach (Archer). This particular approach has the advantage of using limited cell numbers as input and fewer enzymatic manipulations when compared to the 10× Genomics based TCR sequencing.

Sequencing outputs were analyzed using the 10× software and custom bioinformatics pipelines to identify T-cell receptor (TCR) alpha and beta chain pairs as also shown in Supplementary Table 6. Supplementary table 6 further lists the alpha and beta variable (V), joining (J), constant (C), and beta diversity (D) regions, and CDR3 amino acid sequence of the most prevalent TCR clonotypes. Clonotypes were defined as alpha, beta chain pairs of unique CDR3 amino acid sequences. Clonotypes were filtered for single alpha and single beta chain pairs present at frequency above 2 cells to yield the final list of clonotypes per target peptide in patient CU04 (Supplementary Table 6).

In summary, using the method described above with regard to FIG. 23, memory CD8+ T-cells from the peripheral blood of patient CU04, that are neoantigen-specific to patient CU04's tumor neoantigens identified as discussed above with regard to Example 10 in Section XIV., were identified. The TCRs of these identified neoantigen-specific T-cells were sequenced. And furthermore, sequenced TCRs that are neoantigen-specific to patient CU04's tumor neoantigens as identified by the above presentation models, were identified.

XVIII. Example 13: Use of Neoantigen-Specific Memory T-Cells for T-Cell Therapy After T-cells and/or TCRs that are neoantigen-specific to neoantigens presented by a patient's tumor are identified, these identified neoantigen-specific T-cells and/or TCRs can be used for T-cell therapy in the patient. Specifically, these identified neoantigen-specific T-cells and/or TCRs can be used to produce a therapeutic quantity of neoantigen-specific T-cells for infusion into a patient during T-cell therapy. Two methods for producing a therapeutic quantity of neoantigen specific T-cells for use in T-cell therapy in a patient are discussed herein in Sections XVII.A. and XVII.B. The first method comprises expanding the identified neoantigen-specific T-cells from a patient sample (Section XVII.A.). The second method comprises sequencing the TCRs of the identified neoantigen-specific T-cells and cloning the sequenced TCRs into new T-cells (Section XVII.B.). Alternative methods for producing neoantigen specific T-cells for use in T-cell therapy that are not explicitly mentioned herein can also be used to produce a therapeutic quantity of neoantigen specific T-cells for use in T-cell therapy. Once the neoantigen-specific T-cells are obtained via one or more of these methods, these neoantigen-specific T-cells may be infused into the patient for T-cell therapy.

XVIII.A Identification and Expansion of Neoantigen-Specific Memory T-Cells from a Patient Sample for T-Cell Therapy A first method for producing a therapeutic quantity of neoantigen specific T-cells for use in T-cell therapy in a patient comprises expanding identified neoantigen-specific T-cells from a patient sample.

Specifically, to expand neoantigen-specific T-cells to a therapeutic quantity for use in T-cell therapy in a patient, a set of neoantigen peptides that are most likely to be presented by a patient's cancer cells are identified using the presentation models as described above. Additionally, a patient sample containing T-cells is obtained from the patient. The patient sample may comprise the patient's peripheral blood, tumor-infiltrating lymphocytes (TIL), or lymph node cells.

In embodiments in which the patient sample comprises the patient's peripheral blood, the following methods may be used to expand neoantigen-specific T-cells to a therapeutic quantity. In one embodiment, priming may be performed. In another embodiment, already-activated T-cells may be identified using one or more of the methods described above. In another embodiment, both priming and identification of already-activated T-cells may be performed. The advantage to both priming and identifying already-activated T-cells is to maximize the number of specificities represented. The disadvantage both priming and identifying already-activated T-cells is that this approach is difficult and time-consuming. In another embodiment, neoantigen-specific cells that are not necessarily activated may be isolated. In such embodiments, antigen-specific or non-specific expansion of these neoantigen-specific cells may also be performed. Following collection of these primed T-cells, the primed T-cells can be subjected to rapid expansion protocol. For example, in some embodiments, the primed T-cells can be subjected to the Rosenberg rapid expansion protocol (https://www.ncbi.nlm.nih.gov/pmc/articles/PMC2978753/, https://www.ncbi.nlm.nih.gov/pmc/articles/PMC2305721/)[153, 154].

In embodiments in which the patient sample comprises the patient's TIL, the following methods may be used to expand neoantigen-specific T-cells to a therapeutic quantity. In one embodiment, neoantigen-specific TIL can be tetramer/multimer sorted ex vivo, and then the sorted TIL can be subjected to a rapid expansion protocol as described above. In another embodiment, neoantigen-nonspecific expansion of the TIL may be performed, then neoantigen-specific TIL may be tetramer sorted, and then the sorted TIL can be subjected to a rapid expansion protocol as described above. In another embodiment, antigen-specific culturing may be performed prior to subjecting the TIL to the rapid expansion protocol. (https://www.ncbi.nlm.nih.gov/pmc/articles/PMC4607110/, https://onlinelibrary.wiley.com/doi/pdf/10.1002/eji.201545849)[155, 156].

In some embodiments, the Rosenberg rapid expansion protocol may be modified. For example, anti-PD1 and/or anti-41BB may be added to the TIL culture to simulate more rapid expansion. (https://jitc.biomedcentral.com/articles/10.1186/s40425-016-0164-7)[157].

XVIII.B Identification of Neoantigen-Specific T Cells, Sequencing TCRs of Identified Neoantigen-Specific T Cells, and Cloning of Sequenced TCRs into New T-Cells A second method for producing a therapeutic quantity of neoantigen specific T-cells for use in T-cell therapy in a patient comprises identifying neoantigen-specific T-cells from a patient sample, sequencing the TCRs of the identified neoantigen-specific T-cells, and cloning the sequenced TCRs into new T-cells.

First, neoantigen-specific T-cells are identified from a patient sample, and the TCRs of the identified neoantigen-specific T-cells are sequenced. The patient sample from which T cells can be isolated may comprise one or more of blood, lymph nodes, or tumors. More specifically, the patient sample from which T cells can be isolated may comprise one or more of peripheral blood mononuclear cells (PBMCs), tumor-infiltrating cells (TILs), dissociated tumor cells (DTCs), in vitro primed T cells, and/or cells isolated from lymph nodes. These cells may be fresh and/or frozen. The PBMCs and the in vitro primed T cells may be obtained from cancer patients and/or healthy subjects.

After the patient sample is obtained, the sample may be expanded and/or primed. Various methods may be implemented to expand and prime the patient sample. In one embodiment, fresh and/or frozen PBMCs may be simulated in the presence of peptides or tandem mini-genes. In another embodiment, fresh and/or frozen isolated T-cells may be simulated and primed with antigen-presenting cells (APCs) in the presence of peptides or tandem mini-genes. Examples of APCs include B-cells, monocytes, dendritic cells, macrophages or artificial antigen presenting cells (such as cells or beads presenting relevant HLA and co-stimulatory molecules, reviewed in https://www.ncbi.nlm.nih.gov/pmc/articles/PMC2929753). In another embodiment, PBMCs, TILs, and/or isolated T-cells may be stimulated in the presence of cytokines (e.g., IL-2, IL-7, and/or IL-15). In another embodiment, TILs and/or isolated T-cells can be stimulated in the presence of maximal stimulus, cytokine(s), and/or feeder cells. In such embodiments, T cells can be isolated by activation markers and/or multimers (e.g., tetramers). In another embodiment, TILs and/or isolated T cells can be stimulated with stimulatory and/or co-stimulatory markers (e.g., CD3 antibodies, CD28 antibodies, and/or beads (e.g., DynaBeads). In another embodiment, DTCs can be expanded using a rapid expansion protocol on feeder cells at high dose of IL-2 in rich media.

Then, neoantigen-specific T cells are identified and isolated. In some embodiments, T cells are isolated from a patient sample ex vivo without prior expansion. In one embodiment, the methods described above with regard to Section XVI. may be used to identify neoantigen-specific T cells from a patient sample. In an alternative embodiment, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker+) at a relatively higher level (marker$^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a CD4+ or CD8+ selection step is used to separate CD4+ helper and CD8+ cytotoxic T-cells. Such CD4+ and CD8+ populations can be further sorted into sub-populations by positive or negative selection for markers expressed or expressed to a relatively higher degree on one or more naïve, memory, and/or effector T-cell subpopulations.

In some embodiments, CD8+ cells are further enriched for or depleted of naïve, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) J Immunother. 35(9):689-701. In some embodiments, combining TCM-enriched CD8+ T-cells and CD4+ T-cells further enhances efficacy.

In embodiments, memory T cells are present in both CD62L+ and CD62L− subsets of CD8+ peripheral blood lymphocytes. PBMC can be enriched for or depleted of CD62L−CD8+ and/or CD62L+CD8+ fractions, such as using anti-CD8 and anti-CD62L antibodies.

In some embodiments, the enrichment for central memory T (TCM) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a CD8+ population enriched for TCM cells is carried out by depletion of cells expressing CD4, CD14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of CD4+ cells, where both the negative and positive fractions are retained. The negative fraction then is subjected to negative selection based on expression of CD14 and CD45RA or ROR1, and positive selection based on a marker characteristic of central memory T-cells, such as CD62L or CCR7, where the positive and negative selections are carried out in either order.

CD4+T helper cells are sorted into naive, central memory, and effector cells by identifying cell populations that have cell surface antigens. CD4+ lymphocytes can be obtained by standard methods. In some embodiments, naive CD4+T lymphocytes are CD45RO−, CD45RA+, CD62L+, CD4+ T-cells. In some embodiments, central memory CD4+ cells are CD62L+ and CD45RO+. In some embodiments, effector CD4+ cells are CD62L− and CD45RO−.

In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immune-magnetic (or affinity-magnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher Humana Press Inc., Totowa, N.J.).

In some aspects, the sample or composition of cells to be separated is incubated with small, magnetizable or magnetically responsive material, such as magnetically responsive particles or microparticles, such as paramagnetic beads (e.g., such as Dynabeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the affinity-based selection is via magnetic-activated cell sorting (MACS) (Miltenyi Biotech, Auburn, Calif.). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-large T cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotic), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood may be automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) J Immunother. 35(9): 651-660, Terakura et al. (2012) Blood. 1:72-82, and Wang et al. (2012) J Immunother. 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) Lab Chip 10, 1567-1573; and Godin et al. (2008) J Biophoton. 1(5):355-376. In both cases, cells can be labeled with multiple markers, allowing for the isolation of well-defined T-cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This can then be diluted 1:1 with media so that the final concentration of DMSO and HSA are 10% and 4%, respectively. Other examples include Cryostor®, CTL-Cryo™ ABC freezing media, and the like. The cells are then frozen to −80 degrees C. at a rate of 1 degree per minute and stored in the vapor phase of a liquid nitrogen storage tank.

In some embodiments, the provided methods include cultivation, incubation, culture, and/or genetic engineering steps. For example, in some embodiments, provided are methods for incubating and/or engineering the depleted cell populations and culture-initiating compositions.

Thus, in some embodiments, the cell populations are incubated in a culture-initiating composition. The incubation and/or engineering may be carried out in a culture vessel, such as a unit, chamber, well, column, tube, tubing set, valve, vial, culture dish, bag, or other container for culture or cultivating cells.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T-cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the T-cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T-cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some embodiments, the PBMC feeder cells are inactivated with Mytomicin C. In some aspects, the feeder cells are added to culture medium prior to the addition of the populations of T-cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T-cells, such as antigen-specific CD4+ and/or CD8+ T-cells, are obtained by stimulating naive or antigen specific T lymphocytes with antigen. For example, antigen-specific T-cell lines or clones can be generated to cytomegalovirus antigens by isolating T-cells from infected subjects and stimulating the cells in vitro with the same antigen.

In some embodiments, neoantigen-specific T-cells are identified and/or isolated following stimulation with a functional assay (e.g., ELISpot). In some embodiments, neoantigen-specific T-cells are isolated by sorting polyfunctional cells by intracellular cytokine staining. In some embodiments, neoantigen-specific T-cells are identified and/or isolated using activation markers (e.g., CD137, CD38, CD38/HLA-DR double-positive, and/or CD69). In some embodiments, neoantigen-specific CD8+, natural killer T-cells, memory T-cells, and/or CD4+ T-cells are identified and/or isolated using class I or class II multimers and/or activation markers. In some embodiments, neoantigen-specific CD8+ and/or CD4+ T-cells are identified and/or isolated using memory markers (e.g., CD45RA, CD45RO, CCR7, CD27, and/or CD62L). In some embodiments, proliferating cells are identified and/or isolated. In some embodiments, activated T-cells are identified and/or isolated.

After identification of neoantigen-specific T-cells from a patient sample, the neoantigen-specific TCRs of the identified neoantigen-specific T-cells are sequenced. To sequence a neoantigen-specific TCR, the TCR must first be identified. One method of identifying a neoantigen-specific TCR of a T-cell can include contacting the T-cell with an HLA-multimer (e.g., a tetramer) comprising at least one neoantigen; and identifying the TCR via binding between the HLA-multimer and the TCR. Another method of identifying a neoantigen-specific TCR can include obtaining one or more T-cells comprising the TCR; activating the one or more T-cells with at least one neoantigen presented on at least one antigen presenting cell (APC); and identifying the TCR via selection of one or more cells activated by interaction with at least one neoantigen.

After identification of the neoantigen-specific TCR, the TCR can be sequenced. In one embodiment, the methods described above with regard to Section XVI. may be used to sequence TCRs. In another embodiment, TCRa and TCRb of a TCR can be bulk-sequenced and then paired based on frequency. In another embodiment, TCRs can be sequenced and paired using the method of Howie et al., Science Translational Medicine 2015 (doi: 10.1126/scitranslmed.aac5624). In another embodiment, TCRs can be sequenced and paired using the method of Han et al., Nat Biotech 2014 (PMID 24952902, doi 10.1038/nbt.2938). In another embodiment, paired TCR sequences can be obtained using the method described by https://www.biorxiv.org/content/early/2017/05/05/134841 and https://patents.google.com/patent/US20160244825A1/.[158, 159]

In another embodiment, clonal populations of T cells can be produced by limiting dilution, and then the TCRa and TCRb of the clonal populations of T cells can be sequenced. In yet another embodiment, T-cells can be sorted onto a plate with wells such that there is one T cell per well, and then the TCRa and TCRb of each T cell in each well can be sequenced and paired.

Next, after neoantigen-specific T-cells are identified from a patient sample and the TCRs of the identified neoantigen-specific T-cells are sequenced, the sequenced TCRs are cloned into new T-cells. These cloned T-cells contain neoantigen-specific receptors, e.g., contain extracellular domains including TCRs. Also provided are populations of such cells, and compositions containing such cells. In some embodiments, compositions or populations are enriched for such cells, such as in which cells expressing the TCRs make up at least 1, 5, 10, 20, 30, 40, 50, 60, 70, 80, 90, 91, 92, 93, 94, 95, 96, 97, 98, 99, or more than 99 percent of the total cells in the composition or cells of a certain type such as T-cells or CD8+ or CD4+ cells. In some embodiments, a composition comprises at least one cell containing a TCR disclosed herein. Among the compositions are pharmaceutical compositions and formulations for administration, such as for adoptive cell therapy. Also provided are therapeutic methods for administering the cells and compositions to subjects, e.g., patients.

Thus also provided are genetically engineered cells expressing TCR(s). The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T-cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T-cells or other cell types, such as whole T-cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T-cells and/or of CD4+ and/or of CD8+ T-cells are naive T (TN) cells, effector T-cells (TEFF), memory T-cells and sub-types thereof, such as stem cell memory T (TSCM), central memory T (TCM), effector memory T (TEM), or terminally differentiated effector memory T-cells, tumor-infiltrating lymphocytes (TIL), immature T-cells, mature T-cells, helper T-cells, cytotoxic T-cells, mucosa-associated invariant T (MALT) cells, naturally occurring and adaptive regulatory T (Treg) cells, helper T-cells, such as TH1 cells, TH2 cells, TH3 cells, TH17 cells, TH9 cells, TH22 cells, follicular helper T-cells, alpha/beta T-cells, and delta/gamma T-cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

The cells may be genetically modified to reduce expression or knock out endogenous TCRs. Such modifications are described in Mol Ther Nucleic Acids. 2012 December; 1(12): e63; Blood. 2011 Aug. 11; 118(6):1495-503; Blood. 2012 Jun. 14; 119(24): 5697-5705; Torikai, Hiroki et al "HLA and TCR Knockout by Zinc Finger Nucleases: Toward "off-the-Shelf" Allogeneic T-Cell Therapy for CD19+ Malignancies." Blood 116.21 (2010): 3766; Blood. 2018 Jan. 18; 131(3):311-322. doi: 10.1182/blood-2017-05-787598; and WO2016069283, which are incorporated by reference in their entirety.

The cells may be genetically modified to promote cytokine secretion. Such modifications are described in Hsu C, Hughes M S, Zheng Z, Bray R B, Rosenberg S A, Morgan R A. Primary human T lymphocytes engineered with a codon-optimized IL-15 gene resist cytokine withdrawal-induced apoptosis and persist long-term in the absence of exogenous cytokine. J Immunol. 2005; 175:7226-34; Quintarelli C, Vera J F, Savoldo B, Giordano Attianese G M, Pule M, Foster A E, Co-expression of cytokine and suicide genes to enhance the activity and safety of tumor-specific cytotoxic T lymphocytes. Blood. 2007; 110:2793-802; and Hsu C, Jones S A, Cohen C J, Zheng Z, Kerstann K, Zhou J, Cytokine-independent growth and clonal expansion of a primary human CD8+ T-cell clone following retroviral transduction with the IL-15 gene. Blood. 2007; 109:5168-77.

Mismatching of chemokine receptors on T-cells and tumor-secreted chemokines has been shown to account for the suboptimal trafficking of T-cells into the tumor microenvironment. To improve efficacy of therapy, the cells may be genetically modified to increase recognition of chemokines in tumor micro environment. Examples of such modifications are described in Moon, EKCarpenito, CSun, JWang, LCKapoor, VPredina, J Expression of a functional CCR2 receptor enhances tumor localization and tumor eradication by retargeted human T-cells expressing a mesothelin-specific chimeric antibody receptor. Clin Cancer Res. 2011; 17: 4719-4730; and. Craddock, JALu, ABear, APule, MBrenner, MKRooney, C M et al. Enhanced tumor trafficking of GD2 chimeric antigen receptor T-cells by expression of the chemokine receptor CCR2b. J Immunother. 2010; 33: 780-788.

The cells may be genetically modified to enhance expression of costimulatory/enhancing receptors, such as CD28 and 41BB.

Adverse effects of T-cell therapy can include cytokine release syndrome and prolonged B-cell depletion. Introduction of a suicide/safety switch in the recipient cells may improve the safety profile of a cell-based therapy. Accordingly, the cells may be genetically modified to include a suicide/safety switch. The suicide/safety switch may be a gene that confers sensitivity to an agent, e.g., a drug, upon the cell in which the gene is expressed, and which causes the cell to die when the cell is contacted with or exposed to the agent. Exemplary suicide/safety switches are described in Protein Cell. 2017 August; 8(8): 573-589. The suicide/safety switch may be HSV-TK. The suicide/safety switch may be cytosine daminase, purine nucleoside phosphorylase, or nitroreductase. The suicide/safety switch may be RapaCIDe™, described in U.S. Patent Application Pub. No. US20170166877A1. The suicide/safety switch system may be CD20/Rituximab, described in Haematologica. 2009 September; 94(9): 1316-1320. These references are incorporated by reference in their entirety.

The TCR may be introduced into the recipient cell as a split receptor which assembles only in the presence of a heterodimerizing small molecule. Such systems are described in Science. 2015 Oct. 16; 350(6258): aab4077, and in U.S. Pat. No. 9,587,020, which are hereby incorporated by reference.

In some embodiments, the cells include one or more nucleic acids, e.g., a polynucleotide encoding a TCR disclosed herein, wherein the polynucleotide is introduced via genetic engineering, and thereby express recombinant or genetically engineered TCRs as disclosed herein. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

The nucleic acids may include a codon-optimized nucleotide sequence. Without being bound to a particular theory or mechanism, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

A construct or vector may be used to introduce the TCR into the recipient cell. Exemplary constructs are described herein. Polynucleotides encoding the alpha and beta chains of the TCR may in a single construct or in separate constructs. The polynucleotides encoding the alpha and beta chains may be operably linked to a promoter, e.g., a heterologous promoter. The heterologous promoter may be a strong promoter, e.g., EF1alpha, CMV, PGK1, Ubc, beta actin, CAG promoter, and the like. The heterologous promoter may be a weak promoter. The heterologous promoter may be an inducible promoter. Exemplary inducible promoters include, but are not limited to TRE, NFAT, GAL4, LAC, and the like. Other exemplary inducible expression systems are described in U.S. Pat. Nos. 5,514,578; 6,245,531; 7,091,038 and European Patent No. 0517805, which are incorporated by reference in their entirety.

The construct for introducing the TCR into the recipient cell may also comprise a polynucleotide encoding a signal peptide (signal peptide element). The signal peptide may promote surface trafficking of the introduced TCR. Exemplary signal peptides include, but are not limited to CD8 signal peptide, immunoglobulin signal peptides, where specific examples include GM-CSF and IgG kappa. Such signal peptides are described in Trends Biochem Sci. 2006 October; 31(10):563-71. Epub 2006 Aug. 21; and An, et al. "Construction of a New Anti-CD19 Chimeric Antigen Receptor and the Anti-Leukemia Function Study of the Transduced T-cells." Oncotarget 7.9 (2016): 10638-10649. PMC. Web. 16 Aug. 2018; which are hereby incorporated by reference.

In some cases, e.g., cases where the alpha and beta chains are expressed from a single construct or open reading frame, or cases wherein a marker gene is included in the construct, the construct may comprise a ribosomal skip sequence. The ribosomal skip sequence may be a 2A peptide, e.g., a P2A or T2A peptide. Exemplary P2A and T2A peptides are described in Scientific Reports volume 7, Article number: 2193 (2017), hereby incorporated by reference in its entirety. In some cases, a FURIN/PACE cleavage site is introduced upstream of the 2A element. FURIN/PACE cleavage sites are described in, e.g., http://www.nuolan.net/substrates.html. The cleavage peptide may also be a factor Xa cleavage site. In cases where the alpha and beta chains are expressed from a single construct or open reading frame, the construct may comprise an internal ribosome entry site (IRES).

The construct may further comprise one or more marker genes. Exemplary marker genes include but are not limited to GFP, luciferase, HA, lacZ. The marker may be a selectable marker, such as an antibiotic resistance marker, a heavy metal resistance marker, or a biocide resistant marker, as is known to those of skill in the art. The marker may be a complementation marker for use in an auxotrophic host. Exemplary complementation markers and auxotrophic hosts are described in Gene. 2001 Jan. 24; 263(1-2):159-69. Such markers may be expressed via an IRES, a frameshift sequence, a 2A peptide linker, a fusion with the TCR, or expressed separately from a separate promoter.

Exemplary vectors or systems for introducing TCRs into recipient cells include, but are not limited to Adeno-associated virus, Adenovirus, Adenovirus+Modified vaccinia, Ankara virus (MVA), Adenovirus+Retrovirus, Adenovirus+Sendai virus, Adenovirus+Vaccinia virus, Alphavirus (VEE) Replicon Vaccine, Antisense oligonucleotide, *Bifidobacterium longum*, CRISPR-Cas9, *E. coli*, Flavivirus, Gene gun, Herpesviruses, Herpes simplex virus, *Lactococcus lactis*, Electroporation, Lentivirus, Lipofection, *Listeria monocytogenes*, Measles virus, Modified Vaccinia Ankara virus (MVA), mRNA Electroporation, Naked/Plasmid DNA, Naked/Plasmid DNA+Adenovirus, Naked/Plasmid DNA+ Modified Vaccinia Ankara virus (MVA), Naked/Plasmid DNA+RNA transfer, Naked/Plasmid DNA+Vaccinia virus, Naked/Plasmid DNA+Vesicular stomatitis virus, Newcastle disease virus, Non-viral, PiggyBac™ (PB) Transposon, nanoparticle-based systems, Poliovirus, Poxvirus, Poxvirus+ Vaccinia virus, Retrovirus, RNA transfer, RNA transfer+ Naked/Plasmid DNA, RNA virus, *Saccharomyces cerevisiae*, *Salmonella typhimurium*, Semliki forest virus, Sendai virus, *Shigella dysenteriae*, Simian virus, siRNA, Sleeping Beauty transposon, *Streptococcus mutans*, Vaccinia virus, Venezuelan equine encephalitis virus replicon, Vesicular stomatitis virus, and *Vibrio cholera*.

In preferred embodiments, the TCR is introduced into the recipient cell via adeno associated virus (AAV), adenovirus, CRISPR-CAS9, herpesvirus, lentivirus, lipofection, mRNA electroporation, PiggyBac™ (PB) Transposon, retrovirus, RNA transfer, or Sleeping Beauty transposon.

In some embodiments, a vector for introducing a TCR into a recipient cell is a viral vector. Exemplary viral vectors include adenoviral vectors, adeno-associated viral (AAV) vectors, lentiviral vectors, herpes viral vectors, retroviral vectors, and the like. Such vectors are described herein.

Figure 24:
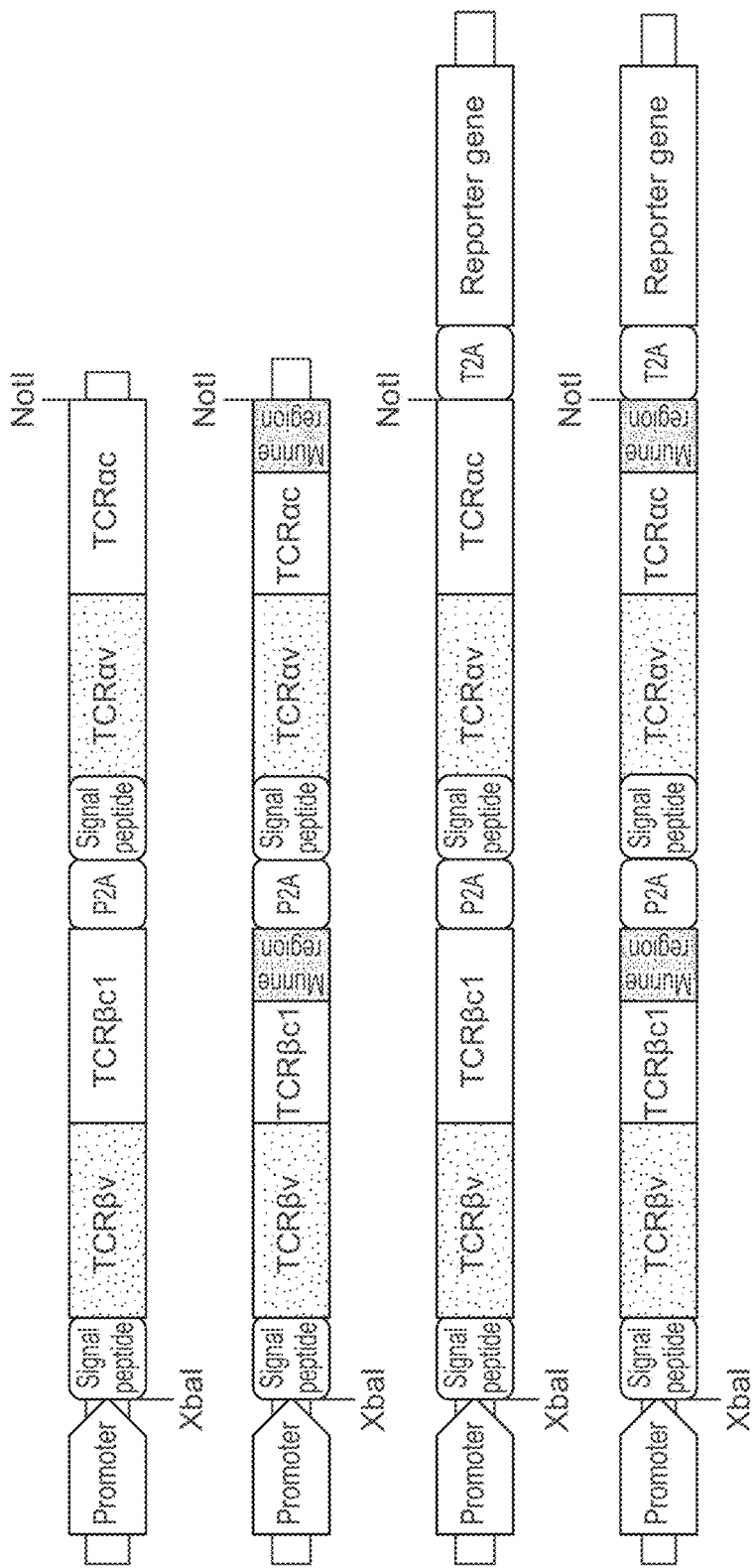
FIG. 24 depicts exemplary embodiments of TCR constructs for introducing a TCR into recipient cells.

Exemplary embodiments of TCR constructs for introducing a TCR into recipient cells is shown in FIG. 24. In some embodiments, a TCR construct includes, from the 5'-3' direction, the following polynucleotide sequences: a promoter sequence, a signal peptide sequence, a TCR β variable (TCRβv) sequence, a TCR β constant (TCRβc) sequence, a cleavage peptide (e.g., P2A), a signal peptide sequence, a TCR α variable (TCRαv) sequence, and a TCR α constant (TCRαc) sequence. In some embodiments, the TCRβc and TCRαc sequences of the construct include one or more murine regions, e.g., full murine constant sequences or human→murine amino acid exchanges as described herein. In some embodiments, the construct further includes, 3' of the TCRαc sequence, a cleavage peptide sequence (e.g., T2A) followed by a reporter gene. In an embodiment, the construct includes, from the 5'-3' direction, the following polynucleotide sequences: a promoter sequence, a signal peptide sequence, a TCR β variable (TCRβv) sequence, a TCR β constant ((TCRβc) sequence containing one or more murine regions, a cleavage peptide (e.g., P2A), a signal peptide sequence, a TCR α variable (TCRαv) sequence, and a TCR α constant (TCRαc) sequence containing one or more murine regions, a cleavage peptide (e.g., T2A), and a reporter gene.

Figure 25:
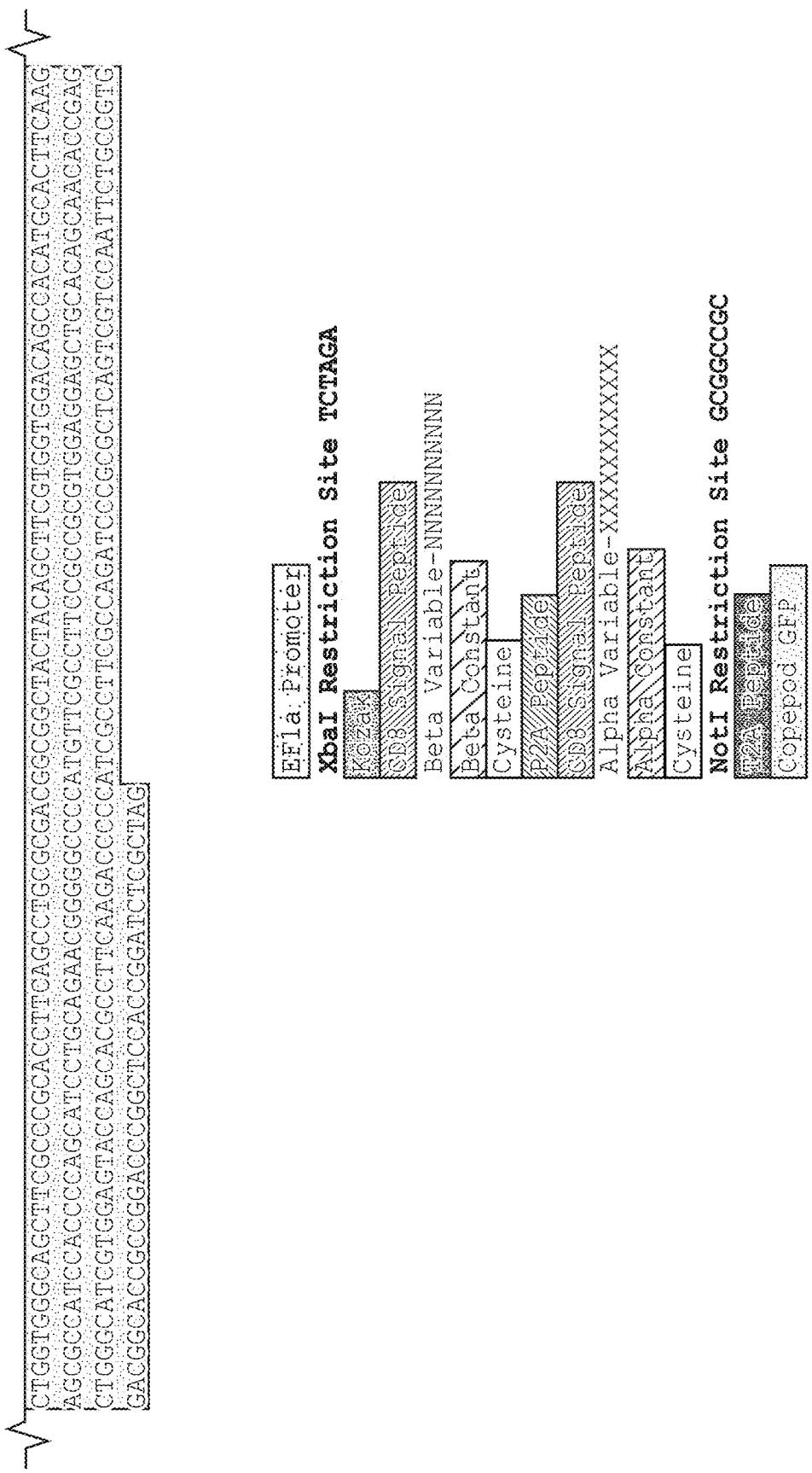
FIG. 25 depicts an exemplary P526 construct backbone nucleotide sequence for cloning TCRs into expression systems for therapy development.

FIG. 25 depicts an exemplary P526 construct backbone nucleotide sequence for cloning TCRs into expression systems for therapy development.

Figure 26:
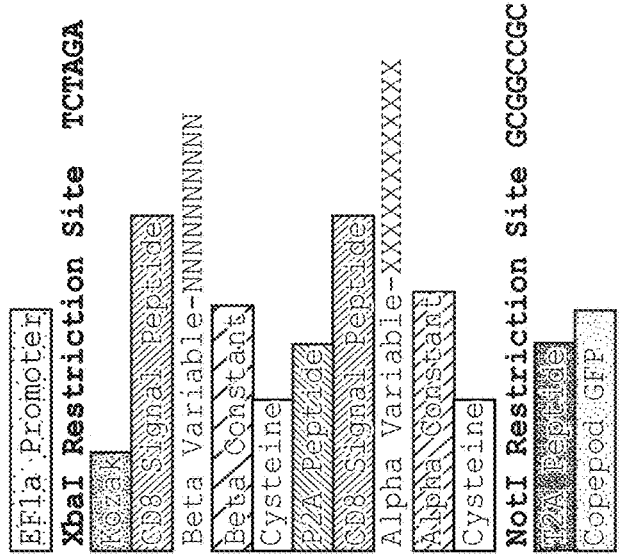
FIG. 26 depicts an exemplary construct sequence for cloning patient neoantigen-specific TCR, clonotype 1 TCR into expression systems for therapy development.

FIG. 26 depicts an exemplary construct sequence for cloning patient neoantigen-specific TCR, clonotype 1 into expression systems for therapy development.

Figure 27:
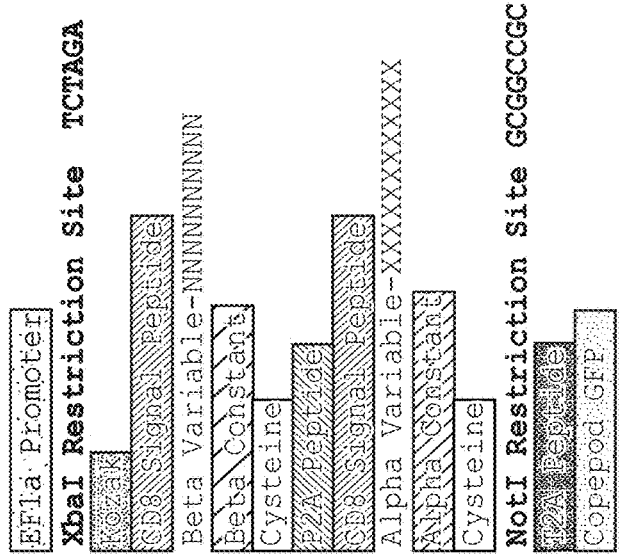
FIG. 27 depicts an exemplary construct sequence for cloning patient neoantigen-specific TCR, clonotype 3 into expression systems for therapy development.

FIG. 27 depicts an exemplary construct sequence for cloning patient neoantigen-specific TCR, clonotype 3 into expression systems for therapy development.

Also provided are isolated nucleic acids encoding TCRs, vectors comprising the nucleic acids, and host cells comprising the vectors and nucleic acids, as well as recombinant techniques for the production of the TCRs.

The nucleic acids may be recombinant. The recombinant nucleic acids may be constructed outside living cells by joining natural or synthetic nucleic acid segments to nucleic acid molecules that can replicate in a living cell, or replication products thereof. For purposes herein, the replication can be in vitro replication or in vivo replication.

For recombinant production of a TCR, the nucleic acid(s) encoding it may be isolated and inserted into a replicable vector for further cloning (i.e., amplification of the DNA) or expression. In some aspects, the nucleic acid may be produced by homologous recombination, for example as described in U.S. Pat. No. 5,204,244, incorporated by reference in its entirety.

Many different vectors are known in the art. The vector components generally include one or more of the following: a signal sequence, an origin of replication, one or more marker genes, an enhancer element, a promoter, and a transcription termination sequence, for example as described in U.S. Pat. No. 5,534,615, incorporated by reference in its entirety.

Exemplary vectors or constructs suitable for expressing a TCR, antibody, or antigen binding fragment thereof, include, e.g., the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as AGT10, AGT11, AZapII (Stratagene), AEMBL4, and ANM1 149, are also suitable for expressing a TCR disclosed herein.

XIX. Treatment Overview Flow Chart

Figure 28:
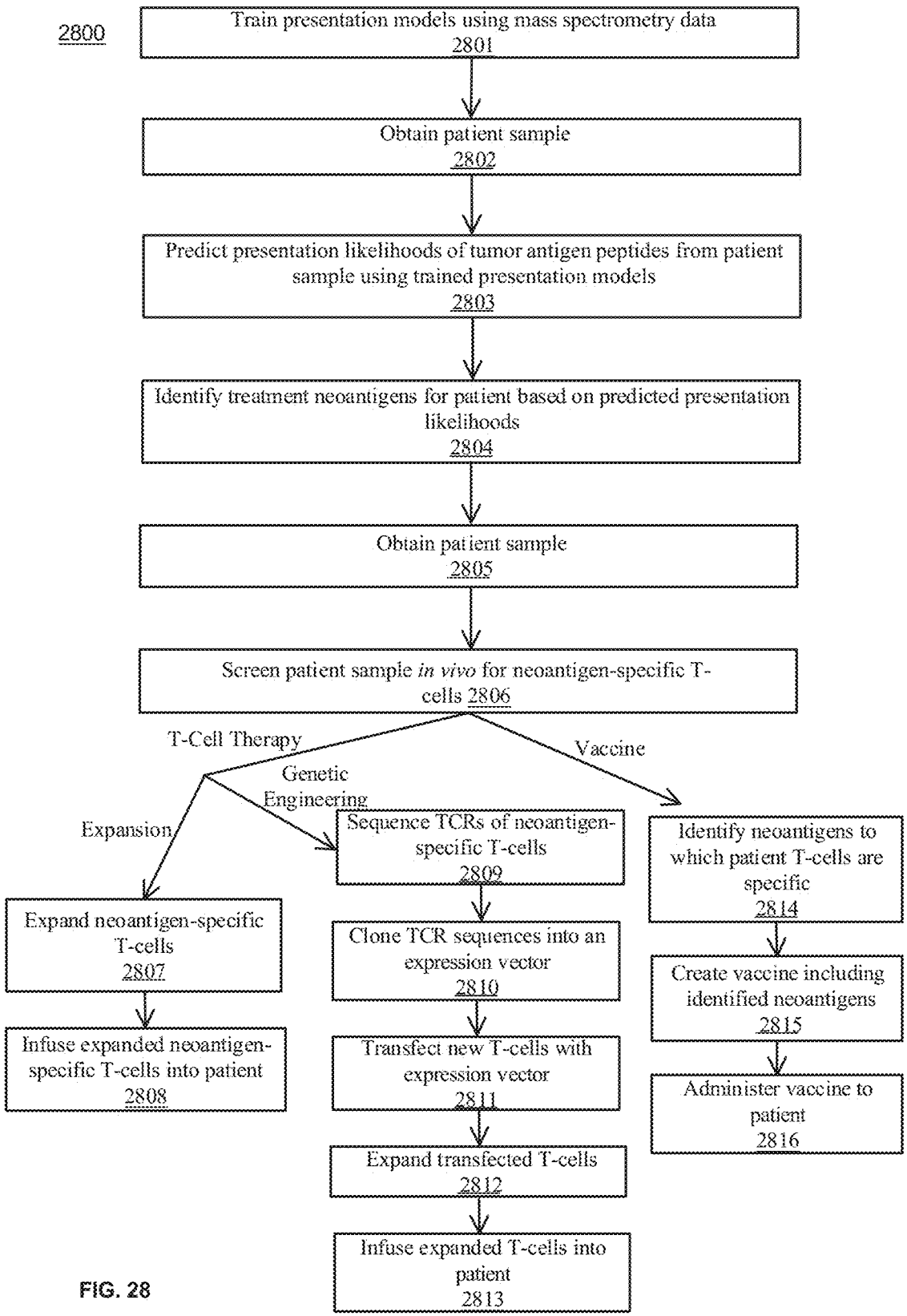
FIG. 28 is a flow chart of a method for providing a customized, neoantigen-specific treatment to a patient, in accordance with an embodiment.

FIG. 28 is a flow chart of a method for providing a customized, neoantigen-specific treatment to a patient, in accordance with an embodiment. In other embodiments, the method may include different and/or additional steps than those shown in FIG. 28. Additionally, steps of the method may be performed in different orders than the order described in conjunction with FIG. 28 in various embodiments.

The presentation models are trained 2801 using mass spectrometry data as described above. A patient sample is obtained 2802. In some embodiments, the patient sample comprises a tumor biopsy and/or the patient's peripheral blood. The patient sample obtained in step 2802 is sequenced to identify data to input into the presentation models to predict the likelihoods that tumor antigen peptides from the patient sample will be presented. Presentation likelihoods of tumor antigen peptides from the patient sample obtained in step 2802 are predicted 2803 using the trained presentation models. Treatment neoantigens are identified 2804 for the patient based on the predicted presentation likelihoods. Next, another patient sample is obtained 2805. The patient sample may comprise the patient's peripheral blood, tumor-infiltrating lymphocytes (TIL), lymph, lymph node cells, and/or any other source of T-cells. The patient sample obtained in step 2805 is screened 2806 in vivo for neoantigen-specific T-cells.

At this point in the treatment process, the patient can either receive T-cell therapy and/or a vaccine treatment. To receive a vaccine treatment, the neoantigens to which the patient's T-cells are specific are identified 2814. Then, a vaccine including the identified neoantigens is created 2815. Finally, the vaccine is administered 2816 to the patient.

To receive T-cell therapy, the neoantigen-specific T-cells undergo expansion and/or new neoantigen-specific T-cells are genetically engineered. To expand the neoantigen-specific T-cells for use in T-cell therapy, the cells are simply expanded 2807 and infused 2808 into the patient.

To genetically engineer new neoantigen-specific T-cells for T-cell therapy, the TCRs of the neoantigen-specific T-cells that were identified in vivo are sequenced 2809. Next, these TCR sequences are cloned 2810 into an expression vector. The expression vector 2810 is then transfected 2811 into new T-cells. The transfected T-cells are 2812 expanded. And finally, the expanded T-cells are infused 2813 into the patient.

A patient may receive both T-cell therapy and vaccine therapy. In one embodiment, the patient first receives vaccine therapy then receives T-cell therapy. One advantage of this approach is that the vaccine therapy may increase the number of tumor-specific T-cells and the number of neoantigens recognized by detectable levels of T-cells.

In another embodiment, a patient may receive T-cell therapy followed by vaccine therapy, wherein the set of epitopes included in the vaccine comprises one or more of the epitopes targeted by the T-cell therapy. One advantage of this approach is that administration of the vaccine may promote expansion and persistence of the therapeutic T-cells.

XX. Example Computer

Figure 29:
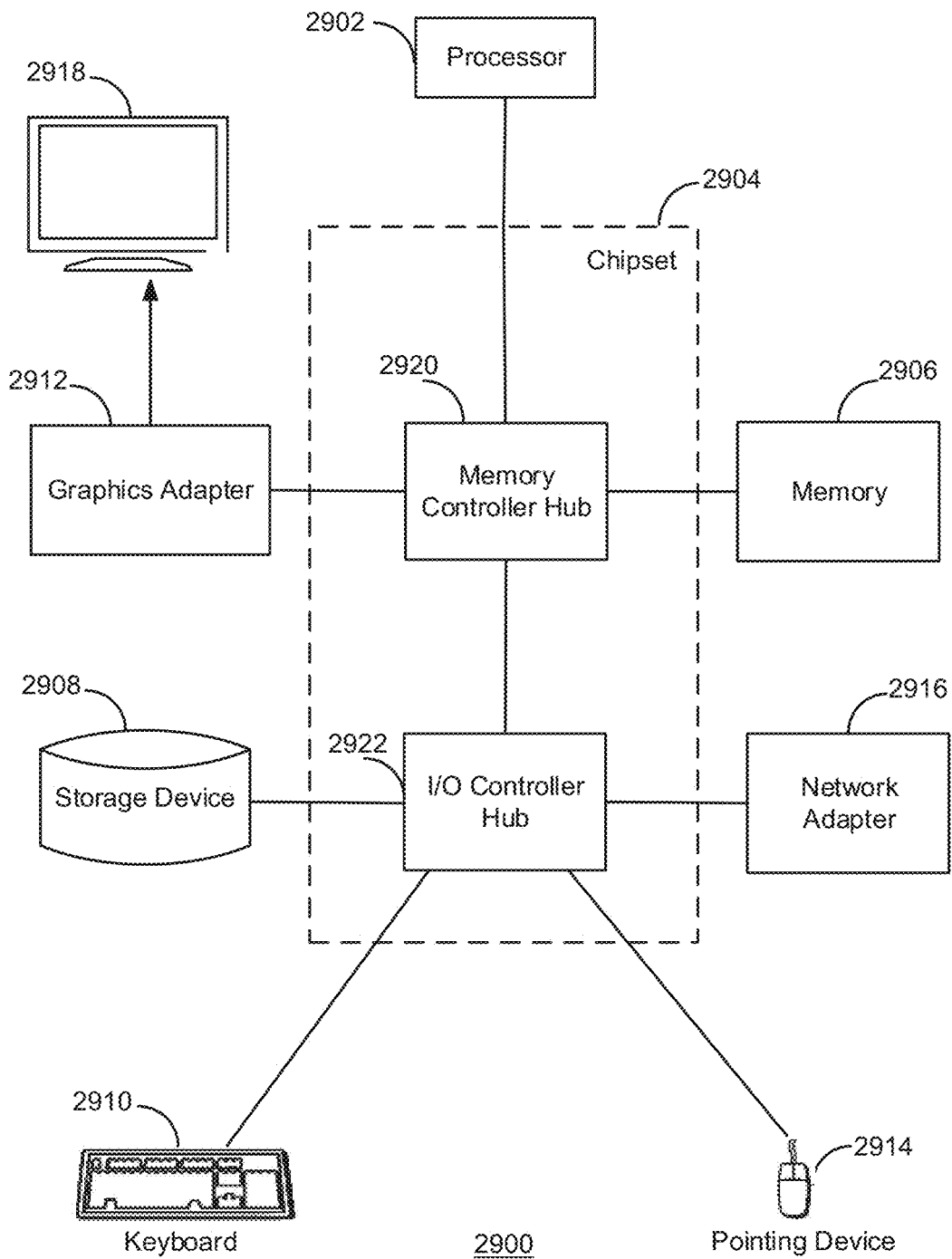
FIG. 29 illustrates an example computer for implementing the entities shown in FIGS. 1 and 3.

FIG. 29 illustrates an example computer 2900 for implementing the entities shown in FIGS. 1 and 3. The computer 2900 includes at least one processor 2902 coupled to a chipset 2904. The chipset 2904 includes a memory controller hub 2920 and an input/output (I/O) controller hub 2922. A memory 2906 and a graphics adapter 2912 are coupled to the memory controller hub 2920, and a display 2918 is coupled to the graphics adapter 2912. A storage device 2908, an input device 2914, and network adapter 2916 are coupled to the I/O controller hub 2922. Other embodiments of the computer 2900 have different architectures.

The storage device 2908 is a non-transitory computer-readable storage medium such as a hard drive, compact disk read-only memory (CD-ROM), DVD, or a solid-state memory device. The memory 2906 holds instructions and data used by the processor 2902. The input interface 2914 is a touch-screen interface, a mouse, track ball, or other type of pointing device, a keyboard, or some combination thereof, and is used to input data into the computer 2900. In some embodiments, the computer 2900 may be configured to receive input (e.g., commands) from the input interface 2914 via gestures from the user. The graphics adapter 2912 displays images and other information on the display 2918. The network adapter 2916 couples the computer 2900 to one or more computer networks.

The computer 2900 is adapted to execute computer program modules for providing functionality described herein. As used herein, the term "module" refers to computer program logic used to provide the specified functionality. Thus, a module can be implemented in hardware, firmware, and/or software. In one embodiment, program modules are stored on the storage device 2908, loaded into the memory 2906, and executed by the processor 2902.

The types of computers 2900 used by the entities of FIG. 1 can vary depending upon the embodiment and the processing power required by the entity. For example, the presentation identification system 160 can run in a single computer 2900 or multiple computers 2900 communicating with each other through a network such as in a server farm. The computers 2900 can lack some of the components described above, such as graphics adapters 2912, and displays 2918.

REFERENCES

1. Desrichard, A., Snyder, A. & Chan, T. A. Cancer Neoantigens and Applications for Immunotherapy. Clin. Cancer Res. Off. J. Am. Assoc. Cancer Res. (2015). doi:10.1158/1078-0432.CCR-14-3175
2. Schumacher, T. N. & Schreiber, R. D. Neoantigens in cancer immunotherapy. Science 348, 69-74 (2015).
3. Gubin, M. M., Artyomov, M. N., Mardis, E. R. & Schreiber, R. D. Tumor neoantigens: building a framework for personalized cancer immunotherapy. J. Clin. Invest. 125, 3413-3421 (2015).
4. Rizvi, N. A. et al. Cancer immunology. Mutational landscape determines sensitivity to PD-1 blockade in non-small cell lung cancer. Science 348, 124-128 (2015).
5. Snyder, A. et al. Genetic basis for clinical response to CTLA-4 blockade in melanoma. N. Engl. J. Med. 371, 2189-2199 (2014).
6. Carreno, B. M. et al. Cancer immunotherapy. A dendritic cell vaccine increases the breadth and diversity of melanoma neoantigen-specific T-cells. Science 348, 803-808 (2015).
7. Tran, E. et al. Cancer immunotherapy based on mutation-specific CD4+ T-cells in a patient with epithelial cancer. Science 344, 641-645 (2014).
8. Hacohen, N. & Wu, C. J.-Y. U.S. patent application Ser. No. 01/029,3637—COMPOSITIONS AND METHODS OF IDENTIFYING TUMOR SPECIFIC NEOANTIGENS. (A1). at <http://appft1.uspto.gov/netacgi/nph-Parser?Sect1=PTO1&Sect2=HITOFF&d=PG01&p=1&u=/netahtml/PTO/srchnum.html&r=1&f=G&1=50&s1=20110293637.PGNR.>
9. Lundegaard, C., Hoof, I., Lund, O. & Nielsen, M. State of the art and challenges in sequence based T-cell epitope prediction. Immunome Res. 6 Suppl 2, S3 (2010).
10. Yadav, M. et al. Predicting immunogenic tumour mutations by combining mass spectrometry and exome sequencing. Nature 515, 572-576 (2014).
11. Bassani-Sternberg, M., Pletscher-Frankild, S., Jensen, L. J. & Mann, M. Mass spectrometry of human leukocyte antigen class I peptidomes reveals strong effects of protein abundance and turnover on antigen presentation. Mol. Cell. Proteomics MCP 14, 658-673 (2015).
12. Van Allen, E. M. et al. Genomic correlates of response to CTLA-4 blockade in metastatic melanoma. Science 350, 207-211 (2015).
13. Yoshida, K. & Ogawa, S. Splicing factor mutations and cancer. Wiley Interdiscip. Rev. RNA 5, 445-459 (2014).
14. Cancer Genome Atlas Research Network. Comprehensive molecular profiling of lung adenocarcinoma. Nature 511, 543-550 (2014).
15. Rajasagi, M. et al. Systematic identification of personal tumor-specific neoantigens in chronic lymphocytic leukemia. Blood 124, 453-462 (2014).
16. Downing, S. R. et al. U.S. patent application Ser. No. 01/202,08706—OPTIMIZATION OF MULTIGENE ANALYSIS OF TUMOR SAMPLES. (A1). at <http://appft1.uspto.gov/netacgi/nph-Parser?Sect1=PTO1&Sect2=HITOFF&d=PG01&p=1&u=/netahtml/PTO/srchnum.html&r=1&f=G&1=50&s1=20120208706.PGNR.>
17. Target Capture for NextGen Sequencing—IDT. at <http://www.idtdna.com/pages/products/nextgen/target-capture>
18. Shukla, S. A. et al. Comprehensive analysis of cancer-associated somatic mutations in class I HLA genes. Nat. Biotechnol. 33, 1152-1158 (2015).
19. Cieslik, M. et al. The use of exome capture RNA-seq for highly degraded RNA with application to clinical cancer sequencing. Genome Res. 25, 1372-1381 (2015).
20. Bodini, M. et al. The hidden genomic landscape of acute myeloid leukemia: subclonal structure revealed by undetected mutations. Blood 125, 600-605 (2015).

21. Saunders, C. T. et al. Strelka: accurate somatic small-variant calling from sequenced tumor-normal sample pairs. Bioinforma. Oxf. Engl. 28, 1811-1817 (2012).
22. Cibulskis, K. et al. Sensitive detection of somatic point mutations in impure and heterogeneous cancer samples. Nat. Biotechnol. 31, 213-219 (2013).
23. Wilkerson, M. D. et al. Integrated RNA and DNA sequencing improves mutation detection in low purity tumors. Nucleic Acids Res. 42, e107 (2014).
24. Mose, L. E., Wilkerson, M. D., Hayes, D. N., Perou, C. M. & Parker, J. S. ABRA: improved coding indel detection via assembly-based realignment. Bioinforma. Oxf. Engl. 30, 2813-2815 (2014).
25. Ye, K., Schulz, M. H., Long, Q., Apweiler, R. & Ning, Z. Pindel: a pattern growth approach to detect break points of large deletions and medium sized insertions from paired-end short reads. Bioinforma. Oxf. Engl. 25, 2865-2871 (2009).
26. Lam, H. Y. K. et al. Nucleotide-resolution analysis of structural variants using BreakSeq and a breakpoint library. Nat. Biotechnol. 28, 47-55 (2010).
27. Frampton, G. M. et al. Development and validation of a clinical cancer genomic profiling test based on massively parallel DNA sequencing. Nat. Biotechnol. 31, 1023-1031 (2013).
28. Boegel, S. et al. HLA typing from RNA-Seq sequence reads. Genome Med. 4, 102 (2012).
29. Liu, C. et al. ATHLATES: accurate typing of human leukocyte antigen through exome sequencing. Nucleic Acids Res. 41, e142 (2013).
30. Mayor, N. P. et al. HLA Typing for the Next Generation. PloS One 10, e0127153 (2015).
31. Roy, C. K., Olson, S., Graveley, B. R., Zamore, P. D. & Moore, M. J. Assessing long-distance RNA sequence connectivity via RNA-templated DNA-DNA ligation. eLife 4, (2015).
32. Song, L. & Florea, L. CLASS: constrained transcript assembly of RNA-seq reads. BMC Bioinformatics 14 Suppl 5, S14 (2013).
33. Maretty, L., Sibbesen, J. A. & Krogh, A. Bayesian transcriptome assembly. Genome Biol. 15, 501 (2014).
34. Pertea, M. et al. StringTie enables improved reconstruction of a transcriptome from RNA-seq reads. Nat. Biotechnol. 33, 290-295 (2015).
35. Roberts, A., Pimentel, H., Trapnell, C. & Pachter, L. Identification of novel transcripts in annotated genomes using RNA-Seq. Bioinforma. Oxf. Engl. (2011). doi: 10.1093/bioinformatics/btr355
36. Vitting-Seerup, K., Porse, B. T., Sandelin, A. & Waage, J. spliceR: an R package forclassification of alternative splicing and prediction of coding potential from RNA-seq data. BMC Bioinformatics 15, 81 (2014).
37. Rivas, M. A. et al. Human genomics. Effect of predicted protein-truncating genetic variants on the human transcriptome. Science 348, 666-669 (2015).
38. Skelly, D. A., Johansson, M., Madeoy, J., Wakefield, J. & Akey, J. M. A powerful and flexible statistical framework for testing hypotheses of allele-specific gene expression from RNA-seq data. Genome Res. 21, 1728-1737 (2011).
39. Anders, S., Pyl, P. T. & Huber, W. HTSeq-a Python framework to work with high-throughput sequencing data. Bioinforma. Oxf. Engl. 31, 166-169 (2015).
40. Furney, S. J. et al. SF3B1 mutations are associated with alternative splicing in uveal melanoma. Cancer Discov. (2013). doi:10.1158/2159-8290.CD-13-0330
41. Zhou, Q. et al. A chemical genetics approach for the functional assessment of novel cancergenes. Cancer Res. (2015). doi:10.1158/0008-5472.CAN-14-2930
42. Maguire, S. L. et al. SF3B1 mutations constitute a novel therapeutic target in breast cancer. J. Pathol. 235, 571-580 (2015).
43. Carithers, L. J. et al. A Novel Approach to High-Quality Postmortem Tissue Procurement: The GTEx Project. Biopreservation Biobanking 13, 311-319 (2015).
44. Xu, G. et al. RNA CoMPASS: a dual approach for pathogen and host transcriptome analysis of RNA-seq datasets. PloS One 9, e89445 (2014).
45. Andreatta, M. & Nielsen, M. Gapped sequence alignment using artificial neural networks: application to the MHC class I system. Bioinforma. Oxf. Engl. (2015). doi:10.1093/bioinformatics/btv639
46. Jørgensen, K. W., Rasmussen, M., Buus, S. & Nielsen, M. NetMHCstab—predicting stability of peptide-MHC-I complexes; impacts for cytotoxic T lymphocyte epitope discovery. Immunology 141, 18-26 (2014).
47. Larsen, M. V. et al. An integrative approach to CTL epitope prediction: a combined algorithm integrating MHC class I binding, TAP transport efficiency, and proteasomal cleavage predictions. Eur. J. Immunol. 35, 2295-2303 (2005).
48. cytotoxic T-cell epitopes: insights obtained from improved predictions of proteasomal cleavage. Immunogenetics 57, 33-41 (2005).
49. Boisvert, F.-M. et al. A Quantitative Spatial Proteomics Analysis of Proteome Turnover in Human Cells. Mol. Cell. Proteomics 11, M111.011429-M111.011429 (2012).
50. Duan, F. et al. Genomic and bioinformatic profiling of mutational neoepitopes reveals new rules to predict anticancer immunogenicity. J. Exp. Med. 211, 2231-2248 (2014).
51. Janeway's Immunobiology: 9780815345312: Medicine & Health Science Books @Amazon.com. at <http://www.amazon.com/Janeways-Immunobiology-Kenneth-Murphy/dp/0815345313>
52. Calis, J. J. A. et al. Properties of MHC Class I Presented Peptides That Enhance Immunogenicity. PLoS Comput. Biol. 9, e1003266 (2013).
53. Zhang, J. et al. Intratumor heterogeneity in localized lung adenocarcinomas delineated by multiregion sequencing. Science 346, 256-259 (2014)
54. Walter, M. J. et al. Clonal architecture of secondary acute myeloid leukemia. N. Engl. J. Med. 366, 1090-1098 (2012).
55. Hunt D F, Henderson R A, Shabanowitz J, Sakaguchi K, Michel H, Sevilir N, Cox A L, Appella E, Engelhard V H. Characterization of peptides bound to the class I MHC molecule HLA-A2.1 by mass spectrometry. Science 1992. 255: 1261-1263.
56. Zarling A L, Polefrone J M, Evans A M, Mikesh L M, Shabanowitz J, Lewis S T, Engelhard V H, Hunt D F. Identification of class I MHC-associated phosphopeptides as targets for cancer immunotherapy. Proc Natl Acad Sci USA. 2006 Oct. 3; 103(40):14889-94.
57. Bassani-Sternberg M, Pletscher-Frankild S, Jensen L J, Mann M. Mass spectrometry of human leukocyte antigen class I peptidomes reveals strong effects of protein abundance and turnover on antigen presentation. Mol Cell Proteomics. 2015 March; 14(3):658-73. doi: 10.1074/mcp.M114.042812.
58. Abelin J G, Trantham P D, Penny S A, Patterson A M, Ward S T, Hildebrand W H, Cobbold M, Bai D L, Shabanowitz J, Hunt D F. Complementary IMAC enrichment methods for HLA-associated phosphopeptide identification by mass spectrometry. Nat Protoc. 2015 September; 10(9):1308-18. doi: 10.1038/nprot.2015.086. Epub 2015 Aug. 6
59. Barnstable C J, Bodmer W F, Brown G, Galfre G, Milstein C, Williams A F, Ziegler A. Production of monoclonal antibodies to group A erythrocytes, HLA and other human cell surface antigens-new tools for genetic analysis. Cell. 1978 May; 14(1):9-20.
60. Goldman J M, Hibbin J, Kearney L, Orchard K, Th'ng K H. HLA-DR monoclonal antibodies inhibit the proliferation of normal and chronic granulocytic leukaemia myeloid progenitor cells. Br J Haematol. 1982 November; 52(3):411-20.
61. Eng J K, Jahan T A, Hoopmann M R. Comet: an open-source MS/MS sequence database search tool. Proteomics. 2013 January; 13(1):22-4. doi: 10.1002/pmic.201200439. Epub 2012 Dec. 4.
62. Eng J K, Hoopmann M R, Jahan T A, Egertson J D, Noble W S, MacCoss MJ. A deeper look into Comet-implementation and features. J Am Soc Mass Spectrom. 2015 November; 26(11):1865-74. doi: 10.1007/s13361-015-1179-x. Epub 2015 Jun. 27.
63. Lukas Käll, Jesse Canterbury, Jason Weston, William Stafford Noble and Michael J. MacCoss. Semi-supervised learning for peptide identification from shotgun proteomics datasets. Nature Methods 4:923-925, November 2007
64. Lukas K O, John D. Storey, Michael J. MacCoss and William Stafford Noble. Assigning confidence measures to peptides identified by tandem mass spectrometry. Journal of Proteome Research, 7(1):29-34, January 2008
65. Lukas Käll, John D. Storey and William Stafford Noble. Nonparametric estimation of posterior error probabilities associated with peptides identified by tandem mass spectrometry. Bioinformatics, 24(16):i42-i48, August 2008
66. Bo Li and C. olin N. Dewey. RSEM: accurate transcript quantification from RNA-Seq data with or without a referenfe genome. BMC Bioinformatics, 12:323, August 2011
67. Hillary Pearson, Tariq Daouda, Diana Paola Granados, Chantal Durette, Eric Bonneil, Mathieu Courcelles, Anja Rodenbrock, Jean-Philippe Laverdure, Caroline Côté, Sylvie Mader, Sébastien Lemieux, Pierre Thibault, and Claude Perreault. MHC class I-associated peptides derive from selective regions of the human genome. The Journal of Clinical Investigation, 2016,
68. Juliane Liepe, Fabio Marino, John Sidney, Anita Jeko, Daniel E. Bunting, Alessandro Sette, Peter M. Kloetzel, Michael P. H. Stumpf, Albert J. R. Heck, Michele Mishto. A large fraction of HLA class I ligands are proteasome-generated spliced peptides. Science, 21, October 2016.
69. Mommen G P., Marino, F., Meiring H D., Poelen, M C., van Gaans-van den Brink, J A., Mohammed S., Heck A J., and van Els C A. Sampling From the Proteome to the Human Leukocyte Antigen-DR (HLA-DR) Ligandome Proceeds Via High Specificity. Mol Cell Proteomics 15(4): 1412-1423, April 2016.
70. Sebastian Kreiter, Mathias Vormehr, Niels van de Roemer, Mustafa Diken, Martin Löwer, Jan Diekmann, Sebastian Boegel, Barbara SchrOrs, Fulvia Vascotto, John C. Castle, Arbel D. Tadmor, Stephen P. Schoenberger, Christoph Huber, Özlem Türeci, and Ugur Sahin. Mutant MHC class II epitopes drive therapeutic immune responses to cancer. Nature 520, 692-696, April 2015.
71. Tran E., Turcotte S., Gros A., Robbins P. F., Lu Y.C., Dudley M. E., Wunderlich J. R., Somerville R. P., Hogan K., Hinrichs C. S., Parkhurst M. R., Yang J. C., Rosenberg S. A. Cancer immunotherapy based on mutation-specific CD4+ T-cells in a patient with epithelial cancer. Science 344(6184) 641-645, May 2014.
72. Andreatta M., Karosiene E., Rasmussen M., Stryhn A., Buus S., Nielsen M. Accurate pan-specific prediction of peptide-MHC class II binding affinity with improved binding core identification. Immunogenetics 67(11-12) 641-650, November 2015.
73. Nielsen, M., Lund, O. NN-align. An artificial neural network-based alignment algorithm for MHC class II peptide binding prediction. BMC Bioinformatics 10:296, September 2009.
74. Nielsen, M., Lundegaard, C., Lund, O. Prediction of MHC class II binding affinity using SMM-align, a novel stabilization matrix alignment method. BMC Bioinformatics 8:238, July 2007.
75. Zhang, J., et al. PEAKS DB: de novo sequencing assisted database search for sensitive and accurate peptide identification. Molecular & Cellular Proteomics. 11(4):1-8. Jan. 2, 2012.
76. Snyder, A. et al. Genetic basis for clinical response to CTLA-4 blockade in melanoma. N. Engl. J. Med. 371, 2189-2199 (2014).
77. Rizvi, N. A. et al. Cancer immunology. Mutational landscape determines sensitivity to PD-1 blockade in non-small cell lung cancer. Science 348, 124-128 (2015).
78. Gubin, M. M., Artyomov, M. N., Mardis, E. R. & Schreiber, R. D. Tumor neoantigens: building a framework for personalized cancer immunotherapy. J. Clin. Invest. 125, 3413-3421 (2015).
79. Schumacher, T. N. & Schreiber, R. D. Neoantigens in cancer immunotherapy. Science 348, 69-74 (2015).
80. Carreno, B. M. et al. Cancer immunotherapy. A dendritic cell vaccine increases the breadth and diversity of melanoma neoantigen-specific T-cells. Science 348, 803-808 (2015).
81. Ott, P. A. et al. An immunogenic personal neoantigen vaccine for patients with melanoma. Nature 547, 217-221 (2017).
82. Sahin, U. et al. Personalized RNA mutanome vaccines mobilize poly-specific therapeutic immunity against cancer. Nature 547, 222-226 (2017).
83. Tran, E. et al. T-Cell Transfer Therapy Targeting Mutant KRAS in Cancer. N. Engl. J. Med. 375, 2255-2262 (2016).
84. Gros, A. et al. Prospective identification of neoantigen-specific lymphocytes in the peripheral blood of melanoma patients. Nat. Med. 22, 433-438 (2016).
85. The problem with neoantigen prediction. Nat. Biotechnol. 35, 97-97 (2017).
86. Vitiello, A. & Zanetti, M. Neoantigen prediction and the need for validation. Nat. Biotechnol. 35, 815-817 (2017).
87. Bassani-Sternberg, M., Pletscher-Frankild, S., Jensen, L. J. & Mann, M. Mass spectrometry of human leukocyte antigen class I peptidomes reveals strong effects of protein abundance and turnover on antigen presentation. Mol. Cell. Proteomics MCP 14, 658-673 (2015).
88. Vita, R. et al. The immune epitope database (IEDB) 3.0. Nucleic *Acids Res.* 43, D405-412 (2015).
89. Andreatta, M. & Nielsen, M. Gapped sequence alignment using artificial neural networks: application to the MHC class I system. Bioinforma. Oxf. Engl. 32, 511-517 (2016).
90. O'Donnell, T. J. et al. MHCflurry: Open-Source Class I MHC Binding Affinity Prediction. Cell Syst. (2018). doi:10.1016/j.cels.2018.05.014

91. Bassani-Sternberg, M. et al. Direct identification of clinically relevant neoepitopes presented on native human melanoma tissue by mass spectrometry. Nat. Commun. 7, 13404 (2016).
92. Abelin, J. G. et al. Mass Spectrometry Profiling of HLA-Associated Peptidomes in Mono-allelic Cells Enables More Accurate Epitope Prediction. Immunity 46, 315-326 (2017).
93. Yadav, M. et al. Predicting immunogenic tumour mutations by combining mass spectrometry and exome sequencing. Nature 515, 572-576 (2014).
94. Stranzl, T., Larsen, M. V., Lundegaard, C. & Nielsen, M. NetCTLpan: pan-specific MHC class I pathway epitope predictions. Immunogenetics 62, 357-368 (2010).
95. Bentzen, A. K. et al. Large-scale detection of antigen-specific T-cells using peptide-MHC-I multimers labeled with DNA barcodes. Nat. Biotechnol. 34, 1037-1045 (2016).
96. Tran, E. et al. Immunogenicity of somatic mutations in human gastrointestinal cancers. Science 350, 1387-1390 (2015).
97. Stronen, E. et al. Targeting of cancer neoantigens with donor-derived T-cell receptor repertoires. Science 352, 1337-1341 (2016).
98. Trolle, T. et al. The Length Distribution of Class I-Restricted T-cell Epitopes Is Determined by Both Peptide Supply and MHC Allele-Specific Binding Preference. J. Immunol. Baltim. Md. 1950 196, 1480-1487 (2016).
99. Di Marco, M. et al. Unveiling the Peptide Motifs of HLA-C and HLA-G from Naturally Presented Peptides and Generation of Binding Prediction Matrices. J. Immunol. Baltim. Md. 1950 199, 2639-2651 (2017).
100. Goodfellow, I., Bengio, Y. & Courville, A. Deep Learning. (MIT Press, 2016).
101. Sette, A. et al. The relationship between class I binding affinity and immunogenicity of potential cytotoxic T-cell epitopes. J. Immunol. Baltim. Md. 1950 153, 5586-5592 (1994).
102. Fortier, M.-H. et al. The MHC class I peptide repertoire is molded by the transcriptome. J. Exp. Med. 205, 595-610 (2008).
103. Pearson, H. et al. MHC class I-associated peptides derive from selective regions of the human genome. J. Clin. Invest. 126, 4690-4701 (2016).
104. Bassani-Sternberg, M. et al. Deciphering HLA-I motifs across HLA peptidomes improves neoantigen predictions and identifies allostery regulating HLA specificity. PLoS Comput. Biol. 13, e1005725 (2017).
105. Andreatta, M., Lund, O. & Nielsen, M. Simultaneous alignment and clustering of peptide data using a Gibbs sampling approach. Bioinforma. Oxf. Engl. 29, 8-14 (2013).
106. Andreatta, M., Alvarez, B. & Nielsen, M. GibbsCluster: unsupervised clustering and alignment of peptide sequences. Nucleic Acids Res. (2017). doi:10.1093/nar/gkx248
107. Gros, A. et al. Prospective identification of neoantigen-specific lymphocytes in the peripheral blood of melanoma patients. Nat. Med. 22, 433-438 (2016).
108. Zacharakis, N. et al. Immune recognition of somatic mutations leading to complete durable regression in metastatic breast cancer. Nat. Med. 24, 724-730 (2018).
109. Chudley, L. et al. Harmonisation of short-term in vitro culture for the expansion of antigen-specific CD8+ T-cells with detection by ELISPOT and HLA-multimer staining. Cancer Immunol. Immunother. 63, 1199-1211 (2014).
110. Van Allen, E. M. et al. Genomic correlates of response to CTLA-4 blockade in metastatic melanoma. Science 350, 207-211 (2015).
111. Anagnostou, V. et al. Evolution of Neoantigen Landscape during Immune Checkpoint Blockade in Non-Small Cell Lung Cancer. Cancer Discov. 7, 264-276 (2017).
112. Carreno, B. M. et al. Cancer immunotherapy. A dendritic cell vaccine increases the breadth and diversity of melanoma neoantigen-specific T-cells. Science 348, 803-808 (2015).
113. Stevanović, S. et al. Landscape of immunogenic tumor antigens in successful immunotherapy of virally induced epithelial cancer. Science 356, 200-205 (2017).
114. Pasetto, A. et al. Tumor- and Neoantigen-Reactive T-cell Receptors Can Be Identified Based on Their Frequency in Fresh Tumor. Cancer Immunol. Res. 4, 734-743 (2016).
115. Gillette, M. A. & Carr, S. A. Quantitative analysis of peptides and proteins in biomedicine by targeted mass spectrometry. Nat. Methods 10, 28-34 (2013).
116. Boegel, S., Löwer, M., Bukur, T., Sahin, U. & Castle, J. C. A catalog of HLA type, HLA expression, and neo-epitope candidates in human cancer cell lines. Oncoimmunology 3, e954893 (2014).
117. Johnson, D. B. et al. Melanoma-specific MHC-II expression represents a tumour-autonomous phenotype and predicts response to anti-PD-1/PD-L1 therapy. Nat. Commun. 7, 10582 (2016).
118. Robbins, P. F. et al. A Pilot Trial Using Lymphocytes Genetically Engineered with an NY-ESO-1-Reactive T-cell Receptor: Long-term Follow-up and Correlates with Response. Clin. Cancer Res. 21, 1019-1027 (2015).
119. Snyder, A. et al. Genetic basis for clinical response to CTLA-4 blockade in melanoma. N. Engl. J. Med. 371, 2189-2199 (2014).
120. Calis, J. J. A. et al. Properties of MHC class I presented peptides that enhance immunogenicity. PLoS Comput. Biol. 9, e1003266 (2013).
121. Duan, F. et al. Genomic and bioinformatic profiling of mutational neoepitopes reveals new rules to predict anticancer immunogenicity. J. Exp. Med. 211, 2231-2248 (2014).
122. Glanville, J. et al. Identifying specificity groups in the T-cell receptor repertoire. Nature 547, 94-98 (2017).
123. Dash, P. et al. Quantifiable predictive features define epitope-specific T-cell receptor repertoires. Nature 547, 89-93 (2017).
124. Hunt, D. F. et al. Pillars article: Characterization of peptides bound to the class I MHC molecule HLA-A2.1 by mass spectrometry. Science 1992. 255: 1261-1263. J. Immunol. Baltim. Md. 1950 179, 2669-2671 (2007).
125. Zarling, A. L. et al. Identification of class I MHC-associated phosphopeptides as targets for cancer immunotherapy. Proc. Natl. Acad. Sci. U.S.A. 103, 14889-14894 (2006).
126. Abelin, J. G. et al. Complementary IMAC enrichment methods for HLA-associated phosphopeptide identification by mass spectrometry. Nat. Protoc. 10, 1308-1318 (2015).
127. Barnstable, C. J. et al. Production of monoclonal antibodies to group A erythrocytes, HLA and other human cell surface antigens-new tools for genetic analysis. Cell 14, 9-20 (1978).
128. Eng, J. K., Jahan, T. A. & Hoopmann, M. R. Comet: an open-source MS/MS sequence database search tool. Proteomics 13, 22-24 (2013).

129. Eng, J. K. et al. A deeper look into Comet-implementation and features. J. Am. Soc. Mass Spectrom. 26, 1865-1874 (2015).
130. Käll, L., Storey, J. D., MacCoss, M. J. & Noble, W. S. Assigning significance to peptides identified by tandem mass spectrometry using decoy databases. J. Proteome Res. 7, 29-34 (2008).
131. Käll, L., Storey, J. D. & Noble, W. S. Non-parametric estimation of posterior errorprobabilities associated with peptides identified by tandem mass spectrometry. Bioinforma. Oxf. Engl. 24, i42-48 (2008).
132. Käll, L., Canterbury, J. D., Weston, J., Noble, W. S. & MacCoss, M. J. Semi-supervised learning for peptide identification from shotgun proteomics datasets. Nat. Methods 4, 923-925 (2007).
133. Li, B. & Dewey, C. N. RSEM: accurate transcript quantification from RNA-Seq data with or without a reference genome. BMC Bioinformatics 12, 323 (2011).
134. Chollet, F. & others. Keras. (2015).
135. Bastien, F. et al. Understanding the difficulty of training deep feedforward neural networks. Proc. Thirteen. Int. Conf. Artif. Intell. Stat. 249-256 (2010).
136. Glorot, X. & Bengio, Y. Understanding the difficulty of training deep feedforward neural networks. in Proceedings of the Thirteenth International Conference on Artificial Intelligence and Statistics 249-256 (2010).
137. Kingma, D. & Ba, J. Adam: A method for stochastic optimization. ArXiv Prepr. ArXiv14126980 (2014).
138. Schneider, T. D. & Stephens, R. M. Sequence logos: a new way to display consensus sequences. Nucleic Acids Res. 18, 6097-6100 (1990).
139. Rubinsteyn, A., O'Donnell, T., Damaraju, N. & Hammerbacher, J. Predicting Peptide-MHC Binding Affinities With Imputed Training Data. biorxiv (2016). doi:https://doi.org/10.1101/054775
140. Tran, E. et al. Immunogenicity of somatic mutations in human gastrointestinal cancers. Science 350, 1387-1390 (2015).
141. Stronen, E. et al. Targeting of cancer neoantigens with donor-derived T-cell receptor repertoires. Science 352, 1337-1341 (2016).
142. Janetzki, S., Cox, J. H., Oden, N. & Ferrari, G. Standardization and validation issues of the ELISPOT assay. Methods Mol. Biol. Clifton N.J. 302, 51-86 (2005).
143. Janetzki, S. et al. Guidelines for the automated evaluation of Elispot assays. Nat. Protoc. 10, 1098-1115 (2015).
144. Li, H. & Durbin, R. Fast and accurate short read alignment with Burrows-Wheeler transform. Bioinforma. Oxf. Engl. 25, 1754-1760 (2009).
145. DePristo, M. A. et al. A framework for variation discovery and genotyping using next-generation DNA sequencing data. Nat. Genet. 43, 491-498 (2011).
146. Garrison, E. & Marth, G. Haplotype-based variant detection from short-read sequencing. arXiv (2012).
147. Cingolani, P. et al. A program for annotating and predicting the effects of single nucleotide polymorphisms, SnpEff: SNPs in the genome of Drosophila melanogaster strain w1118; iso-2; iso-3. Fly (Austin) 6, 80-92 (2012).
148. Szolek, A. et al. OptiType: precision HLA typing from next-generation sequencing data. Bioinforma. Oxf. Engl. 30, 3310-3316 (2014).
149. Cibulskis, K. et al. Sensitive detection of somatic point mutations in impure and heterogeneous cancer samples. Nat. Biotechnol. 31, 213-219 (2013).
150. Scholz, E. M. et al. Human Leukocyte Antigen (HLA)-DRB1*15:01 and HLA-DRB5*01:01 Present Complementary Peptide Repertoires. Front. Immunol. 8, 984 (2017).
151. Ooi, J. D. et al. Dominant protection from HLA-linked autoimmunity by antigen-specific regulatory T-cells. Nature 545, 243-247 (2017).
152. Karosiene, E. et al. NetMHCIIpan-3.0, a common pan-specific MHC class II prediction method including all three human MHC class II isotypes, HLA-DR, HLA-DP and HLA-DQ. Immunogenetics 65, 711-724 (2013).
153. Dudley M E, Gross C A, Langhan M M, et al. CD8+ enriched "young" tumor infiltrating lymphocytes can mediate regression of metastatic melanoma. Clinical cancer research: an official journal of the American Association for Cancer Research. 2010; 16(24):6122-6131. doi: 10.1158/1078-0432.CCR-10-1297.
154. Dudley M E, Wunderlich J R, Shelton T E, Even J, Rosenberg S A. Generation of Tumor-Infiltrating Lymphocyte Cultures for Use in Adoptive Transfer Therapy for Melanoma Patients. Journal of immunotherapy (Hagerstown, Md.: 1997). 2003; 26(4):332-342.
155. Cohen C J, Gartner J J, Horovitz-Fried M, et al. Isolation of neoantigen-specific T cells from tumor and peripheral lymphocytes. The Journal of Clinical Investigation. 2015; 125(10):3981-3991. doi:10.1172/JCI82416.
156. Kelderman, S., Heemskerk, B., Fanchi, L., Philips, D., Toebes, M., Kvistborg, P., Buuren, M. M., Rooij, N., Michels, S., Germeroth, L., Haanen, J. B. and Schumacher, N. M. (2016), Antigen-specific TIL therapy for melanoma: A flexible platform for personalized cancer immunotherapy. Eur. J. Immunol., 46: 1351-1360. doi: 10.1002/eji.201545849.
157. Hall M, Liu H, Malafa M, et al. Expansion of tumor-infiltrating lymphocytes (TIL) from human pancreatic tumors. Journal for Immunotherapy of Cancer. 2016; 4:61. doi:10.1186/s40425-016-0164-7.
158. Briggs A, Goldfless S, Timberlake S, et al. Tumor-infiltrating immune repertoires captured by single-cell barcoding in emulsion. bioRxiv. 2017. doi.org/10.1101/134841.
159. US Patent Application No. 20160244825A1.
160. Koşaloğlu-Yalç, Z. et al. Predicting T cell recognition of MHC class I restricted neoepitopes. J. OncoImmunology, 1-15 (2018).

SUPPLEMENTARY TABLE 1

Predicted Ranks of Mutations with Pre-Existing Response

| Mutation ID | Patient ID | MHCFlurry, TPM > 0 | MHCFlurry, TPM > 1 | MHCFlurry, TPM > 2 | Peptide MS Model, TPM > 1 | Full MS Model |
|---|---|---|---|---|---|---|
| KARS_D356H | 3942 | 81 | 44 | 36 | 26 | 5 |
| NUP98_A359D | 3942 | 13 | 8 | 7 | 0 | 0 |
| CASP8_F67V | 3971 | 13 | 3 | 2 | 3 | 1 |
| KRAS_G12D | 3995 | 36 | 21 | 18 | 2 | 2 |

SUPPLEMENTARY TABLE 1-continued

Predicted Ranks of Mutations with Pre-Existing Response

| Mutation ID | Patient ID | MHCFlurry, TPM > 0 | MHCFlurry, TPM > 1 | MHCFlurry, TPM > 2 | Peptide MS Model, TPM > 1 | Full MS Model |
|---|---|---|---|---|---|---|
| RNF213_N1702S | 3995 | 0 | 0 | 0 | 7 | 7 |
| TUBGCP2_P293L | 3995 | 2 | 2 | 2 | 8 | 6 |
| H3F3B_A48T | 4007 | 33 | 23 | 21 | 13 | 0 |
| SKIV2L_R653H | 4007 | 2 | 1 | 1 | 15 | 17 |
| API5_R243Q | 4032 | 52 | 31 | 27 | 10 | 1 |
| PHLPP1_G566E | 4032 | 54 | 33 | 29 | 72 | 67 |
| RNF10_E572K | 4032 | 43 | 23 | 22 | 46 | 46 |
| ZFYVE27_R6H | 4069 | 35 | 23 | 22 | 0 | 0 |
| CADPS2_R1266H | 4136 | 23 | 22 | 22 | 4 | 5 |
| KIAA0368_S186F | 4136 | 2 | 2 | 2 | 1 | 0 |
| FLNA_R2049C | NCI-3784 | 91 | 85 | 81 | 31 | 5 |
| KIF16B_L1009P | NCI-3784 | 22 | 21 | 19 | 74 | 69 |
| SON_R1927C | NCI-3784 | 37 | 35 | 32 | 105 | 83 |
| KIF1BP_P246S | NCI-3903 | 66 | 35 | 32 | 22 | 7 |
| MAGEA6_E168K | NCI-3998 | 15 | 10 | 9 | 1 | 0 |
| MED13_P1691S | NCI-3998 | 5 | 3 | 2 | 0 | 1 |
| PDS5A_Y1000F | NCI-3998 | 13 | 8 | 7 | 6 | 4 |
| CDK4_R71L | patient1 | 56 | 23 | 20 | 5 | 0 |
| DNAH17_H8302Y | patient1 | 42 | 80 | 59 | 112 | 77 |
| GCN1_L2330P | patient1 | 59 | 25 | 22 | 3 | 1 |
| BRWD1_R925W | patient2 | 80 | 62 | 58 | 74 | 75 |
| PARG_Y427N | patient2 | 88 | 69 | 65 | 51 | 49 |
| | Median | 35.5 | 23 | 21.5 | 9 | 5 |

SUPPLEMENTARY TABLE 2

Demographics of NSCLS Patients

| Patient ID | Age Range (Years) | Gender | Race | Year of Initial (Lung Cancer) Diagnosis | Tumor Stage (At Enrollment) | Location of Primary Tumor | Histological Type |
|---|---|---|---|---|---|---|---|
| 1-001-002 | 81-90 | Male | White | 2010 | IIB | Lung | Non-squamous |
| 1-024-001 | 81-90 | Male | White | 2016 | IV | Lung | Sarcomatoid pulmonary carcinoma |
| 1-024-002 | 51-60 | Female | White | 2016 | IV | Lung | Adenocarcinoma |
| 1-038-001 | 61-70 | Male | White | 2016 | IV | Lung | Adenocarcinoma |

| Systemic NSCLC-Directed Therapy | Current Anti-PD(L)-1 Therapy | HLA-A | HLA-A | HLA-B | HLA-B | HLA-C | HLA-C | Expressed Mutations |
|---|---|---|---|---|---|---|---|---|
| Carboplantin | Nivolumab | A*01:01 | A*01:01 | B*08:01 | B*51:01 | C*01:02 | C*07:01 | 122 |
| | Pernbrolizumab | A*32:01 | A*03:01 | B*27:05 | B*27:05 | C*02:02 | C*02:02 | 83 |
| DOCEtaxel, Bevacizumab, Ramucirumab, Pemetrexed Disodium | Nivolumab | A*68:01 | A*68:01 | B*40:02 | B*40:27 | C*03:04 | C*03:04 | 38 |
| premetexed, Cisplatin | Nivolumab | A*69:01 | A*01:02 | B*41:01 | B*49:01 | C*17:01 | C*07:01 | 158 |

| Nonsynonymous Mutations | Normal DNA Median Exon Coverage | Tumor DNA Median Exon Coverage | RNA PF Unique Reads (M) | Known Drivers | Likely Drivers | Median VAF |
|---|---|---|---|---|---|---|
| 232 | 145 | 552 | 173 | KRAS_G12D, TP53_R213* | STK11_G52fs | 0.22 |
| 143 | 165 | 508 | 131.9 | KRAS_G12C, TP53_R280T | PML_E43* NF2_R341* | 0.093 |
| 69 | 190 | 454 | 114.4 | KRAS_G12S, TP53_Q331* | STK11_E199* | 0.182 |
| 265 | 158 | 983 | 311.8 | KRAS_G12V | KDM5C_E303* | 0.19 |

| Patient ID | Age Range (Years) | Gender | Race | Year of Initial (Lung Cancer) Diagnosis | Tumor Stage (At Enrollment) | Location of Primary Tumor | Histological Type |
|---|---|---|---|---|---|---|---|
| 1-050-001 | 71-80 | Female | White | 2015 | IIB | Lung | Adenocarcinoma |
| CU05 | 71-80 | Female | White | 2013 | IV | Lung | Lung Squamous |

SUPPLEMENTARY TABLE 2-continued

Demographics of NSCLS Patients

| | | | | | | | | |
|---|---|---|---|---|---|---|---|---|
| CU04 | 61-70 | Female | Hispanic or Latino | 2013 | I | Lung | Adenocarcinoma | |
| CU03 | 61-70 | Male | African American | 2016 | I | Lung | Lung Squamous | |
| CU02 | 61-70 | Male | White | 2016 | I | Lung | Lung Squamous | |

| Systemic - NSCLC Directed Therapy | Current Anti-PD(L)-1 Therapy | HLA-A | HLA-A | HLA-B | HLA-B | HLA-C | HLA-C | Expressed Mutations |
|---|---|---|---|---|---|---|---|---|
| ETOPOSIDE, cisplatin | Nivolumab | A*29:02 | A*26:01 | B*44:03 | B*07:05 | C*16:01 | C*15:05 | 53 |
| carboplatin plus pemetrexed | Nivolumab | A*24:02 | A*68:02 | B*14:02 | B*15:17 | C*07:01 | C*08:02 | 65 |
| | durvalumab plus tremelimumab | A*24.:26 | A*26:01 | B*18:01 | B*38:01 | C*12:03 | C*12:03 | 336 |
| | n/a | A*23:01 | A*01:01 | B*08:01 | B*15:03 | C*01:02 | C*12:03 | 105 |
| carboplatin + gemcitabine | n/a | A*02:01 | A*03:01 | B*07:02 | B*57:01 | C*07:02 | C*06:02 | 102 |

| Nonsynonymous Mutations | Normal DNA Median Exon Coverage | Tumor DNA Median Exon Coverage | RNA PE Unique Reads (M) | Known Drivers | Likely Drivers | Median VAF |
|---|---|---|---|---|---|---|
| 92 | 117 | 556 | 119 | | | 0.059 |
| 109 | 191 | 448 | 83.6 | | | 0.095 |
| 511 | 213 | 552 | 240.4 | TP53_R158G | NFBIE_G41fs, CDH1_0346*, NF1_D2163fs, MED12_R730* | 0.224 |
| 187 | 114 | 830 | 182.1 | | | 0.242 |
| 174 | 105 | 738 | 185.3 | TP53_R175H | ATR_Q195* | 0.32 |

TABLE 3

Supplementary Peptides Tested for T-Cell Recognition in NSCLC Patients

| Patient | Peptide | SEQ ID NO: | Individual Peptide Response (Any Time Point) | Individual Peptide Response Notes | Pool ID | Pool Response (Any Time Point) | Mutation |
|---|---|---|---|---|---|---|---|
| 1-001-002 | HSPFTATSL | 28 | N | | 1-001-002_pool_1 | N | chr15_28215653_C_A |
| 1-001-002 | DPEEVLVTV | 29 | N | | 1-001-002_pool_1 | N | chr17_59680958_C_T |
| 1-001-002 | ELDPDIQLEY | 30 | N | | 1-001-002_pool_1 | N | chr13_3021037_C_A |
| 1-001-002 | TPLTKDVTL | 31 | N | | 1-001-002_pool_1 | N | chr5_78100974_A_T |
| 1-001-002 | DGVGKSAL | 32 | N | | 1-001-002_pool_1 | N | chr12_25245350_C_T |
| 1-001-002 | YTTVRALTL | 33 | N | | 1-001-002_pool_1 | N | chr17_28339664_G_T |
| 1-001-002 | TPSAAVKLI | 34 | N | | 1-001-002_pool_1 | N | chr15_81319417_T_C |
| 1-001-002 | WPVLLLNV | 35 | N | | 1-001-002_pool_1 | N | chr3_179025167_AAC_A |
| 1-001-002 | ELNARRCSF | 36 | N | | 1-001-002_pool_1 | N | chr18_79943341_G_A |

| Mutation Type | Gene | Protein Effect | TPM | Most Probable Restriction covered by Full MS Model | Full MS Model Rank | MHCFlurry Rank | MHCFlurry (nM) | Most Probable Restriction covered by MHCFlurry |
|---|---|---|---|---|---|---|---|---|
| snp | HERC2 | A20605 | 41.9 | HLA-C*01:02 | 0 | 95 | 5169.68205 | FALSE |
| snp | CLTC | S989L | 272.1 | HLA-B*51:01 | 1 | 61 | 3455.25069 | TRUE |
| snp | KATNAL1 | D407Y | 12.81 | HLA-A*01:01 | 2 | 1 | 24.2177849 | TRUE |
| snp | AP3B1 | S817T | 44.4 | HLA-B*08:01 | 3 | 2 | 48.9740194 | TRUE |
| snp | KRAS | G12D | 40.75 | HLA-B*08:01 | 4 | 89 | 4714.29522 | TRUE |
| snp | TNFAIP1 | R48L | 45.62 | HLA-B*08:01 | 5 | 26 | 973.417701 | TRUE |
| snp | STARD5 | M108V | 1.95 | HLA-B*51:01 | 6 | 39 | 2030.48603 | TRUE |
| del_fs | ZMAT3 | V240fs | 14.99 | | 7 | 16 | 600.564752 | TRUE |
| snp | PQLC1 | R109C | 33.89 | HLA-B*08:01 | 8 | 5 | 62.0439997 | TRUE |

TABLE 3-continued

Supplementary Peptides Tested for T-Cell Recognition in NSCLC Patients

| Patient Peptide | SEQ ID NO: | Individual Peptide Response (Any Time Point) | Individual Peptide Response Notes | Pool ID | Pool Response (Any Time Point) | Mutation |
|---|---|---|---|---|---|---|
| 1-001-002 QMKNPILEL | 37 | N | | 1-001-002 pool 1 | N | chr9_127663287_G_T |
| 1-001-002 LTEKVSLLK | 38 | N | | 1-001-002 pool_2 | N | chr9_92719180_C_T |
| 1-001-002 SPFTATSL | 39 | N | | 1-001-002 pool_2 | N | chr15_2821565_C_A |
| 1-001-002 NVDMRTISF | 40 | N | | 1-001-002 pool_2 | N | chr9_121353262_T_A |
| 1-001-002 TSIVVSQTL | 41 | N | | 1-001-002 pool_2 | N | chr4_3920569_C_T |
| 1-001-002 HIKIEPVAI | 42 | N | | 1-001-002 pool_2 | N | chr13_73062087_C_T |
| 1-001-002 DSPDGSNGL | 43 | N | | 1-001-002 pool_2 | N | chr20_44197575_C_T |
| 1-001-002 YTAVHYAASY | 44 | N | | 1-001-002 pool_2 | N | chr12_56248788_C_A |
| 1-001-002 VGADGVGKSAL | 45 | N | | 1-001-002 pool_2 | N | chr12_25245350_C_T |

| Mutation Type | Gene | Protein Effect | TPM | Most Probable Restriction covered by Full MS Model | Full MS Model Rank | MHCFlurry Rank | MHCFlurry (nM) | Most Probable Restriction covered by MHCFlurry |
|---|---|---|---|---|---|---|---|---|
| snp | STXBP1 | R171L | 38.76 | HLA-B*08:01 | 9 | 20 | 674.64733 | TRUE |
| snp | BICD2 | E489K | 42.66 | HLA-A*01:01 | 10 | 10 | 428.744925 | TRUE |
| snp | HERC2 | A20605 | 41.9 | HLA-B*08:01 | 11 | 4 | 59.1155419 | TRUE |
| snp | STOM | K93N | 360.6 | HLA-B*08:01 | 12 | 30 | 1490.72261 | TRUE |
| snp | WDR19 | A282V | 18.12 | HLA-B*08:01 | 13 | 176 | 9862.33009 | TRUE |
| snp | KLF5 | T163I | 25.77 | HLA-B*08:01 | 14 | 27 | 1122.27455 | TRUE |
| snp | OSERI | S119N | 20.7 | HLA-C*01:02 | 15 | 471 | 21598.414 | FALSE |
| snp | ANKRD52 | A559S | 18.32 | HLA-A*01:01 | 16 | 0 | 11.5906737 | TRUE |
| snp | KRAS | G12D | 40.75 | HLA-C*01:02 | 17 | 370 | 17985.3612 | FALSE |

TABLE 3-continued

Supplementary Peptides Tested for T-Cell Recognition in NSCLC Patients

| Patient Peptide | SEQ ID NO: | Individual Peptide Response (Any Time Point) | Individual Peptide Response Notes | Pool ID | Pool Response (Any Time Point) | Mutation |
|---|---|---|---|---|---|---|
| 1-001-002 MMPPLPGI | 46 | N | | 1-001-002_pool_2 | N | chr17_32369404_A_T |
| 1-001-002 FPYPGMTNQ | 47 | N | | 1-001-002_pool_2 | N | chr5_109186272_G_T |
| 1-024-001 VTNHAPLSW | 48 | N | | 1-024-001_pool_1 | Y | chr3_125552370_C_A |
| 1-024-001 GTKKDVDVLK | 27 | Y | | 1-024-001_pool_1 | Y | chr20_56513366_G_A |
| 1-024-001 GLNVPVQSNK | 49 | N | | 1-024-001_pool_1 | Y | chr4_88390868_G_T |
| 1-024-001 VVVGACGVGK | 50 | N | | 1-024-001_pool_1 | Y | chr12_2524535_C_A |
| 1-024-001 AQFAGKDQTY | 51 | N | | 1-024-001_pool_1 | Y | chr9_89045819_C_A |
| 1-024-001 KVVLPSDVTSY | 52 | N | | 1-024-001_pool_1 | Y | chr3_48591778_G_T |
| 1-024-001 MLMKNISTK | 53 | N | | 1-024-001_pool_1 | Y | chr12_6959976_G_A |

| Mutation Type | Gene | Protein Effect | TPM | Most Probable Restriction covered by Full MS Model | Full MS Model Rank | MHCFlurry Rank | MHCFlurry (nM) | Most Probable Restriction covered by MHCFlurry |
|---|---|---|---|---|---|---|---|---|
| snp | ZNF207 | Q409L | 186 | HLA-B*51:01 | 18 | 136 | 7609.76602 | TRUE |
| snp | FER | C759F | 67.36 | HLA-B*51:01 | 19 | 38 | 1999.07208 | TRUE |
| snp | OSBPL11 | G489W | 24.12 | HLA-A*32:01 | 0 | 7 | 77.009026 | TRUE |
| snp | RTFDC1 | E177K | 61.32 | HLA-A*03:01 | 1 | 70 | 2168.51668 | TRUE |
| snp | HERC6 | R218L | 8.7 | HLA-A*03:01 | 2 | 4 | 59.675168 | TRUE |
| snp | KRAS | G12C | 40.05 | HLA-A*03:01 | 3 | 11 | 133.648023 | TRUE |
| snp | SHC3 | E376D | 8.88 | HLA-A*32:01 | 4 | 91 | 3715.42819 | TRUE |
| snp | COL7A1 | R4685 | 25.42 | HLA-A*32:01 | 6 | 85 | 3234.15772 | TRUE |
| snp | PTPN6 | E471K | 105.4 | HLA-A*03:01 | 7 | 0 | 12.2301919 | TRUE |

TABLE 3-continued

Supplementary Peptides Tested for T-Cell Recognition in NSCLC Patients

| Patient | Peptide | SEQ ID NO: | Individual Peptide Response (Any Time Point) | Individual Peptide Response Notes | Pool ID | Pool Response (Any Time Point) | Mutation |
|---|---|---|---|---|---|---|---|
| 1-024-001 | DLAGGTFDV | 54 | N | | 1-024-001_pool_1 | Y | chr11_123059991_C_G |
| 1-024-001 | LIFDLAGGTF | 55 | N | | 1-024-001_pool_1 | Y | chr11_123059991_C_G |
| 1-024-001 | NVLIFDLA | 56 | N | | 1-024-001_pool_1 | Y | chr11_123059991_C_G |
| 1-024-001 | VVGACGVGK | 57 | N | | 1-024-001_pool_2 | N | chr12_25245351_C_A |
| 1-024-001 | VIMLNGTKK | 58 | N | | 1-024-001_pool_2 | N | chr20_5651336_G_A |
| 1-024-001 | LAGGTFDV | 59 | N | | 1-024-001_pool_2 | N | chr11_123059991_C_G |
| 1-024-001 | LRNSGGEVF | 60 | N | | 1-024-001_pool_2 | N | chr14_8090602_TC_T |
| 1-024-001 | VVLPSDVTSY | 61 | N | | 1-024-001_pool_2 | N | chr3_48591778_G_T |
| 1-024-001 | IFDLAGGTF | 62 | N | | 1-024-001_pool_2 | N | chr11_123059991_C_G |

| Mutation Type | Gene | Protein Effect | TPM | Most Probable Restriction covered by Full MS Model | Full MS Model Rank | MHCFlurry Rank | MHCFlurry (nM) | Most Probable Restriction covered by MHCFlurry |
|---|---|---|---|---|---|---|---|---|
| snp | HSPA8 | G201A | 736.6 | HLA-B*27:05 | 9 | 353 | 18290.7955 | TRUE |
| snp | HSPA8 | G201A | 736.6 | HLA-C*02:02 | 11 | 57 | 1716.74204 | FALSE |
| snp | HSPA8 | G201A | 736.6 | HLA-A*32:01 | 17 | 621 | 27984.1357 | TRUE |
| snp | KRAS | G12C | 40.05 | HLA-A*03:01 | 5 | 19 | 197.846108 | TRUE |
| snp | RTFDC1 | E177K | 61.32 | HLA-A*03:01 | 8 | 10 | 122.750322 | TRUE |
| snp | HSPA8 | G201A | 736.6 | HLA-C*02:02 | 10 | 632 | 28384.8834 | FALSE |
| del_fs | CEP128 | R102fs | 11.31 | HLA-B*27:05 | 12 | 46 | 1020.95087 | TRUE |
| snp | COL7A1 | R4685 | 25.42 | HLA-A*32:01 | 13 | 62 | 1925.29397 | TRUE |
| snp | HSPA8 | G201A | 736.6 | HLA-C*02:02 | 14 | 427 | 21255.2074 | FALSE |

TABLE 3-continued

Supplementary Peptides Tested for T-Cell Recognition in NSCLC Patients

| Patient | Peptide | SEQ ID NO: | Individual Peptide Response (Any Time Point) | Individual Peptide Response Notes | Pool ID | Pool Response (Any Time Point) | Mutation |
|---|---|---|---|---|---|---|---|
| 1-024-001 | GLLDEAKRLLY | 63 | N | | 1-024-001_pool_2 | N | chr19_57575861_G_T |
| 1-024-001 | SVLLPENYITK | 64 | N | | 1-024-001_pool_2 | N | chr11_122789248_G_T |
| 1-024-001 | DLAGGTFDVS | 65 | N | | 1-024-001_pool_2 | N | chr11_123059991_C_G |
| 1-024-001 | FDLAGGTFDV | 66 | N | | 1-024-001_pool_2 | N | chr11_123059991_C_G |
| 1-024-002 | AEWRNGSTSSL | 67 | N | | 1-024-002_pool_1 | Y | chr3_122703943_C_G |
| 1-024-002 | YVSEKDVISAK | 68 | N | | 1-024-002_pool_1 | Y | chr2_43889858_G_A |
| 1-024-002 | EGSLGISHTR | 69 | N | | 1-024-002_pool_1 | Y | chr18_62157782_C_A |
| 1-024-002 | PASVSAPK | 70 | N | | 1-024-002_pool_1 | Y | chr13_109784018_C_A |
| 1-024-002 | QDVSVOVER | 24 | Y | | 1-024-002_pool_1 | Y | chr9_6441122_T_G |

| Mutation Type | Gene | Protein Effect | TPM | Most Probable Restriction covered by Full MS | Full MS Model Model | MHCFlurry Rank | MHCFlurry Rank | Most Probable Restriction covered by (nM) MHCFlurry |
|---|---|---|---|---|---|---|---|---|
| snp | ZNF416 | Q49K | 11.89 | HLA-A*03:01 | 15 | 24 | 354.82068 | TRUE |
| snp | UBASH3B | G307V | 12.11 | HLA-A*03:01 | 16 | 23 | 228.127132 | TRUE |
| snp | HSPA8 | G201A | 736.6 | HLA-A*32:01 | 18 | 487 | 23357.3292 | TRUE |
| snp | HSPA8 | G201A | 736.6 | HLA-C*02:02 | 19 | 563 | 25887.4267 | FALSE |
| snp | PARP14 | P1095A | 129.5 | HLA-A*68:01 | 0 | 8 | 126.397714 | TRUE |
| snp | LRPPRC | T1335I | 79.08 | HLA-A*68:01 | 1 | 9 | 136.482978 | TRUE |
| snp | PIGN | W83L | 20.74 | HLA-A*68:01 | 2 | 6 | 88.2623459 | TRUE |
| snp | IRS2 | S6791 | 63.55 | HLA-A*68:01 | 3 | 16 | 224.278982 | TRUE |
| snp | ANKRD20A4 | M646R | 8.92 | HLA-A*68:01 | 4 | 14 | 193.974327 | TRUE |

| Patient | Peptide | SEQ ID NO: | Individual Peptide Response (Any Time Point) | Individual Peptide Response Notes | Pool ID | Pool Response (Any Time Point) | Mutation |
|---|---|---|---|---|---|---|---|
| 1-024-002 | LVVVGASGVGK | 71 | N | | 1-024-002_pool_1 | Y | chr12_25245351_C_T |
| 1-024-002 | RATIVPEL | 72 | N | | 1-024-002_pool_1 | Y | ch7_131463253_A_T |

TABLE 3-continued

Supplementary Peptides Tested for T-Cell Recognition in NSCLC Patients

| Patient | Peptide | Mutation Type | Gene | Protein Effect | SEQ ID NO: | TPM | Individual Peptide Response (Any Time Point) | Individual Peptide Response Notes | Most Probable Restriction covered by Full MS Model | Full MS Model Rank | Pool ID | MHCFlurry Rank | MHCFlurry (nM) | Most Probable Restriction covered by MHCFlurry | Mutation |
|---|---|---|---|---|---|---|---|---|---|---|---|---|---|---|---|
| 1-024-002 | SSAAAPFPL | | | | 21 | | Y | | | | 1-024-002_pool_1 | | | | chr6_13711102_T_A |
| 1-024-002 | GVSKIIGGNPK | | | | 73 | | N | | | | 1-024-002_pool_1 | | | | chr4_10116175_C_T |
| 1-024-002 | EQNFVSTSDIK | | | | 74 | | not tested individually | | | | 1-024-002_pool_1 | | | | chr3_25791346_A_C |
| 1-024-002 | RTQDVSVQVER | | | | 75 | | N | | | | 1-024-002_pool_2 | | | | chr9_6441223_T_G |
| 1-024-002 | EAGNNSRVPR | | | | 76 | | N | | | | 1-024-002_pool_2 | | | | chr2_74046630_G_T |
| 1-024-002 | RYVLHVVAA | | | | 77 | | N | | | | 1-024-002_pool_2 | | | | chr3_122703943_C_G |
| 1-024-002 | VSKIIGGNPK | | | | 78 | | N | | | | 1-024-002_pool_2 | | | | chr4_1011675_C_T |
| 1-024-002 | QPSGVPTSL | snp | KRAS | G12S | 79 | 72.77 | N | | HLA-A*68:01 | 6 | 1-024-002_pool_2 | 41 | 1238.56407 | TRUE | chr12_14478436_GG_TT |
| 1-024-002 | DVSVQVER | snp | MKLN1 | D521V | 80 | 84.08 | N | | HLA-C*03:04 | 7 | 1-024-002_pool_2 | 266 | 16010.7063 | FALSE | chr9_64411223_T_G |
| 1-024-002 | FVSTDIKSM | snp | RANBP9 | H135L | 22 | 43.5 | Y | | HLA-C*03:04 | 8 | 1-024-002_pool_2 | 103 | 4565.97417 | FALSE | chr3_25791346_A_C |
| | | snp | WDR1 | D26N | | 134.5 | | | HLA-A*68:01 | 9 | | 125 | 6797.60699 | TRUE | |
| | | snp | OXSM | K109T | | 12.82 | | | HLA-A*68:01 | 17 | | 156 | 9099.70986 | TRUE | |
| | | snp | ANKRD20A4 | M646R | | 8.92 | | | HLA-A*68:01 | 5 | | 53 | 1847.42359 | TRUE | |
| | | snp | TET3 | G238V | | 56.35 | | | HLA-A*68:01 | 10 | | 13 | 161.242762 | TRUE | |
| | | snp | PARP14 | P1095A | | 129.5 | | | HLA-A*68:01 | 11 | | 176 | 10453.627 | TRUE | |
| | | snp | WDR1 | D26N | | 134.5 | | | HLA-A*68:01 | 12 | | 38 | 954.724495 | TRUE | |

TABLE 3-continued

Supplementary Peptides Tested for T-Cell Recognition in NSCLC Patients

| Patient | Peptide | Mutation Type | Gene | Protein Effect | SEQ ID NO: | TPM | Individual Peptide Response (Any Time Point) | Most Probable Restriction covered by Full MS Model | Full MS Model Rank | MHCFlurry Rank | MHCFlurry (nM) | Pool Response (Any Time Point) | Pool ID | Most Probable Restriction covered by MHCFlurry | Mutation |
|---|---|---|---|---|---|---|---|---|---|---|---|---|---|---|---|
| 1-024-002 | FPVVNSHSL | mnp | ATF7113 | G1021L | 81 | 123.2 | N | HLA-A*68:01 | 13 | 139 | 7795.97025 | Y | 1-024-002_pool_2 | TRUE | chr1_116062776_G_C |
| 1-024-002 | APFPLGDSAL | snp | ANKRD20A4 | M646R | 82 | 8.92 | N | HLA-A*68:01 | 14 | 7 | 123.489687 | Y | 1-024-002_pool_2 | TRUE | chr6_13711102_T_A |
| 1-024-002 | ATIVPELNEI | snp | OXSM | K109T | 83 | 12.82 | N | HLA-C*03:04 | 15 | 128 | 7025.56581 | Y | 1-024-002_pool_2 | FALSE | chr7_131463253_A_T |
| 1-038-001 | QEFAPLGTV | snp | SLC22A15 | A396P | 84 | 8.57 | N | HLA-C*03:04 | 16 | 155 | 9082.40652 | see pool results | 1-038-001_pool_1 | FALSE | chr2_219501883_G_T |
| 1-038-001 | MNQVLHAY | snp | RANBP9 | H135L | 85 | 43.5 | not tested individually | HLA-A*68:01 | 18 | 196 | 11590.601 | see pool results | 1-038-001_pool_1 | TRUE | chr14_100354547_C_G |
| 1-038-001 | HEDVKEAI | snp | MKLN1 | D521V | 86 | 84.08 | not tested individually | HLA-A*68:01 | 19 | 365 | 19785.1419 | see pool results | 1-038-001_pool_1 | TRUE | chr8_96231911_C_G |
| | | snp | GMPPA | G92V | | 21.6 | | HLA-B*49:01 | 0 | 31 | 3481.07375 | | | FALSE | |
| | | snp | WARS | D148H | | 757.2 | | HLA-C*07:01 | 12 | 422 | 27180.1513 | | | FALSE | |
| | | snp | UCICRB | D41H | | 174.8 | | HLA-B*49:01 | 16 | 300 | 24830.2411 | | | FALSE | |
| 1-038-001 | GPYPFVQAV | | | | 87 | | not tested individually | | | | | see pool results | 1-038-001_pool_1 | Y | chr1_111242326_C_T |
| 1-038-001 | YEHEDVKEAI | | | | 88 | | not tested individually | | | | | see pool results | 1-038-001_pool_1 | Y | chr8_96231911_C_G |

TABLE 3-continued

Supplementary Peptides Tested for T-Cell Recognition in NSCLC Patients

| | | | | |
|---|---|---|---|---|
| 1-038-001 EESVMLLTV | 89 | not tested individually | see pool results 1-038-001_pool_1 | Y | chr1_15583354_CC_AG |
| 1-038-001 IEEDSAEKI | 90 | not tested individually | see pool results 1-038-001_pool_1 | Y | chr6_84215849_C_A |
| 1-038-001 TEEDVKIKF | 91 | not tested individually | see pool results 1-038-001_pool_1 | Y | chr7_93105459_C_A |
| 1-038-001 NEQSKLLKV | 92 | not tested individually | see pool results 1-038-001_pool_1 | Y | chrX_70375298_C_G |
| 1-038-001 VDNIIIQSI | 93 | not tested individually | see pool results 1-038-001_pool_1 | Y | chr20_2654879_G_T |
| 1-038-001 YEHEDVKEA | 20 | Y | 1-038-001_pool_2 | Y | chr8_96231911_C_G |
| 1-038-001 YVSEVPVSV | 94 | not tested individually | 1-038-001_pool_2 | Y | chr17_2330604_G_A |

| Mutation Type | Gene | Protein Effect | TPM | Most Probable Restriction covered by Full MS Model | Full MS Model Rank | MHCFlurry Rank | MHCFlurry (nM) | Most Probable Restriction covered by MHCFlurry |
|---|---|---|---|---|---|---|---|---|
| snp | CH13L2 | L379F | 122.3 | HLA-B*49:01 | 1 | 19 | 1176.97782 | FALSE |
| snp | UQCRB | D41H | 174.8 | HLA-B*49:01 | 2 | 212 | 22559.0306 | FALSE |
| mnp | AGMAT | G105L | 1.03 | HLA-B*49:01 | 3 | 109 | 17185.8013 | FALSE |
| snp | CEP162 | E82D | 15.62 | HLA-B*49:01 | 4 | 171 | 20568.515 | FALSE |
| snp | SAMD9 | M2131 | 68.23 | HLA-B*49:01 | 5 | 226 | 22894.2742 | FALSE |
| snp | K1F4A | L625V | 19.51 | HLA-B*49:01 | 6 | 141 | 19054.8385 | FALSE |
| snp | NOP56 | M1671 | 89.39 | HLA-B*49:01 | 7 | 119 | 17928.6022 | FALSE |
| snp | UQCRB | D41H | 174.8 | HLA-B*49:01 | 9 | 250 | 23419.567 | FALSE |
| snp | TSR1 | H561Y | 48.21 | HLA-C*17:01 | 10 | 0 | 6.07874308 | FALSE |

TABLE 3-continued

Supplementary Peptides Tested for T-Cell Recognition in NSCLC Patients

| Patient Peptide | SEQ ID NO: | Individual Peptide Response (Any Time Point) | Individual Peptide Response Notes | Pool ID | Pool Response (Any Time Point) | Mutation |
|---|---|---|---|---|---|---|
| 1-038-001 SELTVHQR1 | 95 | not tested individually | | 1-038-001_pool_2 | Y | chr19_37564705_G_C |
| 1-038-001 VGVGKSAL | 96 | not tested individually | | 1-038-001_pool_2 | Y | chr12_25245350_C_A |
| 1-038-001 DMNQVLHAY | 97 | not tested individually | | 1-038-001_pool_2 | Y | chr14_100354547_C_G |
| 1-038-001 NEKGKAL1Y | 98 | not tested individually | | 1-038-001_pool_2 | Y | chr17_51294040_G_T |
| 1-038-001 TEYKLVVVGAV | 99 | not tested individually | | 1-038-001_pool_2 | Y | chr12_25245350_C_A |
| 1-038-001 QEFAPLGTVG | 100 | not tested individually | | 1-038-001_pool_2 | Y | chr2_219501883_G_T |
| 1-038-001 QEVRNTLLNV | 101 | not tested individually | | 1-038-001_pool_2 | Y | chr17_4085728_C_A |
| 1-038-001 VEMLGL1SC | 102 | not tested individually | | 1-038-001_pool_2 | Y | chr4_168427109_C_A |
| 1-050-001 LFHDMNVSY | 103 | N | | 1-050-001_pool_1 | N | chr1_193097666_T_C |

| Mutation Type | Gene | Protein Effect | TPM | Most Probable Restriction covered by Full MS Model | Full MS Model Rank | MHCFlurry Rank | MHCFlurry (nM) | Most Probable Restriction covered by MHCFlurry |
|---|---|---|---|---|---|---|---|---|
| snp | ZNF571 | L575V | 19.07 | HLA-B*49:01 | 11 | 159 | 19886.0407 | FALSE |
| snp | KRAS | G12V | 91.89 | HLA-C*17:01 | 13 | 388 | 26432.7668 | FALSE |
| snp | WARS | D148H | 757.2 | HLA-C*07:01 | 14 | 64 | 10286.4383 | FALSE |
| snp | UTP18 | M5471 | 63.21 | HLA-C*07:01 | 15 | 339 | 25564.2874 | FALSE |
| snp | KRAS | G12V | 91.89 | HLA-B*49:01 | 17 | 233 | 23113.572 | FALSE |
| snp | GMPPA | G92V | 21.6 | HLA-B*49:01 | 18 | 338 | 25558.5468 | FALSE |

TABLE 3-continued

Supplementary Peptides Tested for T-Cell Recognition in NSCLC Patients

| Mutation Type | Gene | Protein Effect | Patient Peptide | SEQ ID NO: | Response (Any Time Point) | TPM | | | | |
|---|---|---|---|---|---|---|---|---|---|---|
| snp | ZZEF1 | G863V | | | | | | | | |
| snp | DDX60L | A6315 | | | | | | | | |
| snp | GLRX2 | N945 | | | | | | | | |
| snp | RNF213 | R2827L | 1-050-001 ISTFRQCAL | 104 | not tested individually | 330.6 | | | | |
| snp | GABRB3 | T185N | 1-050-001 YNTDDIEFY | 105 | not tested individually | 2.2 | | | | |
| snp | TIAM1 | Y283F | 1-050-001 EETPPFSNY | 106 | N | 13.99 | | | | |
| | | | 1-050-001 QASGNHHVW | 107 | not tested individually | | | | | |
| | | | 1-050-001 EEVTPILAI | 108 | not tested individually | | | | | |
| | | | 1-050-001 IEHNIRNAKY | 109 | not tested individually | | | | | |
| | | | 1-050-001 AERLDVKAI | 110 | not tested individually | | | | | |
| | | | 1-050-001 LFQQGKDLQQY | 111 | not tested individually | | | | | |
| | | | 1-050-001 DTSPVAVAL | 112 | not tested individually | | | | | |

| | HLA-B*49:01 | 19 | 124 | 18359.7482 | FALSE |
| | HLA-B*49:01 | 8 | 267 | 23949.2398 | FALSE |
| | HLA-A*29:02 | 0 | 1 | 44.54051 | TRUE |

| Patient Peptide | Individual Peptide Response Notes | Pool ID | Pool Response (Any Time Point) | Mutation |
|---|---|---|---|---|
| 1-050-001 ISTFRQCAL | | 1-050-001_pool_1 | N | chr17_80346815_G_T |
| 1-050-001 YNTDDIEFY | | 1-050-001_pool_1 | N | chr15_26580447_G_T |
| 1-050-001 EETPPFSNY | | 1-050-001_pool_1 | N | chr21_31266125_T_A |
| 1-050-001 QASGNHHVW | | 1-050-001_pool_1 | N | chr22_30893501_T_C |
| 1-050-001 EEVTPILAI | | 1-050-001_pool_1 | N | chr18_5419733_G_A |
| 1-050-001 IEHNIRNAKY | | 1-050-001_pool_1 | N | chr3_52617347_T_G |
| 1-050-001 AERLDVKAI | | 1-050-001_pool_1 | N | chr14_103339252_G_T |
| 1-050-001 LFQQGKDLQQY | | 1-050-001_pool_1 | N | chr17_80346815_G_T |
| 1-050-001 DTSPVAVAL | | 1-050-001_pool_1 | N | chr5_73074790_T_C |

| Most Probable Restriction covered by Full MS Model | Full MS Model Rank | MHCFlurry Rank | Probable Restriction MHCFlurry (nM) | Most covered by MHCFlurry |
|---|---|---|---|---|
| HLA-C*16:01 | 10 | 322 | 22721.4424 | FALSE |
| HLA-A*29:02 | 16 | 20 | 447.152559 | TRUE |
| HLA-B*44:03 | 1 | 26 | 537.02592 | TRUE |

TABLE 3-continued

Supplementary Peptides Tested for T-Cell Recognition in NSCLC Patients

| | | | | | | | Mutation |
|---|---|---|---|---|---|---|---|
| snp | OSBP2 | Y677H | 7.86 | HLA-B*44:03 | 19 | 109 | 7506.81856 | TRUE | chr21_31266125_T_A |
| snp | EPB41L3 | S495L | 51.69 | HLA-B*44:03 | 2 | 17 | 390.306194 | TRUE | chr3_47661451_C_G |
| snp | PBRM1 | D578A | 65.68 | HLA-B*44:03 | 3 | 10 | 186.953378 | TRUE | chr18_5419733_G_A |
| snp | EIF5 | M275I | 89.97 | HLA-B*44:03 | 5 | 34 | 1075.19965 | TRUE | chr14_103339252_G_T |
| snp | RNF213 | R2827L | 330.6 | HLA-A*29:02 | 6 | 54 | 2855.46701 | TRUE | chr7_79453094_C_A |
| snp | FCHO2 | L543S | 43.6 | HLA-A*26:01 | 8 | 91 | 5750.39585 | TRUE | chr1_159535913_A_T |

| Patient Peptide | SEQ ID NO: | Response (Any Time Point) | Individual Peptide Response Notes | Pool ID | Pool Response (Any Time Point) |
|---|---|---|---|---|---|
| 1-050-001 AEETPPFSNY | 113 | N | | 1-050-001_pool_2 | N |
| 1-050-001 AAKAALEDF | 114 | not tested individually | | 1-050-001_pool_2 | N |
| 1-050-001 EVTPI LAIR | 115 | not tested individually | | 1-050-001_pool_2 | N |
| 1-050-001 DVKAIGPLV | 116 | not tested individually | | 1-050-001_pool_2 | N |
| 1-050-001 NETPVAVLTI | 117 | not tested individually | | 1-050-001_pool_2 | N |
| 1-050-001 LFVVFOTVY | 118 | not tested individually | | 1-050-001_pool_2 | N |
| 1-050-001 AEAERLDVKAI | 119 | not tested individually | | 1-050-001_pool_2 | N |
| 1-050-001 ASGNHHVW | 120 | not tested individually | | 1-050-001_pool_2 | N |
| 1-050-001 KLFHDMNVSY | 121 | not tested individually | | 1-050-001_pool_2 | N |

TABLE 3-continued

Supplementary Peptides Tested for T-Cell Recognition in NSCLC Patients

| Mutation Type | Gene | Protein Effect | TPM | Most Probable Restriction covered by Full MS Model | Full MS Model Rank | MHCFlurry Rank | MHCFlurry (nM) | Mutation | Most Probable Restriction covered by MHCFlurry |
|---|---|---|---|---|---|---|---|---|---|
| snp | TIAM1 | Y283F | 13.99 | HLA-B*44:03 | 9 | 16 | 364.187996 | chr21_31266125_T_A | TRUE |
| snp | SMARCC1 | E721D | 39.53 | HLA-C*16:01 | 11 | 307 | 22125.437 | chr4_2241321_C_A | FALSE |
| snp | EPB41L3 | S495L | 51.69 | HLA-A*26:01 | 12 | 125 | 9269.11767 | chr1_37874128_G_C | TRUE |
| snp | EIF5 | M2751 | 89.97 | HLA-A*26:01 | 13 | 90 | 5692.75283 | chr3_9943508_G_C | TRUE |
| snp | MAGI2 | G76V | 2.29 | HLA-B*44:03 | 14 | 13 | 253.431553 | chr12_7066530_C_T | TRUE |
| snp | OR10J5 | L32Q | 0.9 | HLA-A*29:02 | 15 | 9 | 139.510048 | chr7_5752914_T_C | TRUE |
| snp | EIF5 | M2751 | 89.97 | HLA-B*44:03 | 17 | 38 | 1465.22509 | chr1_52268541_A_C | TRUE |
| snp | OSBP2 | Y677H | 7.86 | HLA-C*16:01 | 18 | 173 | 13216.9384 | chr7_135598004_C_G | FALSE |
| snp | GLRX2 | N945 | 17.92 | HLA-A*29:02 | 4 | 21 | 453.621334 | chr14_34713369_C_A | TRUE |

| Patient | Peptide | SEQ ID NO: | Individual Peptide Response (Any Time Point) | Individual Peptide Response Notes | Pool ID | Pool Response (Any Time Point) |
|---|---|---|---|---|---|---|
| 1-050-001 | ETPPFSNYNTL | 122 | not tested individually | | 1-050-001_pool_2 | N |
| CU04 | DENITTIQF | 23 | Y | | CU04_pool_1 | Y |
| CU04 | MELKVESF | 123 | N | | CU04_pool_1 | Y |
| CU04 | EHIPESAGF | 124 | N | | CU04_pool_1 | Y |
| CU04 | YHGDPMPCL | 125 | N | | CU04_pool_1 | Y |
| CU04 | DEERIPVL | 126 | N | | CU04_pool_1 | Y |
| CU04 | EVADAATLTM | 25 | Y | | CU04_pool_1 | Y |
| CU04 | IEVEVNEI | 127 | N | | CU04_pool_1 | Y |
| CU04 | DTVEYPYTSF | 26 | Y | | CU04_pool_1 | Y |

TABLE 3-continued

Supplementary Peptides Tested for T-Cell Recognition in NSCLC Patients

| Mutation Type | Gene | Protein Effect | TPM | Most Probable Restriction covered by Full MS Model | Full MS Model Rank | MHCFlurry Rank | MHCFlurry (nM) | Mutation | Most Probable Restriction covered by MHCFlurry |
|---|---|---|---|---|---|---|---|---|---|
| snp | TIAM1 | Y283F | 13.99 | HLA-A*26:01 | 7 | 172 | 13162.6216 | chr11_62827178_C_G | TRUE |
| snp | ADGRA3 | C734F | 20.67 | HLA-B*18:01 | 0 | 2 | 8.27203164 | ch7_138762364_G_T | TRUE |
| snp | INPP5B | 0606E | 36.85 | HLA-B*18:01 | 1 | 5 | 13.0510076 | chr6_10556704_C_T | TRUE |
| snp | CRELD1 | 0347H | 29.9 | HLA-B*38:01 | 2 | 103 | 4218.0095 | chr4_22413213_C_A | TRUE |
| snp | CIS | P295L | 157.5 | HLA-B*38:01 | 3 | 12 | 76.7416543 | chr14_7517203_C_G | TRUE |
| snp | RNF216 | M45V | 49.2 | HLA-B*18:01 | 4 | 29 | 387.328968 | chrX_40597563_G_A | TRUE |
| snp | ZFYVE9 | K845T | 70.08 | HLA-A*26:01 | 5 | 7 | 38.7340629 | chr17_42104792_T_A | TRUE |
| snp | NUP205 | L691V | 42.37 | HLA-B*18:01 | 6 | 21 | 209.301169 | chr2_67404159_G_C | TRUE |
| snp | CFL2 | D66Y | 16.65 | HLA-A*26:01 | 7 | 9 | 42.7267485 | chr2_85395579_C_T | TRUE |

| Patient | Peptide | SEQ ID NO: | Individual Peptide Response (Any Time Point) | Individual Peptide Response Notes | Pool ID | Pool Response (Any Time Point) |
|---|---|---|---|---|---|---|
| CU04 | VEIEQLTY | 128 | N | | CU04_pool_1 | Y |
| CU04 | LELKAVHAY | 129 | N | | CU04_pool_1 | Y |
| CU04 | EEADFLLAY | 130 | N | | CU04_pool_2 | N |
| CU04 | ENIIIIQFY | 131 | N | | CU04_pool_2 | N |
| CU04 | FHATNPLNL | 132 | N | | CU04_pool_2 | N |
| CU04 | VFKDLSVTL | 133 | N | | CU04_pool_2 | N |
| CU04 | QAVAAVQKL | 134 | N | | CU04_pool_2 | N |
| CU04 | IQDQIQNCI | 135 | N | | CU04_pool_2 | N |
| CU04 | VAKGFISRM | 136 | N | | CU04_pool_2 | N |

TABLE 3-continued

Supplementary
Peptides Tested for T-Cell Recognition in NSCLC Patients

| Mutation Type | Gene | Protein Effect | TPM | Most Probable Restriction covered by Full MS Model | Full MS Model Rank | MHCFlurry Rank | MHCFlurry (nM) | Most Probable Restriction covered by MHCFlurry |
|---|---|---|---|---|---|---|---|---|
| snp | STX5 | E134Q | 83.43 | HLA-B*18:01 | 8 | 3 | 11.6727539 | TRUE |
| snp | ATP6V0A4 | P163H | 47.21 | HLA-B*18:01 | 9 | 0 | 3.63590379 | TRUE |
| snp | GCNT2 | P94L | 25.19 | HLA-B*18:01 | 10 | 1 | 6.48490966 | TRUE |
| snp | ADGRA3 | C734F | 20.67 | HLA-A*26:01 | 11 | 16 | 135.44155 | TRUE |
| snp | NEK9 | D252H | 20.29 | HLA-B*38:01 | 12 | 8 | 39.1165673 | TRUE |
| snp | ATP6AP2 | E145K | 88.26 | HLA-B*38:01 | 13 | 45 | 1080.8332 | TRUE |
| snp | DHX58 | M513L | 35.87 | HLA-C*12:03 | 14 | 136 | 6872.44 | TRUE |
| snp | ETAA1 | E493Q | 38.47 | HLA-B*38:01 | 15 | 59 | 1665.0162 | TRUE |
| snp | CAPG | E314K | 151.7 | HLA-C*12:03 | 16 | 107 | 5236.61406 | TRUE |

| Patient | Peptide | SEQ ID NO: | Individual Peptide Response (Any Time Point) | Individual Peptide Response Notes | Pool ID | Pool Response (Any Time Point) | Mutation |
|---|---|---|---|---|---|---|---|
| CU04 | QTKPASLLY | 137 | N | | CU04_pool_2 | N | chr2_32487684_AG_A |
| CU04 | DHFETIIKY | 138 | N | | CU04_pool_2 | N | chr1_220024376_C_G |
| CU04 | VEYPYTSF | 139 | N | | CU04_pool_2 | N | chr14_34713369_C_A |
| CU05 | SVSDISEYRV | 140 | N | | CU05_pool_1 | N | chr12_15670870_G_C |
| CU05 | YTFEIQGVNGV | 141 | N | | CU05_pool_1 | N | chr12_2865138_C_G |
| CU05 | IYTSSGQLQLF | 142 | N | | CU05_pool_1 | N | chr10_73293336_T_C |
| CU05 | FATPSLHTSV | 143 | N | | CU05_pool_1 | N | chr17_80345147_A_T |
| CU05 | AVSKPGLDYEL | 144 | N | | CU05_pool_1 | N | chr14_77026556_T_A |
| CU05 | KYINKTIRV | 145 | N | | CU05_pool_1 | N | chr19_2328426_C_T |

TABLE 3-continued

Supplementary Peptides Tested for T-Cell Recognition in NSCLC Patients

| Mutation Type | Gene | Protein Effect | TPM | Most Probable Restriction covered by Full MS Model | Full MS Model Rank | MHCFlurry Rank | MHCFlurry (nM) | Most Probable Restriction covered by MHCFlurry |
|---|---|---|---|---|---|---|---|---|
| del_fs | BIRC6 | G2619fs | 111.7 | HLA-A*26:01 | 17 | 47 | 1143.73481 | TRUE |
| snp | EPRS | M2771 | 76.64 | HLA-B*18:01 | 18 | 6 | 29.8996386 | TRUE |
| snp | CFL2 | D66Y | 16.65 | HLA-B*18:01 | 19 | 4 | 12.3783994 | TRUE |
| snp | EPS8 | Q64E | 52.56 | HLA-A*68:02 | 0 | 1 | 6.0399624 | TRUE |
| snp | EPHB2 | A410G | 74.99 | HLA-A*68:02 | 1 | 22 | 132.877429 | TRUE |
| snp | CFAP70 | E636G | 30.45 | HLA-A*24:02 | 2 | 17 | 46.3526841 | TRUE |
| snp | RNF213 | D2271V | 735.3 | HLA-A*68:02 | 4 | 16 | 43.8761927 | TRUE |
| snp | 1RF2BPL | M413L | 58.51 | HLA-A*68:02 | 5 | 274 | 13566.6012 | TRUE |
| snp | LSM7 | D20N | 76.01 | HLA-A*24:02 | 8 | 32 | 318.671051 | TRUE |

| Patient | Peptide | SEQ ID NO: | Individual Peptide Response (Any Time Point) | Individual Peptide Response Notes | Pool ID | Pool Response (Any Time Point) | Mutation |
|---|---|---|---|---|---|---|---|
| CU05 | ETTEEMKYVL | 146 | N | | CU05_pool_1 | N | chr6_80040624_G_A |
| CU05 | VVSHPHLVYW | 147 | N | | CU05_pool_1 | N | chr4_106232956_C_G |
| CU05 | DIFQVVKAI | 148 | N | | CU05_pool_1 | N | chr1_198754369_C_A |
| CU05 | FAFDAVSKPGL | 149 | N | | CU05_pool_1 | N | chr14_77026556_T_A |
| CU05 | SVSDISEYR | 150 | N | | CU05_pool_2 | N | chr12_15670870_G_C |
| CU05 | YTFEIQGV | 151 | N | | CU05_pool_2 | N | chr1_22865138_C_G |
| CU05 | ATPSLHTSV | 152 | N | | CU05_pool_2 | N | chr17_80345147_A_T |
| CU05 | DFATPSLHTSV | 153 | N | | CU05_pool_2 | N | chr17_80345147_A_T |
| CU05 | KYINKTIRVKF | 154 | N | | CU05_pool_2 | N | chr19_2328426_C_T |

TABLE 3-continued

Supplementary Peptides Tested for T-Cell Recognition in NSCLC Patients

| Mutation Type | Gene | Protein Effect | TPM | Most Probable Restriction covered by Full MS Model | Full MS Model Rank | MHCFlurry Rank | MHCFlurry (nM) | Most Probable Restriction covered by MHCFlurry |
|---|---|---|---|---|---|---|---|---|
| snp | TTK | G804E | 17.14 | HLA-A*68:02 | 9 | 37 | 398.324158 | TRUE |
| snp | TBCK | D478H | 71.17 | HLA-A*68:02 | 11 | 235 | 10875.8686 | TRUE |
| snp | PTPRC | L1204I | 104.6 | HLA-A*68:02 | 13 | 36 | 394.198029 | TRUE |
| snp | 1RF2BPL | M413L | 58.51 | HLA-A*68:02 | 18 | 65 | 1067.11951 | TRUE |
| snp | EPS8 | Q64E | 52.56 | HLA-A*68:02 | 3 | 94 | 2050.45825 | TRUE |
| snp | EPHB2 | A410G | 74.99 | HLA-A*68:02 | 6 | 11 | 26.6362167 | TRUE |
| snp | RNF213 | D2271V | 735.3 | HLA-A*68:02 | 7 | 25 | 177.027506 | TRUE |
| snp | RNF213 | D2271V | 735.3 | HLA-A*68:02 | 10 | 185 | 7619.02631 | TRUE |
| snp | LSM7 | D20N | 76.01 | HLA-A*24:02 | 12 | 42 | 538.209517 | TRUE |

| Patient | Peptide | SEQ ID NO: | Individual Peptide Response (Any Time Point) | Individual Peptide Response Notes | Pool ID | Pool Response (Any Time Point) | Mutation |
|---|---|---|---|---|---|---|---|
| CU05 | SVKPHLCSL | 155 | N | | CU05_pool_2 | N | chr17_35363437_C_T |
| CU05 | DISEYRVEHL | 156 | N | | CU05_pool_2 | N | chr12_15670870_G_C |
| CU05 | WVVSHPHLV | 157 | N | | CU05_pool_2 | N | chr4_106232956_C_G |
| CU05 | KVFKLGNKV | 158 | N | | CU05_pool_2 | N | chrX_24810777_G_A |
| CU05 | VSKPGLDYEL | 159 | N | | CU05_pool_2 | N | chr14_77026556_T_A |
| CU02 | SPSKTSLTL | 160 | not tested individually | see pool results | CU02_pool_1 | Y | chr12_132750694_G_T |
| CU02 | ASADGTVKLW | 161 | not tested individually | see pool results | CU01_pool_1 | Y | chr16_1977246_A_G |

TABLE 3-continued

Supplementary Peptides Tested for T-Cell Recognition in NSCLC Patients

| Mutation Type | Gene | Peptide | Protein Effect | SEQ ID NO: | Individual Peptide Response (Any Time Point) | Individual Peptide Response Notes | Most Probable Restriction covered by Full MS Model | TPM | Full MS Model Rank | MHCFlurry Rank | MHCFlurry (nM) | Most Probable Restriction covered by MHCFlurry | Mutation |
|---|---|---|---|---|---|---|---|---|---|---|---|---|---|
| CU02 | | LVGPAQLSHW | 162 | | not tested individually | see pool results | | | | | | Y | chr8_143930249_G_A |
| CU02 | | QTAAAVGVLK | 163 | | not tested individually | see pool results | | | | | | Y | chr7_77773271_A_G |
| snp | SLFN11 | | R124H | | | | HLA-A*68:02 | 91.5 | 14 | 88 | 1897.58723 | | TRUE |
| snp | EPS8 | | Q64E | | | | HLA-A*68:02 | 52.56 | 15 | 59 | 885.161001 | | TRUE |
| snp | TBCK | | D478H | | | | HLA-A*68:02 | 71.17 | 16 | 15 | 40.725305 | | TRUE |
| snp | POLA1 | | E1017K | | | | HLA-A*68:02 | 19.31 | 17 | 61 | 954.869111 | | TRUE |
| snp | IRF2BPL | | M413L | | | | HLA-A*68:02 | 58.51 | 19 | 258 | 12457.5646 | | |
| snp | ANKLE2 | | P266T | | | | HLA-B*07:02 | 43.78 | 0 | 7 | 20.5140939 | | TRUE |
| snp | TBL3 | | I545V | | | | HLA-B*57:01 | 26.23 | 1 | 20 | 77.5504026 | | TRUE |
| snp | PLEC | | P863L | | | | HLA-B*57:01 | 528.5 | 4 | 42 | 287.473059 | | TRUE |
| snp | RSBN1L | | T584A | | | | HLA-A*03:01 | 25.89 | 5 | 19 | 76.1012011 | | TRUE |

| Patient | Peptide | SEQ ID NO: | Pool ID | Pool Response (Any Time Point) | Mutation |
|---|---|---|---|---|---|
| CU02 | FPSPSKTSLTL | 164 | CU02_pool_1 | Y | chr12_132750694_G_T |
| CU02 | SSTSNRSSTW | 165 | CU02_pool_1 | Y | chr10_96604023_G_A |
| CU02 | LVYGPLGAGK | 166 | CU02_pool_1 | Y | chr13_33821175_C_T |
| CU02 | HSYSELCTW | 167 | CU02_pool_1 | Y | chr8_119802006_C_G |

TABLE 3-continued

Supplementary Peptides Tested for T-Cell Recognition in NSCLC Patients

| | | | | | |
|---|---|---|---|---|---|
| CU02 | VTLDVILER | 168 | not tested individually | see pool results | CU02_pool_1 | Y | chr9_108979413_T_G |
| CU02 | HSKPEDTDAW | 169 | not tested individually | see pool results | CU02_pool_1 | Y | chr12_133057238_A_G |
| CU03 | IAASRSVVM | 170 | not tested individually | | CU03_pool_1 | N | chr1_230868472_G_A |
| CU03 | AAIAASRSV | 171 | not tested individually | | CU03_pool_1 | N | chr1_230868472_G_A |
| CU03 | AASRSVVM | 172 | not tested individually | | CU03_pool_1 | N | chr1_230868472_G_A |

| Mutation Type | Gene | Protein Effect | TPM | Most Probable Restriction covered by Full MS Model | Full MS Model Rank | MHCFlurry Rank | MHCFlurry (nM) | Most Probable Restriction covered by MHCFlurry |
|---|---|---|---|---|---|---|---|---|
| snp | ANKLE2 | P266T | 43.78 | HLA-B*07:02 | 6 | 26 | 131.765585 | TRUE |
| snp | PIK3AP1 | R733W | 9.84 | HLA-B*57:01 | 7 | 30 | 162.029882 | TRUE |
| snp | RFC3 | S44L | 9.76 | HLA-A*03:01 | 8 | 2 | 8.21211585 | TRUE |
| snp | TAF2 | D194H | 29.74 | HLA-B*57:01 | 9 | 3 | 10.120376 | TRUE |
| snp | CTNNAL1 | E323D | 32.44 | HLA-B*57:01 | 10 | 136 | 2107.24068 | TRUE |
| snp | ZNF84 | T175A | 29.84 | HLA-B*57:01 | 11 | 23 | 90.7546185 | TRUE |
| snp | C1orf198 | A14V | 36.47 | HLA-C*12:03 | 0 | 19 | 146.699014 | TRUE |
| snp | C1orf198 | A14V | 36.47 | HLA-C*12:03 | 2 | 42 | 492.404622 | TRUE |
| snp | C1orf198 | A14V | 36.47 | HLA-C*12:03 | 6 | 116 | 3437.73836 | TRUE |

TABLE 3-continued

Supplementary Peptides Tested for T-Cell Recognition in NSCLC Patients

| Patient | Peptide | SEQ ID NO: | Individual Peptide Response (Any Time Point) | Individual Peptide Response Notes | Pool ID | Pool Response (Any Time Point) | Mutation |
|---|---|---|---|---|---|---|---|
| CU03 | EMDMHLSDY | 173 | not tested individually | | CU03_pool_1 | N | chr5_37180032_T_A |
| CU03 | VENQKHSL | 174 | not tested individually | | CU03_pool_1 | N | chr12_30728769_C_T |
| CU03 | QYMDSSLVKI | 175 | not tested individually | | CU03_pool_1 | N | chr10_60788061_G_T |
| CU03 | SASLHPATV | 176 | not tested individually | | CU03_pool_1 | N | chr2_25929006_C_T |
| CU03 | VPDQKSKQL | 177 | not tested individually | | CU03_pool_1 | N | chr6_63685063_T_G |
| CU03 | IVFIATSEF | 178 | not tested individually | | CU03_pool_1 | N | chr11_65976483_A_T |
| CU03 | YPAPCIPPVL | 179 | not tested individually | | CU03_pool_1 | N | chr20_44066022_C_A |

| Mutation Type | Gene | Protein Effect | TPM | Most Probable Restriction covered by Full MS Model | Full MS Model Rank | MHCFlurry Rank | MHCFlurry (nM) | Most Probable Restriction covered by MHCFlurry |
|---|---|---|---|---|---|---|---|---|
| snp | C5orf42 | I1908L | 14.78 | HLA-A*01:01 | 8 | 7 | 35.7275148 | TRUE |
| snp | CAPRIN2 | S554N | 6.69 | HLA-B*08:01 | 10 | 124 | 3970.47602 | TRUE |
| snp | CDK1 | S107I | 26.84 | HLA-A*23:01 | 7 | 8 | 50.3301427 | TRUE |
| snp | KIF3C | R785H | 17.29 | HLA-C*12:03 | 9 | 30 | 260.370195 | TRUE |
| snp | PHF3 | N447K | 47.53 | HLA-B*08:01 | 13 | 130 | 4071.14261 | TRUE |
| snp | SART1 | N554I | 70.53 | HLA-B*15:03 | 5 | 3 | 17.4168253 | TRUE |
| snp | TOX2 | S382Y | 11.56 | HLA-B*08:01 | 11 | 101 | 2455.95947 | TRUE |

SUPPLEMENTARY TABLE 4

|  |  | Donor ID | | | | |
| --- | --- | --- | --- | --- | --- | --- |
| Analyte (average) | Stimulus | 1-038-001 | CU04 | 1-024-001 | 1-024-002 | CU02 |
| Granzyme B (pg/ml)* | DMSO | 1786.73 | 1383.53 | 2639.03 | 854.78 | 1449.74 |
|  | Peptide Pool 1 | 1672.60 | 4269.64 | 2449.23 | 1281.54 | 1132.49 |
|  | DMSO | 1874.02 | 3747.71 | 2382.01 | 626.20 | n/a |
|  | Peptide Pool 2 | 3118.30 | 3191.90 | 2006.73 | 872.89 | n/a |
| TNFalpha (pg/ml)# | DMSO | 37.58 | 34.64 | 21.76 | 38.07 | 1.22 |
|  | Peptide Pool 1 | 53.02 | 217.57 | 42.05 | 57.13 | 7.44 |
|  | DMSO | 16.58 | 80.81 | 24.98 | 24.77 | n/a |
|  | Peptide Pool 2 | 61.54 | 75.70 | 33.70 | 48.84 | n/a |
| IL-2 (pg/ml)# | DMSO | 1.78 | 3.86 | 4.24 | 0.23 | 6.67 |
|  | Peptide Pool 1 | 15.53 | 9.88 | 7.75 | 0.00 | 0.00 |
|  | DMSO | 26.66 | 27.25 | 5.72 | 10.20 | n/a |
|  | Peptide Pool 2 | 0.00 | 19.15 | 11.48 | 0.00 | n/a |
| IL-5 (pg/ml)# | DMSO | 26.47 | 5.20 | 20.92 | 11.96 | 18.91 |
|  | Peptide Pool 1 | 10.48 | 14.65 | 26.72 | 9.42 | 17.64 |
|  | DMSO | 27.31 | 19.65 | 11.01 | 29.93 | n/a |
|  | Peptide Pool 2 | 26.47 | 25.43 | 20.11 | 40.11 | n/a |

Positive values are shown in italics. * Granzyme B ELISA: Values ●5-fold over DMSO background were considered positive. # U-Plex MSD assay: Values ●.5-fold over DMSO background were considered positive Supplementary Table 5
TSNA and Infectious Disease Epitopes in IVS Control Experiments

| Peptide Name | Sequence | SEQ ID NO: | Origin (Cell Line, Gene) | Predicted HLA Restriction | Predicted Binding Affinity | Mutation Position | Mutation Nucleotide |
| --- | --- | --- | --- | --- | --- | --- | --- |
| Neoantigen_A1 | APKKKSIKL | 180 | H2009 PPFIA3 | B*07:02 | 125 | chr19-49140014 | C-to-T |
| Neoantigen_A2 | LLLEVVWHL | 181 | H128 FANCA | A*02:01 | 6 | chr16-89808348 | C-to-T |
| Neoantigen_A3 | FTDEKVKAY | 182 | H2122 PDE10A | A*01:01 | 41 | chr6-165543564 | G-to-T |
| Neoantigen_A6 | RTAKQNPLTK | 183 | H2122 GPR183 | A*03:01 | 138 | chr13-99295446 | G-to-A |
| Neoantigen_A7 | FLAPTGVPV | 184 | H128 NTM | A*02:01 | 8 | chr11-131911555 | T-to-C |
| Neoantigen_A10 | RLADAEKLFQL | 185 | H128 PLEKHG4 | A*02:01 | 201 | chr16-67284435 | G-to-A |
| Neoantigen_A11 | RTAKQNPLTKK | 186 | H2122 GPR183 | A*03:01 | 131 | chr13-99295446 | G-to-A |
| Neoantigen_B2 | IMYLTGMVNK | 187 | H2009 GSPT1 | A*03:01 | 33 | chr16-11891120 | G-to-A |
| Neoantigen_B3 | TLQELSHAL | 188 | H128 PRPF19 | A*02:01 | 106 | chr11-60902829 | G-to-T |
| Neoantigen_B6 | VSQPVAPSY | 189 | Colo829 KIAA0319L | A*01:01 | 948 | chr1-35479047 | C-to-T |
| Neoantigen_B7 | RLFTPISAGY | 190 | H2126 CYP26B1 | A*03:01 | 157 | chr2-72133060 | G-to-C |
| Neoantigen_B8 | ITEEPILMTY | 191 | H2122 RP1L1 | A*01:01 | 308 | chr8-10611205 | C-to-A |
| Neoantigen_B10 | KVTGHRWLK | 192 | H2009 BSG | A*03:01 | 51 | chr19-579577 | G-to-A |
| Neoantigen_B12 | KLSEQILKK | 193 | H2009 TLR5 | A*03:01 | 39 | chr1-223110532 | C-to-G |
| Neoantigen_C3 | GTKPNPHVY | 194 | H2126 OAS3 | A*03:01 | 7336 | chr12-112961105 | G-to-T |

Supplementary Table 5
TSNA and Infectious Disease Epitopes in IVS Control Experiments

| Peptide Name | Sequence | SEQ ID NO: | Origin (Cell Line, Gene) | Predicted HLA Restriction | Predicted Binding Affinity | Mutation Position | Mutation Nucleotide |
|---|---|---|---|---|---|---|---|
| Neoantigen_C4 | QQQQVVTNK | 195 | H2126 LRP1 | A*03:01 | 2361 | chr12-57162861 | G-to-T |
| Neoantigen_C5 | KVLGKGSFAK | 196 | H2126 PLK2 | A*03:01 | 40 | chr5-58459089 | G-to-A |
| Neoantigen_C6 | SVQAPVPPK | 197 | H2009 ENGASE | A*03:01 | 279 | chr17-79084548 | C-to-G |
| EBV RAKF | RAKFKQLL | 198 | EBV BZLF-1 | B*08:01 | 457 | Nan | Nan |
| Flu CTEL | CTELKLSDY | 199 | Influenza NP | A*01:01 | 39 | Nan | Nan |
| Flu ELRS | ELRSRYWAI | 200 | Influenza A | B*08:01 | 12 | Nan | Nan |
| CMV NLVP | NLVPMVATV | 201 | CMV pp65 | A*02:01 | 45 | Nan | Nan |
| Flu GILG | GILGFVFTL | 202 | Influenza MP | A*02:01 | 20 | Nan | Nan |
| HCV KLVA | KLVALGINAV | 203 | HCV NS3 | A*02:01 | 49 | Nan | Nan |
| HIV LKE | ILKEPVHGV | 204 | HIV pol | A*02:01 | 144 | Nan | Nan |
| RSV NPKA | NPKASLLSL | 205 | RSV NP | B*07:02 | 60 | Nan | Nan |
| *Mutated peptides in neoantigen sequences are underlined. | | | | | NaN | Nan | Nan |
| **Tumor cell lines: Colo829, H128, H2009, H2122, H2126 | | | | | NaN | Nan | Nan |

Supplementary Table 6

| Clonotype | Frequency | Proportion | TRAV | TRAJ | TRAC | TRBV | TRBD | TRBJ | TRBC |
|---|---|---|---|---|---|---|---|---|---|
| clonotype1 | 386 | 0.49171975 | TRAV8-4 | TRAJ5 | TRAC | TRBV2 | TRBD2 | TRBJ2-5 | TRBC2 |
| clonotype3 | 53 | 0.06751592 | TRAV6 | TRAJ31 | TRAC | TRBV6-1 | TRBD2 | TRBJ14 | TRBC1 |
| clonotype9 | 7 | 0.0089172 | TRAV22 | TRAJ33 | TRAC | TRBV20-1 | TRBD1 | TRBJ1-5 | TRBC1 |
| clototype10 | 5 | 0.00636943 | TRAV17 | TRAJ57 | TRAC | TRBV7-6 | TRBD1 | TRBJ2-3 | TRBC2 |
| clonotype14 | 4 | 0.00509554 | TRAV13-1 | TRAJ33 | TRAC | TRBV28 | TRBD2 | TRBJ2-7 | TRBC2 |

Supplementary Table 6

| ALPHA CDR3 | SEQ ID NO: | BETA CDR3 | SEQ ID NO: | Full Length ALPHA VJ | SEQ ID NO: |
|---|---|---|---|---|---|
| CAVTVTGRRALTF | 206 | CASNPPDAARGQETQYF | 211 | MLLLLVPVLEVIFTLGGTRAQSVTQLGSHVSVSEGALVLLRCN YSSSVPPYLFWYVQYPNQGLQLLLLKYTTGATLVKGINGFEAEF KKSETSFHLTKPSAHMSDAAEYFCAVTVTGRRALTFGSGTRL QVQ | 216 |
| CALNARLMF | 207 | CASSYREYNTEAFF | 212 | MAFWLRRLGLHFRPHLGRRMESFLGGVLLILWLQVDWVKS QKIEQNSEALNIQEGKTATLTCNYTNYSPAYLQWYRQDPGR GPVFLLLIRENEKEKRKERLKVTFDTTLKQSLFHITASQPADSA TYLCALNARLMFGDGTQLVVK | 217 |
| CAVVLDSNYQLIW | 208 | CSATRGHLSNQPQHF | 213 | MKRILGALLGLLSAQVCCVRGIQVEQSPPDLILQEGANSTLRC NFSDSVNNLQWFHQNPWGQLINLFYIPSGTKQNGRLSATTV ATERYSLLYISSSQTTDSGVYFCAVVLDSNYQLIWGAGTKLIIK | 218 |

| | | | | |
|---|---|---|---|---|
| CATASRQGGSEKLVF | 209 | CASSRGGGTDTQYF | 214 | METLLGVSLVILWLQLARVNSQQGEEDPQALSIQEGENATM NCSYKTSINNLQWYRQNSGRGLVHLILIRSNEREKHSGRLRVT LDTSKKSSSLLITASRAADTASYFCATASRQGGSEKLVFGKGTK LTVN | 219 |
| CAASSNYQLIW | 210 | CASSLGLAYEQYF | 215 | MTSIRAVFIFLWLQLDLVNGENVEQHPSTLSVQEGDSAVIKC TYSDSASNYFPWYKQELGKGPQLIIDIRSNVGEKKDQRIAVTL NKTAKHFSLHITETQPEDSAVYFCAASSNYQLIWGAGTKLIIK | 220 |

Supplementary Table 6

| Full Length BETA V(D)J | SEQ ID NO: |
|---|---|
| MDTWLVCWAIFSLLKAGLTEPEVTQTPSHQVTQMGQEVILRCVPISNHLYFYW YRQILGQKVEFLVSFYNNEISEKSEIFDDQFSVERPDGSNFTLKIRSTKLEDSAMYF CASNPPDAARGQETQYFGPGTRLLVL | 221 |
| MSIGLLCCVAFSLLWASPVNAGVTQTPKFQVLKTGQSMTLQCAQDMNHNSM YWYRQDPGMGLRLIYYSASEGTTDKGEVPNGYNVSRLNKREFSLRLESAAPSQT SVYFCASSYREYNTEAFFGQGTRLTVV | 222 |
| MLLLLLLLGPGSGLGAVVSQHPSRVICKSGTSVKIECRSLDFQATTMFWYRQFPK QSLMLMATSNEGSKATYEQGVEKDKFLINHASLTLSTLTVTSAHPEDSSFYICSA TRGHLSNQPQHFGDGTRLSIL | 223 |
| MGTSLLCWVVLGFLGTDHTGAGVSQSPRYKVTKRGQDVALRCDPISGHVSLY WYRQALGQGPEFLTYFNYEAQQDKSGLPNDRFSAERPEGSISTLTIQRTEQRDS AMYRCASSRGGGTDTQYFGPGTRLTVL | 224 |
| MGIRLLCRVAFCFLAVGLVDVKVTQSSRYLVKRTGEKVFLECVQDMDHENMF WYRQDPGLGLRLIYFSYDVKMKEKGDIPEGYSVSREKKERFSLILESASTNQTSM YLCASSLGLAYEQYFGPGTRLTVT | 225 |

The invention claimed is:

1. A method for identifying one or more neoantigens from one or more tumor cells of a subject that are likely to be presented on a surface of the tumor cells, the method comprising the steps of:
   (a) obtaining at least one of exome, transcriptome, or whole genome nucleotide sequencing data from the tumor cells and normal cells of the subject, wherein the nucleotide sequencing data is used to obtain data representing peptide sequences of each of a set of neoantigens identified by comparing the nucleotide sequencing data from the tumor cells and the nucleotide sequencing data from the normal cells, wherein the peptide sequence of each neoantigen comprises at least one alteration that makes it distinct from the corresponding wild-type peptide sequence identified from the normal cells of the subject;
   (b) encoding the peptide sequence of each of the neoantigens into a corresponding numerical vector, each numerical vector including information regarding a plurality of amino acids that make up the peptide sequence and a set of positions of the amino acids in the peptide sequence;
   (c) associating the peptide sequence of each of the neoantigens with one or more k-mer blocks of a plurality of k-mer blocks of the nucleotide sequencing data of the subject;
   (d) determining, using a neural network model stored in a non-transitory computer readable medium of one or more computing devices, a set of presentation likelihoods for the set of neoantigens, each presentation likelihood in the set representing the likelihood that a corresponding neoantigen is presented by one or more MEW alleles on the surface of the tumor cells of the subject, the neural network model comprising:
      (i) two or more layers comprising a first layer and a second layer, each layer comprising one or more nodes, wherein said nodes comprise a memory location for one or more input values;
      (ii) a plurality of connections between nodes of said first layer and one or more nodes of said second layer;
      (iii) optimized parameters stored in memory locations, wherein the optimized parameters transform input values of nodes of the first layer into input values for nodes of the second layer connected to the nodes of the first layer,
      (iv) wherein the optimized parameters are identified using at least a training data set comprising:
         (A) training peptide sequences encoded as numerical vectors including information regarding a plurality of amino acids that make up the peptide sequences and a set of positions of the amino acids in the peptide sequences;
         (B) at least one MHC allele associated with the training peptide sequences;
         (C) for each of the training peptide sequences, one or more labels indicating associations between the training peptide sequence and one or more k-mer blocks of a plurality of k-mer blocks of the nucleotide sequencing data of the training peptide sequences; and
         (D) for each of the training peptide sequences, a label indicating whether the training peptide was presented by the at least one MHC allele,
            wherein a subset of the optimized parameters represent a presence or absence of a presentation hotspot for the one or more k-mer blocks; and
   (v)
   (e) wherein said determining comprises:
      (i) forward feeding the numerical vectors, using a computer processor, through nodes of the first layer and the second layer of the neural network model, said forward feeding comprising transforming values of the numerical vectors as they are fed from nodes of the first layer to nodes of the second layer using the optimized parameters;
      (ii) generating, using a computer processor, the set of presentation likelihoods for the set of antigens from the transformed numerical vectors, each presentation likelihood in the set representing the likelihood that a corresponding antigen is presented by one or more class I MEW alleles on the surface of the tumor cells of the subject;
   (f) selecting a subset of the set of neoantigens based on the set of presentation likelihoods to generate a set of selected neoantigens; and
   (g) returning the set of selected neoantigens.

2. The method of claim 1, wherein generating the set of presentation likelihoods for the set of antigens comprises:
   (a) generating a dependency score for each of the one or more MHC alleles indicating whether the MEW allele will present the neoantigen based on the particular amino acids at the particular positions of the peptide sequence.

3. The method of claim 2, wherein generating the set of presentation likelihoods for the set of antigens further comprises:
   (a) transforming the dependency scores to generate a corresponding per-allele likelihood for each MEW allele indicating a likelihood that the corresponding MEW allele will present the corresponding neoantigen; and
   (b) combining the per-allele likelihoods to generate the presentation likelihood of the neoantigen.

4. The method of claim 3, wherein the transforming the dependency scores models the presentation of the neoantigen as mutually exclusive across the one or more MHC alleles.

5. The method of claim 2, wherein generating the set of presentation likelihoods for the set of antigens further comprises:
   (a) transforming a combination of the dependency scores to generate the presentation likelihood, wherein transforming the combination of the dependency scores models the presentation of the neoantigen as interfering between the one or more MHC alleles.

6. The method of claim 2, wherein the set of presentation likelihoods are further identified by at least one or more allele noninteracting features, and further comprising:
    (a) applying the neural network model to the allele noninteracting features to generate a dependency score for the allele noninteracting features indicating whether the peptide sequence of the corresponding neoantigen will be presented based on the allele noninteracting features.

7. The method of claim 6, further comprising:
    (a) combining the dependency score for each MHC allele in the one or more MHC alleles with the dependency score for the allele noninteracting features;
    (b) transforming the combined dependency scores for each MHC allele to generate a per-allele likelihood for each MHC allele indicating a likelihood that the corresponding MHC allele will present the corresponding neoantigen; and
    (c) combining the per-allele likelihoods to generate the presentation likelihood.

8. The method of claim 6, further comprising:
    (a) combining the dependency scores for each of the MHC alleles and the dependency score for the allele noninteracting features; and
    (b) transforming the combined dependency scores to generate the presentation likelihood.

9. The method of claim 6, wherein the at least one or more allele noninteracting features comprises associations between the peptide sequence of the neoantigen and one or more k-mer blocks of a plurality of k-mer blocks of the nucleotide sequencing data of the neoantigen.

10. The method of claim 1, wherein the one or more MHC alleles include two or more different MHC alleles.

11. The method of claim 1, wherein the peptide sequences comprise peptide sequences having lengths other than 9 amino acids.

12. The method of claim 1, wherein encoding the peptide sequence comprises encoding the peptide sequence using a one-hot encoding scheme.

13. The method of claim 1, wherein the label indicating whether the training peptide was presented by the at least one MHC allele is identified as present in at least one of a plurality of samples, the plurality of samples comprising at least one of:
    (a) one or more cell lines engineered to express a single MHC allele;
    (b) one or more cell lines engineered to express a plurality of MHC alleles;
    (c) one or more human cell lines obtained or derived from a plurality of patients;
    (d) fresh or frozen tumor samples obtained from a plurality of patients; and
    (e) fresh or frozen tissue samples obtained from a plurality of patients.

14. The method of claim 1, wherein the training data set further comprises at least one of:
    (a) data associated with peptide-MHC binding affinity measurements for at least one of the training peptide sequences; and
    (b) data associated with peptide-MHC binding stability measurements for at least one of the training peptide sequences.

15. The method of claim 1, wherein the set of presentation likelihoods are further identified by at least expression levels of the one or more MHC alleles in the subject, as measured by RNA-seq or mass spectrometry.

16. The method of claim 1, wherein the set of presentation likelihoods are further identified by features comprising at least one of:
    (a) predicted affinity between a neoantigen in the set of neoantigens and the one or more MHC alleles; and
    (b) predicted stability of the neoantigen encoded peptide-MHC complex.

17. The method of claim 1, wherein the set of numerical likelihoods are further identified by features comprising at least one of:
    (a) the C-terminal sequences flanking the neoantigen encoded peptide sequence within its source protein sequence; and
    (b) the N-terminal sequences flanking the neoantigen encoded peptide sequence within its source protein sequence.

18. The method of claim 1, wherein selecting the set of selected neoantigens comprises selecting neoantigens that have an increased likelihood of being presented on the tumor cell surface relative to unselected neoantigens.

19. The method of claim 1, wherein selecting the set of selected neoantigens comprises selecting neoantigens that have an increased likelihood of being capable of inducing a tumor-specific immune response in the subject relative to unselected neoantigens.

20. The method of claim 1, wherein selecting the set of selected neoantigens comprises selecting neoantigens that have an increased likelihood of being capable of being presented to naive T-cells by professional antigen presenting cells (APCs) relative to unselected neoantigens, optionally wherein the APC is a dendritic cell (DC).

21. The method of claim 1, wherein selecting the set of selected neoantigens comprises selecting neoantigens that have a decreased likelihood of being subject to inhibition via central or peripheral tolerance relative to unselected neoantigens.

22. The method of claim 1, wherein selecting the set of selected neoantigens comprises selecting neoantigens that have a decreased likelihood of being capable of inducing an autoimmune response to normal tissue in the subject relative to unselected neoantigens.

23. The method of claim 1, wherein the one or more tumor cells are selected from the group consisting of: lung cancer, melanoma, breast cancer, ovarian cancer, prostate cancer, kidney cancer, gastric cancer, colon cancer, testicular cancer, head and neck cancer, pancreatic cancer, brain cancer, B-cell lymphoma, acute myelogenous leukemia, chronic myelogenous leukemia, chronic lymphocytic leukemia, and T-cell lymphocytic leukemia, non-small cell lung cancer, and small cell lung cancer.

24. The method of claim 1, further comprising generating an output for constructing a personalized cancer vaccine from the set of selected neoantigens.

25. The method of claim 24, wherein the output for the personalized cancer vaccine comprises at least one peptide sequence or at least one nucleotide sequence encoding the set of selected neoantigens.

26. The method of claim 1, wherein the neural network model includes a plurality of network models for the MHC alleles, each network model assigned to a corresponding MHC allele of the MHC alleles and including a series of nodes arranged in one or more layers.

27. The method of claim 26, wherein the neural network model is trained by updating parameters of the neural network model, and wherein the parameters of at least two network models of the neural network model are jointly updated for at least one training iteration.

28. The method of claim 1, wherein two or more optimized parameters transform an input value for a node of the first layer into an input value of a node in the second layer.

29. A computer system comprising:
   (a) a computer processor;
   (b) a memory storing computer program instructions that when executed by the computer processor cause the computer processor to:
      (i) obtain at least one of exome, transcriptome, or whole genome nucleotide sequencing data from the tumor cells and normal cells of the subject, wherein the nucleotide sequencing data is used to obtain data representing peptide sequences of each of a set of neoantigens identified by comparing the nucleotide sequencing data from the tumor cells and the nucleotide sequencing data from the normal cells, wherein the peptide sequence of each neoantigen comprises at least one alteration that makes it distinct from the corresponding wild-type peptide sequence identified from the normal cells of the subject;
      (ii) encode the peptide sequence of each of the neoantigens into a corresponding numerical vector, each numerical vector including information regarding a plurality of amino acids that make up the peptide sequence and a set of positions of the amino acids in the peptide sequence;
      (iii) associate the peptide sequence of each of the neoantigens with one or more k-mer blocks of a plurality of k-mer blocks of the nucleotide sequencing data of the subject;
      (iv) determine, using a neural network model, a set of presentation likelihoods for the set of neoantigens, each presentation likelihood in the set representing the likelihood that a corresponding neoantigen is presented by one or more MHC alleles on the surface of the tumor cells of the subject, the neural network model comprising:
         (A) a plurality of connections between nodes of said first layer and one or more nodes of said second layer,
         (B) optimized parameters stored in memory locations, wherein the optimized parameters transform input values of nodes of the first layer into input values for nodes of the second layer connected to the nodes of the first layer,
         (C) two or more layers comprising a first layer and a second layer, each layer comprising one or more nodes, wherein said nodes comprise a memory location for one or more input values;
         (D) wherein the optimized parameters are generated using a training data set comprising:
            (1) training peptide sequences encoded as numerical vectors including information regarding a plurality of amino acids that make up the peptide sequences and a set of positions of the amino acids in the peptide sequences;
            (2) at least one MHC allele associated with the training peptide sequences;
            (3) for each of the training peptide sequences, one or more labels indicating associations between the training peptide sequence and one or more k-mer blocks of the k-mer blocks of the nucleotide sequencing data of the training peptide sequences; and
            (4) for each of the training peptide sequences, a label indicating whether the training peptide was presented by the at least one WIC allele, wherein a subset of the optimized parameters represent a presence or absence of a presentation hotspot for the one or more k-mer blocks;
         wherein said determination of the set of presentation likelihoods comprises:
            (A) forward feeding the numerical vectors, using a computer processor, through nodes of the first layer and the second layer of the neural network model, said forward feeding comprising transforming values of the numerical vectors as they are fed from nodes of the first layer to nodes of the second layer using the optimized parameters;
            (B) generating, using a computer processor, the set of presentation likelihoods for the set of antigens from the transformed numerical vectors, each presentation likelihood in the set representing the likelihood that a corresponding antigen is presented by one or more class I MHC alleles on the surface of the tumor cells of the subject;
      (v) select a subset of the set of neoantigens based on the set of presentation likelihoods to generate a set of selected neoantigens; and
      (vi) return the set of selected neoantigens.

* * * * *

UNITED STATES PATENT AND TRADEMARK OFFICE
CERTIFICATE OF CORRECTION

PATENT NO. : 11,264,117 B2  
APPLICATION NO. : 16/403331  
DATED : March 1, 2022  
INVENTOR(S) : Brendan Bulik-Sullivan et al.

Page 1 of 1

It is certified that error appears in the above-identified patent and that said Letters Patent is hereby corrected as shown below:

On the Title Page

Item (57), under Abstract, Line 7, replace "subject; The" with --subject. The--.

In the Claims

In Column 243, Claim 1, Line 43, replace "MEW" with --MHC--.

In Column 243, Claim 1, Line 56, replace "layer," with --layer;--.

In Column 244, Claim 1, Line 20, delete "and".

In Column 244, Claim 1, Line 21, delete "(v)".

In Column 244, Claim 1, Line 35, replace "MEW" with --MHC--.

In Column 244, Claim 2, Line 44, replace "MEW" with --MHC--.

In Column 244, Claim 3, Line 52, replace "MEW" with --MHC--.

In Column 244, Claim 3, Line 54, replace "MEW" with --MHC--.

In Column 248, Claim 29, Line 4, replace "values;" with --values,--.

In Column 248, Claim 29, Line 22, replace "WIC" with --MHC--.

Signed and Sealed this  
Twenty-seventh Day of December, 2022

Katherine Kelly Vidal  
*Director of the United States Patent and Trademark Office*